(12) United States Patent
Huang et al.

(10) Patent No.: US 8,450,343 B2
(45) Date of Patent: May 28, 2013

(54) GAMMA SECRETASE MODULATORS

(76) Inventors: Xianhai Huang, Warren, NJ (US);
Anandan Palani, Bridgewater, NJ (US);
Jun Qin, Somerset, NJ (US); Robert G. Aslanian, Rockaway, NJ (US);
Zhaoning Zhu, Plainsboro, NJ (US);
William Greenlee, Teaneck, NJ (US);
Hubert Josien, Jersey City, NJ (US);
Wei Zhou, Scotch Plains, NJ (US);
Xiaohong Zhu, Edison, NJ (US); Chad E. Bennett, Metuchen, NJ (US); Dmitri Pissarnitski, Scotch Plains, NJ (US);
Mihirbaran Mandal, Scotch Plains, NJ (US); Pawan Dhondi, Elizabeth, NJ (US); Troy McCracken, Hoboken, NJ (US); Thomas Bara, Linden, NJ (US);
Zhiqiang Zhao, Scotch Plains, NJ (US);
Duane Burnett, Bernardsville, NJ (US);
John Clader, Cranford, NJ (US)

( * ) Notice: Subject to any disclaimer, the term of this patent is extended or adjusted under 35 U.S.C. 154(b) by 74 days.

(21) Appl. No.: 12/746,041

(22) PCT Filed: Dec. 4, 2008

(86) PCT No.: PCT/US2008/085515
§ 371 (c)(1),
(2), (4) Date: Sep. 24, 2010

(87) PCT Pub. No.: WO2009/073777
PCT Pub. Date: Jun. 11, 2009

(65) Prior Publication Data
US 2011/0015190 A1 Jan. 20, 2011

Related U.S. Application Data

(60) Provisional application No. 60/992,839, filed on Dec. 6, 2007.

(51) Int. Cl.
| | | |
|---|---|---|
| *A01N 43/42* | (2006.01) | |
| *A61K 31/44* | (2006.01) | |
| *C07D 471/02* | (2006.01) | |
| *C07D 491/02* | (2006.01) | |
| *C07D 498/02* | (2006.01) | |
| *C07D 513/02* | (2006.01) | |
| *C07D 515/02* | (2006.01) | |

(52) U.S. Cl.
USPC .......................................... 514/303; 546/119

(58) Field of Classification Search
None
See application file for complete search history.

(56) References Cited

U.S. PATENT DOCUMENTS
| | | |
|---|---|---|
| 4,937,258 A | 6/1990 | Shaw |
| 5,026,712 A | 6/1991 | Davey |
| 2005/0042284 A1 | 2/2005 | Hobden et al. |
| 2006/0004013 A1 | 1/2006 | Kimura et al. |

FOREIGN PATENT DOCUMENTS
| | | |
|---|---|---|
| WO | WO2004/071431 | 8/2004 |
| WO | WO2004/110350 | 12/2004 |
| WO | WO2005/063756 | 7/2005 |
| WO | WO2006/001877 | 1/2006 |
| WO | WO2006/045554 | 5/2006 |

OTHER PUBLICATIONS

Borisy, et. al., Proceedings of the National Academy of Sciences of the United States of America, 100(13) 7977-7982.*
Burger's Medicinal Chemistry and Drug Discovery, 5th Ed. Part 1, pp. 975-977 (1995).*
Banker, et. al., (1996), Modern Pharmaceuticals, p. 596.*
Vippagunta et. al. Advanced Drug Delivery Reviews 48 (2001) 3-26.*
International Search Report for PCT/EP2008/085515 filed Apr. 12, 2008 mailed on Mar. 10, 2009; 3 pages.
Written Opinion for PCT/EP2008/085515 filed Apr. 12, 2008 mailed on Mar. 10, 2009; 8 pages.

* cited by examiner

*Primary Examiner* — Jeffrey Murray
(74) *Attorney, Agent, or Firm* — Susan L. Hess; Henry Jeanette; Gerard M. Devlin

(57) ABSTRACT

This invention provides novel compounds that are modulators of gamma secretase. The compounds have the formula (I) wherein $R^2$ is a fused bicyclic ring of the formula (II). Also disclosed are methods of modulating gamma secretase activity and methods of treating Alzheimer's disease using the compounds of formula (I).

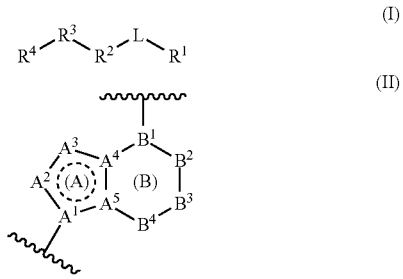

8 Claims, No Drawings

GAMMA SECRETASE MODULATORS

REFERENCE TO RELATED APPLICATION

This Application claims the benefit of U.S. Provisional Application Ser. No. 60/992,839 filed Dec. 6, 2007.

CROSS REFERENCE TO RELATED APPLICATION

This application is entered into national stage examination under 37 U.S.C. 371 and stems from international patent application No. PCT/US2008/085515 filed on Apr. 12, 2008.

FIELD OF THE INVENTION

The present invention relates to certain heterocyclic compounds useful as gamma secretase modulators, pharmaceutical compositions containing the compounds, and methods of treatment using the compounds and compositions to treat various diseases including central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed tor creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22, suggest a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute the main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer disease and Down syndrome*, Proceeding National Academy of Science USA, June 1985, 82(12), p. 4245-4249.).

Furthermore, it is known that mutations of APP and presenelin genes, which are observed in familial Alzheimer's disease, increase production of Aβ40 and Aβ42 (for example, see Gouras G K, et al, *Intraneuronal Aβ142 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and normeuronal cells*, Journal of Biological Chemistry, Dec. 19, 1997, 272(51), p. 32247-32253.). Therefore, compounds which reduce production of Aβ40 and Aβ42 are expected to be agents for controlling progress of Alzheimer's disease or for preventing the disease.

These Aβs are produced when APP is cleaved by beta secretase and subsequently cleaved by gamma secretase. In consideration of this, creation of inhibitors of γ-secretase and β-secretase has been attempted for the purpose of reducing production of Aβs. Many of these known secretase inhibitors are peptides or peptidomimetics such as L-685,458. L-685, 458, an aspartyl protease transition state mimic, is a potent inhibitor of γ-secretase activity, (Biochemistry; Aug. 1, 2000, 39(30), p. 8698-8704).

Also of interest in connection with the present invention are: US 2007/0117798 (Eisai, published May 24, 2007); US 2007/0117839 (Eisai, published May 24, 2007); US 2006/0004013 (Eisai, published Jan. 5, 2006); WO 2005/110422 (Boehringer Ingelheim, published Nov. 24, 2005); WO 2006/045554 (Cellzone A G, published May 4, 2006); WO 2004/110350 (Neurogenetics, published Dec. 23, 2004); WO 2004/071431 (Myriad Genetics, published Aug. 26, 2004); US 2005/0042284 (Myriad Genetics, published Feb. 23, 2005) and WO 2006/001877 (Myriad Genetics, published Jan. 5, 2006).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as gamma secretase modulators (including inhibitors, antagonists and the like), methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the Aβ using such compounds or pharmaceutical compositions.

One embodiment, of the present invention is directed to compounds of formula (I):

(I)

or a pharmaceutically acceptable salt, solvate, ester or prodrug thereof, wherein $R^1$, $R^2$, $R^3$, $R^4$, and L are as defined below.

This invention also provides compounds of formula (I).

This invention also provides compounds of formula (I) in pure and isolated form.

This invention also provides compounds of formula (I) selected from the group consisting of: compounds of formulas IA to 35A, 35A.1, 35A2, 45A-49A, 52A to 79A, 82A to 88A, 91A to 97A, 100A and 101A.

This invention also provides compounds of formula (I) selected from the group consisting of: compounds of formulas IA.1, IA, IB.1, IB, IC, ID.1, ID, IE.1, IE, B2, B3, B5-B9, B11, B13-B35, B45 to B49, B52 to B74, B45.1 to B49.1, B52.1 to B74.1, B75 to B77, and 1 to 162 (identified below).

This invention also provides compounds of formula (I) selected from the group consisting of: compounds of formulas B2, B3, B5-B9, B11, B13-B35, B45 to B49, B52 to B74, B45.1 to B49.1, B52.1 to B74.1, B75 to B77, and 1 to 162 (identified below).

This invention also provides compounds of formula (I) selected from the group consisting of: compounds of formulas B2, B3, B5-B9, B11, and B13 to B35.

This invention also provides compounds of formula (I) selected from the group consisting of: compounds of formulas B45 to B49 and B52 to B74.1.

This invention also provides compounds of formula (I) selected from the group consisting of: compounds of formulas B45.1 to B49.1 and B52.1 to B74.1.

This invention also provides compounds of formula (I) selected from the group consisting of: compounds of formulas B75 to B77.

This invention also provides compounds of formula (I) selected from the group consisting of: compounds of formulas 1 to 162 (identified below).

This invention also provides pharmaceutical compositions comprising an effective amount of one or more (e.g., one) compounds of formula (I), or a pharmaceutically acceptable salt, ester or solvate thereof, and a pharmaceutically acceptable carrier.

This invention also provides pharmaceutical compositions comprising an effective amount of one or more (e.g., one) compounds of formula (I), or a pharmaceutically acceptable salt, ester or solvate thereof, and an effective amount of one or more (e.g., one) other pharmaceutically active ingredients (e.g., drugs), and a pharmaceutically acceptable carrier.

The compounds of formula (I) can be useful as gamma secretase modulators and can be useful in the treatment and prevention of diseases such as, for example, central nervous system disorders such as Alzheimers disease and Downs Syndrome.

Thus, this invention also provides methods for: (1) method for modulating (including inhibiting, antagonizing and the like) gamma-secretase; (2) treating one or more neurodegenerative diseases; (3) inhibiting the deposition of amyloid protein (e.g., amyloid beta protein) in, on or around neurological tissue (e.g., the brain); (4) Alzheimer's disease: and (5) treating Downs syndrome; wherein each method comprises administering an effective amount of one or more (e.g., one) compounds of formula (I) to a patient in need of such treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula (I) and the administration of an effective amount of one or more (e.g., one) other pharmaceutical active ingredients (e.g., drugs).

This invention also provides methods for (1) treating mild cognitive impairment; (2) treating glaucoma; (3) treating cerebral amyloid angiopathy; (4) treating stroke; (5) treating dementia; (6) treating microgliosis; (7) treating brain inflammation; and (8) treating olfactory function loss; wherein each method comprises administering an effective amount of one or more (e.g., one) compounds of formula (I) to a patient in need of such treatment.

This invention also provides a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described below), the combined quantities of the compound of formula (I) and the other pharmaceutically active ingredient being effective to treat the diseases or conditions mentioned in any of the above methods.

This invention also provides any of the above mentioned methods, pharmaceutical compositions or kit wherein the compound of formula (I) is selected from the group consisting of: compounds of formulas IA to 35A, 35A.1, 35A.2, 45A-79A, 82A to 88A, 91A to 97A, 100A and 101A.

This invention also provides any of the above mentioned methods, pharmaceutical compositions or kit wherein the compound of formula (I) is selected from the group consisting of: compounds IA.1, IA, IB.1, IB, IC, ID.1, ID, IE.1, IE, B2, B3, B5-B9, B11, B13-B35, B45 to B74, B45.1 to B74.1, B75 to B77, and 1 to 162 (identified below).

This invention also provides any of the above mentioned methods, pharmaceutical compositions or kit wherein the compound of formula (I) is selected from the group consisting of: compounds B2, B3, B5-B9, B11, B13-B35, B45 to B74, B45.1 to B74.1, B75 to B77, and 1 to 162 (identified below).

This invention also provides any of the above mentioned methods, pharmaceutical compositions or kit wherein the compound of formula (I) is selected from the group consisting of: compounds B2, B3, B5-B9, B11, and B13 to B35.

This invention also provides any of the above mentioned methods, pharmaceutical compositions or kit wherein the compound of formula (I) is selected from the group consisting of: compounds B45 to B74.

This invention also provides any of the above mentioned methods, pharmaceutical compositions or kit wherein the compound of formula (I) is selected from the group consisting of: compounds B45.1 to B74.1.

This invention also provides any of the above mentioned methods, pharmaceutical compositions or kit wherein the compound of formula (I) is selected from the group consisting of: compounds B75 to B77.

This invention also provides any of the above mentioned methods, pharmaceutical compositions or kit wherein the compound of formula (I) is selected from the group consisting of: compounds 1 to 162 (identified below).

DETAILED DESCRIPTION OF THE INVENTION

This invention provides compounds, useful as gamma secretase modulators, of formula (I):

(I)

or a pharmaceutically acceptable salt, solvate, ester or prodrug thereof, wherein:

$R^1$, $R^2$, $R^3$, $R^4$ and L are each independently selected;

$R^1$ is selected from the group consisting of: alkyl, alkenyl, alkynyl, cycloalkyl, heterocyclyl (e.g., heterocycloalkyl), cycloalkenyl, aryl (e.g., phenyl), heteroaryl (e.g., pyridyl), heterocyclenyl (i.e., heterocycloalkenyl), fused cycloalkylaryl- (i.e., cycloalkyfusedlaryl-), fused heterocycloalkylaryl- (i.e., heterocycloalkyfusedaryl-), fused cycloalkylheteroaryl-(i.e., cycloalkylfusedheteroary-), fused heterocycloalkylheteroaryl-(i.e., heterocycloalkylfusedheteroaryl-), fused benzocycloalkylalkyl-(i.e., benzefusedcycloalkylalkyl-), fused benzoheterocycloalkylalkyl-(i.e., benzofusedheterocycloalkylalkyl-), fused heteroarylcycloalkylalkyl-(i.e., heteroarylfusedcycloalkylalkyl-), fused heteroarylheterocycloalkylalkyl-(i.e., heteroarylfusedheterocycloalkylalkyl-), fused cycloalkylarylalkyl-(i.e., cycloalkyfusedlarylalkyl-), fused heterocycloalkylarylalkyl-(i.e., heterocycloalkylfusedarylalkyl-), fused cycloalkylheteroarylalkyl-(i.e., cycloalkylfusedheteroarylalkyl-), fused heterocycloalkyll heteroarylalkyl-(i.e., heterocycloalkylfusedheteroarylalkyl-), and wherein each of said: alkyl, alkenyl, alkynyl, cycloalkyl, heterocyclyl, cycloalkenyl, aryl, heteroaryl, heterocyclenyl, fused cycloalkylaryl, fused heterocycloalkylaryl-, fused cycloalkylheteroaryl-, fused heterocycloalkylheteroaryl-, fused benzocycfoalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, and fused heterocycloalkylheteroarylalkyl-$R^1$ groups is optionally substituted with 1-5 independently selected $R^{21}$ groups;

L is selected from the group consisting of: L is a direct bond, —O—, —N($R^5$)—, —C($R^6$)($R^7$)—, —(C=O)—, —(C=N$R^{21A}$)—, —S—, —S(O)—, and —S(O)$_2$—;

$R^2$ is the fused bicyclic ring:

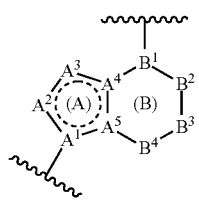

wherein:

(1) Ring (A) is a five membered heteroaryl ring comprising atoms $A^1$ to $A^5$, or Ring (A) is a five membered heterocycloalkenyl ring comprising atoms $A^1$ to $A^5$ (wherein the dashed circle in Ring A represents a sufficient number of bonds for Ring (A) to be a heteroaryl ring, or for Ring (A) to be a heterocycloalkenyi ring, thus the dashed circle represents at feast one bond), and:

(i) when Ring (A) is a heteroaryl ring:
  (a) $A^1$, $A^4$, and $A^5$ are each independently selected from the group consisting of C and N,
  (b) $A^2$ and $A^3$ are each independently selected from the group consisting of: N, S, O or C, and wherein each substitutable C is optionally substituted with one $R^{21B}$ group and each $R^{21B}$ for each C is independently selected, and wherein each substitutable N is optionally substituted with one $R^{21A}$ group and each $R^{21A}$ for each N is independently selected,
  (c) provided that at least one (e.g., 1 to 3, or 1 to 2, or 1) of $A^1$ to $A^5$ is a heteroatom (i.e., at least one of $A^1$ to $A^5$ is selected from the group consisting of N, S and O), and provided that the total number of heteroatoms in Ring (A) is 1 to 3, and
  (d) provided that Ring (A) does not contain two adjacent ring O atoms, and does not contain adjacent O and S atoms (i.e., there are no —O—O—, and no —O—S—, and no —S—O— ring members in Ring (A)), and (ii) when ring (A) is a heterocycloalkenyl ring:
  (a) $A^1$, $A^4$, and $A^5$ are each independently selected from the group consisting of C and N, and wherein each substitutable C is optionally substituted with one $R^{21B}$ group and each $R^{21B}$ for each C is independently selected, and wherein each substitutable N is optionally substituted with one $R^{21A}$ group and each $R^{21A}$ for each N is independently selected,
  (b) $A^2$ and $A^3$ are each independently selected from the group), and wherein each substitutable C is optionally substituted with one $R^{21B}$ group and each $R^{21B}$ for each C is independently selected, and wherein each substitutable N is optionally substituted with one $R^{21A}$ group and each $R^{21A}$ for each N is independently selected,
  (c) provided that at least one (e.g., 1 to 3, or 1 to 2, or 1) of $A^1$ to $A^5$ is a heteroatom (i.e., at least one of $A^1$ to $A^5$ is selected from the group consisting of N, S, SO, SO$_2$ and O), and provided that the total number of heteroatoms in Ring (A) is 1 to 3, and
  (d) provided that Ring (A) does not contain two adjacent ring O atoms, and does not contain two adjacent S groups (e.g., does not contain two adjacent groups selected from the group consisting of —S—, —S(O)— and —S(O)$_2$), and does not contain adjacent O atom and S groups (i.e., there are no —O—O—, and no —O—S—, and no —O—SO—, and no O—SO$_2$—, and no —S—O— ring members in Ring (A)), (2) Ring (B) (which comprises atoms $A^4$, $A^5$, and $B^1$ to $B^4$) is a cycloalkyl, cycloalkenyl, heterocycloalkyl, heterocycloalkenyl, heteroaryl or phenyl ring, and
  (a) $A^4$ and $A^5$ are as defined for Ring (A) above,
  (b) in said phenyl Ring (B):
    (i) $A^4$, $A^5$, and $B^1$ to $B^4$ are C, and
    (ii) $B^2$, $B^3$, and $B^4$ are each optionally substituted with one $R^{21B}$ group (and the substitution on each carbon is independent of the substitutions on the remaining carbons),
  (c) in said cycloalkyl Ring (B):
    (i) $A^4$, $A^5$, and $B^1$ are C,
    (ii) $B^2$, $B^3$, and $B^4$ are each independently selected from the group consisting of: C, —(C=O)— and —(C=N$R^{21A}$)— (e.g., —(C=N—O$R^{15}$)—, and —(C=N—N($R^{15}$)($R^{16}$))—), provided that there are only 0 to 2 moieties selected from the group consisting of —(C=O)— and —(C=N$R^{21A}$)— (i.e. in said cycloalkyl Ring (B) either $B^2$, $B^3$, and $B^4$ are all C, or one of $B^2$, $B^3$, and $B^4$ is C and the remaining two are selected from the group consisting of —(C=O)— and —(C=N$R^{21A}$)—, or two of $B^2$, $B^3$, and $B^4$ are C and the remaining one is selected from the group consisting of: —(C=O)— and —(C=N$R^{21A}$)—), and (iii) each substitutable $A^4$, $A^5$, and $B^1$ to $B^4$ C is optionally substituted with 1 or 2 independently selected $R^{21B}$ groups (and the substitution on each carbon is independent of the substitutions on the remaining carbons, and those skilled in the art will appreciate that the total number of optional substituents on a carbon is determined by the number bonds in the ring to the ring atom), (d) in said cycloalkenyl Ring (B):
  (i) $A^4$, $A^5$, and $B^1$ are C,
  (ii) $B^2$, $B^3$, and $B^4$ are each independently selected from the group consisting of: C, —(C=O)— and —(C=NR$^{21A}$)— (e.g., —(C=N—OR$^{15}$)—, and —(C=N—N(R$^{15}$)(R$^{16}$))—), provided that there are only 0 to 2 moieties selected from the group consisting of C=O and —C=NR$^{21A}$ (i.e. in said cycloalkenyl Ring (B) either $B^2$, $B^3$, and $B^4$ are all C, or one of $B^2$, $B^3$, and $B^4$ is C and the remaining two are selected from the group consisting of —(C=O)— and —(C=NR$^{21A}$)—, or two of $B^2$, $B^3$, and $B^4$ are C and the remaining one is selected from the group consisting of: —(C=O)— and
  (iii) each substitutable $A^4$, $A^5$, and $B^1$ to $B^4$ C is optionally substituted with 1 or 2 independently selected $R^{21B}$ groups (and the substitution on each carbon is independent of the substitutions on the remaining carbons, and those skilled in the art will appreciate that the total number of optional substituents on a carbon is determined by the number bonds in the ring to the ring atom), and
  (iv) said cycloalkenyl Ring (B) comprises one or two double bonds (and in one example one double bond, and in another example two double bonds), (e) in said heterocycloalkyl Ring (B):
  (i) $B^1$ is selected from the group consisting of N and C,
  (ii) $B^2$, $B^3$ and $B^4$ are each independently selected from the group consisting of: N, C, —(C=O)— and —(C=NR$^{21A}$)— e.g., —(C=N—OR$^{15}$)—, and —(C=N—N(R$^{15}$)(R$^{16}$))—) O, S, S(O), and S(O)$_2$, and provided that there are no —O—O— bonds, no —O—S— bonds, no O—S(O) bonds, no —O—S(O)$_2$ bonds, and no —N—S— bonds in the ring, and provided that the ring does not comprise three adjacent nitrogen atoms,
  (iii) at least one (e.g., 1 to 3, or 1 to 2, or 1) of $A^4$, $A^5$, and $B^1$ to $B^4$ is a heteroatom, provided that when $A^4$ is a heteroatom said heteroatom is N, and when $A^5$ is a heteroatom said heteroatom is N, and when $B^1$ is a heteroatom said heteroatom is N, and the heteroatoms for $B^2$ to $B^4$ (when one or more of $B^2$ to $B^4$ are heteroatoms) are selected from the group consisting of: N, O, S, S(O), and S(O)$_2$,
  (iv) the total number of heteroatoms in said heterocycloalkyl Ring (B) is 1 to 4, and
  (v) each substitutable $A^4$, $A^5$, and $B^1$ to $B^4$ C is optionally substituted with 1 or 2 independently selected $R^{21B}$ groups (and the substitution on each carbon is independent of the substitutions on the remaining carbons, and those skilled in the art will appreciate that the total number of optional substituents on a carbon is determined by the number bonds in the ring to the ring atom), and
  (vi) each substitutable $B^2$ to $B^4$ N is optionally substituted with one $R^{21A}$ group and each $R^{21A}$ for each N is independently selected, (f) in said heterocycloalkenyl Ring (B):
  (i) $B^1$ is selected from the group consisting of N and C,
  (ii) $B^2$, $B^3$ and $B^4$ are each independently selected from the group consisting of: N, C, —(C=O)— and —(C=NR$^{21A}$)— (e.g., —(C=N—OR$^{15}$)—, and —(C=N—N(R$^{15}$)(R$^{16}$))—), O, S, S(O), and S(O)$_2$, and provided that there are no —O—O— bonds, no —O—S— bonds, no O—S(O) bonds, no —O—S(O)$_2$ bonds, and no —N—S— bonds in the ring, and provided that the ring does not comprise three adjacent nitrogen atoms,
  (iii) at least one (e.g., 1 to 3, or 1 to 2, or 1) of $A^4$, $A^5$, and $B^1$ to $B^4$ is a heteroatom, provided that when $A^4$ is a heteroatom said heteroatom is N, and when $A^5$ is a heteroatom said heteroatom is N, and when $B^1$ is a heteroatom said heteroatom is N, and the heteroatoms for $B^2$ to $B^4$ (when one or more of $B^2$ to $B^4$ are heteroatoms) are selected from the group consisting of: N, O, S, S(O), and S(O)$_2$,
  (iv) the total number of heteroatoms in said heterocycloalkenyl Ring (B) is 1 to 4, and
  (v) each substitutable $A^4$, $A^5$, and $B^1$ to $B^4$ C is optionally substituted with 1 or 2 independently selected $R^{21B}$ groups (and the substitution on each carbon is independent of the substitutions on the remaining carbons, and those skilled in the art will appreciate that the total number of optional substituents on a carbon is determined by the number bonds in the ring to the ring atom),
  (vi) each substitutable $B^2$ to $B^4$ N is optionally substituted with one $R^{21A}$ group and each $R^{21A}$ for each N is independently selected, and
  (vii) said heterocycloalkenyl Ring (B) comprises one or two double bonds (and in one example one double bond, and in another example two double bonds); and (g) in said heteroaryl Ring (B):
  (i) $B^1$ is C,
  (ii) $B^2$ to $B^4$ are each independently selected from the group consisting of C and N,
  (iii) at least one (e.g., 1 to 4, or 1 to 3, or 1 to 2, or 1) of $A^4$, $A^5$, and $B^2$ to $B^4$ is a heteroatom (e.g., at least one of $A^4$ or $A^5$ is N, or at least one of $B^2$ to $B^4$ is N), and
  (iv) the total number of heteroatoms in said heteroaryl Ring (B) is 1 to 3 and wherein each substitutable $B^2$ to $B^4$ C is optionally substituted with one $R^{21B}$ group (and the substitution on each carbon is independent of the substitutions on the remaining carbons);

$R^3$ is selected from the group consisting of: aryl-(e.g., phenyl), heteroaryl-(e.g., pyridyl), cycloalkyl-, cycloalkenyl, cycloalkylalkyl-, heterocyclyl-, heterocyclenyl-, heterocyclylalkyl-, heterocyclyalkenyl-, fused benzocycloalkyl-(i.e., benzofusedcycloalkyl-), fused benzoheterocycbalkyl-(i.e., benzofusedheterocycloalkyl-), fused heteroarylcycloalkyl-(i.e., heteroarylfusedcycloalkyl-), fused heteroarylheterocycloalkyl-(i.e., heteroarylfusedheterocycloalkyl-), fused cycloalkylaryl (i.e., cycloalkyfusedlaryl-), fused heterocycloalkylaryl-(i.e., heterocycloalkylfusedaryl-), fused cycloalkylheteroaryl-(i.e., cycloalkylfusedheteroaryl-), fused heterocycloalkylheteroaryl-(i.e., heterocycloalkylfusedheteroaryl-),

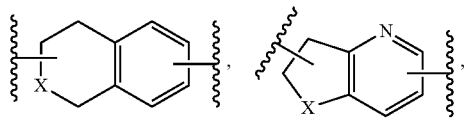

-continued

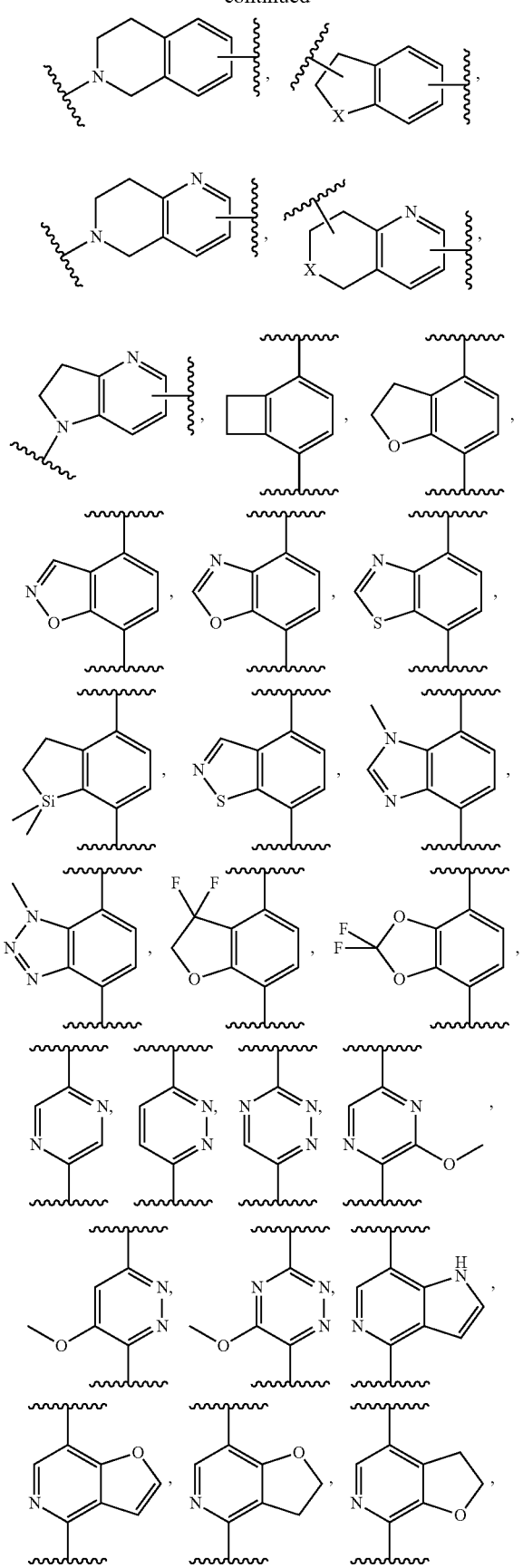

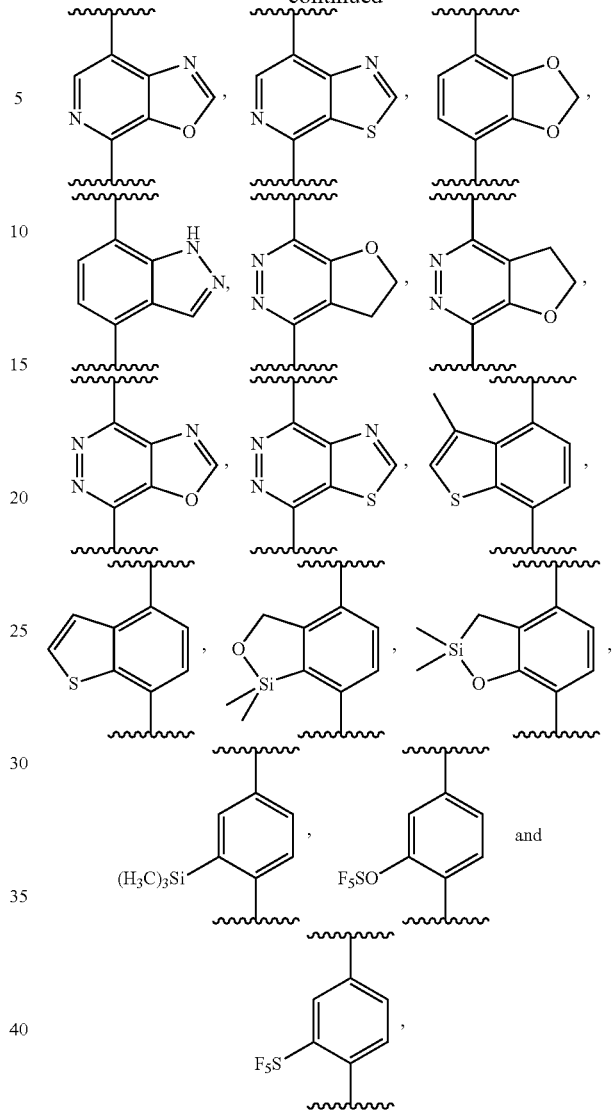

wherein X is selected from the group consisting of: O, —N(R$^{14}$)— and —S—; and wherein each of said R$^3$ moieties is optionally substituted with 1-5 independently selected R$^{21}$ groups;

R$^4$ is selected from the group consisting of: arylalkoxy-, heteroarylalkoxy-, arylalkylamino-, heteroarylalkylamino-, aryl, heteroaryl, cycloalkyl-, cycloalkenyl, heterocyclyl, heterocyclenyl, and heterocyclyalkyl-, wherein each of said R$^4$ arylalkoxy-, heteroarylalkoxy-, arylalkylamino-, heteroarylalkylamino-, aryl, heteroaryl, heterocyclyl, heterocyclenyl, and heterocyclyalkyl-is optionally substituted with 1-5 independently selected R$^{21}$ groups; or R$^3$ and R$^4$ are linked together to form a fused tricyclic ring system wherein R$^3$ and R$^4$ are as defined above and the ring linking R$^3$ and R$^4$ is an alkyl ring, or a heteroalkyl ring, or an aryl ring, or a heteroaryl ring, or an alkenyl ring, or a heteroalkenyl ring (for example, the tricyclic ring system is formed by linking the atoms adjacent to the atoms by which R$^3$ and R$^4$ are bound together);

R$^5$ is selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$); or R$^5$ taken together with R$^1$ and the nitrogen to which they are bound form a heterocycloalkyl or heterocycloalkenyl ring fused to said R$^1$ ring, said fused ring is optionally substituted with 1 to 5 independently selected R$^{21}$ groups;

R$^6$ and R$^7$ are each independently selected from the group consisting of: H, alkyl, alkenyl, alkynyl, aryl, arylalkyl-, alkylaryl-, cycloalkyl, cycloalkylalkyl-, heteroaryl, heteroarylalkyl-, heterocyclyl (i.e., heterocycloalkyl) and heterocyclylalkyl-(i.e., heterocycloalkenyl), wherein independently each of said alkyl, alkenyl and alkynyl, aryl, arylalkyl-, alkylaryl-, cycloalkyl, cycloalkylalkyl-, heteroaryl, heteroarylalkyl-, heterocyclyl and heterocyclylalkyl-is optionally substituted with 1 to 5 independently selected R$^{21}$ groups; or R$^6$ taken together with R$^1$ and the carbon to which they are bound form a cycloalkyl, cycloalkenyl, heterocycloalkyl or heterocycloalkenyl ring fused to said R$^1$ ring, said fused ring is optionally substituted with 1 to 5 independently selected R$^{21}$ groups; or R$^6$ and R$^7$ taken together with the carbon to which they are bound form a spirocycloalkyl ring, a spirocycloalkenyl ring, a spiroheterocycloalkyl ring, or a spiroheterocyclalkenyl ring, and wherein the Spiro ring is optionally substituted with 1-5 independently selected R$^{21}$ groups;

R$^{15A}$ and R$^{16A}$ are independently selected from the group consisting of alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, (R$^{16}$)$_q$-alkyl, (R$^{18}$)$_q$-cycloalkyl, (R$^{18}$)$_q$-cycloalkylalkyl, (R$^{18}$)$_q$-heterocyclyl, (R$^{18}$)$_q$-heterocyclylalkyl, (R$^{18}$)$_q$-aryl, (R$^{18}$)$_q$-arylalkyl, (R$^{18}$)$_q$-heteroaryl and (R$^{18}$)$_q$-heteroarylalkyl, wherein q is 1 to 5 and each R$^{18}$ is independently selected (and those skilled in the art will appreciate that the R$^{18}$ moieties can be bound to any available substitutable atom);

R$^{15}$, R$^{16}$ and R$^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, (R$^{18}$)$_q$-alkyl, (R$^{18}$)$_q$-cycloalkyl, (R$^{18}$)$_q$-cycloalkylalkyl, (R$^{18}$)$_q$-heterocyclyl, (R$^{18}$)$_q$-heterocyclylalkyl, (R$^{18}$)$_q$-aryl, (R$^{18}$)$_q$-arylalkyl, (R$^{18}$)$_q$-heteroaryl and (R$^{18}$)$_q$-heteroarylalkyl, wherein q is 1 to 5 and each R$^{18}$ is independently selected (and those skilled in the art will appreciate that the R$^{18}$ moieties can be bound to any available substitutable atom);

each R$^{18}$ is independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)R$^{18}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{20}$, —O-heterocyclyl, —O-cycloalkylalkyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl); or alternately, two R$^{18}$ moieties on adjacent carbons can be linked together to form:

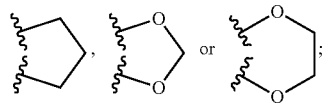

R$^{19}$ is alkyl, cycloalkyl, aryl, arylalkyl or heteroarylalkyl;

R$^{20}$ is alkyl, cycloalkyl, aryl, halo substituted aryl, arylalkyl, heteroaryl or heteroarylalkyl;

each R$^{21}$ group is independently selected from the group consisting of alkyl, alkenyl, alkynyl, cycloalkyl, cycloalkylalkyl, cycloalkenyl, heterocyclyl (i.e., heterocycloalkyl), heterocyclylalkyl (i.e., heterocycloalkylalkyl), aryl, arylalkyl, heteroaryl, heteroarylalkyl, halo, —CN, —OR$^{15}$, —C(O)R$^{15}$, —C(O)OR$^{16}$, —C(O)N(R$^{15}$)(R$^{16}$), —P(O)(CH$_3$)$_2$, —SO(=NR$^{15}$)R$^{16}$—, —SF$_5$, —OSF$_5$, —Si(R$^{15A}$)$_3$ wherein each R$^{15A}$ is independently selected, —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$, —CH$_2$N(R$^{15}$)(R$^{16}$), —N(R$^{15}$)S(O)R$^{16A}$, —N(R$^{15}$)S(O)$_2$R$^{16A}$, —CH$_2$—N(R$^{15}$)S(O)$_2$R$^{16A}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15A}$, =NOR$^{15}$, —N$_3$, —NO$_2$, —S(O)$_2$R$^{15A}$, —O—N=C(R$^{15}$)$_2$ (wherein each R$^{15}$ is independently selected), and —O—N=O(R$^{15}$)$_2$ wherein said R$^{15}$ groups are taken together with the carbon atom to which they are bound to form a 5 to 10 membered ring and wherein said ring optionally contains 1 to 3 heteroatoms independently selected from the group consisting of —O—, —S—, —S(O)—, —S(O)$_2$—, and —NR$^{21A}$;

each R$^{21A}$ is independently selected from the group consisting of H, alkyl, alkenyl, alkynyl, cycloalkyl, cycloalkylalkyl, cycloalkenyl, heterocyclyl (i.e., heterocycloalkyl), heterocyclylalkyl (i.e., heterocycloalkylalkyl), aryl, arylalkyl, heteroaryl, heteroarylalkyl, halo, —OR$^{15}$, —CN, -alkyl-(R$^{15}$)(R$^{16}$), —CH(R$^{15}$)(R$^{16}$), —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —C(O)R$^{15}$, —C(O)OR$^{15}$, —C(O)N(R$^{15}$)(R$^{16}$), —C(=NOR$^{15}$)R$^{16}$, —CH$_2$—N(R$^{15}$)S(O)$_2$R$^{16A}$, —CH$_2$—N(R$^{15}$)C(O)N(R$^{16}$)(R$^{17}$), —CH$_2$—N(R$^{15}$)C(O)OR$^{16}$, —C(R$^{15}$)=NOR$^{16}$, —S(O)R$^{15A}$; —S(O)(OR$^{15}$), —S(O)$_2$(OR$^{15}$), —S(O)$_2$R$^{15A}$, —S(O)N(R$^{15}$)(R$^{16}$), —S(O)$_2$N(R$^{15}$)(R$^{16}$), —P(O)(OR$^{15}$)(OR$^{16}$), —N(R$^{15}$)(R$^{16}$), —N(R$^{15}$)C(O)R$^{16}$, —N(R$^{15}$)S(O)R$^{16A}$, —N(R$^{15}$)S(O)$_2$R$^{16A}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —N(R$^{15}$)C(O)OR$^{16}$, —N$_3$, —NO$_2$, —P(O)(CH$_3$)$_2$, —SO(=NR$^{15}$)R$^{16}$—, —SF$_5$, and —OSF$_5$;

each R$^{21B}$ group is independently selected from the group consisting of H, alkyl, alkenyl, alkynyl, cycloalkyl, cycloalkylalkyl, cycloalkenyl, heterocyclyl (i.e., heterocycloalkyl), heterocyclylalkyl (i.e., heterocycloalkylalkyl), aryl, arylalkyl, heteroaryl, heteroarylalkyl, halo, —OR$^{15}$, —ON, -alkyl-(R$^{15}$)(R$^{16}$), —CH(R$^{15}$)(R$^{16}$), —CH$_2$—N(R$^{15}$)C(O)R$^{16}$, —CH$_2$—N(R$^{15}$)C(O)N(R$^{16}$)(R$^{17}$), —CH$_2$—R$^{15}$, —CH$_2$N(R$^{15}$)(R$^{16}$), —C(O)R$^{15}$, —C(O)OR$^{15}$, —C(O)N(R$^{15}$)(R$^{16}$), —C(=NOR$^{15}$)R$^{16}$, —CH$_2$—N(R$^{15}$)S(O)$_2$R$^{16A}$, —CH$_2$—N(R$^{15}$)C(O)N(R$^{16}$)(R$^{17}$), —CH$_2$—N(R$^{15}$)C(O)OR$^{16}$, —C(R$^{15}$)=NOR$^{16}$, —SR$^{15}$; —S(O)R$^{15A}$; —S(O)(OR$^{15}$), —S(O)$_2$(OR$^{15}$), —S(O)$_2$R$^{15A}$, —S(O)N(R$^{15}$)(R$^{16}$), —S(O)$_2$N(R$^{15}$)(R$^{16}$), —P(O)(OR$^{15}$)(OR$^{16}$), —N(R$^{15}$)(R$^{16}$), —N(R$^{15}$)C(O)R$^{16}$, —N(R$^{15}$)S(O)R$^{16A}$, —N(R$^{15}$)S(O)$_2$R$^{16A}$, —N(R$^{15}$)S(O)$_2$N(R$^{16}$)(R$^{17}$), —N(R$^{15}$)S(O)N(R$^{16}$)(R$^{17}$), —N(R)C(O)N(R$^{16}$)(R$^{17}$), —N(R$^{15}$)C(O)OR$^{16}$, —N$_3$, —$NO_2$, —$P(O)(CH_3)_2$, —$SO(=NR^{15})R^{16}$—, —$SF_5$, —$OSF_5$, and —$Si(R^{15A})_3$ wherein each $R^{15A}$ is independently selected;

Independently, each alkyl, cycloalkenyl, cycloalkyl, cycloalkylalkyl, heterocyclyl, heterocyclylalkyl, aryl, arylalkyl, heteroaryl, heteroarylalkyl, alkenyl and alkynyl $R^{21}$, $R^{21A}$, and $R^{21B}$ group is optionally substituted by 1 to 5 independently selected $R^{22}$ groups wherein each $R^{22}$ group is independently selected from the group consisting of alkyl, cycloalkyl, cycloalkenyl, heterocyclyl, aryl, heteroaryl, halo, —$CF_3$, —CN, —$OR^{13}$, —$C(O)R^{15}$, —$C(O)OR^{15}$, -alkyl-C(O)$OR^{15}$, C(O)N($R^{15}$)($R^{16}$), —S(O)N($R^{15}$)($R^{16}$), —S(O)$_2$N($R^{15}$)($R^{16}$), —C(=NOR$^{15}$)R$^{16}$, —P(O)(OR$^{15}$)(OR$^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)S(O)$_2$ $R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{18}$)($R^{17}$), —N($R^{15}$)C(O)N($R^{16}$)($R^{17}$), —$CH_2$—N($R^{13}$)C(O)N($R^{16}$)($R^{17}$), —N($R^{15}$)C(O)$OR^{16}$, —$CH_2$—N($R^{15}$)C(O)$OR^{16}$, —$N_3$, =$NOR^{15}$, —$NO_2$, —S(O)$R^{15A}$ and —S(O)$_2R^{15A}$; and With the proviso that when $R^3$ is aryl and $R^1$ comprises a 5 or 6-membered aryl or heteroaryl ring, then said 5 or 6-membered aryl or heteroaryl ring is not substituted with an $R^{21}$ group that is selected from the group consisting of the moieties: —O-(5 or 6 membered aryl), —S-(5 or 6 membered aryl), —S(O)$_2$-(5 or 6 membered aryl), —N($R^{15}$)-(5 or 6 membered aryl), —C(O)-(5 or 6 membered aryl), -alkyl-(5 or 6 membered aryl), —O-(5 or 6 membered heteroaryl), —S-(5 or 6 membered heteroaryl), —S(O)$_2$-(5 or 6 membered heteroaryl), —N($R^{15}$)-(5 or 6 membered heteroaryl), —C(O)-(5 or 6 membered heteroaryl), and -alkyl-(5 or 6 membered heteroaryl).

Those skilled in the art will appreciate that the above proviso means that when $R^3$ is aryl and $R^1$ comprises a 5 or 6-membered aryl or heteroaryl ring, then said 5 or 6-membered aryl or heteroaryl ring is not substituted with —O-(5 or 6 membered aryl), —S-(5 or 6 membered aryl), —S(O)$_2$-(5 or 6 membered aryl), —N($R^{15}$)-(5 or 6 membered aryl), —C(O)-(5 or 6 membered aryl), -alkyl-(5 or 6 membered aryl), —O-(5 or 6 membered heteroaryl), —S-(5 or 6 membered heteroaryl), —S(O)$_2$-(5 or 6 membered heteroaryl), —N($R^{15}$)-(5 or 6 membered heteroaryl), —C(O)-(5 or 6 membered heteroaryl), or -alkyl-(5 or 6 membered heteroaryl).

The compounds of this invention are useful for treating central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

Thus, for example, the compounds of this invention can be used to treat the following diseases or conditions: Alzheimers disease, mild cognitive impairment (MC1), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci. USA 95, 6448-53 (1998)), and Olfactory function loss (Getchell, et. al. Neurobiology of Aging, 663-673, 24, 2003).

In one embodiment of this invention $R^1$ is selected from the group consisting of: alkyl, alkenyl, alkynyl, cycloalkyl, heterocyclyl (e.g., heterocycloalkyl), cycloalkenyl, aryl (e.g., phenyl), heteroaryl (e.g., pyridyl), heterocyclenyl (i.e., heterocycloalkenyl), wherein each of said: alkyl, alkenyl, alkynyl, cycloalkyl, heterocyclyl, cycloalkenyl, aryl, heteroaryl, and heterocyclenyl $R^1$ groups is optionally substituted with 1-5 independently selected $R^{21}$ groups.

In another embodiment of this invention Ring (A) is heteroaryl wherein:
(a) $A^1$, $A^4$, and $A^5$ are each independently selected from the group consisting of C and N,
(b) $A^2$ and $A^3$ are each independently selected from the group consisting of: N, S, O or C, and wherein each substitutable C is optionally substituted with one $R^{21B}$ group and each $R^{21B}$ for each C is independently selected, and wherein each substitutable N is optionally substituted with one $R^{21A}$ group and each $R^{21A}$ for each N is independently selected,
(c) provided that at least one (e.g., 1 to 3, or 1 to 2, or 1) of $A^1$ to $A^5$ is a heteroatom (i.e., at least one of $A^1$ to $A^5$ is selected from the group consisting of N, S and O), and provided that the total number of heteroatoms in Ring (A) is 1 to 3, and
(d) provided that Ring (A) does not contain two adjacent ring O atoms, and does not contain adjacent O and S atoms (i.e., there are no —O—O—, and no —O—S—, and no —S—O— ring members in Ring (A)).

In another embodiment of this invention $R^3$ is selected from the group consisting of: phenyl and pyridyl, wherein said $R^3$ group is optionally substituted with 1 to 4 independently selected $R^{21}$ groups.

In another embodiment of this invention $R^4$ is a five membered heteroaryl ring optionally substituted with 1 to 4 independently selected $R^{21}$ groups.

In one embodiment of this invention:
$R^1$ is selected from the group consisting of: alkyl, alkenyl, alkynyl, cycloalkyl, heterocyclyl (e.g., heterocycloalkyl), cycloalkenyl, aryl (e.g., phenyl), heteroaryl (e.g., pyridyl), heterocyclenyl (i.e., heterocycloalkenyl), wherein each of said: alkyl, alkenyl, alkynyl, cycloalkyl, heterocyclyl, cycloalkenyl, aryl, heteroaryl, and heterocyclenyl $R^1$ groups is optionally substituted with 1-5 independently selected $R^{21}$ groups;
Ring (A) is heteroaryl wherein:
(a) $A^1$, $A^4$, and $A^5$ are each independently selected from the group consisting of C and N,
(b) $A^2$ and $A^3$ are each independently selected from the group consisting of: N, S, O or C, and wherein each substitutable C is optionally substituted with one $R^{21B}$ group and each $R^{21B}$ for each C is independently selected, and wherein each substitutable N is optionally substituted with one $R^{21A}$ group and each $R^{21A}$ for each N is independently selected,
(c) provided that at least one (e.g., 1 to 3, or 1 to 2, or 1) of $A^1$ to $A^5$ is a heteroatom (i.e., at least one of $A^1$ to $A^5$ is selected from the group consisting of N, S and O), and provided that the total number of heteroatoms in Ring (A) is 1 to 3, and
(d) provided that Ring (A) does not contain two adjacent ring O atoms, and does not contain adjacent O and S atoms (i.e there are no —O—O—, and no —O—S—, and no —S—O— ring members in Ring (A));
$R^3$ is selected from the group consisting of: phenyl and pyridyl, wherein said $R^3$ group is optionally substituted with 1 to 4 independently selected $R^{21}$ groups; and
$R^4$ is a five membered heteroaryl ring optionally substituted with 1 to 4 independently selected $R^{21}$ groups.

Examples of moieties formed when $R^3$ and $R^4$ are linked together to form a fused tricyclic ring system include, but are not limited to:

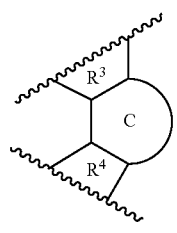

wherein R³ and R⁴ are as defined for formula (I), and Ring C is the ring linking R³ and R⁴, that is Ring C is an alkyl ring, or a heteroalkyl ring, or an aryl ring, or a heteroaryl ring, or an alkenyl ring, or a heteroalkenyl ring.

Examples of moieties formed when R³ and R⁴ are linked together to form a fused tricyclic ring system include, but are not limited to:

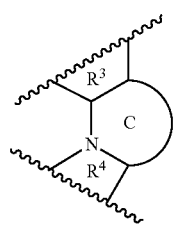

wherein R³ and R⁴ are as defined for formula (I), and Ring C is the ring linking R³ and R⁴, that is Ring C is a heteroalkyl ring, or a heteroaryl ring, or a heteroalkenyl ring.

In one example, the fused tricyclic ring system formed when R³ and R⁴ are linked together is

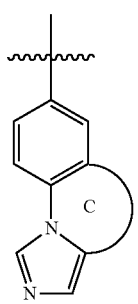

wherein Ring C is a heteroalkyl ring, or a heteroaryl ring, or a heteroalkenyl ring, thus, for example, the tricyclic ring system is formed by linking the atoms adjacent to the atoms by which R³ and R⁴ are bound together), and wherein said fused tricyclic ring system is optionally substituted with 1 to 5 independently selected R²¹ groups.

Other examples of moieties formed when R³ and R⁴ are linked together to form a fused tricyclic ring system include, but are not limited to:

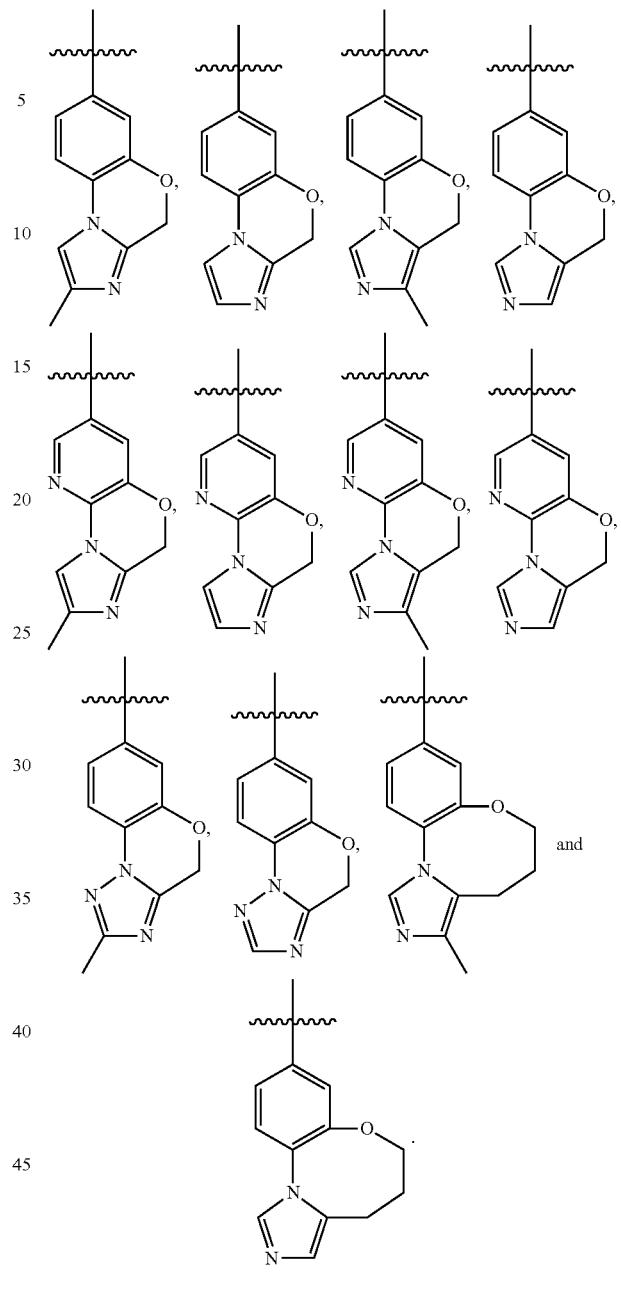

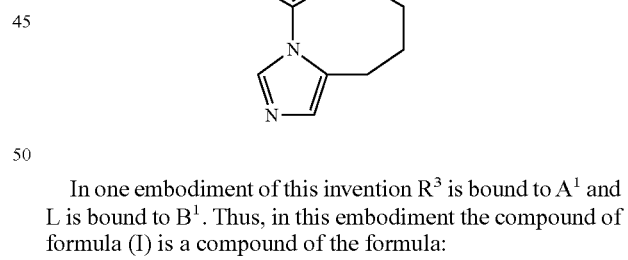

In one embodiment of this invention R³ is bound to A¹ and L is bound to B¹. Thus, in this embodiment the compound of formula (I) is a compound of the formula:

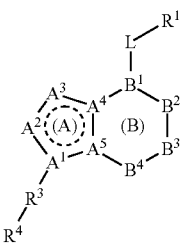

(IA.1)

In one embodiment of this invention R³ is bound to A¹ and L is bound to B¹. Thus, in this embodiment the compound of formula (I) is a compound of the formula:

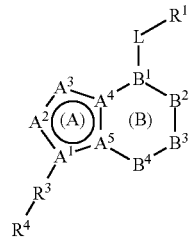

(IA)

In another embodiment of this invention R³ is bound to B¹ and L is bound to A¹. Thus, in this embodiment the compound of formula (I) is a compound of the formula:

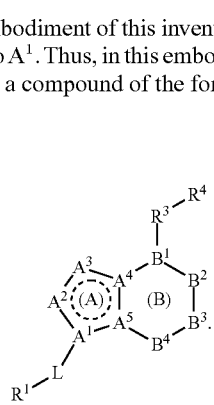

(IB.1)

In another embodiment of this invention R³ is bound to B¹ and L is bound to A¹. Thus, in this embodiment the compound of formula (I) is a compound of the formula:

(IB)

In another embodiment of this invention the R⁴—R³— moiety is:

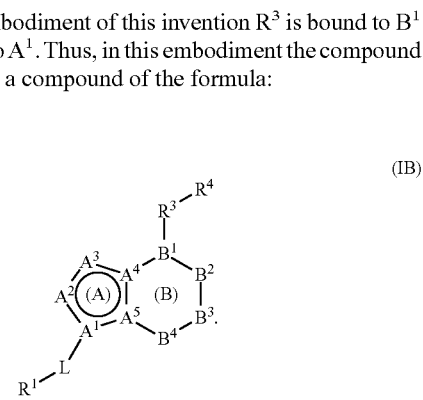

Thus, in another embodiment of this invention the compound of formula (I) is a compound of the formula:

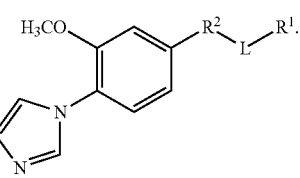

(IC)

In another embodiment of this invention the compound of formula a compound of the formula:

(ID.1)

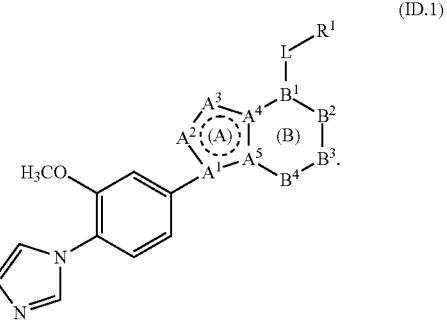

In another embodiment of this invention the compound of formula (I) is a compound of the formula:

(ID)

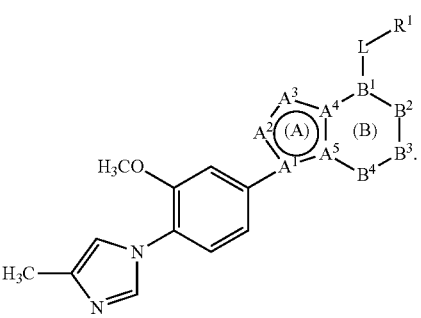

In another embodiment of this invention the compound of formula (I) is a compound the formula:

(IE.1)

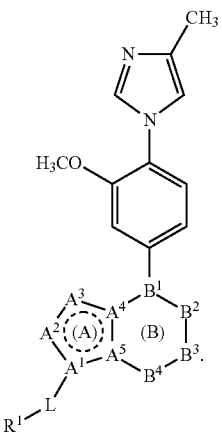

In another embodiment of this invention the compound of formula (I) is a compound the formula:

(IE)

[Chemical structure showing a methyl-substituted imidazole attached to a methoxyphenyl group connected to ring system (A)-(B) with substituents $A^1$-$A^5$, $B^1$-$B^4$, and $R^1$-L]

Another embodiment of this is directed to compounds of formula (I) wherein at least one (e.g., 1 to 3, or 1-2, or 1) group selected from the group consisting of: —SF$_5$, —OSF$_5$, and —Si(R$^{15A}$)$_3$ is present, and wherein each R$^{15A}$ is independently selected, and wherein when there is more than one group, each group is independently selected.

Another embodiment of this is directed to compounds of formula (I) wherein at least one (e.g., 1 to 3, or 1-2, or 1) group selected from the group consisting of: —SF$_5$ and —OSF$_5$ is present, and wherein when there is more than one group, each group is independently selected.

In one embodiment of this invention one group selected from the group consisting of: —SF$_5$, —OSF$_5$, and —Si(R$^{15A}$)$_3$ (wherein each R$^{15A}$ is independently selected) is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected) are present in the compounds of formula (I), wherein at least one group is other than —Si(R$^{15A}$)$_3$.

In another embodiment of this invention three groups selected from the group consisting of: —SF$_5$, —OSF$_5$, and —Si(R$^{15A}$)$_3$ (wherein each R$^{15A}$ is independently selected) are present in the compounds of formula (I), wherein at least one group is other than —Si(R$^{15A}$)$_3$.

In another embodiment of this invention one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I), wherein at least one group is other than —Si(R$^{15A}$)$_3$.

In another embodiment of this invention three groups selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I), wherein at least one group is other than —Si(R$^{15A}$)$_3$.

In another embodiment of this invention one group selected from the group consisting of: —SF$_5$, —OSF$_5$, and —Si(R$^{15A}$)$_3$ (wherein each R$^{15A}$ is independently selected from the group consisting of methyl, ethyl and phenyl) is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I), wherein at least one group is other than —Si(R$^{15A}$)$_3$.

In another embodiment of this invention three groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I), wherein at least one group is other than —Si(R$^{15A}$)$_3$.

In another embodiment of this invention one group selected from the group consisting of: —SF$_5$, —OSF$_5$, and —Si(R$^{15A}$)$_3$ (wherein each R$^{15A}$ is independently selected from the group consisting of methyl and ethyl) is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl and ethyl) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected from the group consisting of methyl and ethyl) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl and ethyl) are present in the compounds of formula (I), wherein at least one group is other than —Si(R$^{15A}$)$_3$.

In another embodiment of this invention three groups selected from the group consisting of: —SF$_5$, —OSF$_5$, and —Si(R$^{15A}$)$_3$ (wherein each R$^{15A}$ is independently selected from the group consisting of methyl and ethyl) are present in the compounds of formula (I), wherein at least one group is other than —Si(R$^{15A}$)$_3$.

In another embodiment of this invention one group selected from the group consisting of: —SF$_5$, —OSF$_5$, and —Si(R$^{15A}$)$_3$ is present in the compounds of formula (I), and said —Si(R$^{15A}$)$_3$ group is selected from the group consisting of: —Si(CH$_3$)$_3$, —Si(CH$_3$)$_2$phenyl, and —Si(CH$_2$CH$_3$)$_2$CH$_8$.

In another embodiment of this invention two groups selected from the group consisting of: —SF$_5$, —OSF$_5$, and —Si(R$^{15A}$)$_3$ are present in the compounds of formula (I) and said —Si(R$^{15A}$)$_3$ group is selected from the group consisting of: —Si(CH$_3$)$_3$, —Si(CH$_3$)$_2$phenyl, and —Si(CH$_2$CH$_3$)$_2$CH$_3$.

In another embodiment of this invention three groups selected from the group consisting of: —SF$_5$, —OSF$_5$, and —Si(R$^{15A}$)$_3$ are present in the compounds of formula (I), and said —Si(R$^{15A}$)$_3$ group is selected from the group consisting of: —Si(CH$_3$)$_3$, —Si(CH$_3$)$_2$phenyl, and —Si(CH$_2$CH$_3$)$_2$CH$_3$.

In another embodiment of this invention two groups selected from the group consisting of: —SF$_5$, —OSF$_5$, and —Si(R$^{15A}$)$_3$ are present in the compounds of formula (I), wherein at least one group is other than —Si(R$^{15A}$)$_3$, and said —Si(R$^{15A}$)$_3$ group is selected from the group consisting of: —Si(CH$_3$)$_3$, —Si(CH$_3$)$_2$phenyl, and —Si(CH$_2$CH$_3$)$_2$CH$_3$.

In another embodiment of this invention three groups selected from the group consisting of: —SF$_5$, —OSF$_5$, and —Si(R$^{15A}$)$_3$ are present in the compounds of formula (I), wherein at least one group is other than —Si(R$^{15A}$)$_3$, and said —Si(R$^{15A}$)$_3$ group is selected from the group consisting of: —Si(CH$_3$)$_3$, —Si(CH$_3$)$_2$phenyl, and —Si(CH$_2$CH$_3$)$_2$CH$_3$.

In another embodiment of this invention one group selected from the group consisting of: —SF$_5$, —OSF$_5$, and —Si(R$^{15A}$)$_3$ is present in the compounds of formula (I), and said —Si(R$^{15A}$)$_3$ group is selected from the group consisting of: —Si(CH$_3$)$_3$ and —Si(CH$_2$CH$_3$)$_2$CH$_3$.

In another embodiment of this invention two groups selected from the group consisting of: —SF$_5$, —OSF$_5$, and —Si(R$^{15A}$)$_3$ are present in the compounds of formula (I), and said —Si(R$^{15A}$)$_3$ group is selected from the group consisting of: —Si(CH$_3$)$_3$ and —Si(CH$_2$CH$_3$)$_2$CH$_3$.

In another embodiment of this invention three groups selected from the group consisting of: —SF$_5$, —OSF$_5$, and —Si(R$^{15A}$)$_3$ are present in the compounds of formula (I), and said —Si(R$^{15A}$)$_3$ group is selected from the group consisting of: —Si(CH$_3$)$_3$ and —Si(CH$_2$CH$_3$)$_2$CH$_3$.

In another embodiment of this invention two groups selected from the group consisting of: —SF$_5$, —OSF$_5$, and —Si(R$^{15A}$)$_3$ are present in the compounds of formula (I), wherein at least one group is other than —Si(R$^{15A}$)$_3$, and said —Si(R$^{15A}$)$_3$ group is selected from the group consisting of: —Si(CH$_3$)$_3$ and —Si(CH$_2$CH$_3$)$_2$CH$_3$.

In another embodiment of this invention three groups selected from the group consisting of: —SF$_5$, —OSF$_5$, and —Si(R$^{15A}$)$_3$ are present in the compounds of formula (I), wherein at least one group is other than —Si(R$^{15A}$)$_3$, and said —Si(R$^{15A}$)$_3$ group is selected from the group consisting of: —Si(CH$_3$)$_3$, —Si(CH$_3$)$_2$phenyl, and —Si(CH$_2$CH$_3$)$_2$CH$_3$ In another embodiment of this invention one group selected from the group consisting of: —SF$_5$, —OSF$_5$, and —Si(CH$_3$)$_3$ is present.

In another embodiment of this invention two groups selected from the group consisting of: —SF$_5$, —OSF$_5$, and —Si(CH$_3$)$_3$ are present in the compounds of formula (I).

In another embodiment of this invention three groups selected from the group consisting of: —SF$_5$, —OSF$_5$, and —Si(CH$_3$)$_3$ are present in the compounds of formula (I).

In another embodiment of this invention two groups selected from the group consisting of: —SF$_5$, —OSF$_5$, and —Si(CH$_3$)$_3$ are present in the compounds of formula (I), wherein at least one group is other than —Si(CH$_3$)$_3$.

In another embodiment of this invention three groups selected from the group consisting of: —SF$_5$, —OSF$_5$, and —Si(R$^{24}$)$_3$ are present in the compounds of formula (I), wherein at least one group is other than —Si(CH$_3$)$_3$.

In another embodiment of this invention one group selected from the group consisting of: —SF$_5$ and —OSF$_5$ is present in the compounds of formula (I).

In another embodiment of this invention two groups selected from the group consisting of: —SF$_5$ and —OSF$_5$ are present in the compounds of formula (I).

In another embodiment of this invention three groups selected from the group consisting of: —SF$_5$ and —OSF$_5$ are present in the compounds of formula (I).

In another embodiment of this invention one —SF$_5$ group is present in the compounds of formula (I).

In another embodiment of this invention two —SF$_5$ groups are present in the compounds of formula (I).

In another embodiment of this invention three —SF$_5$ groups are present in the compounds of formula (I).

In another embodiment of this invention one —OSF$_5$ group is present in the compounds of formula (I).

In another embodiment of this invention two —OSF$_5$ groups are present in the compounds of formula (I).

In another embodiment of this invention three —OSF$_5$ groups are present in the compounds of formula (I).

In another embodiment of this invention one —Si(R$^{15A}$)$_3$ (wherein each R$^{15A}$ is independently selected) group is present in the compounds of formula (I).

In another embodiment of this invention two —Si(R$^{15A}$)$_3$ (wherein each R$^{15A}$ is independently selected) groups are present in the compounds of formula (I).

In another embodiment of this invention three —Si(R$^{15A}$)$_3$ (wherein each R$^{15A}$ is independently selected) groups are present in the compounds of formula (I).

In another embodiment of this invention one —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention two —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention three —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention one —Si(R$^{15A}$)$_3$ (wherein each R$^{15A}$ is independently selected from the group consisting of methyl, ethyl and phenyl) is present in the compounds of formula (I).

In another embodiment of this invention two —Si(R$^{15A}$)$_3$ (wherein each R$^{15A}$ is independently selected from the group consisting of methyl, ethyl and phenyl) is present in the compounds of formula (I).

In another embodiment of this invention three —Si(R$^{15A}$)$_3$ (wherein each R$^{15A}$ is independently selected from the group consisting of methyl, ethyl and phenyl) is present in the compounds of formula (I).

In another embodiment of this invention one —Si(R$^{15A}$)$_3$ (wherein each R$^{15A}$ is independently selected from the group consisting of methyl and ethyl) is present in the compounds of formula (I).

In another embodiment of this invention two —Si(R$^{15A}$)$_3$ (wherein each R$^{15A}$ is independently selected from the group consisting of methyl and ethyl) is present in the compounds of formula (I).

In another embodiment of this invention three —Si(R$^{15A}$)$_3$ (wherein each R$^{15A}$ is independently selected from the group consisting of methyl and ethyl) is present in the compounds of formula (I).

In another embodiment of this invention one —Si(R$^{15A}$)$_3$ group is present in the compounds of formula (I), and said —Si(R$^{15A}$)$_3$ group is selected from the group consisting of: —Si(CH$_3$)$_3$, —Si(CH$_3$)$_2$phenyl, and —Si(CH$_2$CH$_3$)$_2$CH$_3$ In another embodiment of this invention two —Si(R$^{15A}$)$_3$ groups are present in the compounds of formula (I), and said —Si(R$^{15A}$)$_3$ groups are independently selected from the group consisting of: —Si(CH$_3$)$_3$, —Si(CH$_3$)$_2$phenyl, and —Si(CH$_2$CH$_3$)$_2$CH$_3$.

In another embodiment of this invention three —Si(R$^{15A}$)$_3$ groups are present in the compounds of formula (I), and said —Si(R$^{15A}$)$_3$ groups are independently selected from the group consisting of: —Si(CH$_3$)$_3$, —Si(CH$_3$)$_2$phenyl, and —Si(CH$_2$CH$_3$)$_2$CH$_3$.

In another embodiment of this invention one —Si(R$^{15A}$)$_3$ group is present in the compounds of formula (I), and said —Si(R$^{15A}$)$_3$ group is selected from the group consisting of: —Si(CH$_3$)$_3$ and —Si(CH$_2$CH$_3$)$_2$CH$_3$.

In another embodiment of this invention two —Si(R$^{15A}$)$_3$ groups are present in the compounds of formula (I), and said —Si(R$^{15A}$)$_3$ groups are independently selected from the group consisting of: —Si(CH$_3$)$_3$ and —Si(CH$_2$CH$_3$)$_2$CH$_3$.

In another embodiment of this invention three —Si(R$^{15A}$)$_3$ groups are present in the compounds of formula (I), and said —Si(R$^{15A}$)$_3$ groups are independently selected from the group consisting of: —Si(CH$_3$)$_3$ and —Si(CH$_2$CH$_3$)$_2$CH$_3$.

In another embodiment of this invention one —Si(R$^{15A}$)$_3$ group is present in the compounds of formula (I), and said —Si(R$^{15A}$)$_3$ group is —Si(CH$_3$)$_3$.

In another embodiment of this invention two —Si(R$^{15A}$)$_3$ groups are present in the compounds of formula (I), and said —Si(R$^{15A}$)$_3$ groups are —Si(CH$_3$)$_3$.

In another embodiment of this invention three —Si(R$^{15A}$)$_3$ groups are present the compounds of formula (I), and said —Si(R$^{15A}$)$_3$ groups are —Si(CH$_3$)$_3$.

In another embodiment of this invention one group selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$) is present in the compounds of formula (I).

In another embodiment of this invention one group selected from the group consisting of: —SF$_5$, —OSF$_5$, —Si(CH$_3$)$_3$, and —Si(CH$_2$CH$_3$)$_2$CH$_3$) is present in the compounds of formula (I).

In another embodiment of this invention one group selected from the group consisting of: —SF$_5$, —OSF$_5$, and —Si(CH$_3$)$_3$, is present in the compounds of formula (I).

In another embodiment of this invention one —SF$_5$ group is present in the compounds of formula (I), and one or two additional groups selected from the group consisting of: —SF$_5$, —OSF$_5$, and —Si(R$^{15A}$)$_3$ (wherein each R$^{15A}$ is independently selected) are also present in the compounds of formula (I).

In another embodiment of this invention one —SF$_5$ group is present in the compounds of formula (I), and one or two additional groups selected from the group consisting of: —OSF$_5$, and —Si(R$^{15A}$)$_3$ (wherein each R$^{15A}$ is independently selected) are also present in the compounds of formula (I).

In another embodiment of this invention one —OSF$_5$ group is present in the compounds of formula (I), and one or two additional groups selected from the group consisting of: —SF$_5$, —OSF$_5$, and —Si(R$^{15A}$)$_3$ (wherein each R$^{15A}$ is independently selected) are also present in the compounds of formula (I).

In another embodiment of this invention one —OSF$_5$ group is present in the compounds of formula (I), and one or two additional groups selected from the group consisting of: —SF$_5$ and —Si(R$^{15A}$)$_3$ (wherein each R$^{15A}$ is independently selected) are also present in the compounds of formula (I).

In another embodiment of this invention one —SF$_5$ group is present in the compounds of formula (I), and one or two additional groups selected from the group consisting of: —SF$_5$ and —OSF$_5$ are also present in the compounds of formula (I).

In another embodiment of this invention one —OSF$_5$ group is present in the compounds of formula (I), and one or two additional groups selected from the group consisting of: —SF$_5$ and —OSF$_5$ are also present in the compounds of formula (I).

In another embodiment of this invention one —Si(R$^{15A}$)$_3$ (wherein each R$^{15A}$ is independently selected) group is present in the compounds of formula (I), and one or two groups selected from the group consisting of: —SF$_5$, —OSF$_5$, and —Si(R$^{15A}$ (wherein each R$^{15A}$ is independently selected) are also present in the compounds of formula (I).

In another embodiment of this invention one —Si(R$^{15A}$)$_3$ (wherein each R$^{15A}$ is independently selected) group is present in the compounds of formula (I), and one or two groups selected from the group consisting of: —SF$_5$ and —OSF$_5$ are also present in the compounds of formula (I).

In another embodiment of this invention at least one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention at least one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) is present in the compounds of formula (I).

In another embodiment of this invention at least one group selected from the group consisting of: —SF$_5$, —OSF$_5$, and —Si(R$^{15A}$)$_3$ (wherein each R$^{15A}$ is independently selected from the group consisting of methyl, ethyl and phenyl) is present in the compounds of formula (I).

In another embodiment of this invention at least one group selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$) is present in the compounds of formula (I).

In another embodiment of this invention at least one group selected from the group consisting of: —SF$_5$, —OSF$_5$, and —Si(CH$_3$)$_3$ is present in the compounds of formula (I).

In another embodiment of this invention one group selected from the group consisting of: —SF$_5$, —OSF$_5$, and —Si(R$^{15A}$)$_3$ (wherein each R$^{15A}$ is independently selected) is present in the compounds of formula (I).

In another embodiment of this invention one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) is present in the compounds of formula (I).

In another embodiment of this invention one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) is present in the compounds of formula (I).

In another embodiment of this invention one group selected from the group consisting of: —SF$_5$, —OSF$_5$, and —Si(R$^{15A}$)$_3$ (wherein each R$^{15A}$ is independently selected from the group consisting of methyl ethyl and phenyl) is present in the compounds of formula (I).

In another embodiment of this invention one group selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$) is present in the compounds of formula (I).

In another embodiment of this invention one group selected from the group consisting of: —SF$_5$, —OSF$_5$, —Si(CH$_3$)$_3$, and —Si(CH$_2$CH$_3$)$_2$CH$_3$) is present in the compounds of formula (I).

In another embodiment of this invention one group selected from the group consisting of: —SF$_5$, —OSF$_5$, and —Si(CH$_3$)$_3$, is present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected) are present in the compounds of formula (I).

In another embodiment of this invention two groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I).

In another embodiment of this invention two groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) are present in the compounds of formula (I).

In another embodiment of this invention two groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I).

In another embodiment of this invention two groups independently selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$) is present in the compounds of formula (I).

In another embodiment of this invention two groups independently selected from the group consisting of: —SF$_5$, —OSF$_5$, —Si(CH$_3$)$_3$, and —Si(CH$_2$CH$_3$)$_2$CH$_3$) are present in the compounds of formula (I).

In another embodiment of this invention two groups independently selected from the group consisting of: —SF$_5$, —OSF$_5$, and —Si(CH$_3$)$_3$ are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected) are present in the compounds of formula (I)I.

In another embodiment of this invention three groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I).

In another embodiment of this invention three groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) are present in the compounds of formula (I).

In another embodiment of this invention three groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I).

In another embodiment of this invention three groups independently selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$) is present in the compounds of formula (I).

In another embodiment of this invention three groups independently selected from the group consisting of: —SF$_5$, —OSF$_5$, —Si(CH$_3$)$_3$, and —Si(CH$_2$CH$_3$)$_2$CH$_3$) are present in the compounds of formula (I).

In another embodiment of this invention three groups independently selected from the group consisting of: —SF$_5$, —OSF$_5$, and —Si(CH$_3$)$_3$ are present in the compounds of formula (I).

In another embodiment of this invention at least one group selected from the group consisting of: —SF$_5$, —OSF$_5$, and —Si(R$^{15A}$)$_3$ (wherein each R$^{15A}$ is the same or different alkyl group) is present in the compounds of formula (I).

In another embodiment of this invention at least one group selected from the group consisting of: —SF$_5$, —OSF$_5$, and —Si(R$^{15A}$)$_3$ (wherein each R$^{15A}$ is independently selected from the group consisting of methyl and ethyl) is present in the compounds of formula (I).

In another embodiment of this invention one —SF$_5$ group is present in the compounds of formula (I), and one or two groups selected from the group consisting of: —SF$_5$ and —OSF$_5$ are also present in the compounds of formula (I).

In another embodiment of this invention one —OSF$_5$ group is present in the compounds of formula (I), and one or two groups selected from the group consisting of: —SF$_5$ and —OSF$_5$ are also present in the compounds of formula (I).

In another embodiment of this invention L is —C(R$^6$)(R$^7$)—.

In another embodiment of this invention L is —C(R$^6$)(R$^7$)— wherein R$^6$ and R$^7$ are taken together with the carbon atom to which they are bound to form a spirocycloalkyl ring (e.g., cyclopropyl).

In another embodiment of this invention L is —C(R$^6$)(R$^7$)— wherein R$^6$ and R$^7$ are taken together with the carbon atom to which they are bound to form a spirocycloalkenyl ring.

In another embodiment of this invention L is —C(R$^6$)(R$^7$)— wherein R$^6$ and R$^7$ are taken together with the carbon atom to which they are bound to form a spiroheterocycloalkyl ring.

In another embodiment of this invention L is —C(R$^6$)(R$^7$)— wherein R$^6$ and R$^7$ are taken together with the carbon atom to which they are bound to form a spiroheterocycloalkenyl ring.

In another embodiment of this invention L is —C(R$^6$)(R$^7$)— wherein R$^6$ and R$^7$ are independently selected from the group consisting of: H, alkyl, and alkyl substituted with one R$^{21}$ group.

In another embodiment of this invention L is —C(R$^6$)(R$^7$)— wherein R$^6$ and R$^7$ are independently selected from the group consisting of: H, methyl, and methyl substituted with one R$^{21}$ group.

In another embodiment of this invention L is —C(R$^6$)(R$^7$)— wherein R$^6$ and R$^7$ are independently selected from the group consisting of: H, alkyl, and alkyl substituted with one R$^{21}$ group wherein said R$^{21}$ group is —OR$^{15}$.

In another embodiment of this invention L is —C(R$^6$)(R$^7$)— wherein R$^6$ and R$^7$ are independently selected from the group consisting of: H, alkyl, and alkyl substituted with one R$^{21}$ group wherein said R$^{21}$ group is —OR$^{15}$, and said R$^{15}$ is H (i.e., said R$^{21}$ group is —OH).

In another embodiment of this invention L is selected from the group consisting of:

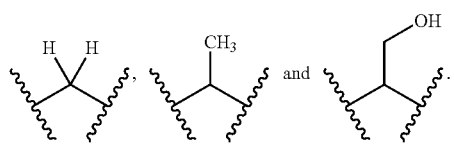

In another embodiment of this invention L is —CH$_2$—.

In another embodiment of this invention L is —CH(CH$_3$)—.

In another embodiment of this invention L is —CH(CH$_2$OH)—.

In another embodiment of this invention R$^1$ is phenyl.

In another embodiment of this invention R$^1$ is phenyl substituted with 1 to 3 halo atoms.

In another embodiment of this invention R$^1$ is phenyl substituted with 1 to 3 F atoms.

In another embodiment of this invention R$^1$ is selected from the group consisting of:

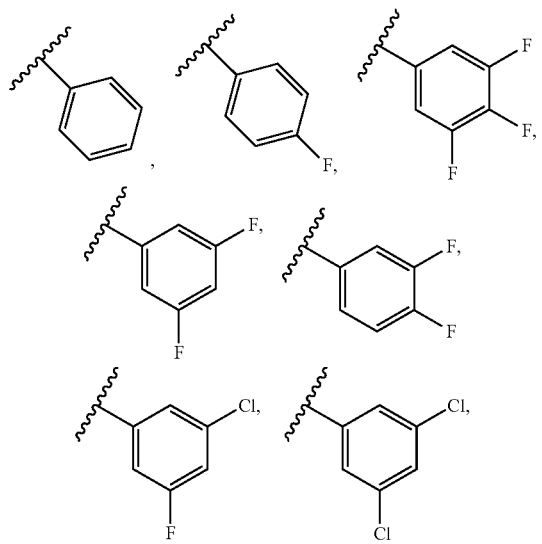

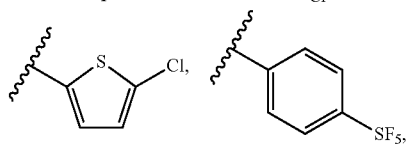

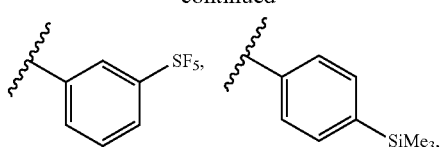

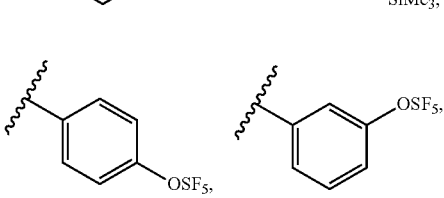

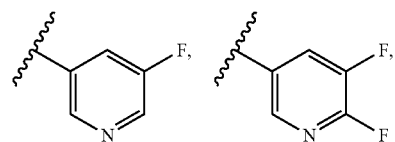

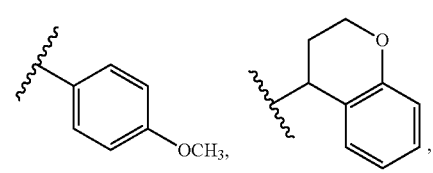

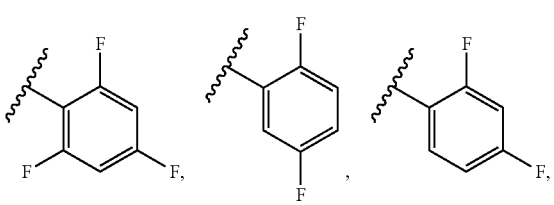

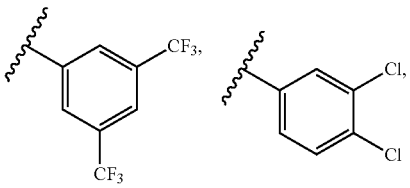

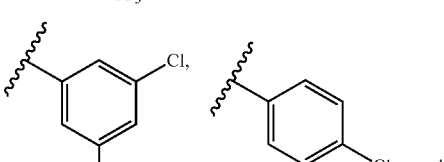

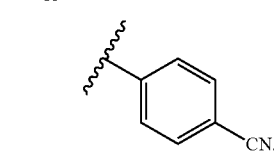

In another embodiment of this invention R$^1$ is selected from the group consisting of:

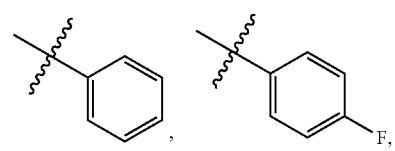

-continued

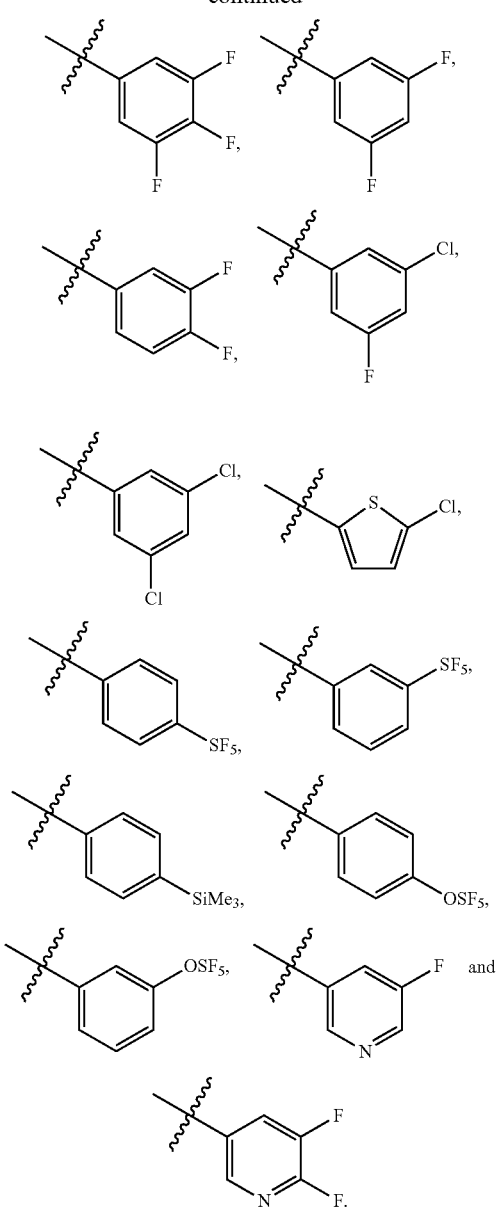

In another embodiment of this invention R¹ is selected from the group consisting of:

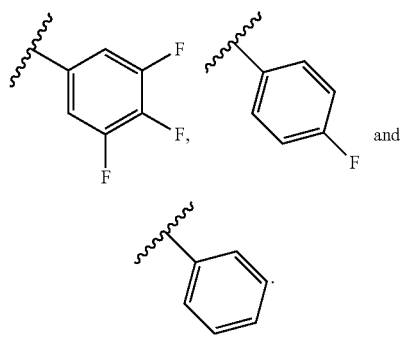

In another embodiment of this invention R¹ is selected from the group consisting of:

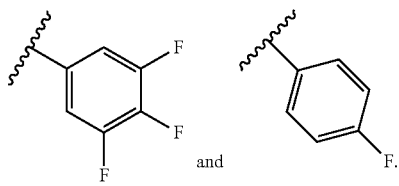 [SMILES: *c1cc(F)c(F)c(F)c1 ; "and" ; *c1ccc(F)cc1]

In another embodiment of this invention R¹ is phenyl.
In another embodiment of this invention R¹ is:

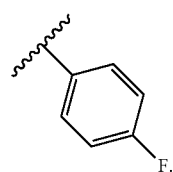 [SMILES: *c1ccc(F)cc1]

In another embodiment of this invention R¹ is:

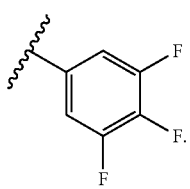 [SMILES: *c1cc(F)c(F)c(F)c1]

In another embodiment of his invention R¹ is:

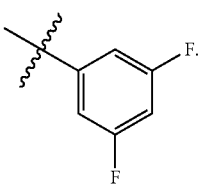 [SMILES: *c1cc(F)cc(F)c1]

In another embodiment of this invention R¹ is:

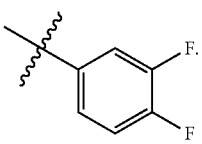 [SMILES: *c1ccc(F)c(F)c1]

In another embodiment of this invention R¹ is:

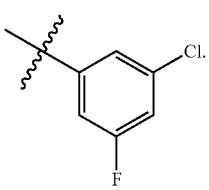 [SMILES: *c1cc(F)cc(Cl)c1]

In another embodiment of this invention R¹ is:

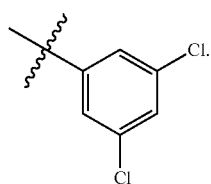 [SMILES: *c1cc(Cl)cc(Cl)c1]

In another embodiment of this invention R¹ is:

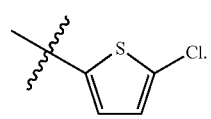 [SMILES: *c1ccc(Cl)s1]

In another embodiment of this invention R¹ is:

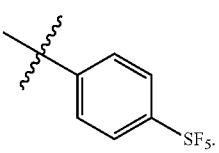

In another embodiment of this invention R¹ is:

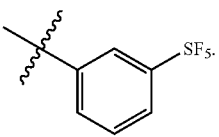

In another embodiment of this invention R¹ is

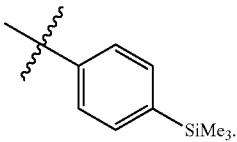 [SMILES: *c1ccc([Si](C)(C)C)cc1]

In another embodiment of this invention R¹ is:

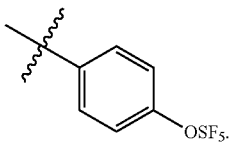

In another embodiment of this invention R¹ is:

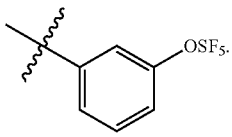

In another embodiment of this invention R¹ is:

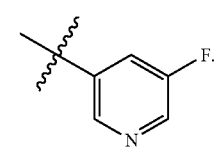

In another embodiment of this invention R¹ is:

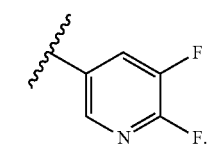 [SMILES: *c1cnc(F)c(F)c1]

In another embodiment of this invention R¹ is:

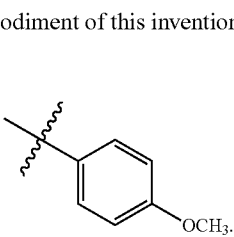

In another embodiment of this invention R¹ is:

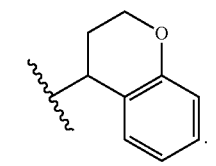

In another embodiment of this invention R¹ is:

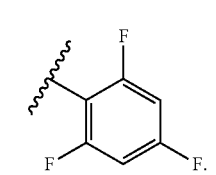 [SMILES: *c1c(F)cc(F)cc1F]

In another embodiment of this invention $R^1$ is:

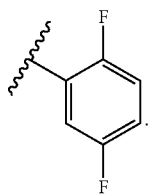 [SMILES: *c1cc(F)ccc1F]

In another embodiment of this invention $R^1$ is:

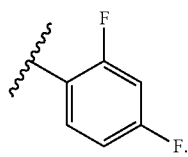 [SMILES: *c1ccc(F)cc1F]

In another embodiment of this invention $R^1$ is:

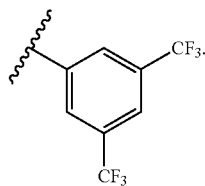 [SMILES: *c1cc(C(F)(F)F)cc(C(F)(F)F)c1]

In another embodiment of this invention $R^1$ is:

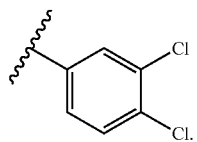 [SMILES: *c1ccc(Cl)c(Cl)c1]

In another embodiment of this invention $R^1$ is:

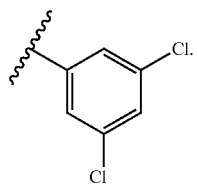 [SMILES: *c1cc(Cl)cc(Cl)c1]

In another embodiment of this invention $R^1$ is:

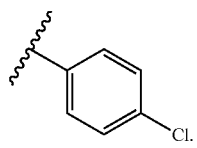 [SMILES: *c1ccc(Cl)cc1]

In another embodiment of this invention $R^1$ is:

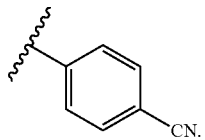 [SMILES: *c1ccc(C#N)cc1]

In another embodiment, $R^1$ is phenyl substituted with 1-3 halos independently selected from the group consisting of F and Cl. In one example said phenyl is substituted with one F and one Cl.

In another embodiment $R^1$ is aryl (e.g., phenyl) substituted with 1 to 3 independently selected $R^{21}$ moieties wherein at least one $R^{21}$ moiety is selected from the group consisting of —$SF_5$, —$OSF_5$ and —$Si(R^{15A})_3$ (and in one example each $R^{15A}$ is the same or different alkyl, and in another example the —$Si(R^{24})_3$ group is —$Si(CH_3)_3$ or —$Si(CH_2CH_3)_2CH_3$, and in another example the —$Si(R^{24})_3$ group is —$Si(C_{1-13})_3)_3$.

In another embodiment $R^1$ is aryl (e.g., phenyl) substituted with 1 to 3 independently selected $R^{21}$ moieties wherein at least one $R^{21}$ moiety is selected from the group consisting of —$SF_5$ and —$OSF_5$.

In another embodiment $R^1$ is aryl (e.g., phenyl) substituted with 1 to 3 $R^{21}$ moieties independently selected from the group consisting of: halo (e.g., F), —$SF_5$, —$OSF_5$ and —$Si(R^{15A})_3$ (and in one example each $R^{15A}$ is the same or different alkyl, and in another example the —$Si(R^{15A})_3$ group is —$Si(CH_3)_3$ or —$Si(CH_2CH_3)_2CH_3$, and in another example the —$Si(R^{15A})_3$ group is —$Si(CH_3)_3$), and wherein at least one $R^{21}$ moiety is selected from the group consisting of —$SF_5$, —$OSF_5$ and —$Si(R^{15A})_3$ (and in one example each $R^{15A}$ is the same or different alkyl, and in another example the —$Si(R^{15A})_3$ group is —$Si(CH_3)_3$ or —$Si(CH_2CH_3)_2CH_3$, and in another example the —$Si(R^{24})_3$ group is —$Si(CH_3)_3$).

In another embodiment $R^1$ is aryl (e.g., phenyl) substituted with 1 to 3 $R^{21}$ moieties independently selected from the group consisting of: halo (e.g., F), —$SF_5$ and —$OSF_5$, and wherein at least one $R^{21}$ moiety is selected from the group consisting of —$SF_5$ and —$OSF_5$.

In another embodiment $R^1$ is aryl (e.g., phenyl) substituted with 1 to 3 independently selected $R^{21}$ moieties wherein at least one $R^{21}$ moiety is selected from the group consisting of —$SF_5$, —$OSF_5$ and —$Si(R^{15A})_3$ (and in one example each $R^{15A}$ is the same or different alkyl, and in another example the —$Si(R^{15A})_3$ group is —$Si(CH_3)_3$ or —$Si(CH_2CH_3)_2CH_3$, and in another example the —$Si(R^{15A})_3$ group is —$Si(CH_3)_3$).

In another embodiment, $R^1$ is phenyl substituted with 1-3 $R^{21}$ groups independently selected from the group consisting of halos, —$SF_5$ and —$OSF_5$, wherein at least one $R^{21}$ group is —$SF_5$ or —$OSF_5$.

In another embodiment, $R^1$ is phenyl substituted with 1-3 $R^{21}$ groups independently selected from the group consisting of halos, —$SF_5$ and —$OSF_5$, wherein at least one $R^{21}$ group is —$SF_5$ or —$OSF_5$.

In another embodiment, $R^1$ is phenyl substituted with 1-3 $R^{21}$ groups independently selected from the group consisting of F, Cl, —$SF_5$ and —$OSF_5$.

In another embodiment, $R^1$ is phenyl substituted with 1-3 $R^{21}$ groups independently selected from the group consisting of —$SF_5$ and —$OSF_5$.

In another embodiment, $R^1$ is phenyl substituted with 1-3 $R^{21}$ groups independently selected from the group consisting of F, —$SF_5$ and —$OSF_5$, wherein at least one $R^{21}$ group is —$SF_5$ or —$OSF_5$.

In another embodiment, R¹ is phenyl substituted with one —SF₅ group.

In another embodiment. R¹ is phenyl substituted with two —SF₅ groups.

In another embodiment, R¹ is phenyl substituted with three —SF₅ groups.

In another embodiment, R¹ is phenyl substituted with one —OSF₅ group.

In another embodiment, R¹ is phenyl substituted with two —OSF₅ groups.

In another embodiment, R¹ is phenyl substituted with three —OSF₅ groups.

In another embodiment, R¹ is phenyl substituted with 1 F.

In another embodiment, R¹ is phenyl substituted with 1 F, and also substituted with 1 to 2 groups independently selected from the group consisting of —SF₅ and —OSF₅.

In another embodiment R¹ is phenyl substituted with 2 F,

In another embodiment R¹ is phenyl substituted with 3F.

In another embodiment of this invention L is selected from the group consisting of:

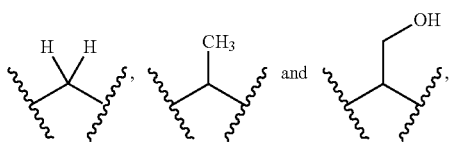

and R¹ is selected from the group consisting of:

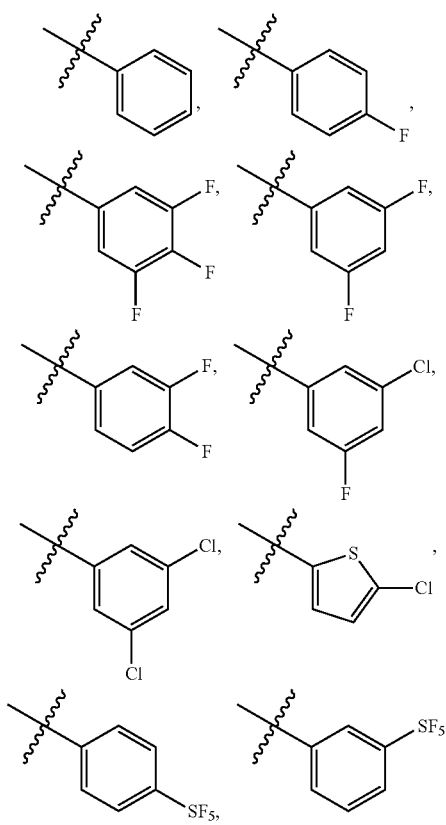

-continued

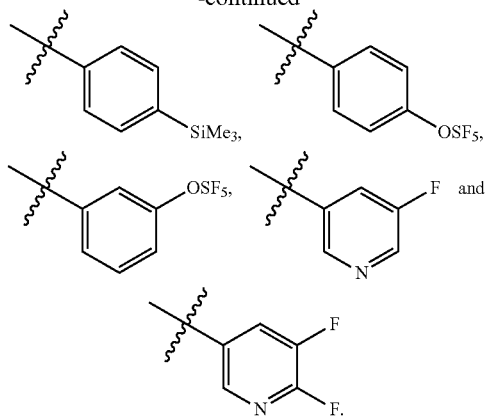

In another embodiment of this invention L is selected from the group consisting of:

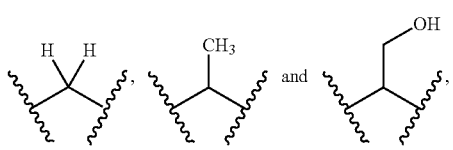

and R¹ is selected from the group consisting of:

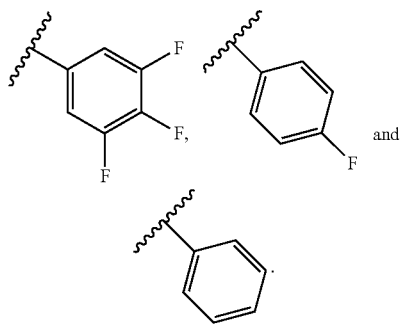

In another embodiment of this invention, the compound of formula (I) is selected from the group consisting of the compounds of formulas (IA), (IB), (IC), (ID), and (IE), L is selected from the group consisting of:

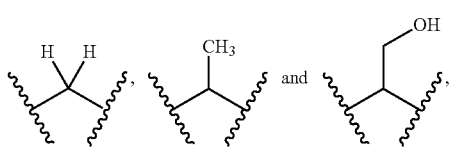

and R¹ is selected from the group consisting of:

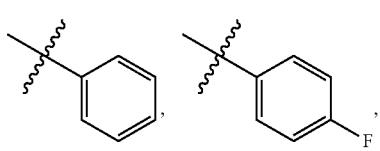

-continued

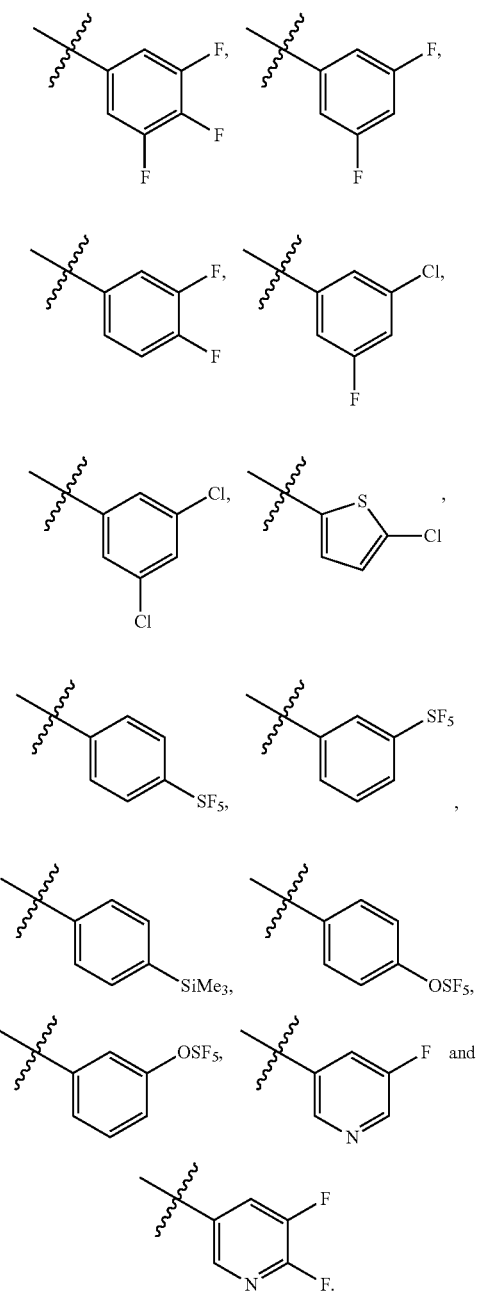

In another embodiment of this invention, the compound of formula (I) is selected from the group consisting of the compounds of formulas (IA), (IB), (IC), (ID), and (IE), L is selected from the group consisting of:

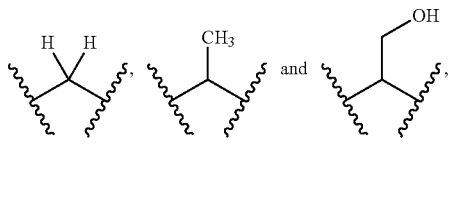

and $R^1$ is selected from the group consisting of:

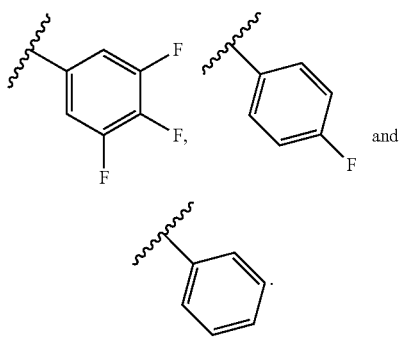

In another embodiment of this invention, the compound of formula (I) is selected from the group consisting of the compounds of formulas (IA.1), (IB.1), (ID.1), and (IE.1), L is selected from the group consisting of:

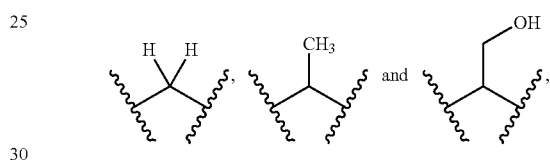

and $R^1$ is selected from the group consisting of:

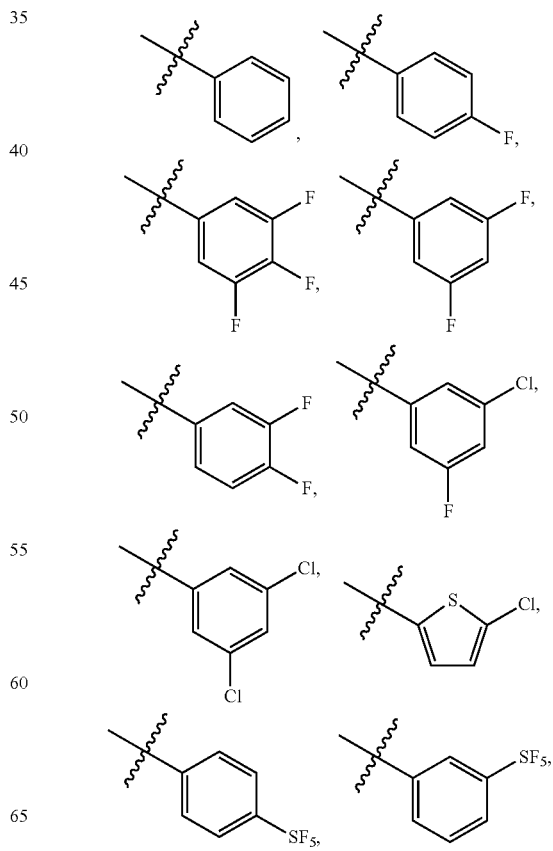

-continued

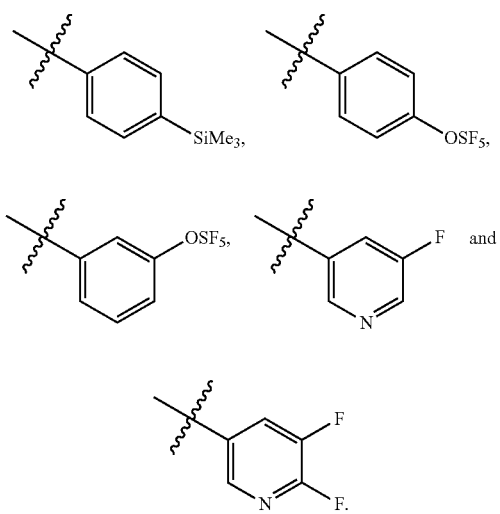

In another embodiment of this invention, the compound of formula (I) is selected from the group consisting of the compounds of formulas (IA.1), (IB.1), (ID.1), and (IE.1), L is selected from the group consisting of:

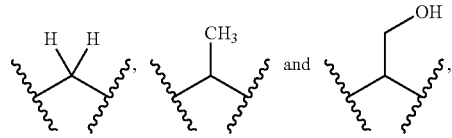

and $R^1$ is selected from the group consisting of:

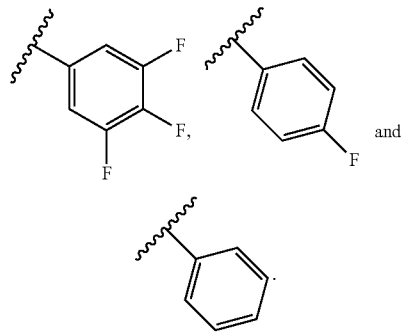

In another embodiment of this invention, the compound of formula (I) is the compound of formula (IA.1), L is selected from the group consisting of:

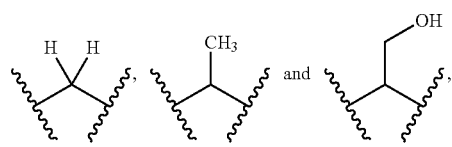

and $R^1$ is selected from the group consisting of:

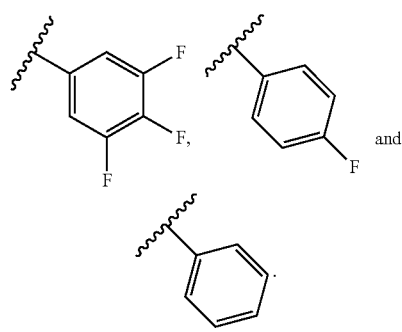

In another embodiment of this invention, the compound of formula (I) is the compound of formulas (IB.1), L is selected from the group consisting of:

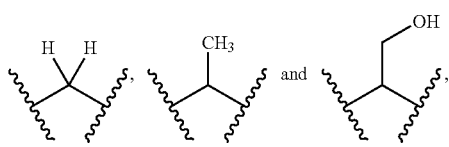

and $R^1$ is selected from the group consisting of:

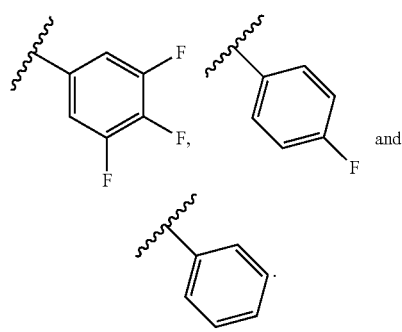

In another embodiment of this invention, the compound of formula (I) is the compounds of formula (ID.1), L is selected from the group consisting of:

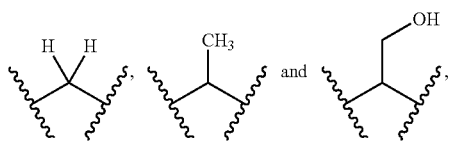

and $R^1$ is selected from the group consisting of:

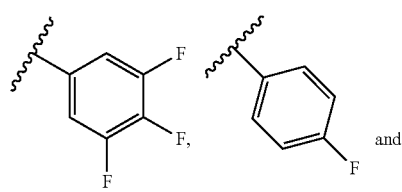

-continued

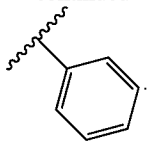

In another embodiment of this invention, the compound of formula (I) is the compounds of formula (IE1), L is selected from the group consisting of:

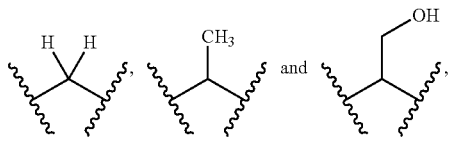

and $R^1$ is selected from the group consisting of:

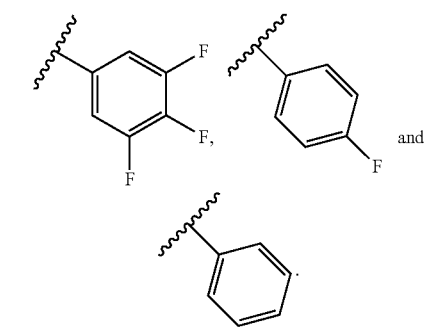

In another embodiment of this invention, the compound of formula (I) is the compound of formula (IA), L is selected from the group consisting of:

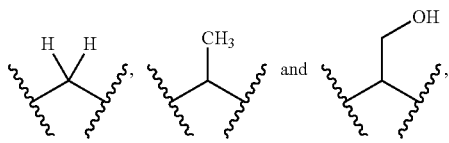

and $R^1$ is selected from the group consisting of:

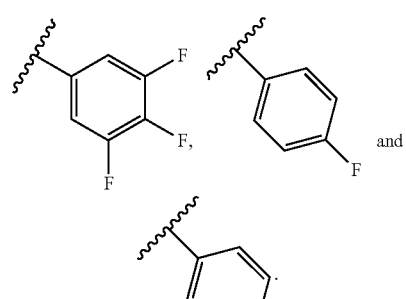

In another embodiment of this invention, the compound of formula (I) is the compound of formulas (IB), L is selected from the group consisting of:

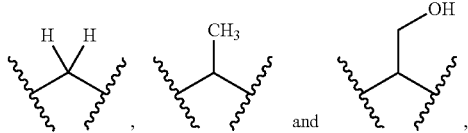

and $R^1$ is selected from the group consisting of:

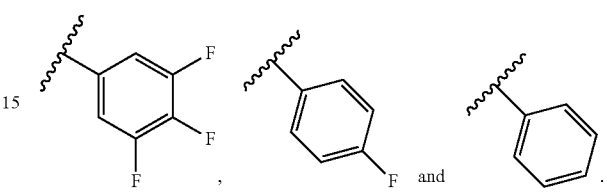

In another embodiment of this invention, the compound of formula (I) is the compounds of formula (IC), L is selected from the group consisting of:

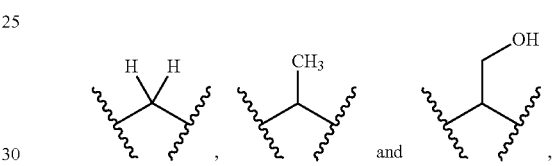

and $R^1$ is selected from the group consisting of:

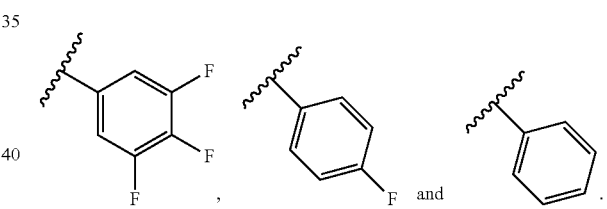

In another embodiment of this invention, the compound of formula the compounds of formula (ID), L is selected from the group consisting of:

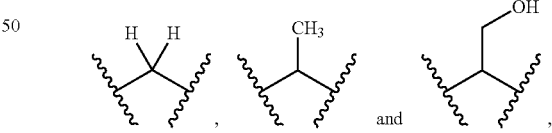

and $R^1$ from the group consisting of:

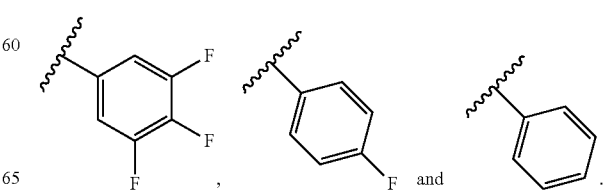

In another embodiment of this invention, the compound of formula (I) is the compounds of formula (IE), L is selected from the group consisting of:

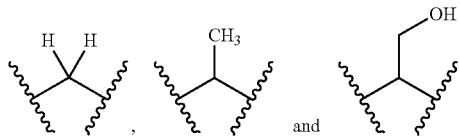

and R[1] is selected from the group consisting of:

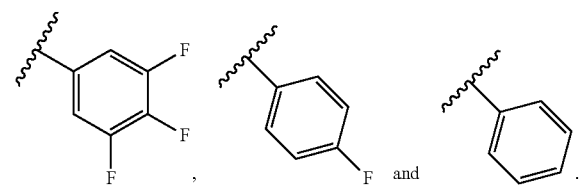 [SMILES: *c1cc(F)c(F)c(F)c1 ; *c1ccc(F)cc1 ; *c1ccccc1]

In another embodiment of this invention, the compound of formula (I) is the compound of formula (IA.1), L is selected from the group consisting of:

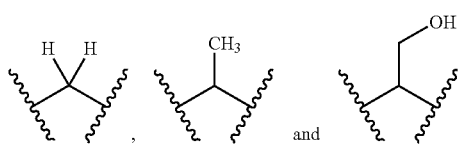

and R[1] is selected from the group consisting of:

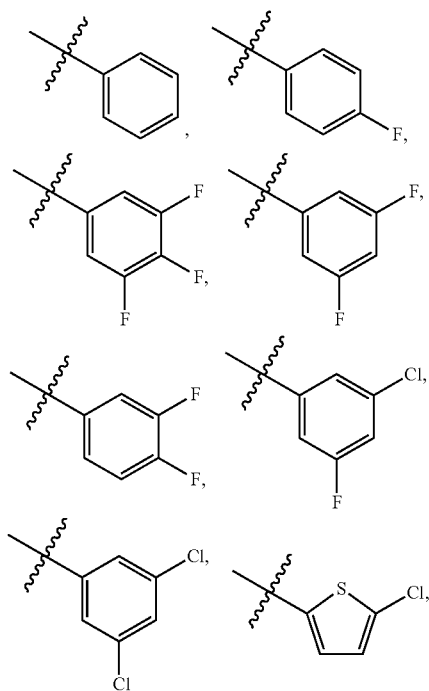

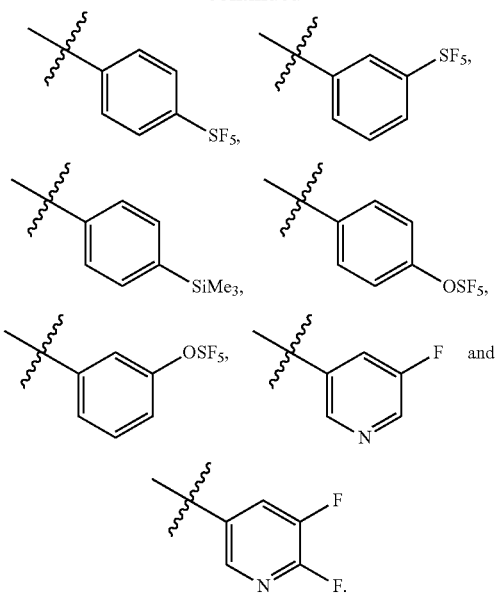

In another embodiment of this invention, the compound of formula (I) is the compound of formulas (IB.1), L is selected from the group consisting of:

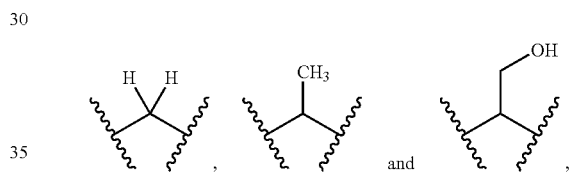

and R[1] is selected from the group consisting of:

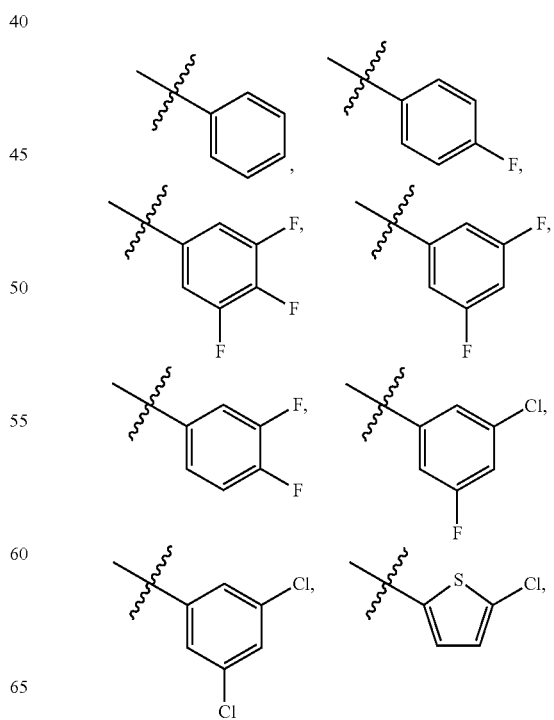

-continued

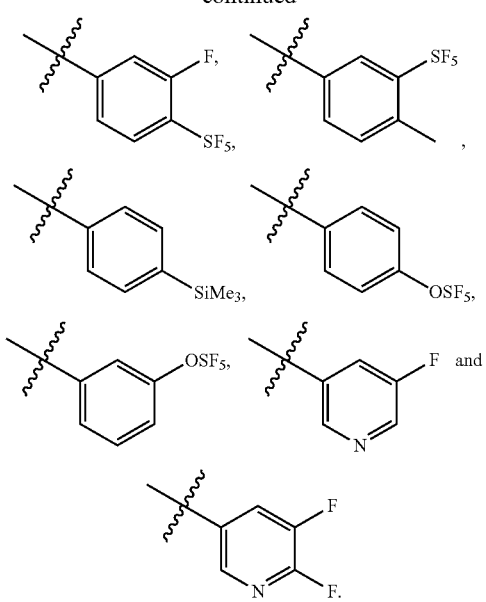

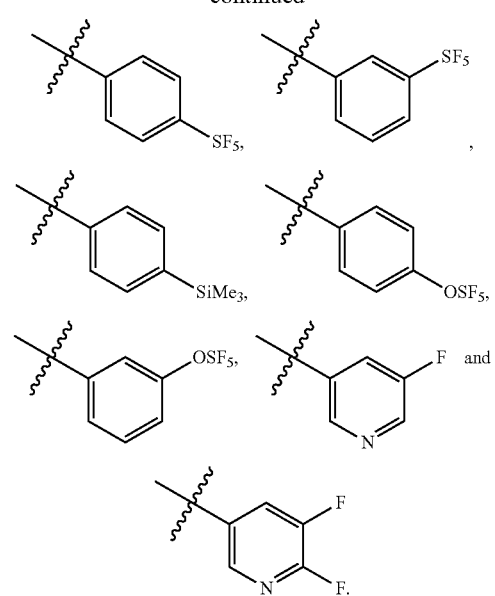

In another embodiment of this invention, the compound of formula is the compounds of formula (ID.1), L is selected from the group consisting of:

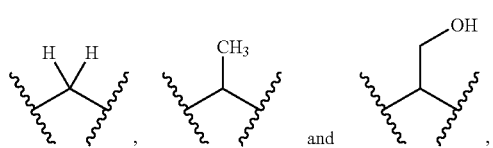

and R¹ selected from the group consisting of:

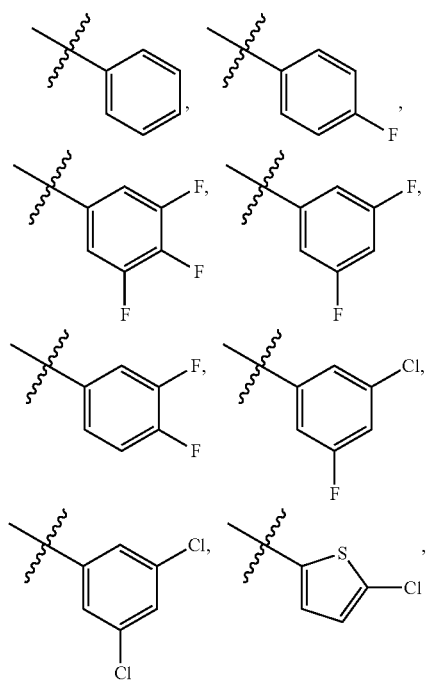

In another embodiment of this invention, the compound of formula (I) is the compounds of formula (IE.1), L is selected from the group consisting of:

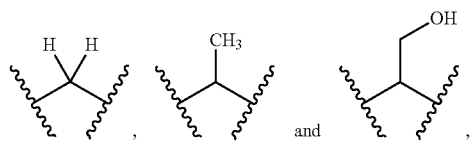

and R¹ is selected from the group consisting of:

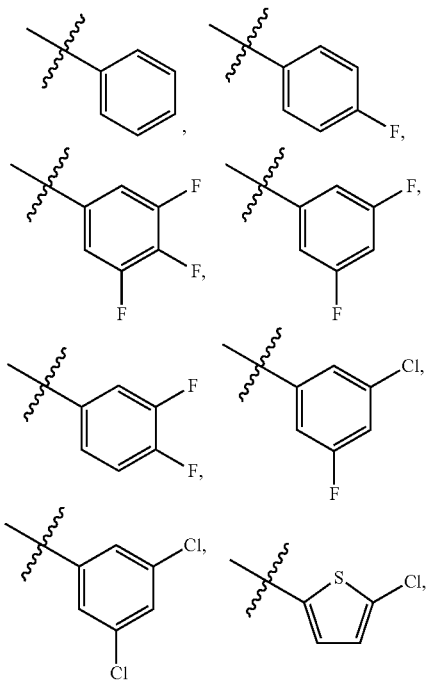

-continued

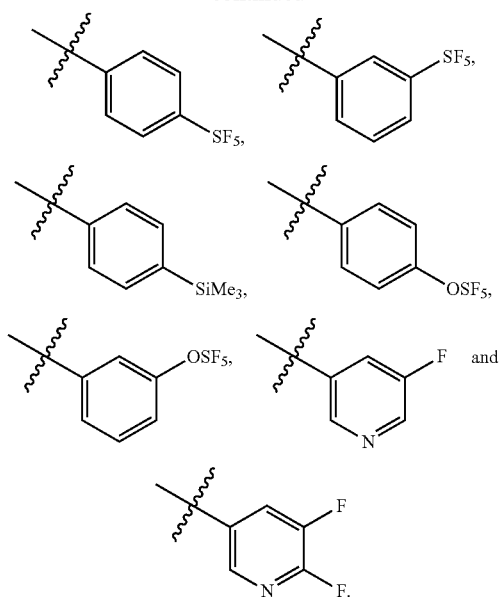

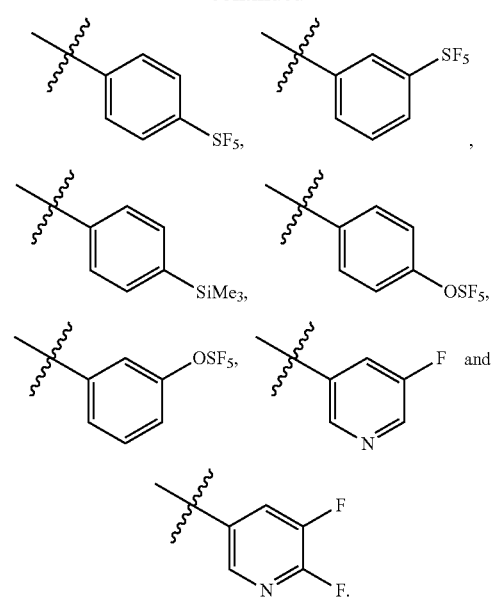

In another embodiment of this invention, the compound of formula (I) is the compound of formula (IA), L is selected from the group consisting of:

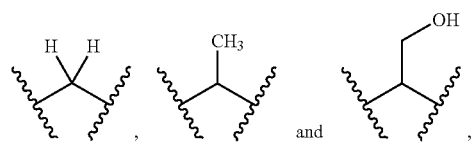

and $R^1$ is selected from the group consisting of:

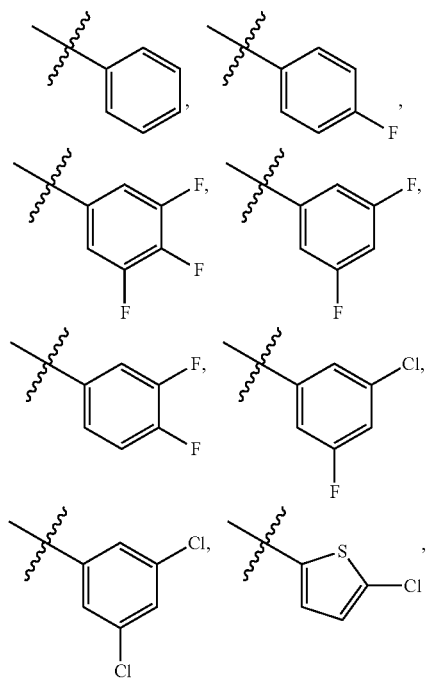

In another embodiment of this invention, the compound of formula (I) is the compound of formulas (IB), L is selected from the group consisting of:

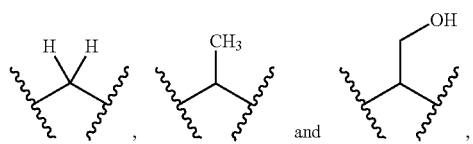

and $R^1$ is selected from the group consisting of:

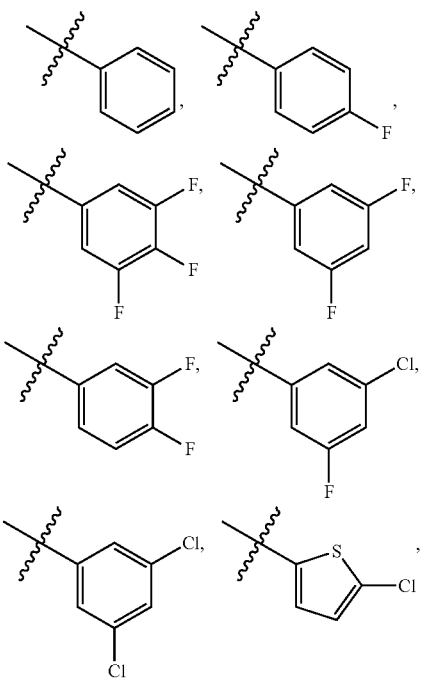

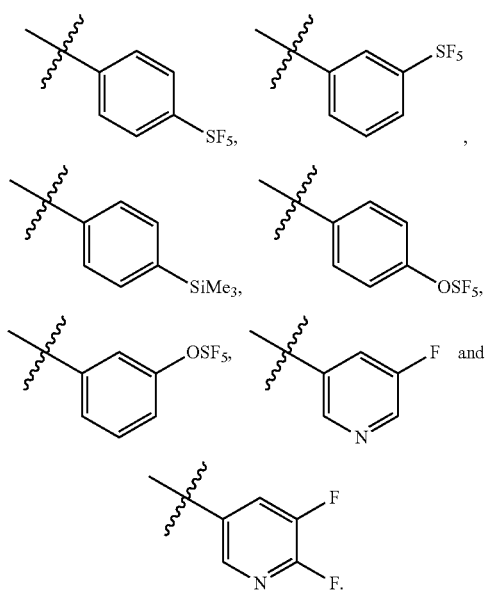

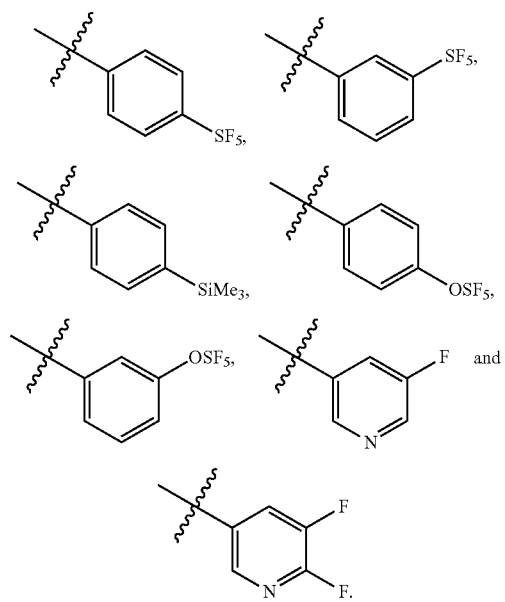

In another embodiment of this invention, the compound of formula (I) is the compounds of formula (IC), L is selected from the group consisting of:

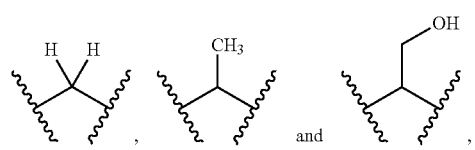

and R[1] is selected from the group consisting of:

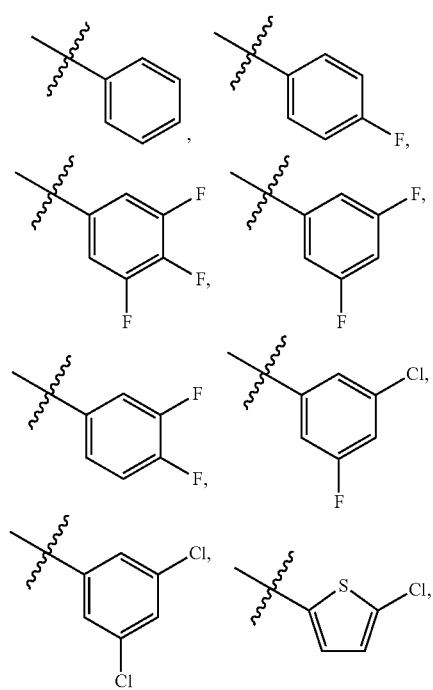

In another embodiment of this invention, the compound of formula (I) is the compounds of formula (ID), L is selected from the group consisting of:

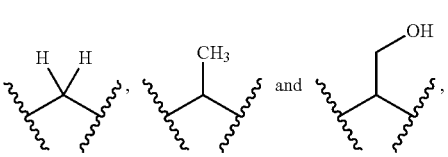

and R[1] is selected from the group consisting of:

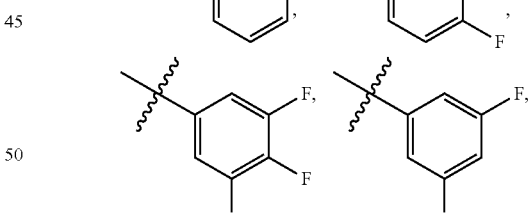

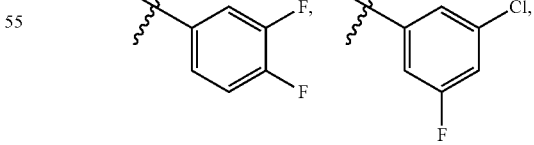

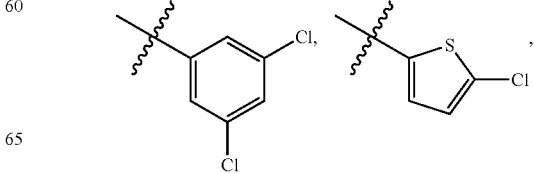

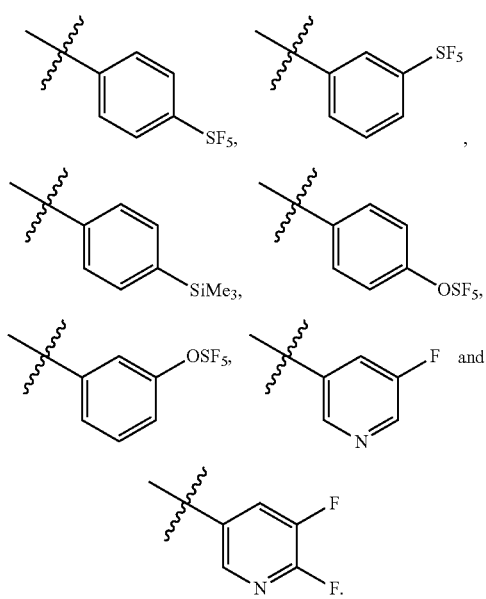

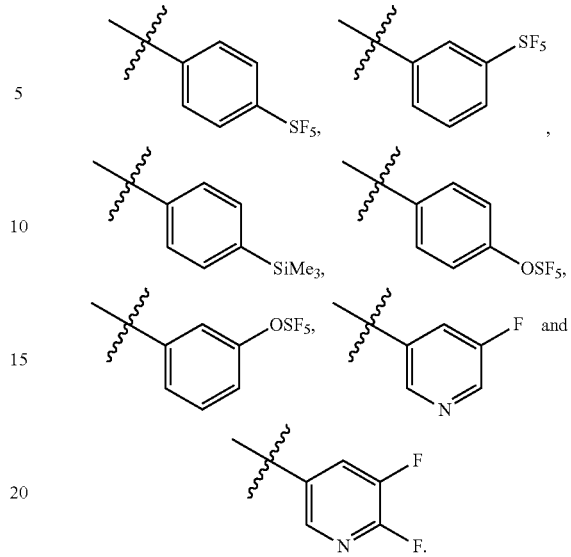

In another embodiment of this invention, the compound of formula (I) is the compounds of formula (IE), L is selected from the group consisting of:

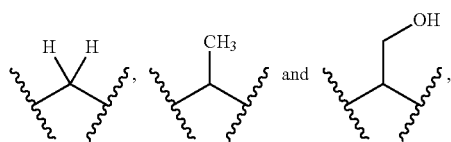

and $R^1$ is selected from the oup consisting of:

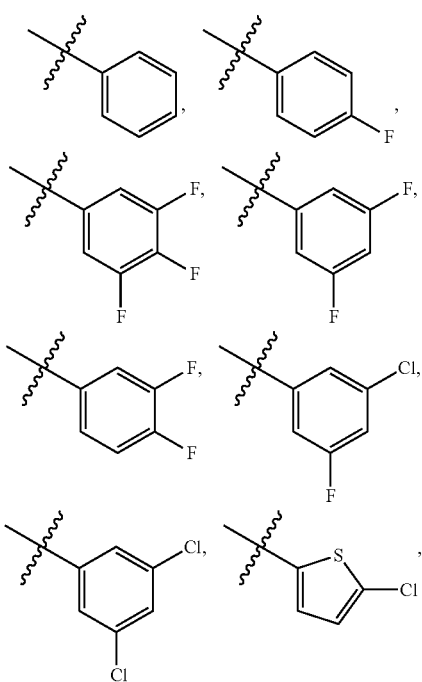

In another embodiment of this invention, $R^5$ is taken together with $R^1$ and the carbon to which they are bound to form a heterocycloalkyl or heterocycloalkenyl ring fused to said $R^1$ ring, said fused ring is optionally substituted with 1 to 5 independently selected $R^{21}$ groups.

In another embodiment of this invention, $R^5$ is taken together with $R^1$ and the carbon to which they are bound to form a 5 to 7 membered heterocycloalkyl or heterocycloalkenyl ring fused to said $R^1$ ring, and wherein said heterocycloalkyl and said heterocylcloalkenyl rings comprise 1 to 4 (including the atoms common to both rings) heteroatoms selected from the group consisting of: —N—, —O—, —S—, —S(O)—, and —S(O)$_2$—, and wherein said 5 to 7 membered ring is optionally substituted with 1 to 5 independently selected $R^{21}$ groups.

In another embodiment of this invention, $R^6$ is taken together with $R^1$ and the carbon to which they are bound to form a cycloalkyl, cycloalkenyl, heterocycloalkyl or heterocycloalkenyl ring fused to said $R^1$ ring, said fused ring is optionally substituted with 1 to 5 independently selected $R^{21}$ groups.

In another embodiment of this invention, $R^6$ is taken together with and the carbon to which they are bound to form a 5 to 7 membered cycloalkyl, cycloalkenyl, heterocycloalkyl or heterocycloalkenyl ring fused to said $R^1$ ring, and wherein said heterocycloalkyl and said heterocylcloalkenyl rings comprise 1 to 4 (including the atoms common to both rings) heteroatoms selected from the group consisting of: —N—, —O—, —S—, —S(O)—, and —S(O)$_2$—, and wherein said 5 to 7 membered ring is optionally substituted with 1 to 5 independently selected $R^{21}$ groups.

In another embodiment of this invention, Ring (B) is a cycloalkyl ring.

In another embodiment of this invention, Ring (B) is a cycloalkenyl ring.

In another embodiment of this invention, Ring (B) is a heterocycloalkyl ring.

In another embodiment of this invention, Ring (B) is a heterocycloalkenyl ring.

In another embodiment of this invention, Ring (B) is an phenyl ring.

In another embodiment of this invention, Ring (B) is a heteroaryl ring.

In another embodiment of this invention Ring (B) is a cycloalkyl ring wherein $B^1$ to $B^4$ are carbon.

In another embodiment of this invention Ring (B) is a cycloalkyl ring wherein $B^1$ is carbon, one of $B^2$, $B^3$, or $B^4$ is C and the remaining two are selected from the group consisting of: —(C=O)— and —(C=NR$^{21A}$)— (e.g., —(C=N—OR$^{15}$)—, and —(C=N—N(R$^{15}$)(R$^{16}$))—).

In another embodiment of this invention Ring (B) is a cycloalkyl ring wherein $B^1$ is carbon, two of $B^2$, $B^3$, or $B^4$ are C and the remaining one is selected from the group consisting of: —(O=O)— and —(C=NR$^{21A}$)— (e.g., —(C=N—OR$^{15}$)—, and —(C=N—N(R$^{15}$)(R$^{16}$))—).

In another embodiment of this invention Ring (B) is a heterocycloalkyl ring wherein one of $B^2$, $B^3$, or $B^4$ is selected from the group consisting of: —(C=O)— and —(C=NR$^{21A}$)— (e.g., —(C=N—OR$^{15}$)—, and —(C=N—N(R$^{15}$)(R$^{16}$))—).

In another embodiment of this invention Ring (B) is a heterocycloalkenyl ring wherein one of $B^2$, $B^3$, or $B^4$ is selected from the group consisting of: —(C=O)— and —(C=NR$^{21A}$)— (e.g., —(C=N—OR$^{15}$)—, and —(C=N—N(R$^{15}$)(R$^{16}$))—).

In another embodiment of this invention L is a direct bond.
In another embodiment of this invention L is —O—.
In another embodiment of this invention L is —NR$^5$—.
In another embodiment of this invention L is —S—.
In another embodiment of this invention L is —SO—.
In another embodiment of this invention L is —S(O)$_2$—.
In another embodiment of this invention L is —(C=O)—.
In another embodiment of this invention L is —(C=NR$^{21A}$)—.
In another embodiment $A^1$ is C.
In another embodiment $A^1$ is N.
In another embodiment $A^5$ is C.
In another embodiment $A^5$ is N.
In another embodiment $A^4$ is C.
In another embodiment $A^4$ is N.
In another embodiment $B^1$ is CH.
In another embodiment $B^1$ is C.
In another embodiment $B^1$ is N.
In another embodiment of this invention $R^3$ is phenyl.
In another embodiment of this invention $R^3$ is phenyl substituted with 1 to 3 independently selected $R^{21}$ groups.
In another embodiment of this invention $R^3$ is phenyl substituted with 1 $R^{21}$ group.
In another embodiment of this invention $R^3$ is phenyl substituted with 1 $R^{21}$ group wherein said $R^{21}$ group is halo.
In another embodiment of this invention $R^3$ is phenyl substituted with 1 $R^{21}$ group wherein said $R^{21}$ group is halo, and said halo is F.
In another embodiment of this invention $R^3$ is phenyl substituted with 1 $R^{21}$ group, wherein said $R^{21}$ group is —OR$^{15}$.
In another embodiment of this invention $R^3$ is phenyl substituted with 1 $R^{21}$ group, wherein said $R^{21}$ group is —OR$^{15}$, and wherein said $R^{15}$ is alkyl (e.g., methyl).
In another embodiment of this invention $R^3$ is pyridyl.
In another embodiment of this invention $R^3$ is pyridyl substituted with 1 to 3 independently selected $R^{21}$ groups.
In another embodiment of this invention $R^3$ in formula (I) is selected from the group consisting of:

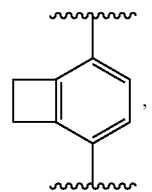
1AA

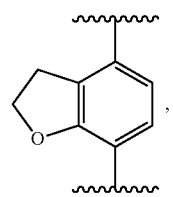
2AA

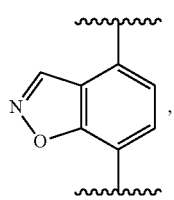
3AA

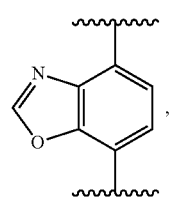
4AA

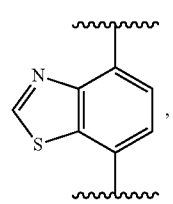
5AA

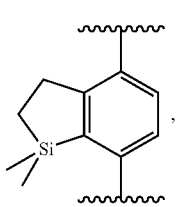
6AA

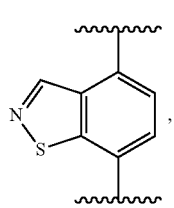
7AA

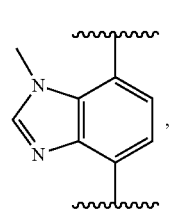
8AA

9AA 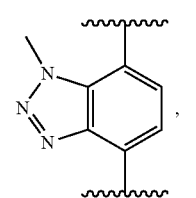
10AA 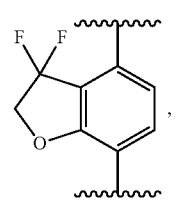
11AA 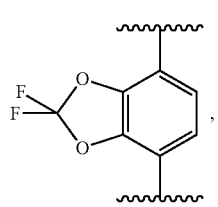
12AA 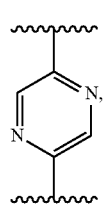
13AA 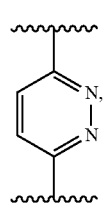
14AA 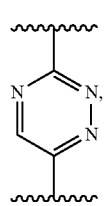
15AA 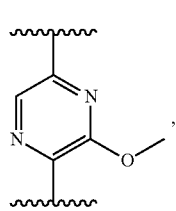
16AA 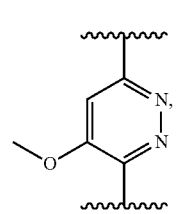
17AA 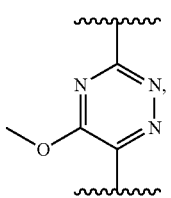
18AA 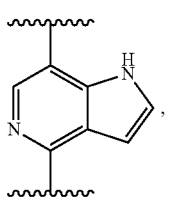
19AA 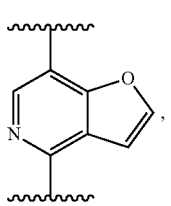
20AA 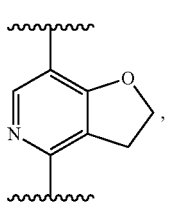
21AA 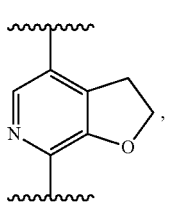
22AA 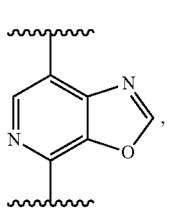
23AA 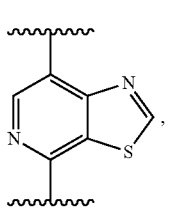
24AA 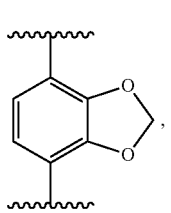

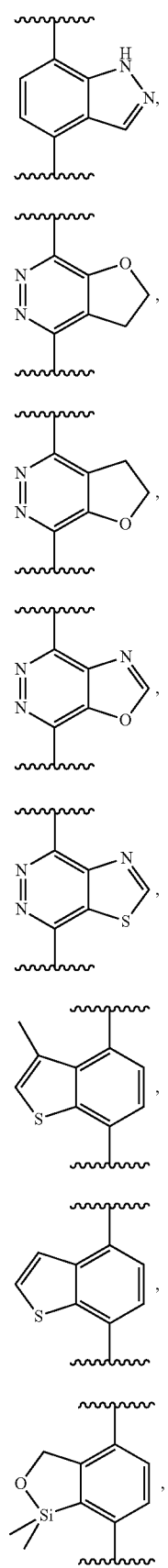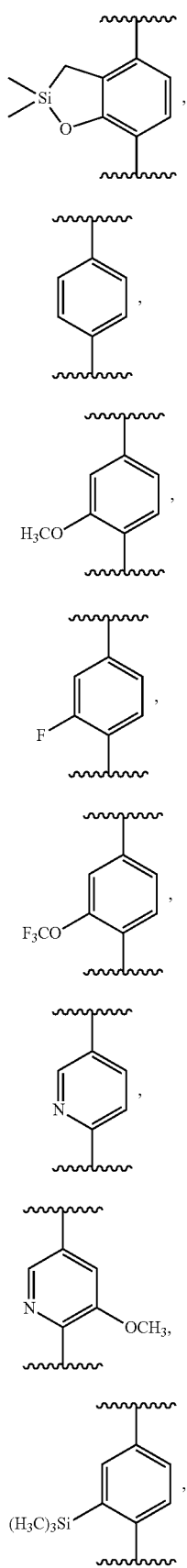

41AA

[Structure: benzene ring with F$_5$SO substituent, labeled "and"]

42AA

[Structure: benzene ring with F$_5$S substituent]

In another embodiment of this invention R$^3$ is group 1AA. In another embodiment of this invention R$^3$ is group 2AA. In another embodiment of this invention R$^3$ is group 3AA. In another embodiment of this invention R$^3$ is group 4AA. In another embodiment of this invention R$^3$ is group 5AA. In another embodiment of this invention R$^3$ is group 6AA. In another embodiment of this invention R$^3$ is group 7AA. In another embodiment of this invention R$^3$ is group 8AA. In another embodiment of this invention R$^3$ is group 9AA. In another embodiment of this invention R$^3$ is group 10AA. In another embodiment of this invention R$^3$ is group 11AA. In another embodiment of this invention R$^3$ is group 12AA, in another embodiment of this invention R$^3$ is group 13AA. In another embodiment of this invention R$^3$ is group 14AA. In another embodiment of this invention R$^3$ is group 15AA. In another embodiment of this invention R$^3$ is group 16AA. In another embodiment of this invention R$^3$ is group 17AA. In another embodiment of this invention R$^3$ is group 18AA. In another embodiment of this invention R$^3$ is group 19AA. In another embodiment of this invention R$^3$ is group 20AA. In another embodiment of this invention R$^3$ is group 21AA. In another embodiment of this invention R$^3$ is group 22AA. In another embodiment of this invention R$^3$ is group 23AA. In another embodiment of this invention R$^3$ is group 24AA. In another embodiment of this invention R$^3$ is group 25AA. In another embodiment of this invention R$^3$ is group 26AA. In another embodiment of this invention R$^3$ is group 27AA. In another embodiment of this invention R$^3$ is group 28AA. In another embodiment of this invention R$^3$ is group 29AA. In another embodiment of this invention R$^3$ is group 30AA. In another embodiment of this invention R$^3$ is group 31AA. In another embodiment of this invention R$^3$ is group 32AA. In another embodiment of this invention R$^3$ is group 33AA. In another embodiment of this invention R$^3$ is group 34AA. In another embodiment of this invention R$^3$ is group 35AA. In another embodiment of this invention R$^3$ is group 36AA. In another embodiment of this invention R$^3$ is group 37AA. In another embodiment of this invention R$^3$ is group 38AA. In another embodiment of this invention R$^3$ is group 39A. In another embodiment of this invention R$^3$ is group 40AA. In another embodiment of this invention R$^3$ is group 41AA. In another embodiment of this invention R$^3$ is group 42AA.

In another embodiment of this invention one group selected from the group consisting of: —SF$_5$, —OSF$_5$, and —Si(R$^{15A}$)$_3$ (wherein each R$^{15A}$ is independently selected) is present in the compounds of formula (I), and R$^3$ is selected from the consisting of 1AA to 42AA.

In another embodiment of this invention one group selected from the group consisting of: —SF$_5$, —OSF$_5$, and —Si(R$^{15A}$)$_3$ (wherein each R$^{15A}$ is independently selected) is present in the compounds of formula (I), and R$^3$ is selected from the consisting of 1AA to 42AA.

In another embodiment of this invention two groups selected from the group consisting of: —SF$_5$, —OSF$_5$, and —Si(R$^{15A}$)$_3$ (wherein each R$^{15A}$ is independently selected) are present in the compounds of formula (I), and R$^3$ is selected from the group consisting of 1AA to 42AA.

In another embodiment of this invention three groups selected from the group consisting of: —SF$_5$, —OSF$_5$, and —Si(R$^{15A}$)$_3$ (wherein each R$^{15A}$ is independently selected) are present in the compounds of formula (I), and R$^3$ is selected from the group consisting of 1AA to 42AA.

In another embodiment of this invention at least one group selected from the group consisting of: —SF$_5$ and —OSF$_5$ is present in the compounds of formula (I), and R$^3$ is selected from the group consisting of 1AA to 42AA.

In another embodiment of this invention one group selected from the group consisting of: —SF$_5$ and —OSF$_5$ is present in the compounds of formula (I), and R$^3$ is selected from the group consisting of 1AA to 42AA.

In another embodiment of this invention two groups selected from the group consisting of: —SF$_5$ and —OSF$_5$ are present in the compounds of formula (I), and R$^3$ is selected from the group consisting of 1AA to 42AA.

In another embodiment of this invention three groups selected from the group consisting of: —SF$_5$ and —OSF$_5$ are present in the compounds of formula (I), and R$^3$ is selected from the group consisting of 1AA to 42AA.

In another embodiment of this invention one —SF$_5$ group is present in the compounds of formula (I), and R$^3$ is selected from the group consisting of 1AA to 42AA.

In another embodiment of this invention two —SF$_5$ groups are present in the compounds of formula (I), and R$^3$ is selected from the group consisting of 1AA to 42AA.

In another embodiment of this invention three —SF$_5$ groups are present in the compounds of formula (I), and R$^3$ is selected from the group consisting of 1AA to 42AA.

In another embodiment of this invention one —OSF$_5$ group is present in the compounds of formula (I), and R$^3$ is selected from the group consisting of 1AA to 42AA.

In another embodiment of this invention two —OSF$_5$ groups are present in the compounds of formula (I), and R$^3$ is selected from the group consisting of 1AA to 42AA.

In another embodiment of this invention three —OSF$_5$ groups are present in the compounds of formula (I), and R$^3$ is selected from the group consisting of 1AA to 42AA.

In another embodiment of this invention one —Si(R$^{15A}$)$_3$ (wherein each R$^{15A}$ is independently selected) group is present in the compounds of formula (I), and R$^3$ is selected from the group consisting of 1AA to 42AA.

In another embodiment of this invention two —Si(R$^{15A}$)$_3$ (wherein each R$^{15A}$ is independently selected) groups are present in the compounds of formula (I), and R$^3$ is selected from the group consisting of 1AA to 42AA.

In another embodiment of this invention three —Si(R$^{15A}$)$_3$ (wherein each R$^{15A}$ is independently selected) groups are present in the compounds of formula (I), and R$^3$ is selected from the group consisting of 1AA to 42AA.

In another embodiment of this invention one —Si(R$^{15A}$)$_3$ (wherein each R$^{15A}$ is independently selected from the group consisting of alkyl (e.g., methyl and ethyl) and aryl (e.g., phenyl)) is present in the compounds of formula (I), and R$^3$ is selected from the group consisting of 1AA to 42AA.

In another embodiment of this invention two —Si(R$^{15A}$)$_3$ (wherein each R$^{15A}$ is independently selected from the group consisting of alkyl (e.g., methyl and ethyl) and aryl (e.g., phenyl)) is present in the compounds of formula (I), and R$^3$ is selected from the group consisting of 1AA to 42AA.

In another embodiment of this invention three —Si(R$^{15A}$)$_3$ (wherein each R$^{15A}$ is independently selected from the group consisting of alkyl (e.g., methyl and ethyl) and aryl (e.g., phenyl)) is present in the compounds of formula (I), and R$^3$ is selected from the group consisting of 1AA to 42AA.

In another embodiment of this invention one —Si(R$^{15A}$)$_3$ (wherein each R$^{15A}$ is independently selected from the group consisting of methyl, ethyl and phenyl) is present in the compounds of formula (I), and R$^3$ is selected from the group consisting of 1AA to 42AA.

In another embodiment of this invention two —Si(R$^{15A}$)$_3$ (wherein each R$^{15A}$ is independently selected from the group consisting of methyl, ethyl and phenyl) is present in the compounds of formula (I), and R$^3$ is selected from the group consisting of 1AA to 42AA.

In another embodiment of this invention three —Si(R$^{15A}$)$_3$ (wherein each R$^{15A}$ is independently selected from the group consisting of methyl, ethyl and phenyl) is present in the compounds of formula (I), and R$^3$ is selected from the group consisting of 1AA to 42AA.

In another embodiment of this invention one —Si(R$^{15A}$)$_3$ (wherein each R$^{15A}$ is independently selected from the group consisting of methyl and ethyl) is present in the compounds of formula (I), and R$^3$ is selected from the group consisting of 1AA to 42AA.

In another embodiment of this invention two —Si(R$^{15A}$)$_3$ (wherein each R$^{15A}$ is independently selected from the group consisting of methyl and ethyl) is present in the compounds of formula (I), and R$^3$ is selected from the group consisting of 1AA to 42AA.

In another embodiment of this invention three —Si(R$^{15A}$)$_3$ (wherein each R$^{15A}$ is independently selected from the group consisting of methyl and ethyl) is present in the compounds of formula (I), and R$^3$ is selected from the group consisting of 1AA to 42AA.

In another embodiment of this invention one —Si(R$^{24}$)$_3$ group is present in the compounds of formula (I), and said —Si(R$^{15A}$)$_3$ group is selected from the group consisting of: —Si(CH$_3$)$_3$, —Si(CH$_3$)$_2$phenyl, and —Si(CH$_2$CH$_3$)$_2$CH$_3$ and R$^3$ is selected from the group consisting of 1AA to 42AA.

In another embodiment of this invention two —Si(R$^{15A}$)$_3$ groups are present in the compounds of formula (I), and said —Si(R$^{15A}$)$_3$ groups are independently selected from the group consisting of: —Si(CH$_3$)$_3$, —Si(CH$_3$)$_2$phenyl, and —Si(CH$_2$CH$_3$)$_2$CH$_3$ and R$^3$ is selected from the group consisting of 1AA to 42AA.

In another embodiment of this invention three —Si(R$^{15A}$)$_3$ groups are present in the compounds of formula (I), and said —Si(R$^{15A}$)$_3$ groups are independently selected from the group consisting of: —Si(CH$_3$)$_3$, —Si(CH$_3$)$_2$phenyl, and —Si(CH$_2$CH$_3$)$_2$CH$_3$ and R$^3$ is selected from the group consisting of 1AA to 42AA.

In another embodiment of this invention one —Si(R$^{15A}$)$_3$ group is present in the compounds of formula (I), and said —Si(R$^{15A}$)$_3$ group is selected from the group consisting of: —Si(CH$_3$)$_3$ and —Si(CH$_2$CH$_3$)$_2$CH$_3$ and R$^3$ is selected from the group consisting of 1AA to 42AA.

In another embodiment of this invention two —Si(R$^{15A}$)$_3$ groups are present in the compounds of formula (I), and said —Si(R$^{15A}$)$_3$ groups are independently selected from the group consisting of: —Si(CH$_3$)$_3$ and —Si(CH$_2$CH$_3$)$_2$CH$_3$ and R$^{10}$ is selected from the group consisting of 1AA to 42AA.

In another embodiment of this invention three —Si(R$^{15A}$)$_3$ groups are present in the compounds of formula (I), and said —Si(R$^{15A}$)$_3$ groups are independently selected from the group consisting of: —Si(CH$_3$)$_3$ and —Si(CH$_2$CH$_3$)$_2$CH$_3$ and R$^3$ is selected from the group consisting of 1AA to 42AA.

In another embodiment of this invention one —Si(R$^{15A}$)$_3$ group is present in the compounds of formula (I), and said —Si(R$^{15A}$)$_3$ group is —Si(CH$_3$)$_3$ and R$^3$ is selected from the group consisting of 1AA to 42AA.

In another embodiment of this invention two —Si(R$^{15A}$)$_3$ groups are present in the compounds of formula (I), and said —Si(R$^{15A}$)$_3$ groups are —Si(CH$_3$)$_3$ and R$^3$ is selected from the group consisting of 1AA to 42AA.

In another embodiment of this invention three —Si(R$^{15A}$)$_3$ groups are present in the compounds of formula (I), and said —Si(R$^{15A}$)$_3$ groups are —Si(CH$_3$)$_3$ and R$^3$ is selected from the group consisting of 1AA to 42AA.

In another embodiment of this invention one group selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$) is present in the compounds of formula (I), and R$^3$ is selected from the group consisting of 1AA to 42AA.

In another embodiment of this invention one group selected from the group consisting of: —SF$_5$, —Si(CH$_3$)$_3$, and —Si(CH$_2$CH$_3$)$_2$CH$_3$) is present in the compounds of formula (I), and R$^3$ is selected from the group consisting of 1AA to 42AA.

In another embodiment of this invention one group selected from the group consisting of: —SF$_5$, —OSF$_5$, and —Si(CH$_3$)$_3$, is present in the compounds of formula (I), and R$^3$ is selected from the group consisting of 1AA to 42AA.

In another embodiment of this invention one —SF$_5$ group is present in the compounds of formula (I), and one or two additional groups selected from the group consisting of: —SF$_5$, —OSF$_6$, and —Si(R$^{15A}$)$_3$ (wherein each R$^{15A}$ is independently selected) are also present in the compounds of formula (I), and R$^3$ is selected from the group consisting of 1AA to 42AA.

In another embodiment of this invention one —SF$_5$ group is present in the compounds of formula (I), and one or two additional groups selected from the group consisting of: —OSF$_5$, and —Si(R$^{15A}$)$_3$ (wherein each R$^{15A}$ is independently selected) are also present in the compounds formula (I), and R$^3$ is selected from the group consisting of 1AA to 42AA.

In another embodiment of this invention one —SF$_5$ group is present in the compounds of formula (I), and one or two additional groups selected from the group consisting of: —SF$_5$ and —OSF$_5$ are also present in the compounds of formula (I), and R$^3$ is selected from the group consisting of 1AA to 42AA.

In another embodiment of this invention one —OSF$_5$ group is present in the compounds of formula (I), and one or two additional groups selected from the group consisting of: —SF$_5$, —OSF$_5$, and —Si(R$^{15A}$)$_3$ (wherein each R$^{15A}$ is independently selected) are also present in the compounds of formula (I)I, and R$^3$ is selected from the group consisting of 1AA to 42AA.

In another embodiment of this invention one —OSF$_5$ group is present in the compounds of formula (I), and one or two additional groups selected from the group consisting of: —SF$_5$ and —Si(R$^{15A}$)$_3$ (wherein each R$^{15A}$ is independently selected) are also present in the compounds of formula (I), and R$^3$ is selected from the group consisting of 1AA to 42AA.

In another embodiment of this invention one —OSF$_5$ group is present in the compounds of formula (I), and one or two additional groups selected from the group consisting of: —SF$_5$ and —OSF$_5$ are also present in the compounds of formula (I), and R$^{10}$ is selected from the group consisting of 1AA to 42AA.

In another embodiment of this invention one —Si(R$^{15A}$)$_3$ (wherein each R$^{15A}$ is independently selected) group is present in the compounds of formula (I), and one or two additional groups selected from the group consisting of: —SF$_5$, —OSF$_5$, and —Si(R$^{15A}$)$_3$ (wherein each R$^{15A}$ is independently selected) are also present in the compounds of formula (I), and R$^3$ is selected from the group consisting of 1AA to 42AA.

In another embodiment of this invention one —Si(R$^{15A}$)$_3$ (wherein each R$^{15A}$ is independently selected) group is present in the compounds of formula (I), and one or two additional groups selected from the group consisting of: —SF$_5$ and —OSF$_5$ are also present in the compounds of formula (I), and R$^3$ is selected from the group consisting of 1AA to 42AA.

In another embodiment of this invention at least one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) is present in the compounds of formula (I), and R$^3$ is selected from the group consisting of 1AA to 42AA.

In another embodiment of this invention at least one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) is present in the compounds of formula (I), and R$^3$ is selected from the group consisting of 1AA to 42AA.

In another embodiment of this invention at least one group selected from the group consisting of: —SF$_5$, —OSF$_5$, and —Si(R$^{15A}$)$_3$ (wherein each R$^{15A}$ is independently selected from the group consisting of methyl, ethyl and phenyl) is present in the compounds of formula (I), and R$^3$ is selected from the group consisting of 1AA to 42AA.

In another embodiment of this invention at least one group selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$) is present in the compounds of formula (I), and R$^3$ is selected from the group consisting of 1AA to 42AA.

In another embodiment of this invention at least one group selected from the group consisting of: —SF$_5$, —OSF$_5$, and —Si(CH$_3$)$_3$ is present in the compounds of formula (I), and R$^3$ is selected from the group consisting of 1AA to 42AA.

In another embodiment of this invention one group selected from the group consisting of: —SF$_5$, —OSF$_5$, and —Si(R$^{15A}$)$_3$ (wherein each R$^{15A}$ is independently selected) is present in the compounds of formula (I), and R$^3$ is selected from the group consisting of 1AA to 42AA.

In another embodiment of this invention one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) is present in the compounds of formula (I), and R$^3$ is selected from the group consisting of 1AA to 42AA.

In another embodiment of this invention one group selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and phenyl) is present in the compounds of formula (I), and R$^3$ is selected from the group consisting of 1AA to 42AA.

In another embodiment of this invention one group selected from the group consisting of: —SF$_5$, —OSF$_5$, and —Si(R$^{15A}$)$_3$ (wherein each R$^{15A}$ is independently selected from the group consisting of methyl, ethyl and phenyl) is present in the compounds of formula (I), and R$^3$ is selected from the group consisting of 1AA to 42AA.

In another embodiment of this invention one group selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$) is present in the compounds of formula (I), and R$^3$ is selected from the group consisting of 1AA to 42AA.

In another embodiment of this invention one group selected from the group consisting of: —SF$_5$, —OSF$_5$, —Si(CH$_3$)$_3$, and —Si(CH$_2$CH$_3$)$_2$CH$_3$) is present in the compounds of formula (I), and R$^3$ is selected from the group consisting of 1AA to 42AA.

In another embodiment of this invention one group selected from the group consisting of: —SF$_5$, —OSF$_5$, and —Si(CH$_3$)$_3$, is present in the compounds of formula (I), and R$^3$ is selected from the group consisting of 1AA to 42AA.

In another embodiment of this invention two groups selected from the group consisting of: —SF$_5$, —OSF$_5$, and —Si(R$^{15A}$)$_3$ (wherein each R$^{15A}$ is independently selected) are present in the compounds of formula (I), and R$^3$ is selected from the group consisting of 1AA to 42AA.

In another embodiment of this invention two groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I), and R$^3$ is selected from the group consisting of 1AA to 42AA.

In another embodiment of this invention two groups independently selected from the group consisting of: —SF$_5$, —OSF$_5$, and —Si(R$^{15A}$)$_3$ (wherein each R$^{15A}$ is independently selected from the group consisting of alkyl (e.g. methyl and ethyl) and phenyl) are present in the compounds of formula (I), and R$^3$ is selected from the group consisting of 1AA to 42AA.

In another embodiment of this invention two groups selected from the group consisting of: —SF$_5$, —OSF$_5$, and —Si(R$^{15A}$)$_3$ (wherein each R$^{15A}$ is independently selected from the group consisting of methyl, ethyl and phenyl) are present in the compounds of formula (I), and R$^3$ is selected from the group consisting of 1AA to 42AA.

In another embodiment of this invention two groups independently selected from the group consisting of: —SF$_5$, —OSF$_5$, —Si(CH$_3$)$_2$phenyl, and —Si(CH$_2$CH$_3$)$_2$CH$_3$) is present in the compounds of formula (I), and R$^3$ is selected from the group consisting of 1AA to 42AA.

In another embodiment of this invention two groups independently selected from the group consisting of: —SF$_5$, —OSF$_5$, —Si(CH$_3$)$_3$, and —Si(CH$_2$CH$_3$)$_2$CH$_3$) are present in the compounds of formula (I), and R$^3$ is selected from the group consisting of 1AA to 42AA.

In another embodiment of this invention two groups independently selected from the group consisting of: —SF$_5$, —OSF$_5$, and —Si(CH$_3$)$_3$ are present in the compounds of formula (I), and R$^3$ is selected from the group consisting of 1AA to 42AA.

In another embodiment of this invention three groups selected from the group consisting of: —SF$_5$, —OSF$_5$, and —Si(R$^{15A}$)$_3$ (wherein each R$^{15A}$ is independently selected) are present in the compounds of formula (I), and R$^3$ is selected from the group consisting of 1AA to 42AA.

In another embodiment of this invention three groups independently selected from the group consisting of: —SF$_5$, —OSF$_5$, and —Si(R$^{15A}$)$_3$ (wherein each R$^{15A}$ is independently selected from the group consisting of alkyl (e.g., methyl and ethyl) and aryl (e.g., phenyl)) are present in the compounds of formula (I), and $R^3$ is selected from the group consisting of 1AA to 42AA.

In another embodiment of this invention three groups independently selected from the group consisting of: —$SF_5$, —$OSF_5$, and —$Si(R^{15A})_3$ (wherein each $R^{15A}$ is independently selected from the group consisting of alkyl (e.g., methyl and ethyl) and phenyl) are present in the compounds of formula (I), and $R^3$ is selected from the group consisting of 1AA to 42AA.

In another embodiment of this invention three groups selected from the group consisting of: —$SF_5$, —$OSF_5$, and —$Si(R^{15A})_3$ (wherein each $R^{15A}$ is independently selected from the group consisting of methyl, ethyl and phenyl) are present in the compounds of formula (I), and $R^3$ is selected from the group consisting of 1A to 42A.

In another embodiment of this invention three groups independently selected from the group consisting of: —$SF_5$, —$OSF_5$, —$Si(CH_3)_3$, —$Si(CH_3)_2$phenyl, and —$Si(CH_2CH_3)_2CH_3$) is present in the compounds of formula (I), and $R^3$ is selected from the group consisting of 1AA to 42AA.

In another embodiment of this invention three groups independently selected from the group consisting of: —$SF_5$, —$OSF_5$, —$Si(CH_3)_3$, and —$Si(CH_2CH_3)_2CH_3$) are present in the compounds of formula (I), and $R^3$ is selected from the group consisting of 1AA to 42AA.

In another embodiment of this invention three groups independently selected from the group consisting of: —$SF_5$, —$OSF_5$, and —$Si(CH_3)_3$ are present in the compounds of formula (I), and $R^3$ is selected from the group consisting of 1AA to 42AA.

In another embodiment of this invention at least one group selected from the group consisting of: —$SF_5$, —$OSF_5$, and —$Si(R^{15A})_3$ (wherein each $R^{15A}$ is the same or different alkyl group) is present in the compounds of formula (I), and $R^3$ is selected from the group consisting of 1AA to 42AA.

In another embodiment of this invention at least one group selected from the group consisting of: —$SF_5$, —$OSF_5$, and —$Si(R^{15A})_3$ (wherein each $R^{15A}$ is independently selected from the group consisting of methyl and ethyl) is present in the compounds of formula (I), and $R^3$ is selected from the group consisting of 1AA to 42AA.

Other embodiments of this invention are directed to any one of the embodiments above directed to the groups —$SF_5$, —$OSF_5$, or —$Si(R^{15A})_3$ wherein $R^3$ is 35AA.

In another embodiment of this invention $R^4$ is heteroaryl.

In another embodiment of this invention $R^4$ is heteroaryl substituted with 1 to 3 independently selected $R^{21}$ groups.

In another embodiment of this invention $R^4$ is heteroaryl substituted with 1 $R^{21}$ group.

In another embodiment of this invention $R^4$ is heteroaryl substituted with 1 to 3 independently selected $R^{21}$ groups, wherein said $R^{21}$ groups are the same or different alkyl group.

In another embodiment of this invention $R^4$ is heteroaryl substituted with 1 $R^{21}$ group, wherein said $R^{21}$ group is alkyl (e.g., methyl).

In another embodiment of this invention $R^4$ is imidazolyl.

In another embodiment of this invention $R^4$ is the imidazolyl:

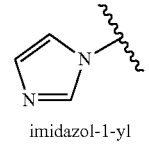

imidazol-1-yl

In another embodiment of this invention $R^4$ is imidazolyl substituted with 1 to 3 independently selected $R^{21}$ groups.

In another embodiment of this invention $R^4$ is imidazolyl substituted with 1 $R^{21}$ group.

In another embodiment of this invention $R^4$ is imidazolyl substituted with 1 to 3 independently selected $R^{21}$ groups, wherein said $R^{21}$ groups are the same or different alkyl group.

In another embodiment of this invention $R^4$ is imidazolyl substituted with 1 $R^{21}$ group, wherein said $R^{21}$ group is alkyl (e.g., methyl).

In another embodiment of this invention $R^4$ is:

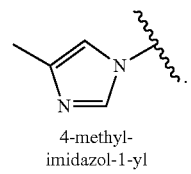 [SMILES: *n1cnc(C)c1]

4-methyl-imidazol-1-yl

In another embodiment of this invention $R^4$ is selected from the group consisting of:

1gg

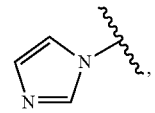

2gg

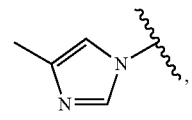

3gg

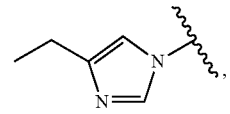

4gg

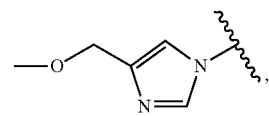

5gg

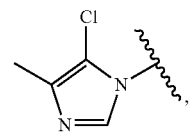

6gg

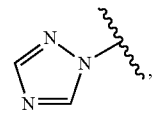

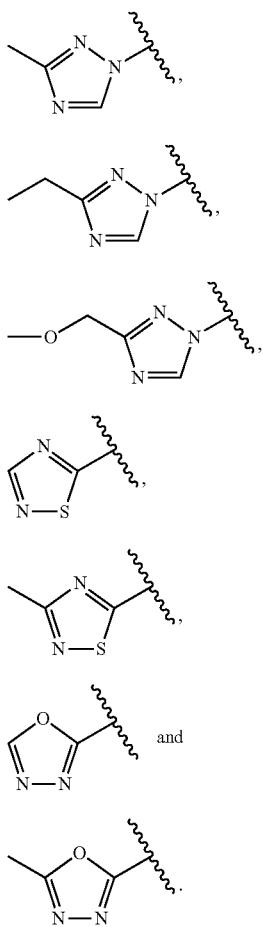

7gg

8gg

9gg

10gg

11gg

12gg and

13gg

In another embodiment of this invention R⁴ is 3gg. In another embodiment of this invention R⁴ is 4gg. In another embodiment of this invention R⁴ is 5gg, in another embodiment of this invention R⁴ is 6gg. In another embodiment of this invention R⁴ is 7gg. In another embodiment of this invention R⁴ is 8gg. In another embodiment of this invention R⁴ is 9gg. In another embodiment of this invention R⁴ is 10gg. In another embodiment of this invention R⁴ is 11gg. In another embodiment of this invention R⁴ is 12gg. In another embodiment of this invention R⁴ is 13gg.

In another embodiment of this invention R³ is selected from the group consisting of 1AA to 42AA, and R⁴ is selected from the group consisting of 1gg to 13gg.

In another embodiment of this invention R³ is selected from the group consisting of 1AA to 42AA, and R⁴ is 2gg.

Examples of the R⁴—R³— moiety include, but are not limited to:

1bb

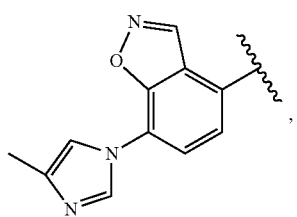

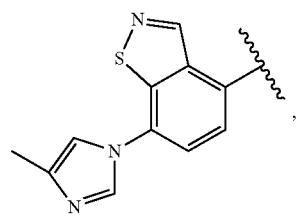

2bb

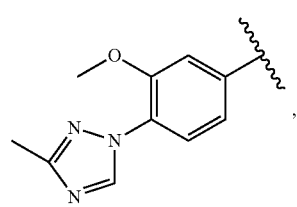

3bb

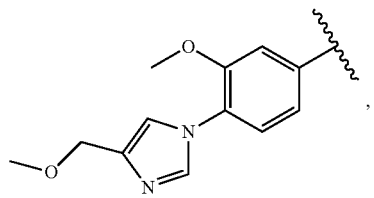

4bb

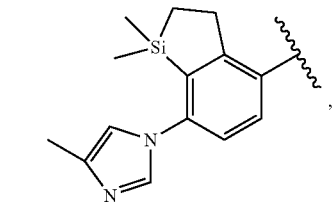

5bb

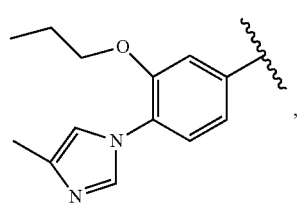

6bb

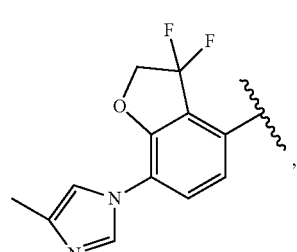

7bb

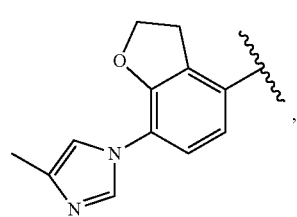

8bb

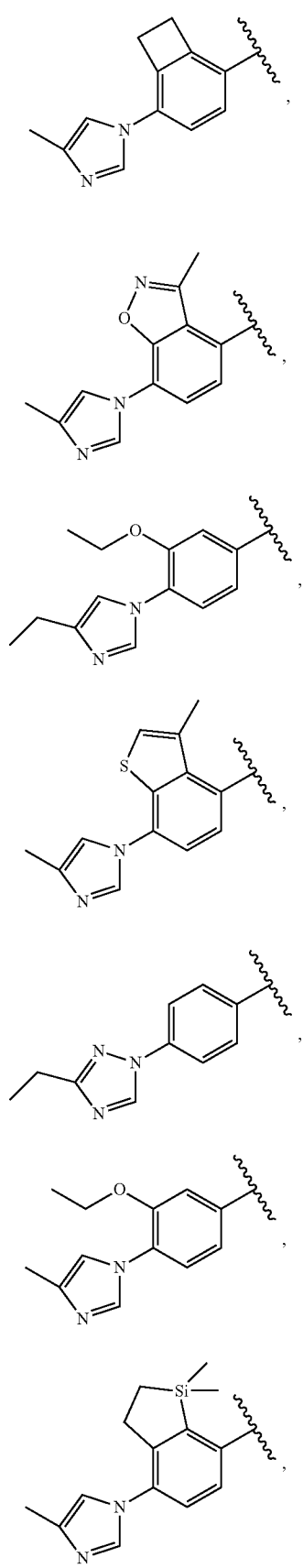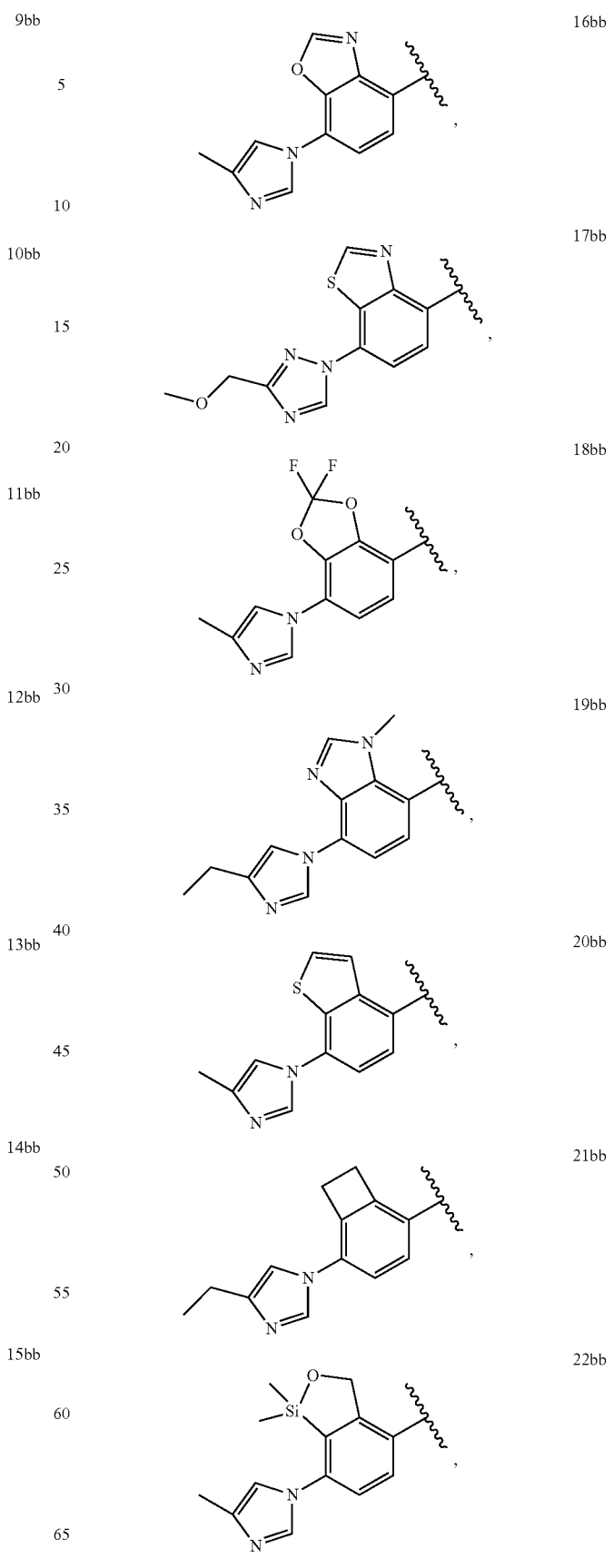

23bb 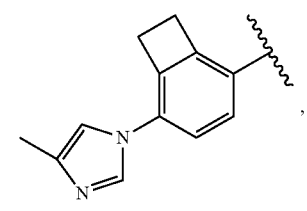
24bb 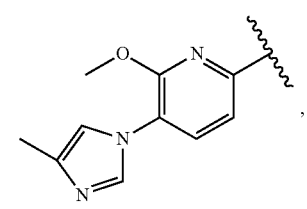
25bb 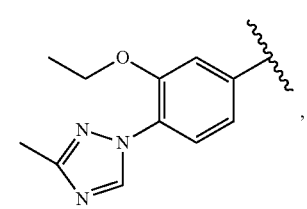
26bb 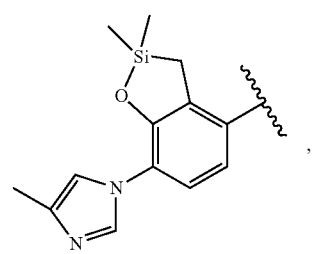
27bb 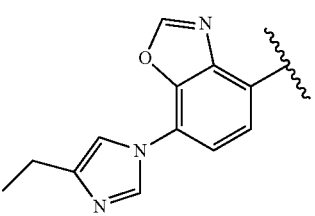
28bb 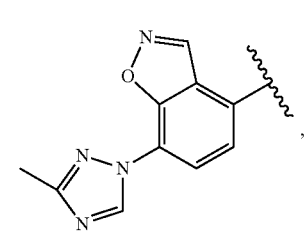
29bb 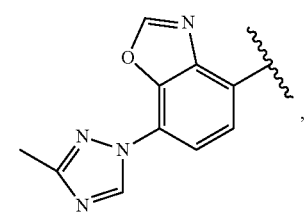
30bb 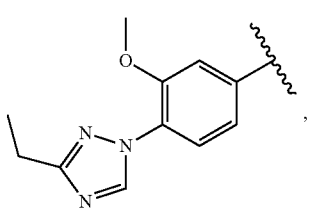
31bb 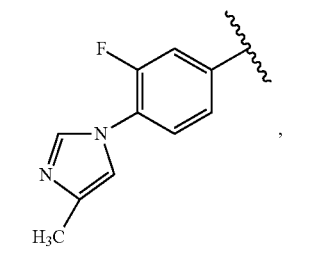
32bb 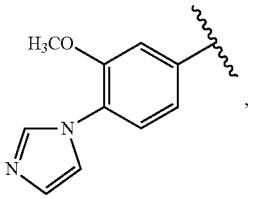
33bb 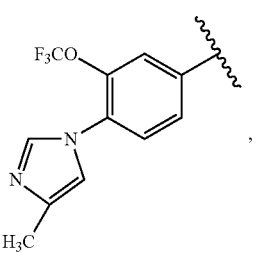
34bb 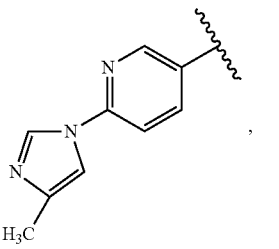
35bb 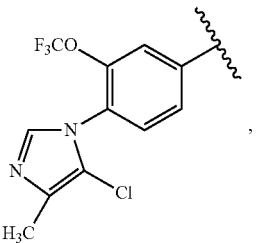

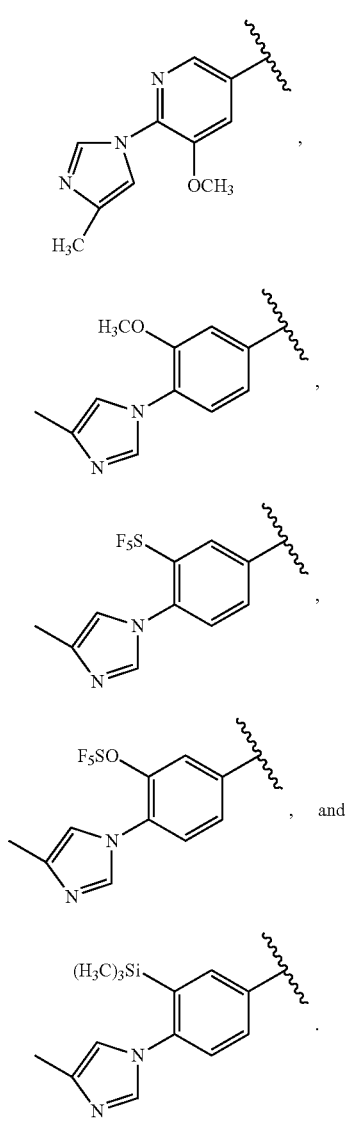

In another embodiment the R⁴—R³— moiety is 1bb. In another embodiment the R⁴—R³— moiety is 2bb. In another embodiment the R⁴—R³— moiety is 3bb. In another embodiment the R⁴—R³— moiety is 4bb. In another embodiment the R⁴—W— moiety is 5bb. In another embodiment the R⁴—R³— moiety is 6bb. In another embodiment the R⁴—R³— moiety is 7bb. In another embodiment the R⁴—R³— moiety is 8bb. In another embodiment the R⁴—R³— moiety is 9bb. In another embodiment the R⁴—R³— moiety is 10bb. In another embodiment the R⁴—R³— moiety is 11bb. In another embodiment the R⁴—R³— moiety is 12bb. In another embodiment the R⁴—R³— moiety is 13bb. In another embodiment the R⁴—R³— moiety is 14bb. In another embodiment the R⁴—R³— moiety is 15bb. In another embodiment the R⁴—R³— moiety is 16bb. In another embodiment the R⁴—R³— moiety is 17bb. In another embodiment the R⁴—R³— moiety is 18bb. In another embodiment the R⁴—R³— moiety is 19bb. In another embodiment the R⁴—R³— moiety is 20bb. In another embodiment the R⁴—R³— moiety is 21 bb. In another embodiment the R⁴—R³— moiety is 22bb. In another embodiment the R⁴—R³— moiety is 23bb. In another embodiment the R⁴—R³— moiety is 24bb. In another embodiment the R⁴—R³— moiety is 25bb. In another embodiment the R⁴—R³— moiety is 26bb. In another embodiment the R⁴—R³— moiety is 27bb. In another embodiment the R⁴—R³— moiety is 28bb. In another embodiment the R⁴—R³— moiety is 29bb. In another embodiment the R⁴—R³— moiety is 30bb. In another embodiment the R⁴—R³— moiety is 31 bb. In another embodiment the R⁴—R³— moiety is 32bb. In another embodiment the R⁴—R³— moiety is 33bb. In another embodiment the R⁴—R³— moiety is 34bb. In another embodiment the R⁴—R³— moiety is 35bb. In another embodiment the R⁴—R³— moiety is 36bb. In another embodiment the R⁴—R³— moiety is 37bb. In another embodiment the R⁴—R³— moiety is 38bb. In another embodiment the R⁴—R³— moiety is 39bb. In another embodiment the R⁴—R³— moiety is 40bb.

In another embodiment of the invention:

$R^3$ is selected from the group consisting of: (1) heteroaryl and (2) hetereoaryl substituted with 1 to 3 independently selected $R^{21}$ groups; and $R^4$ is selected from the group consisting of: (1) heteroaryl (e.g., imidazolyl, such as, for example imidazol-1-yl), (2) heteroaryl (e.g., imidazolyl, such as, for example imidazol-1-yl) substituted with 1 to 3 independently selected $R^{21}$ groups, (3) heteroaryl (e.g., imidazolyl, such as, for example imidazol-1-yl) substituted with 1 $R^{21}$ group, (4) heteroaryl (e.g., imidazolyl, such as, for example imidazol-1-yl) substituted with 1 to 3 independently selected $R^{21}$ groups, wherein said $R^{21}$ groups are the same or different alkyl group, and (5) heteroaryl (e.g., imidazolyl, such as, for example imidazol-1-yl) substituted with 1 $R^{21}$ group, wherein said $R^{21}$ group is alkyl (e.g., methyl).

In another embodiment of this invention the —R³—R⁴ moiety is:

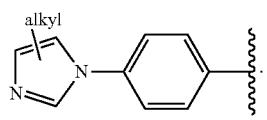

In another embodiment of this invention the —R³—R⁴ moiety is:

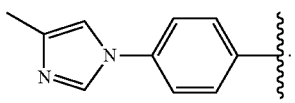 [SMILES: *c1ccc(-n2cnc(C)c2)cc1 ; "."]

In another embodiment of this invention the —R³—R⁴ moiety is:

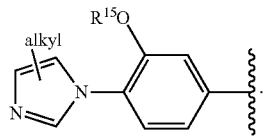

In another embodiment of this invention the —R³—R⁴ moiety is:

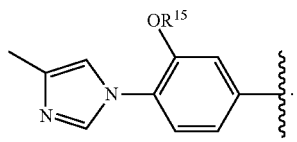

In another embodiment of this invention the —R³—R⁴ moiety is:

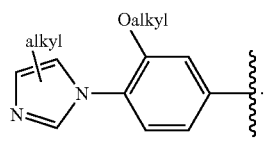

In another embodiment of this invention the —R³—R⁴ moiety is:

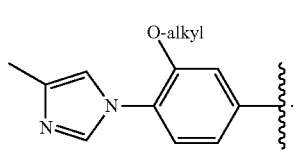

In another embodiment of this invention the —R³—R⁴ moiety is:

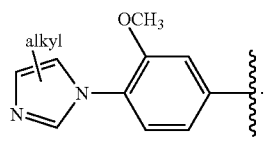

In another embodiment of this invention the —R³—R⁴ moiety is:

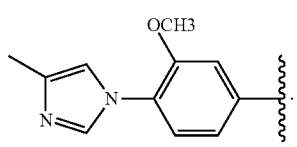 [SMILES: *c1ccc(-n2cnc(C)c2)c(OC)c1 ; "."]

In another embodiment of this invention the —R³—R⁴ moiety is:

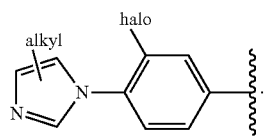

In another embodiment of this invention the —R³—R⁴ moiety is:

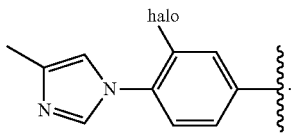

In another embodiment of this invention the —R³—R⁴ moiety is:

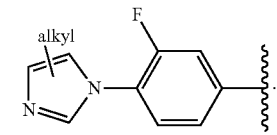

In another embodiment of this invention the —R³—R⁴ moiety is:

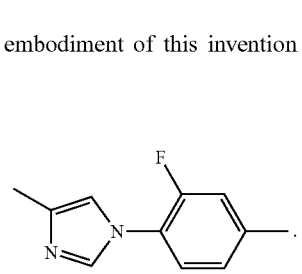

In another embodiment of this invention the —R³—R⁴ moiety is:

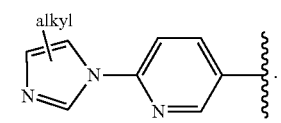

In another embodiment of this invention the —R³—R⁴ moiety is:

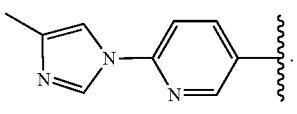

In another embodiment of this invention the —R³—R⁴ moiety is:

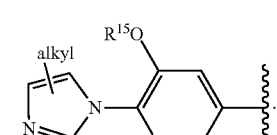

In another embodiment of this invention the —R³—R⁴ moiety is:

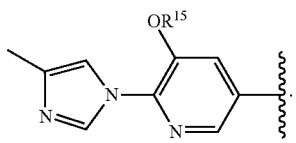

In another embodiment of this invention the —R³—R⁴ moiety is:

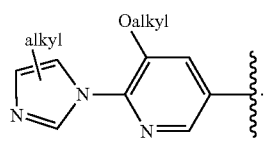

In another embodiment of this invention the —R³—R⁴ moiety is:

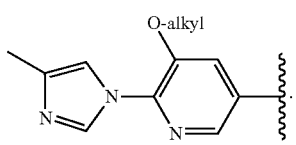

In another embodiment of this invention the —R³—R⁴ moiety is:

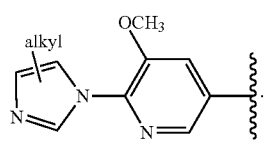

In another embodiment of this invention the —R³—R⁴ moiety is:

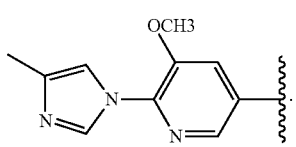 [SMILES: *c1cnc(-n2cnc(C)c2)c(OC)c1]

In another embodiment of this invention the —R³—R⁴ moiety is:

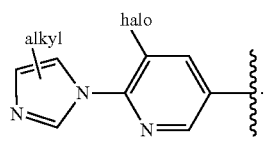

In another embodiment of this invention the —R³—R⁴ moiety is:

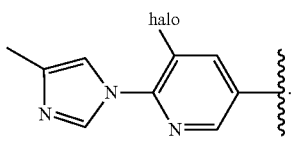

In another embodiment of this invention the —R³—R⁴ moiety is:

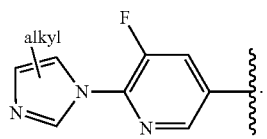

In another embodiment of this invention the —R³—R⁴ moiety is:

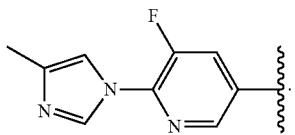 [SMILES: *c1cnc(-n2cnc(C)c2)c(F)c1]

In another embodiment of this invention R¹ is H.
In another embodiment of this invention R¹ is alkyl.
In another embodiment of this invention R¹ is aryl.
In another embodiment of this invention R¹ is aryl substituted with 1 to 3 independently selected R²¹ groups.
In another embodiment of this invention R¹ is aryl substituted with 1 to 3 independently selected R²¹ groups wherein said R²¹ groups are halo.
In another embodiment of this invention R¹ is aryl substituted with 1 to 3 independently selected R²¹ groups wherein said R²¹ groups are F.
In another embodiment of this invention R¹ is aryl substituted with 1 R²¹ group.
In another embodiment of this invention R¹ is aryl substituted with 2 R²¹ groups.
In another embodiment of this invention R¹ is aryl substituted with 3 R²¹ groups.
In another embodiment of this invention R¹ is aryl substituted with 1 R²¹ group wherein said R²¹ group is halo.
In another embodiment of this invention R¹ is aryl substituted with 2 R²¹ groups wherein said R²¹ groups are the same or different halo.
In another embodiment of this invention R¹ is aryl substituted with 3 R²¹ groups wherein said R²¹ groups are the same or different halo.
In another embodiment of this invention R¹ is phenyl substituted with 1 to 3 independently selected R²¹ groups.
In another embodiment of this invention R¹ is phenyl substituted with 1 to 3 independently selected R²¹ groups wherein said R²¹ groups are halo.
In another embodiment of this invention R¹ is phenyl substituted with 1 to 3 independently selected R²¹ groups wherein said R²¹ groups are F.

In another embodiment of this invention R$^1$ is

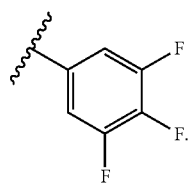 [SMILES: *c1cc(F)c(F)c(F)c1]

In another embodiment of this invention is phenyl substituted with 1 R$^{21}$ group.

In another embodiment of this invention R$^1$ is phenyl substituted with 2 R$^{21}$ groups.

In another embodiment of this invention R$^1$ is phenyl substituted with 3 R$^{21}$ groups.

In another embodiment of this invention R$^1$ is phenyl substituted with 1 R$^{21}$ group wherein said R$^{21}$ group is halo.

In another embodiment of this invention is phenyl substituted with 2 R$^{21}$ groups wherein said R$^{21}$ groups are the same or different halo.

In another embodiment of this invention R$^1$ is phenyl substituted with 3 R$^{21}$ groups wherein said R$^{21}$ groups are the same or different halo.

In another embodiment of this invention R$^1$ is 4-F-phenyl.

In another embodiment of this invention the -L-R$^1$ moiety is:

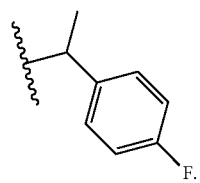 [SMILES: *C(C)c1ccc(F)cc1]

In another embodiment of this invention the moiety is:

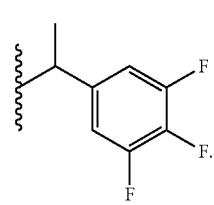 [SMILES: *C(C)c1cc(F)c(F)c(F)c1]

In another embodiment of this invention the -L-R$^1$ moiety is:

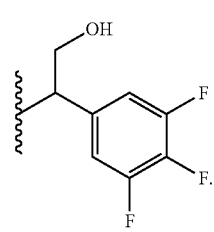 [SMILES: *C(CO)c1cc(F)c(F)c(F)c1]

In another embodiment of this invention the -L-R$^1$ moiety is:

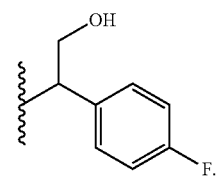 [SMILES: *C(CO)c1ccc(F)cc1]

In another embodiment of this invention the -L-R$^1$ moiety is selected from the group consisting of:

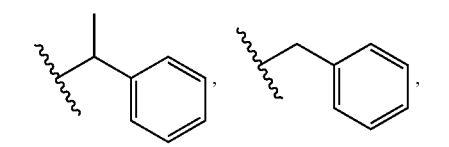

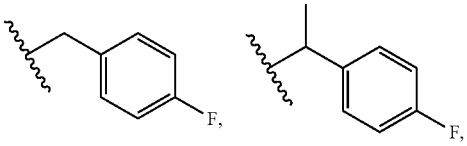

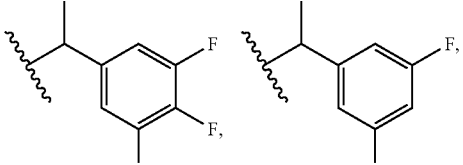

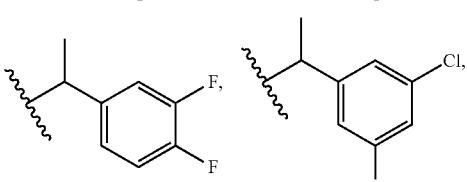

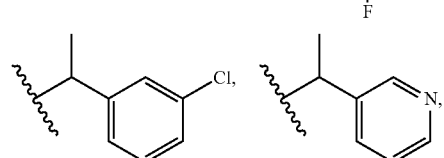

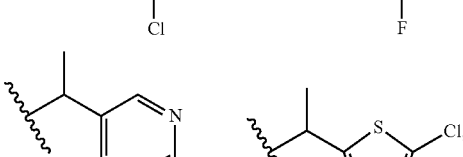

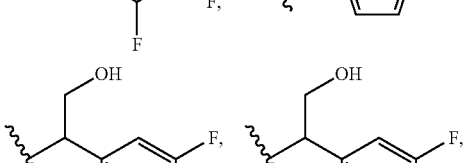

-continued

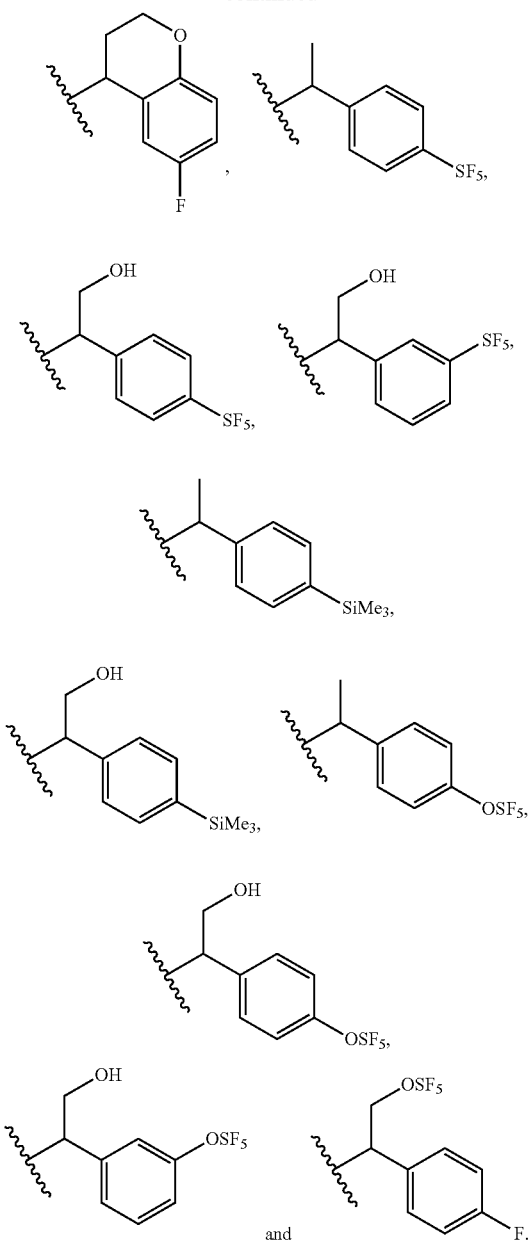

In another embodiment of this invention the -L-R$^1$ moiety is selected from the group consisting of:

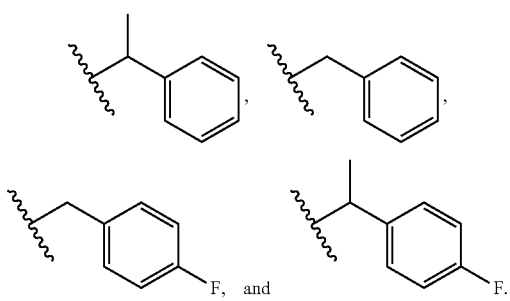

In another embodiment of this invention the -L-R$^1$ moiety is selected from the group consisting of:

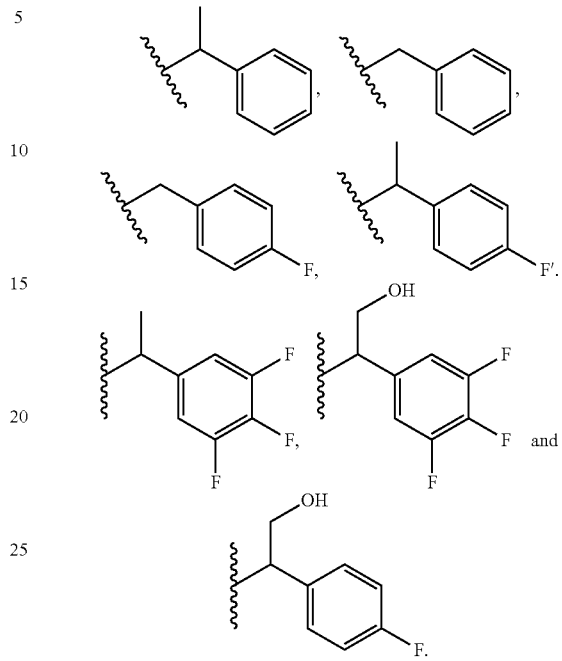

In another embodiment of this invention R$^3$ is selected from the group consisting of phenyl and phenyl substituted with one or more R$^2$ groups, and said R$^4$ group is selected from the group consisting of heteroaryl and heteroaryl substituted with one or more R$^{21}$ groups, and wherein each R$^{21}$ is independently selected.

In another embodiment of this invention: (a) L is —C(R$^6$)(R$^7$)— wherein R$^6$ and R$^7$ are independently selected from the group consisting of H and alkyl (e.g., methyl), and in one example one of R$^6$ and R$^7$ is H and the other is alkyl (e.g., methyl), and in another example both R$^6$ and R$^7$ are H. (b) R$^1$ is aryl (e.g. phenyl) substituted with 1 to 3 independently selected R$^{21}$ groups wherein said R$^{21}$ groups are halo (e.g., F), and in one example R$^1$ is phenyl substituted with two F, and in another example R$^1$ is phenyl substituted with 1 F, (c) R$^3$ is selected from the group consisting of phenyl and phenyl substituted with one or more independently selected R$^{21}$ groups, and (d) R$^4$ is selected from the group consisting of heteroaryl and heteroaryl substituted with one or more independently selected R$^{21}$ groups.

In another embodiment of this invention: (a) L is —C(R$^6$)(R$^7$)— wherein R$^6$ and R$^7$ are independently selected from the group consisting of H and alkyl (e.g., methyl), and in one example one of R$^6$ and R$^7$ is H and the other is alkyl (e.g., methyl), and in another example both R$^6$ and R$^7$ are H, (b) R$^1$ is aryl (e.g. phenyl) substituted with 1 to 3 independently selected R$^{21}$ groups wherein said R$^{21}$ groups are halo (e.g., F), and in one example 1R$^1$ is phenyl substituted with two F, and in another example R$^1$ is phenyl substituted with 1 F, (c) R$^3$ is selected from the group consisting of phenyl and phenyl substituted with one or more independently selected R$^{21}$ groups, and (d) R$^4$ is selected from the group consisting of imidazolyl and imidazolyl substituted with one or more independently selected R$^{21}$ groups.

In another embodiment of this invention: (a) L is —C(R$^6$)(R$^7$)— wherein R$^6$ and R$^7$ are independently selected from the group consisting of H and alkyl (e.g., methyl), and in one example one of $R^6$ and $R^7$ is H and the other is alkyl (e.g., methyl), and in another example both $R^6$ and $R^7$ are H, (b) $R^1$ is aryl (e.g. phenyl) substituted with 1 to 3 independently selected $R^{21}$ groups wherein said $R^{21}$ groups are halo (e.g., F), and in one example $R^1$ is phenyl substituted with two F, and in another example $R^1$ is phenyl substituted with 1 F, (c) $R^3$ is selected from the group consisting of phenyl and phenyl substituted with one or more independently selected —$OR^{15}$ groups, and (d) $R^4$ is selected from the group consisting of imidazolyl and imidazolyl substituted with one or more independently selected alkyl groups.

In another embodiment of this invention: (a) L is —$C(R^6)(R^7)$— wherein $R^3$ and $R^4$ are independently selected from the group consisting of H and alkyl (e.g., methyl), and in one example one of $R^6$ and $R^7$ is H and the other is alkyl (e.g., methyl), and in another example both $R^6$ and $R^7$ are H, (b) $R^1$ is aryl (e.g. phenyl) substituted with 1 to 3 independently selected $R^{21}$ groups wherein said $R^{21}$ groups are halo (e.g., F), and in one example $R^1$ is phenyl substituted with two F, and in another example $R^1$ is phenyl substituted with 1 F, (c) $R^3$ is selected from the group consisting of phenyl and phenyl substituted with one or two independently selected —$OR^{15}$ groups, wherein $R^{15}$ is alkyl, and (d) $R^4$ is selected from the group consisting of imidazolyl and imidazolyl substituted with one or two independently selected alkyl groups groups.

In another embodiment of this invention: (a) L is —$C(R^6)(R^7)$— wherein $R^3$ and $R^4$ are independently selected from the group consisting of H and alkyl (e.g., methyl), and in one example one of $R^6$ and $R^7$ is H and the other is alkyl (e.g., methyl), and in another example both $R^6$ and $R^7$ are H, (b) $R^1$ is aryl (e.g. phenyl) substituted with 1 to 3 independently selected $R^{21}$ groups wherein said $R^{21}$ groups are halo (e.g., F), and in one example $R^1$ is phenyl substituted with two F, and in another example $R^1$ is phenyl substituted with 1 F, (c) $R^3$ is selected from the group consisting of phenyl and phenyl substituted with one or two independently selected —$OR^{15}$ groups, wherein $R^{15}$ is methyl, and (d) $R^4$ is selected from the group consisting of imidazolyl and imidazolyl substituted with one or two independently selected methyl groups groups.

In another embodiment of this invention: (a) L is —$C(R^6)(R^7)$— wherein $R^6$ and $R^7$ are independently selected from the group consisting of H and alkyl (e.g., methyl), and in one example one of $R^6$ and $R^7$ is H and the other is alkyl (e.g., methyl), and in another example both $R^6$ and $R^7$ are H, (b) $R^1$ is aryl (e.g. phenyl) substituted with 1 to 3 independently selected $R^{21}$ groups wherein said $R^{21}$ groups are halo (e.g., F), and in one example $R^1$ is phenyl substituted with two F, and in another example $R^1$ is phenyl substituted with 1 F, (c) $R^3$ is phenyl substituted with one —$OR^{15}$ group, wherein $R^{15}$ is methyl, and (d) $R^4$ is selected from the group consisting of imidazolyl and imidazolyl substituted with one methyl group.

In another embodiment of this invention the -L-$R^1$ moiety is selected from the group consisting of:

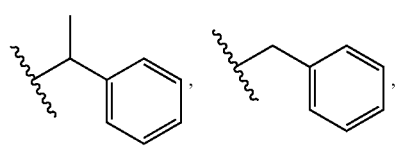

-continued

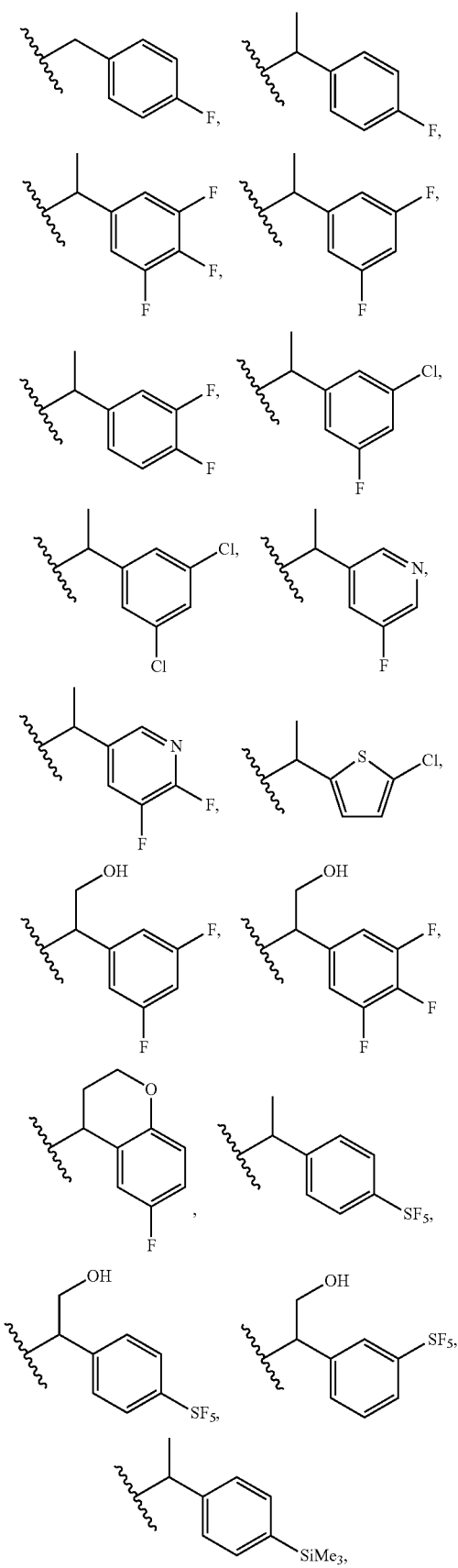

-continued
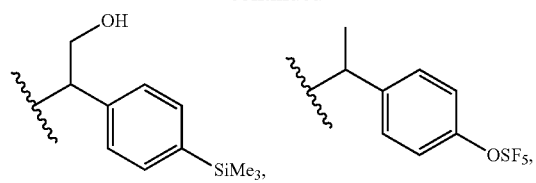
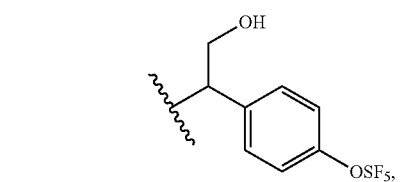
and
the R⁴—R³— moiety is:
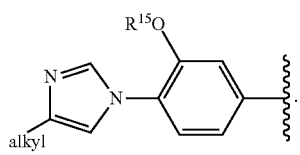
In another embodiment of this invention the -L-R¹ moiety is selected from the group consisting of:
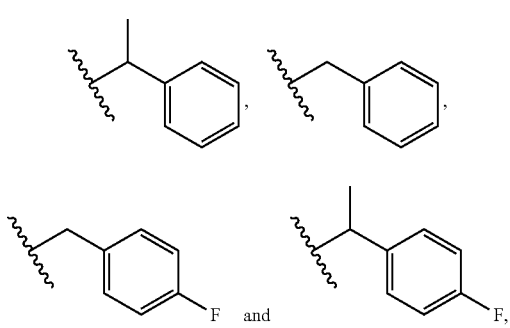
and the R⁴—R³— moiety is:
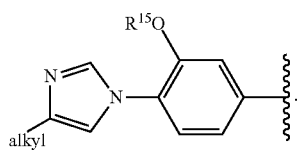
In another embodiment of this invention the -L-R¹ moiety is selected from the group consisting of:
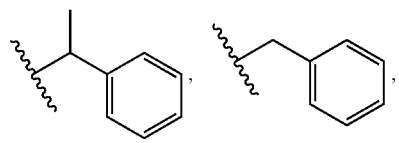
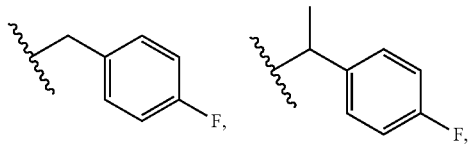
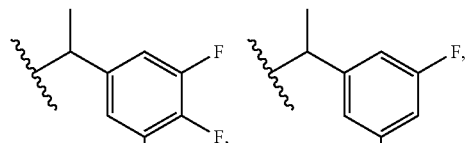
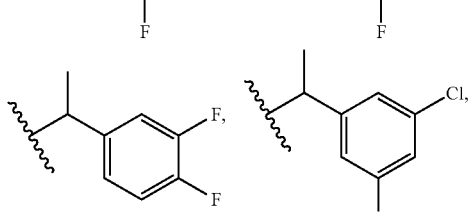
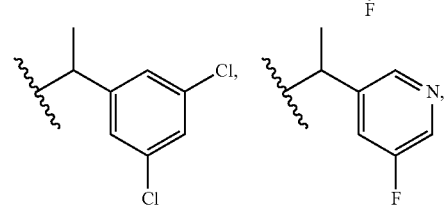
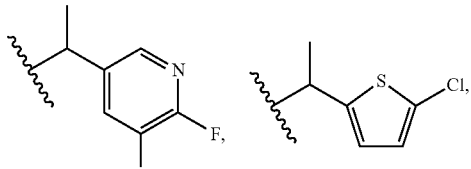
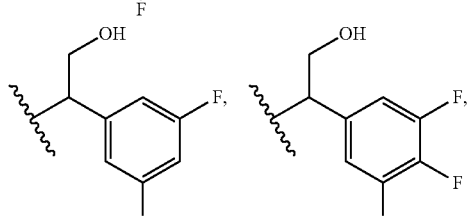
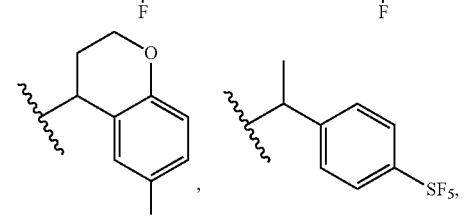
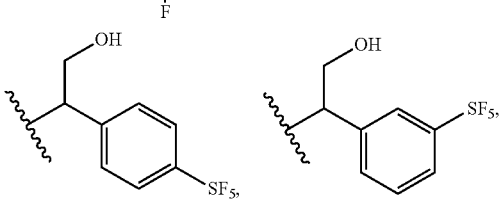

-continued

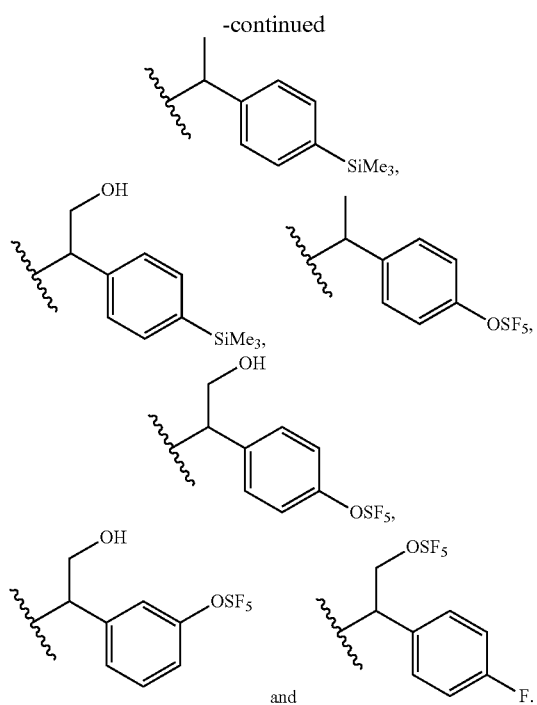

the R³—R⁴— moiety is:

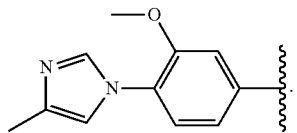 [SMILES: *c1ccc(-n2cnc(C)c2)c(OC)c1]

In another embodiment of this invention the -L-R¹ moiety is selected from the group consisting of:

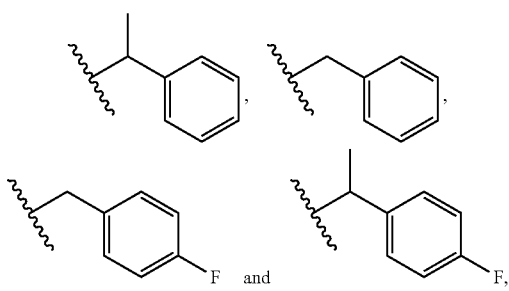

and the R³—R⁴— moiety is:

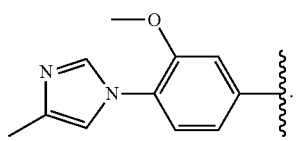 [SMILES: *c1ccc(-n2cnc(C)c2)c(OC)c1]

In another embodiment of this invention: (a) L is —C(R⁶)(R⁷)— wherein R⁶ and R⁷ are independently selected from the group consisting of H and alkyl (e.g., methyl), and in one example one of R⁶ and R⁷ is H and the other is alkyl (e.g., methyl), and in another example both R⁶ and R⁷ are H, (b) R¹ is aryl (e.g. phenyl) substituted with 1 to 3 independently selected R²¹ groups wherein said R²¹ groups are halo (e.g., F), and in one example R¹ is phenyl substituted with two F, and in another example R¹ is phenyl substituted with 1 F, (c) R³ is selected from the group consisting of phenyl and phenyl substituted with one or two independently selected —OR¹⁵ groups, wherein R methyl, and (d) R⁴ is selected from the group consisting of imidazolyl and imidazolyl substituted with one or two independently selected methyl groups groups.

In another embodiment of this invention: (a) L is —C(R⁶)(R⁷)— wherein R⁶ and R⁷ are independently selected from the group consisting of H and alkyl (e.g., methyl), and in one example one of R⁶ and R⁷ is H and the other is alkyl (e.g., methyl), and in another example both R⁶ and R⁷ are H, (b) R¹ is aryl (e.g. phenyl) substituted with 1 to 3 independently selected R²¹ groups wherein said R²¹ groups are halo (e.g., F), and in one example R¹ is phenyl substituted with two F, and in another example R¹ is phenyl substituted with 1 F, (c) R³ is phenyl substituted with one —OR¹⁵ group, wherein R¹⁵ is methyl, and (d) R⁴ is selected from the group consisting of imidazolyl and imidazolyl substituted with one methyl group.

In another embodiment the -L-R¹ moiety is selected from the group consisting of:

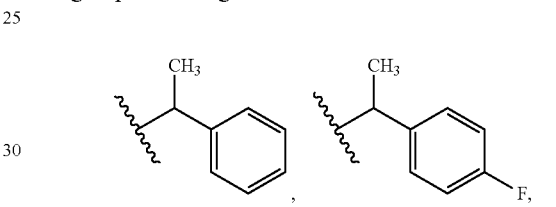

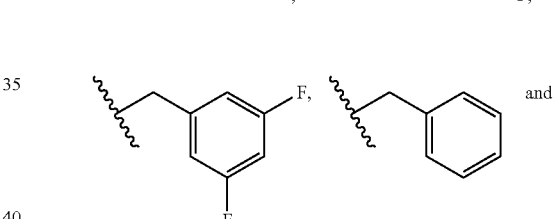

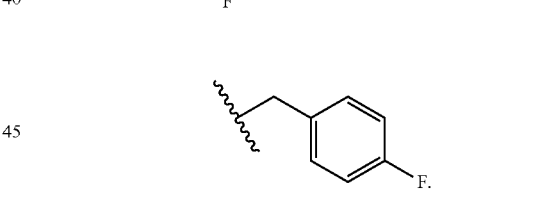

Other embodiments of this invention are directed to compounds of formula (I) wherein R³ is phenyl or phenyl substituted with one or more (e.g., one or two, or one) R²¹ groups (e.g., —OR¹⁵, wherein, for example, R¹⁵ is alkyl, such as, for example, methyl), and R⁹ is heteroaryl (e.g., imidazolyl) or heteroaryl (e.g., imidazolyl) substituted with one or more (e.g., one or two, or one) R²¹ groups (e.g., alkyl, such as, for example, methyl).

Thus, examples of the

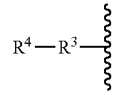

moiety of the compounds of this invention include, but are not limited to:
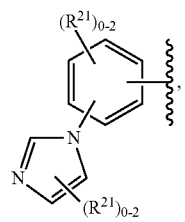
such as, for example,
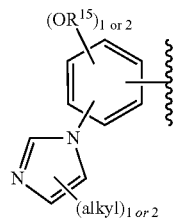
wherein $R^{15}$ is alkyl (e.g., methyl), such as, for example,
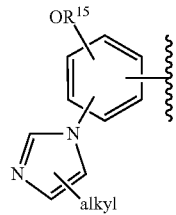
wherein $R^{15}$ is alkyl (e.g., methyl), such as, for example,
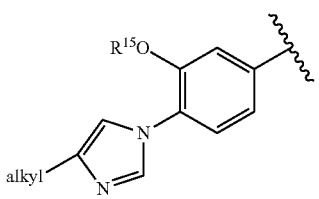
wherein $R^{15}$ is alkyl (e.g., methyl), such as, for example,
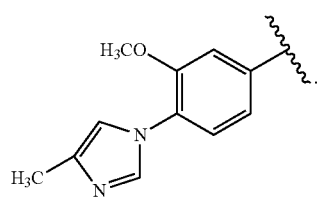 [SMILES: *c1ccc(-n2cnc(C)c2)c(OC)c1]
Representative (A) and (B) fused rings for formula (I) include but are not limited to:
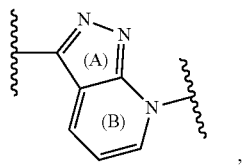
1A
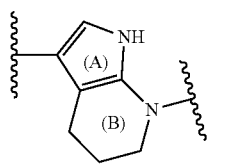
2A
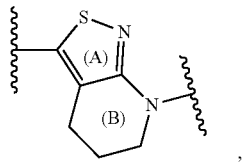
3A
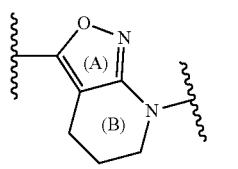
4A
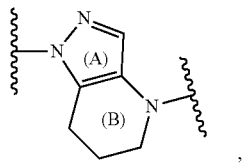
5A
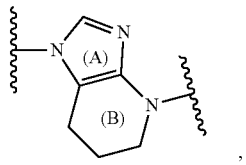
6A
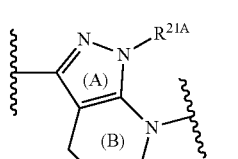
7A
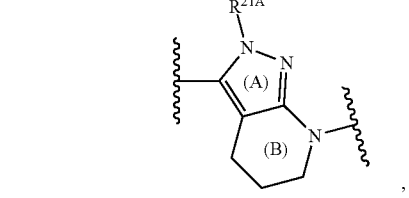
8A

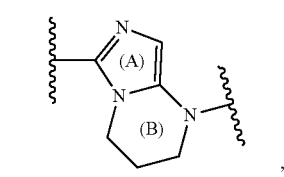
9A
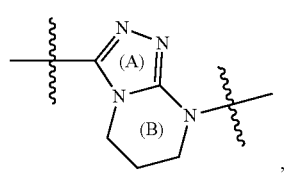
10A
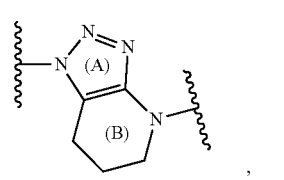
11A
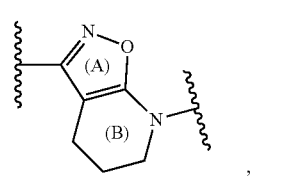
12A
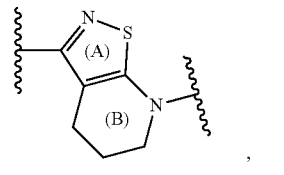
13A
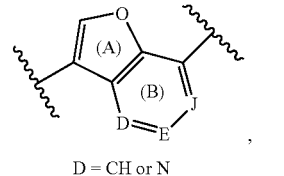
14A
D = CH or N
E = CH or N
J = CH or N
D, E and J are independently selected
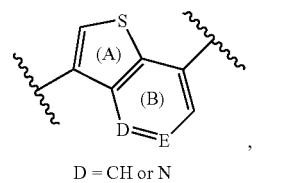
15A
D = CH or N
E = CH or N
D and E are independently selected
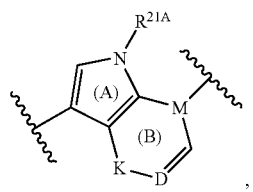
16A
K = CH$_2$ or NR$^{21A}$
(e.g., R$^{21A}$ is H)
D = CH or N
M = CH or N
K, D and M are independently selected
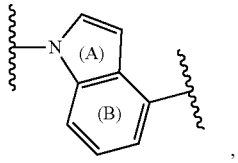
17A
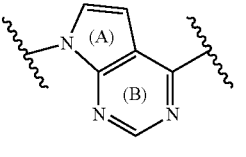
18A
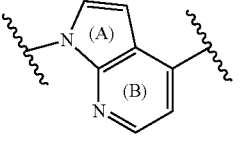
19A
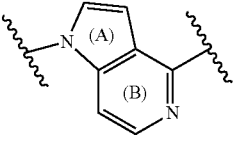
20A
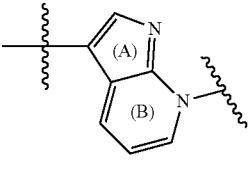
21A
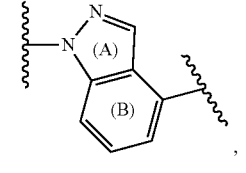
22A
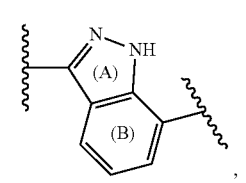
23A 24A
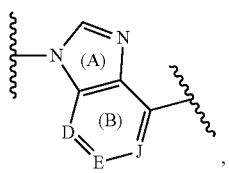
D = CH or N
E = CH or N
J = CH or N
D, E and J are independently selected
25A
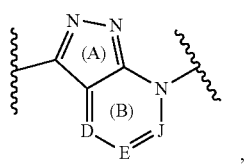
D = CH or N
E = CH or N
J = CH or N
D, E and J are independently selected
26A
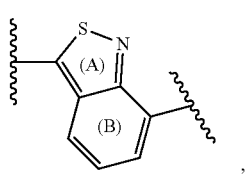
27A
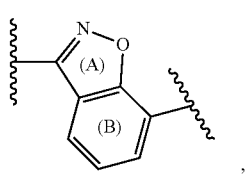
28A
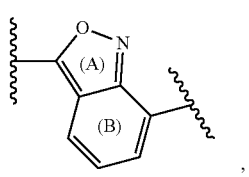
29A
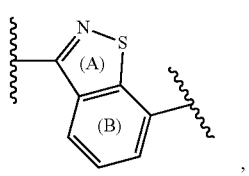
30A
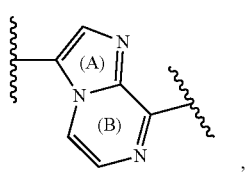
31A
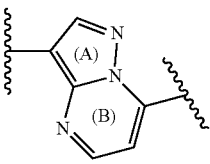
32A
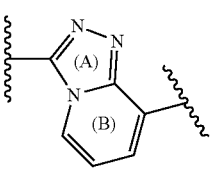
33A
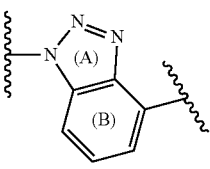
34A
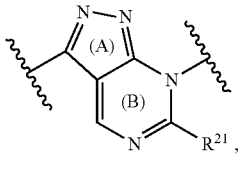
35A
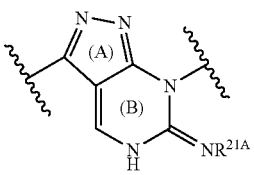
35A.1
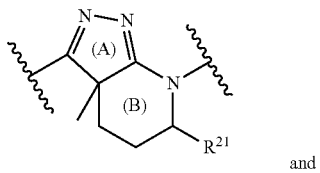
and
35A.2
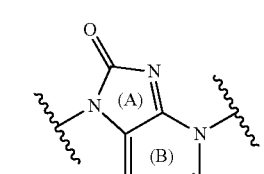
wherein $R^{21A}$ is as defined for formula (I).

Representative (A) and (B) fused rings for formula (I) also include but are not limited to:
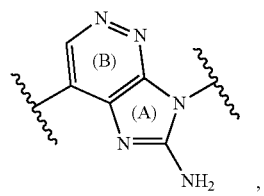 45A
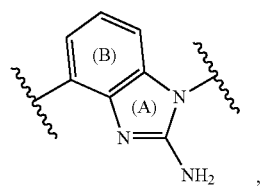 46A
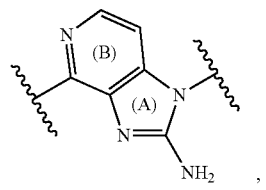 47A
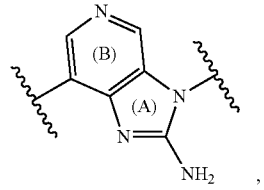 48A
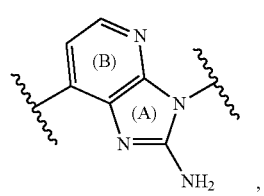 49A
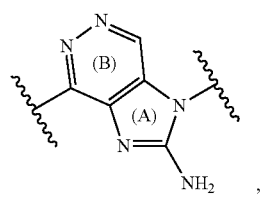 52A
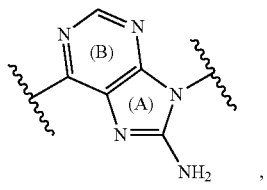 53A
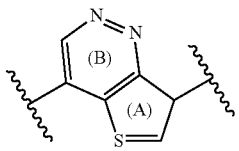 54A
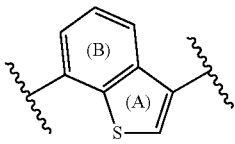 55A
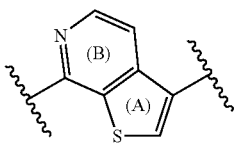 56A
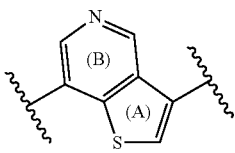 57A
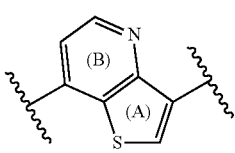 58A
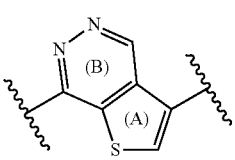 59A
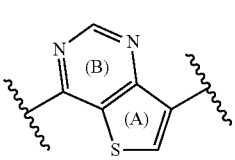 60A
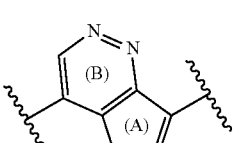 61A
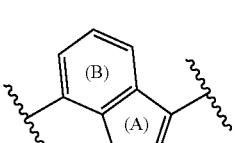 62A
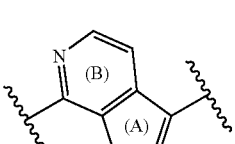 63A

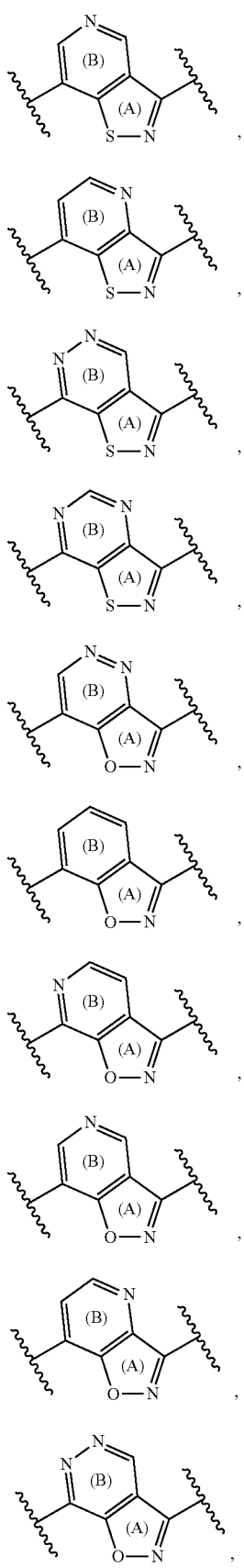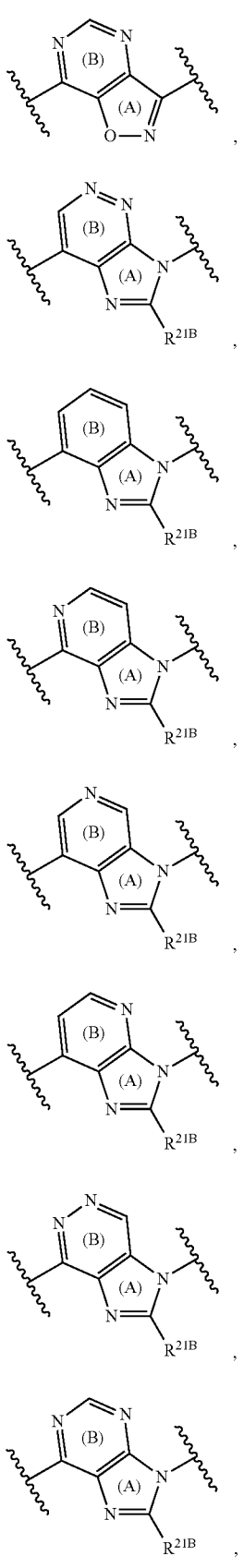

-continued

84A
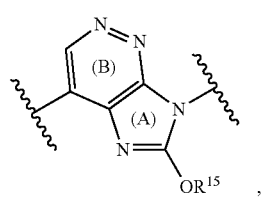

85A
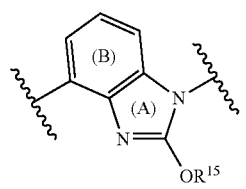

86A
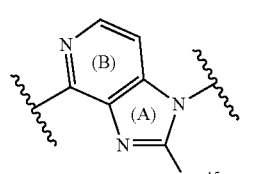

87A
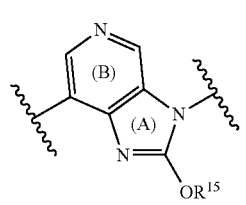

88A
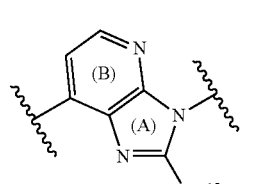

91A
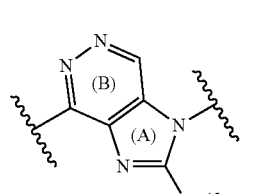

92A

93A
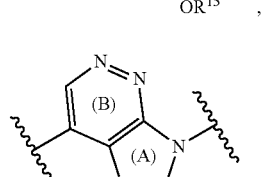

-continued

94A
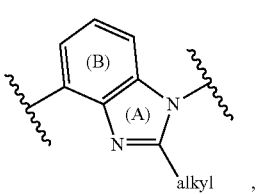

95A
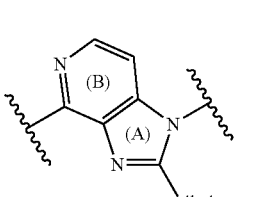

96A
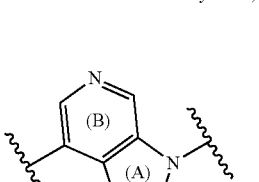

97A
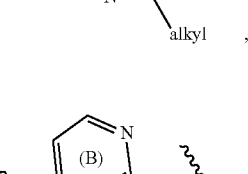

100A
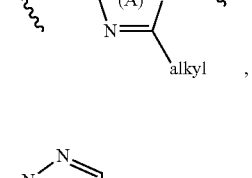
, and

101A
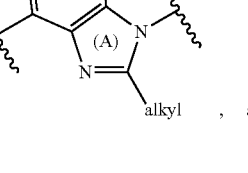
.

Other embodiments of this invention are directed to any of the embodiments above that are directed to L, $R^1$, $R^3$, and $R^4$ (or any combinations thereof) wherein the fused rings are selected from the group consisting of: 1A to 35A.

Other embodiments of this invention are directed to any one of the embodiments above that are directed to L, $R^1$, $R^3$, and $R^4$ (or any combinations thereof) wherein the fused rings are selected from the group consisting of: 45A to 101A.

Representative compounds of formula (I) include but are not limited to:
B2
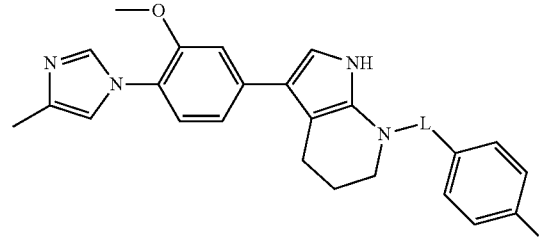
B3
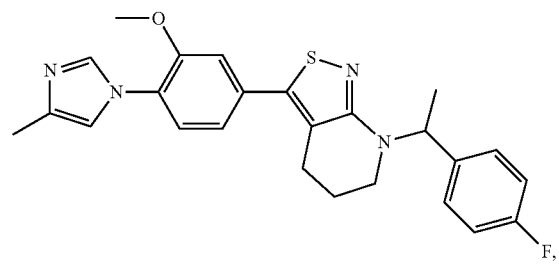
B5
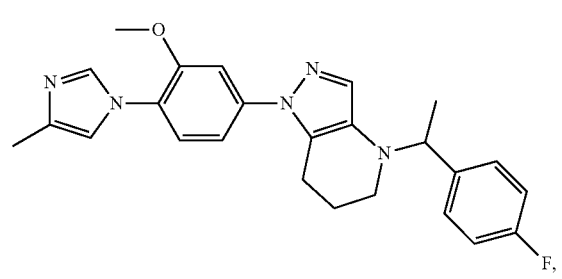
B6
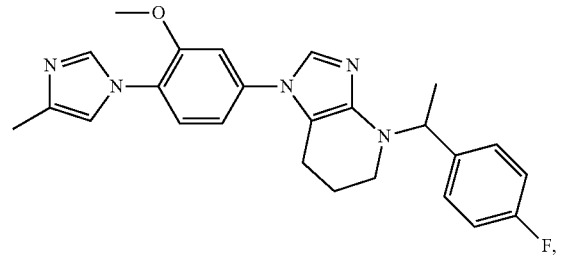
B7

B8
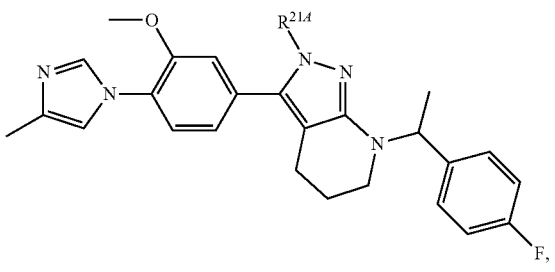
B9
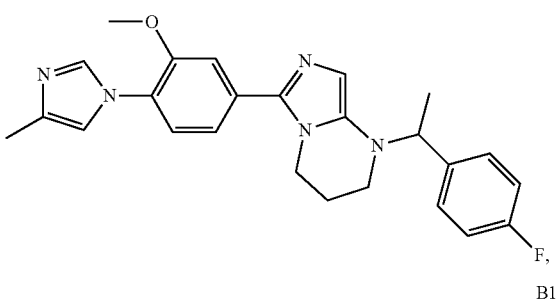
B11
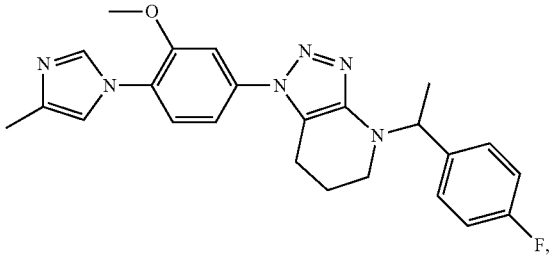
B13
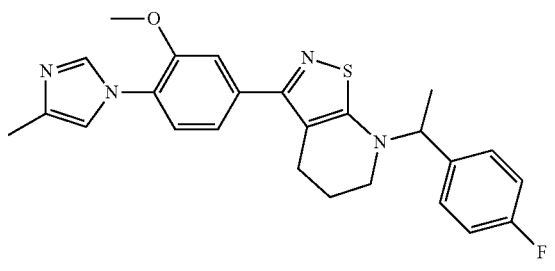
B14
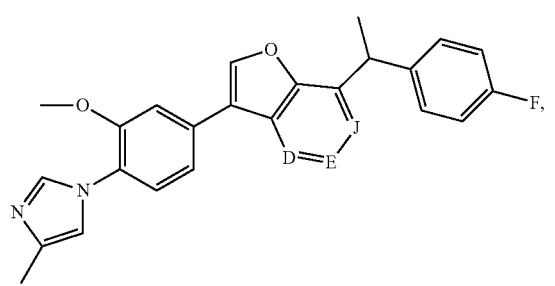
D = CH or N
E = CH or N
J = CH or N
D, E and J are independently selected B15
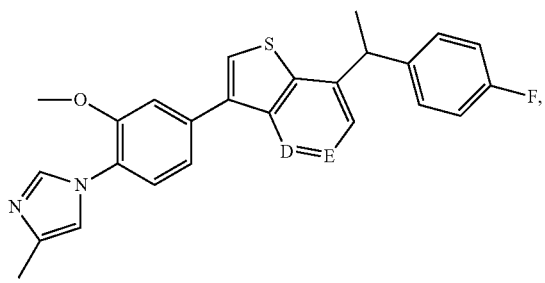
D = CH or N
E = CH or N
D and E are independently selected
B19
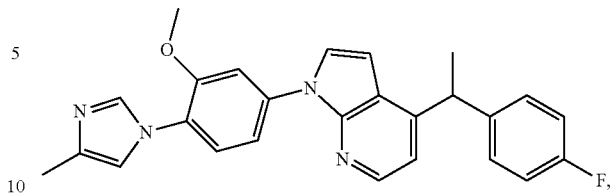
B20
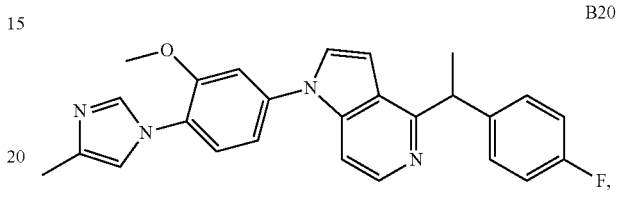
B16
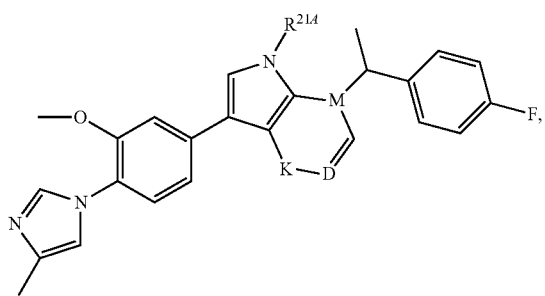
K = CH$_2$ or NR$^{214}$
(e.g., R$^{214}$ is H)
D = CH or N
M = CH or N
K, D and M are independently selected
B21
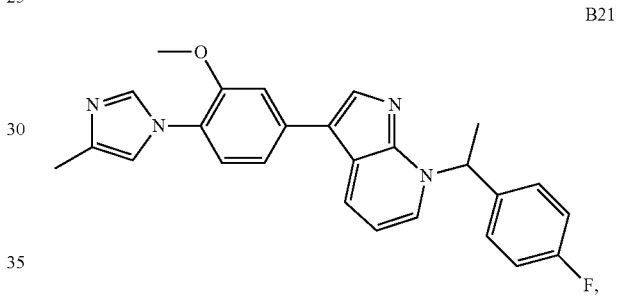
B17
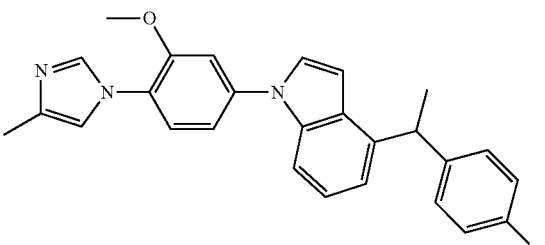
B22
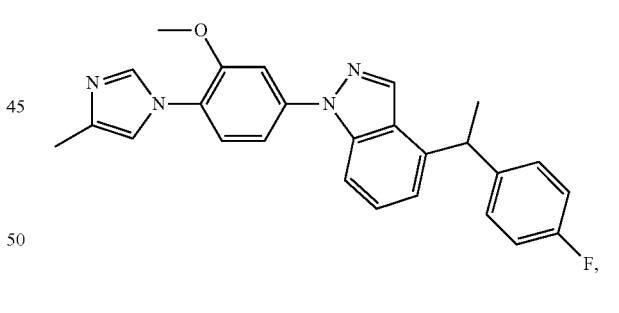
B18
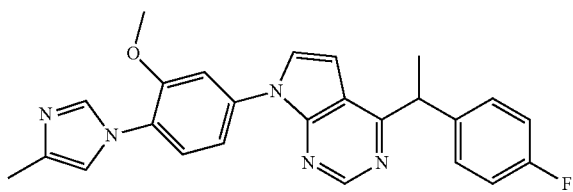
B23
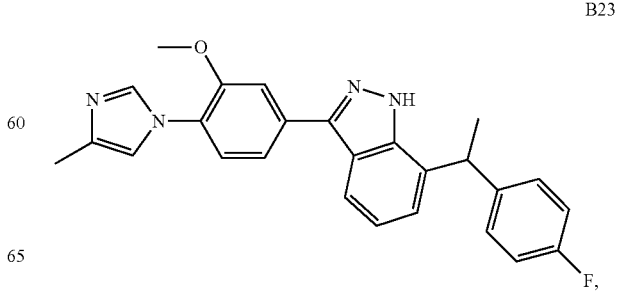

-continued
B24
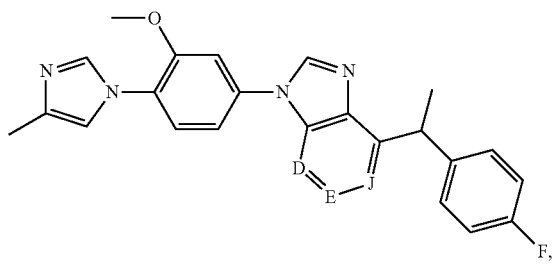
D = CH or N
E = CH or N
J = CH or N
D, E and J are independently selected
B25
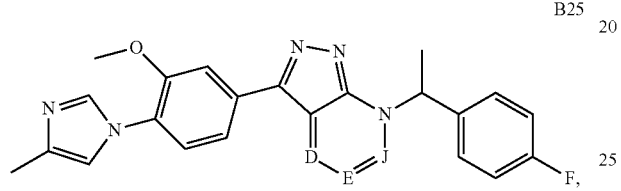
D = CH or N
E = CH or N
J = CH or N
D, E and J are independently selected
B26
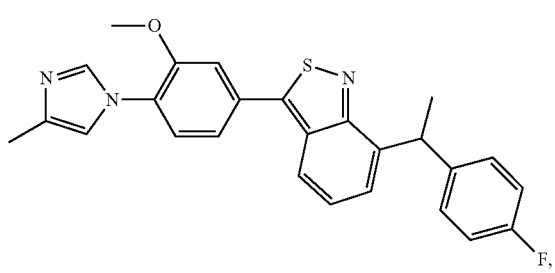
B27
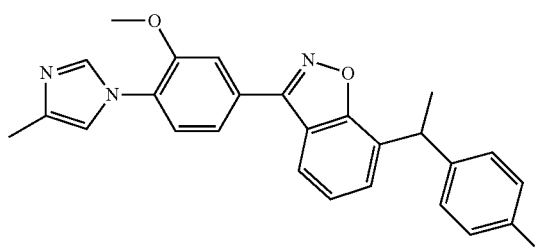
B28
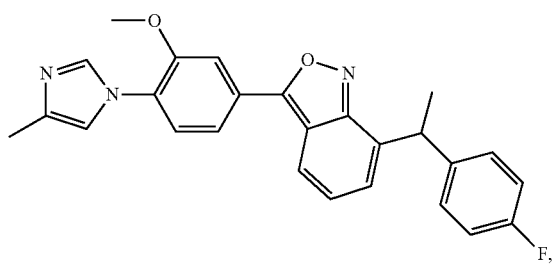
-continued
B29
B30
B31
B32
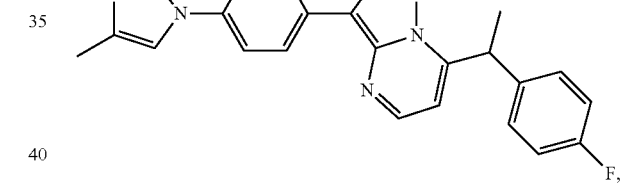
B33
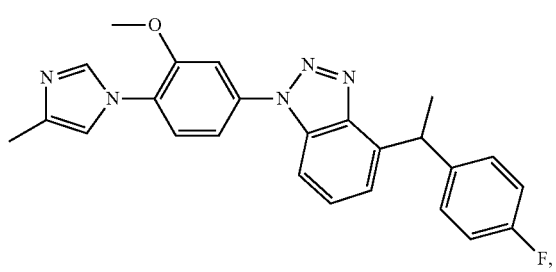

-continued

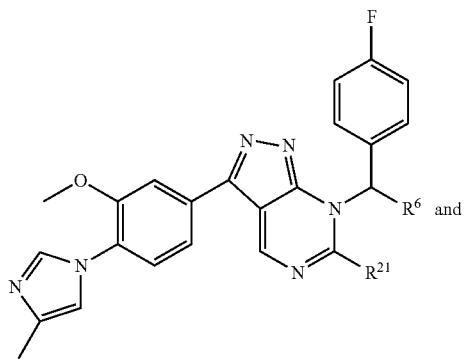
B34

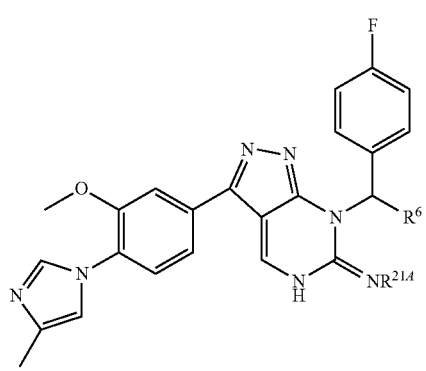
B35 wherein R²¹ᴬ, R⁶ and R²¹ are as defined in formula (I).

Representative compounds of formula (I) also include, but are not limited to:

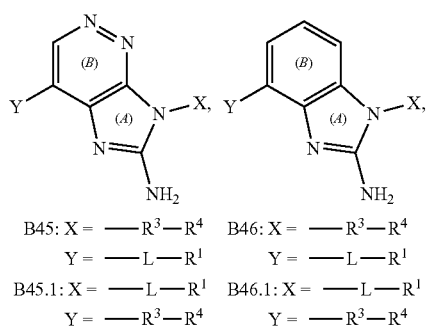

B45: X = —R³—R⁴    B46: X = —R³—R⁴
     Y = —L—R¹          Y = —L—R¹
B45.1: X = —L—R¹    B46.1: X = —L—R¹
       Y = —R³—R⁴          Y = —R³—R⁴

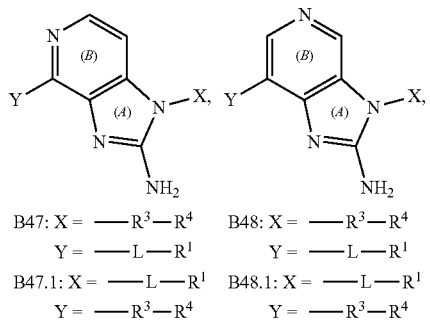

B47: X = —R³—R⁴    B48: X = —R³—R⁴
     Y = —L—R¹          Y = —L—R¹
B47.1: X = —L—R¹    B48.1: X = —L—R¹
       Y = —R³—R⁴          Y = —R³—R⁴

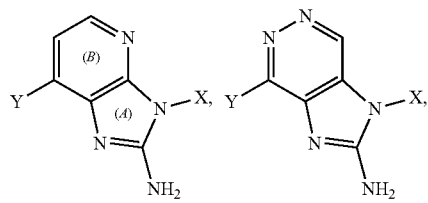

B49: X = —R³—R⁴    B52: X = —R³—R⁴
     Y = —L—R¹          Y = —L—R¹
B49.1: X = —L—R¹    B52.1: X = —L—R¹
       Y = —R³—R⁴          Y = —R³—R⁴

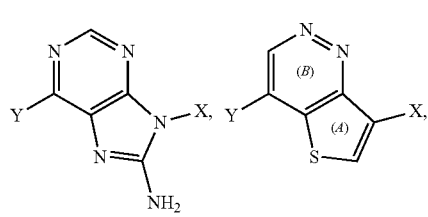

B53: X = —R³—R⁴    B54: X = —R³—R⁴
     Y = —L—R¹          Y = —L—R¹
B53.1: X = —L—R¹    B54.1: X = —L—R¹
       Y = —R³—R⁴          Y = —R³—R⁴

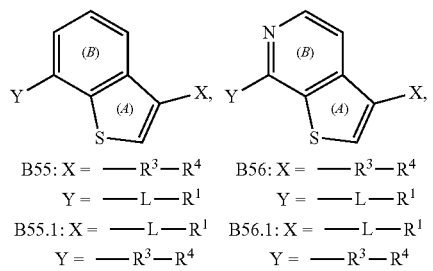

B55: X = —R³—R⁴    B56: X = —R³—R⁴
     Y = —L—R¹          Y = —L—R¹
B55.1: X = —L—R¹    B56.1: X = —L—R¹
       Y = —R³—R⁴          Y = —R³—R⁴

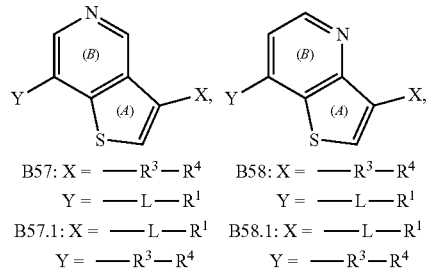

B57: X = —R³—R⁴    B58: X = —R³—R⁴
     Y = —L—R¹          Y = —L—R¹
B57.1: X = —L—R¹    B58.1: X = —L—R¹
       Y = —R³—R⁴          Y = —R³—R⁴

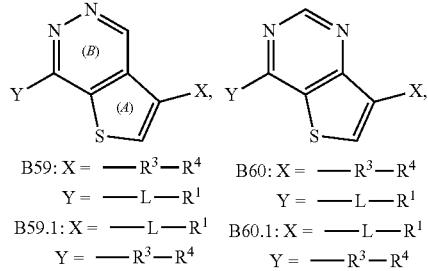

B59: X = —R³—R⁴    B60: X = —R³—R⁴
     Y = —L—R¹          Y = —L—R¹
B59.1: X = —L—R¹    B60.1: X = —L—R¹
       Y = —R³—R⁴          Y = —R³—R⁴

-continued

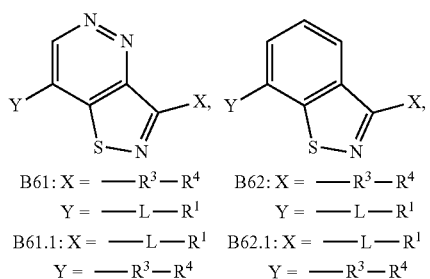

B61: X = —R³—R⁴  B62: X = —R³—R⁴
Y = —L—R¹   Y = —L—R¹
B61.1: X = —L—R¹  B62.1: X = —L—R¹
Y = —R³—R⁴   Y = —R³—R⁴

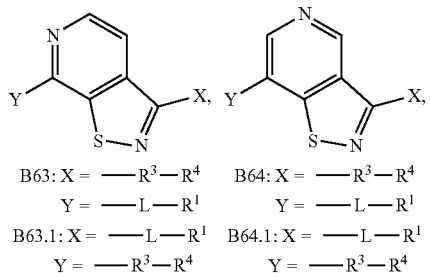

B63: X = —R³—R⁴  B64: X = —R³—R⁴
Y = —L—R¹   Y = —L—R¹
B63.1: X = —L—R¹  B64.1: X = —L—R¹
Y = —R³—R⁴   Y = —R³—R⁴

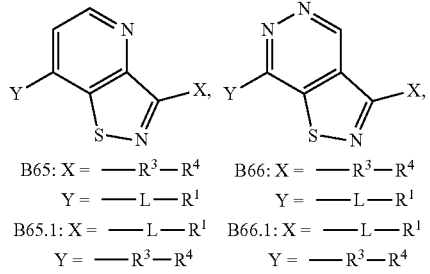

B65: X = —R³—R⁴  B66: X = —R³—R⁴
Y = —L—R¹   Y = —L—R¹
B65.1: X = —L—R¹  B66.1: X = —L—R¹
Y = —R³—R⁴   Y = —R³—R⁴

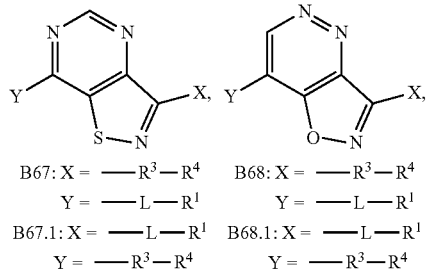

B67: X = —R³—R⁴  B68: X = —R³—R⁴
Y = —L—R¹   Y = —L—R¹
B67.1: X = —L—R¹  B68.1: X = —L—R¹
Y = —R³—R⁴   Y = —R³—R⁴

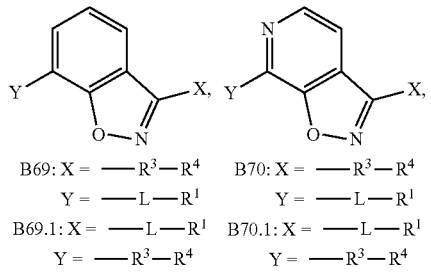

B69: X = —R³—R⁴  B70: X = —R³—R⁴
Y = —L—R¹   Y = —L—R¹
B69.1: X = —L—R¹  B70.1: X = —L—R¹
Y = —R³—R⁴   Y = —R³—R⁴

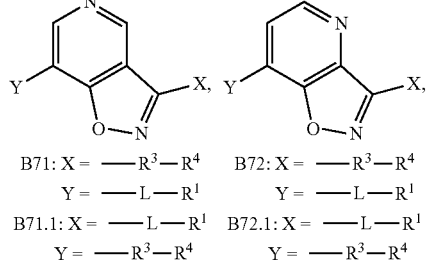

B71: X = —R³—R⁴  B72: X = —R³—R⁴
Y = —L—R¹   Y = —L—R¹
B71.1: X = —L—R¹  B72.1: X = —L—R¹
Y = —R³—R⁴   Y = —R³—R⁴

-continued

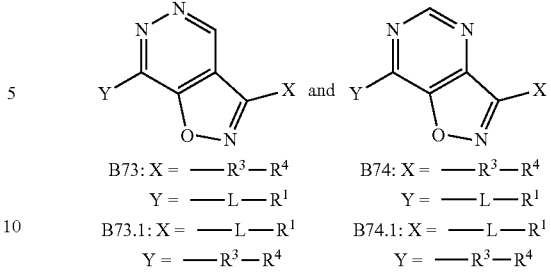

B73: X = —R³—R⁴  B74: X = —R³—R⁴
Y = —L—R¹   Y = —L—R¹
B73.1: X = —L—R¹  B74.1: X = —L—R¹
Y = —R³—R⁴   Y = —R³—R⁴ wherein $R^1$, $R^3$, $R^4$, and L are as defined for formula (I),

Representative compounds of formula (I) also include:

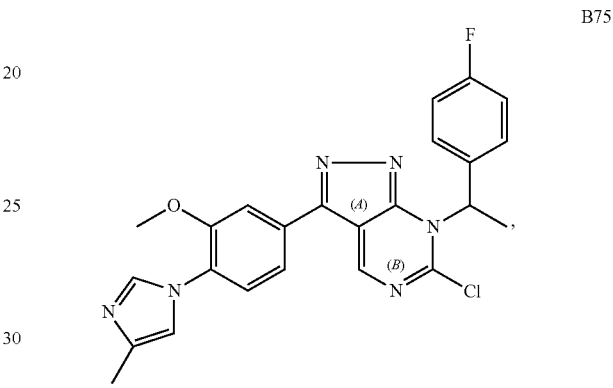

B75

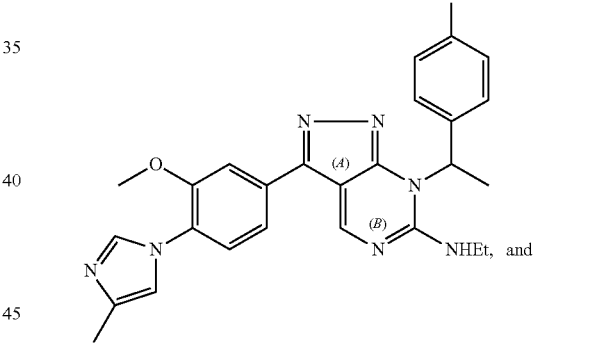

B76

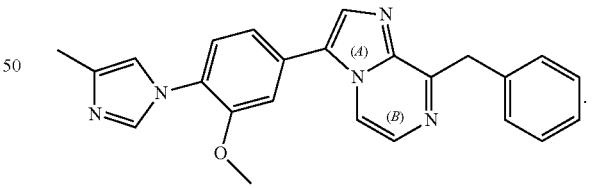

B77

Another embodiment of this invention is directed to a compound of formula (I) selected from the group consisting of: compounds IA.1, IA, IB.1, IB, IC, ID.1, ID, IE.1, IE, B2, B3, B5-B9, B11, B13-B35, B45 to B49, B52 to B74, B45.1 to B49.1, B52.1 to B74.1, B75 to B77, and 1 to 162 (identified below).

Another embodiment of this invention is directed to a compound of formula (I) selected from the group consisting of: compounds B2, B3, B5-B9, B11, B13-B35, B45 to B49, B52 to B74, B45.1 to B49.1, B52.1 to B74.1, B75 to B77, and 1 to 162 (identified below).

Another embodiment of this invention is directed to a compound of formula (I) selected from the group consisting of: compounds B2, B3, B5-B9, B11, and B13 to B35.

Another embodiment of this invention is directed to a compound of formula (I) selected from the group consisting of: compounds B45 to B49 and B52 to B74.

Another embodiment of this invention is directed to a compound of formula (I) selected from the group consisting of: compounds B45.1 to B49.1 and B52.1 to B74.1.

Another embodiment of this invention is directed to a compound of formula (I) selected from the group consisting of: compounds B75 to B77.

Another embodiment of this invention is directed to a compound of formula (I) selected from the group consisting of: compounds 1 to 162 (identified below).

Another embodiment of this invention is directed to compound IA.1.

Another embodiment of this invention is directed to compound IA.

Another embodiment of this invention is directed to compound IB.1.

Another embodiment of this invention is directed to compound IB.

Another embodiment of this invention is directed to compound IC.

Another embodiment of this invention is directed to compound ID.1.

Another embodiment of this invention is directed to compound ID.

Another embodiment of this invention is directed to compound IE1.

Another embodiment of this invention is directed to compound IE.

Another embodiment of this invention is directed to compound B2.

Another embodiment of this invention is directed to compound B3.

Another embodiment of this invention is directed to compound B5.

Another embodiment of this invention is directed to compound B6.

Another embodiment of this invention is directed to compound B7.

Another embodiment of this invention is directed to compound B8.

Another embodiment of this invention is directed to compound B9.

Another embodiment of this invention is directed to compound B11.

Another embodiment of this invention is directed to compound B13.

Another embodiment of this invention is directed to compound B14.

Another embodiment of this invention is directed to compound B15.

Another embodiment of this invention is directed to compound B16.

Another embodiment of this invention is directed to compound B17.

Another embodiment of this invention is directed to compound B18.

Another embodiment of this invention is directed to compound B19.

Another embodiment of this invention is directed to compound B20.

Another embodiment of this invention is directed to compound B21.

Another embodiment of this invention is directed to compound B22.

Another embodiment of this invention is directed to compound B23.

Another embodiment of this invention is directed to compound B24.

Another embodiment of this invention is directed to compound B25.

Another embodiment of this invention is directed to compound B26.

Another embodiment of this invention is directed to compound B27.

Another embodiment of this invention is directed to compound B28.

Another embodiment of this invention is directed to compound B29.

Another embodiment of this invention is directed to compound B30.

Another embodiment of this invention is directed to compound B31.

Another embodiment of this invention is directed to compound B32.

Another embodiment of this invention is directed to compound B33.

Another embodiment of this invention is directed to compound B34.

Another embodiment of this invention is directed to compound B35.

Another embodiment of this invention is directed to compound B45.

Another embodiment of this invention is directed to compound B46.

Another embodiment of this invention is directed to compound B47.

Another embodiment of this invention is directed to compound B48.

Another embodiment of this invention is directed to compound B49.

Another embodiment of this invention is directed to compound B52.

Another embodiment of this invention is directed to compound B53.

Another embodiment of this invention is directed to compound B54.

Another embodiment of this invention is directed to compound B55.

Another embodiment of this invention is directed to compound B56.

Another embodiment of this invention is directed to compound B57.

Another embodiment of this invention is directed to compound B58.

Another embodiment of this invention is directed to compound B59.

Another embodiment of this invention is directed to compound B60.

Another embodiment of this invention is directed to compound B61.

Another embodiment of this invention is directed to compound B62.

Another embodiment of this invention is directed to compound B63.

Another embodiment of this invention is directed to compound B64.

Another embodiment of this invention is directed to compound B65.

Another embodiment of this invention is directed to compound B66.

Another embodiment of this invention is directed to compound B67.

Another embodiment of this invention is directed to compound B68.

Another embodiment of this invention is directed to compound B69.

Another embodiment of this invention is directed to compound B70.

Another embodiment of this invention is directed to compound B71.

Another embodiment of this invention is directed to compound B72.

Another embodiment of this invention is directed to compound B73.

Another embodiment of this invention is directed to compound B74.

Another embodiment of this invention is directed to compound B45.1.

Another embodiment of this invention is directed to compound B46.1.

Another embodiment of this invention is directed to compound B47.1.

Another embodiment of this invention is directed to compound B48.1.

Another embodiment of this invention is directed to compound B49.1.

Another embodiment of this invention is directed to compound B52.1

Another embodiment of this invention is directed to compound B53.1

Another embodiment of this invention is directed to compound B54.1.

Another embodiment of this invention is directed to compound B55.1.

Another embodiment of this invention is directed to compound B56.1.

Another embodiment of this invention is directed to compound B57.1.

Another embodiment of this invention is directed to compound B58.1.

Another embodiment of this invention is directed to compound B59.1.

Another embodiment of this invention is directed to compound B60.1.

Another embodiment of this invention is directed to compound B61.1.

Another embodiment of this invention is directed to compound B62.1.

Another embodiment of this invention is directed to compound B63.1.

Another embodiment of this invention is directed to compound B64.1.

Another embodiment of this invention is directed to compound B65.1.

Another embodiment of this invention is directed to compound B66.1.

Another embodiment of this invention is directed to compound BB67.1.

Another embodiment of this invention is directed to compound B66.1.

Another embodiment of this invention is directed to compound B69.1.

Another embodiment of this invention is directed to compound B70.1.

Another embodiment of this invention is directed to compound B71.1.

Another embodiment of this invention is directed to compound B72.1.

Another embodiment of this invention is directed to compound B73.1.

Another embodiment of this invention is directed to compound B74.1.

Another embodiment of this invention is directed to compound B75.

Another embodiment of this invention is directed to compound B76.

Another embodiment of this invention is directed to compound B77.

Another embodiment of this invention is directed to compound 1.

Another embodiment of this invention is directed to compound 2.

Another embodiment of this invention is directed to compound 3.

Another embodiment of this invention is directed to compound 4.

Another embodiment of this invention is directed to compound 5.

Another embodiment of this invention is directed to compound 6.

Another embodiment of this invention is directed to compound 7.

Another embodiment of this invention is directed to compound 8.

Another embodiment of this invention is directed to compound 9.

Another embodiment of this invention is directed to compound 10.

Another embodiment of this invention is directed to compound 11.

Another embodiment of this invention is directed to compound 12.

Another embodiment of this invention is directed to compound 13.

Another embodiment of this invention is directed to compound 14.

Another embodiment of this invention is directed to compound 15.

Another embodiment of this invention is directed to compound 16.

Another embodiment of this invention is directed to compound 17.

Another embodiment of this invention is directed to compound 18.

Another embodiment of this invention is directed to compound 19.

Another embodiment of this invention is directed to compound 20.

Another embodiment of this invention is directed to compound 21.

Another embodiment of this invention is directed to compound 22.

Another embodiment of this invention is directed to compound 23.

Another embodiment of this invention is directed to compound 24.

Another embodiment of this invention is directed to compound 25.

Another embodiment of this invention is directed to compound 26.

Another embodiment of this invention is directed to compound 27.

Another embodiment of this invention is directed to compound 28,

Another embodiment of this invention is directed to compound 29.

Another embodiment of this invention is directed to compound 30.

Another embodiment of this invention is directed to compound 31.

Another embodiment of this invention is directed to compound 32.

Another embodiment of this invention is directed to compound 33.

Another embodiment of this invention is directed to compound 34.

Another embodiment of this invention is directed to compound 35.

Another embodiment of this invention is directed to compound 45.

Another embodiment of this invention is directed to compound 46.

Another embodiment of this invention is directed to compound 47.

Another embodiment of this invention is directed to compound 48.

Another embodiment of this invention is directed to compound 49.

Another embodiment of this invention is directed to compound 50.

Another embodiment of this invention is directed to compound 51.

Another embodiment of this invention is directed to compound 52.

Another embodiment of this invention is directed to compound 53.

Another embodiment of this invention is directed to compound 54.

Another embodiment of this invention is directed to compound 55.

Another embodiment of this invention is directed to compound 56.

Another embodiment of this invention is directed to compound 57.

Another embodiment of this invention is directed to compound 58.

Another embodiment of this invention is directed to compound 59.

Another embodiment of this invention is directed to compound 60.

Another embodiment of this invention is directed to compound 61.

Another embodiment of this invention is directed to compound 62.

Another embodiment of this invention is directed to compound 63.

Another embodiment of this invention is directed to compound 64.

Another embodiment of this invention is directed to compound 65.

Another embodiment of this invention is directed to compound 66.

Another embodiment of this invention is directed to compound 67.

Another embodiment of this invention is directed to compound 68.

Another embodiment of this invention is directed to compound 69.

Another embodiment of this invention is directed to compound 70.

Another embodiment of this invention is directed to compound 71.

Another embodiment of this invention is directed to compound 72.

Another embodiment of this invention is directed to compound 73.

Another embodiment of this invention is directed to compound 74.

Another embodiment of this invention is directed to compound 75.

Another embodiment of this invention is directed to compound 76.

Another embodiment of this invention is directed to compound 77.

Another embodiment of this invention is directed to compound 78.

Another embodiment of this invention is directed to compound 79.

Another embodiment of this invention is directed to compound 80.

Another embodiment of this invention is directed to compound 81.

Another embodiment of this invention is directed to compound 82.

Another embodiment of this invention is directed to compound 83.

Another embodiment of this invention is directed to compound 84.

Another embodiment of this invention is directed to compound 85.

Another embodiment of this invention is directed to compound 86.

Another embodiment of this invention is directed to compound 87.

Another embodiment of this invention is directed to compound 88.

Another embodiment of this invention is directed to compound 89.

Another embodiment of this invention is directed to compound 90.

Another embodiment of this invention is directed to compound 91.

Another embodiment of this invention is directed to compound 92.

Another embodiment of this invention is directed to compound 93.

Another embodiment of this invention is directed to compound 94.

Another embodiment of this invention is directed to compound 95.

Another embodiment of this invention is directed to compound 96.

Another embodiment of this invention is directed to compound 97.

Another embodiment of this invention is directed to compound 98.

Another embodiment of this invention is directed to compound 99.

Another embodiment of this invention is directed to compound 100.

Another embodiment of this invention is directed to compound 101.

Another embodiment of this invention is directed to compound 102.
Another embodiment of this invention is directed to compound 103.
Another embodiment of this invention is directed to compound 104.
Another embodiment of this invention is directed to compound 105.
Another embodiment of this invention is directed to compound 106.
Another embodiment of this invention is directed to compound 107.
Another embodiment of this invention is directed to compound 108.
Another embodiment of this invention is directed to compound 109.
Another embodiment of this invention is directed to compound 110.
Another embodiment of this invention is directed to compound 111.
Another embodiment of this invention is directed to compound 112.
Another embodiment of this invention is directed to compound 113.
Another embodiment of this invention is directed to compound 114.
Another embodiment of this invention is directed to compound 115.
Another embodiment of this invention is directed to compound 116.
Another embodiment of this invention is directed to compound 117.
Another embodiment of this invention is directed to compound 118.
Another embodiment of this invention is directed to compound 119.
Another embodiment of this invention is directed to compound 120.
Another embodiment of this invention is directed to compound 121.
Another embodiment of this invention is directed to compound 122.
Another embodiment of this invention is directed to compound 123.
Another embodiment of this invention is directed to compound 124.
Another embodiment of this invention is directed to compound 125.
Another embodiment of this invention is directed to compound 126.
Another embodiment of this invention is directed to compound 127.
Another embodiment of this invention is directed to compound 128.
Another embodiment of this invention is directed to compound 129.
Another embodiment of this invention is directed to compound 130.
Another embodiment of this invention is directed to compound 131.
Another embodiment of this invention is directed to compound 132.
Another embodiment of this invention is directed to compound 133
Another embodiment of this invention is directed to compound 134.
Another embodiment of this invention is directed to compound 135.
Another embodiment of this invention is directed to compound 136.
Another embodiment of this invention is directed to compound 137.
Another embodiment of this invention is directed to compound 138.
Another embodiment of this invention is directed to compound 139.
Another embodiment of this invention is directed to compound 140.
Another embodiment of this invention is directed to compound 141.
Another embodiment of this invention is directed to compound 142.
Another embodiment of this invention is directed to compound 143.
Another embodiment of this invention is directed to compound 144.
Another embodiment of this invention is directed to compound 145.
Another embodiment of this invention is directed to compound 146.
Another embodiment of this invention is directed to compound 147.
Another embodiment of this invention is directed to compound 148.
Another embodiment of this invention is directed to compound 149.
Another embodiment of this invention is directed to compound 150.
Another embodiment of this invention is directed to compound 151.
Another embodiment of this invention is directed to compound 152.
Another embodiment of this invention is directed to compound 153.
Another embodiment of this invention is directed to compound 154.
Another embodiment of this invention is directed to compound 155.
Another embodiment of this invention is directed to compound 156.
Another embodiment of this invention is directed to compound 157.
Another embodiment of this invention is directed to compound 158.
Another embodiment of this invention is directed to compound 159.
Another embodiment of this invention is directed to compound 160.
Another embodiment of this invention is directed to compound 161.
Another embodiment of this invention is directed to compound 162.
Another embodiment of this invention is directed to compound 1A.
Another embodiment of this invention is directed to compound 2A.
Another embodiment of this invention is directed to compound 3A.
Another embodiment of this invention is directed to compound 4A.
Another embodiment of this invention is directed to compound 5A.

Another embodiment of this invention is directed to compound 6A.

Another embodiment of this invention is directed to compound 7A.

Another embodiment of this invention is directed to compound 8A.

Another embodiment of this invention is directed to compound 9A.

Another embodiment of this invention is directed to compound 10A.

Another embodiment of this invention is directed to compound 11A.

Another embodiment of this invention is directed to compound 12A.

Another embodiment of this invention is directed to compound 13A.

Another embodiment of this invention is directed to compound 14A.

Another embodiment of this invention is directed to compound 15A.

Another embodiment of this invention is directed to compound 16A.

Another embodiment of this invention is directed to compound 17A.

Another embodiment of this invention is directed to compound 18A.

Another embodiment of this invention is directed to compound 19A.

Another embodiment of this invention is directed to compound 20A.

Another embodiment of this invention is directed to compound 21A.

Another embodiment of this invention is directed to compound 22A.

Another embodiment of this invention is directed to compound 23A.

Another embodiment of this invention is directed to compound 24A.

Another embodiment of this invention is directed to compound 25A.

Another embodiment of this invention is directed to compound 26A.

Another embodiment of this invention is directed to compound 27A.

Another embodiment of this invention is directed to compound 28A.

Another embodiment of this invention is directed to compound 29A.

Another embodiment of this invention is directed to compound 30A.

Another embodiment of this invention is directed to compound 31A.

Another embodiment of this invention is directed to compound 32A.

Another embodiment of this invention is directed to compound 33A.

Another embodiment of this invention is directed to compound 34A.

Another embodiment of this invention is directed to compound 35A.

Another embodiment of this invention is directed to compound 35A.1.

Another embodiment of this invention is directed to compound 35A.2.

Another embodiment of this invention is directed to compound 45A.

Another embodiment of this invention is directed to compound 46A.

Another embodiment of this invention is directed to compound 47A.

Another embodiment of this invention is directed to compound 48A.

Another embodiment of this invention is directed to compound 49A.

Another embodiment of this invention is directed to compound 52A.

Another embodiment of this invention is directed to compound 53A.

Another embodiment of this invention is directed to compound 54A.

Another embodiment of this invention is directed to compound 55A.

Another embodiment of this invention is directed to compound 56A.

Another embodiment of this invention is directed to compound 57A.

Another embodiment of this invention is directed to compound 58A.

Another embodiment of this invention is directed to compound 59A.

Another embodiment of this invention is directed to compound 60A.

Another embodiment of this invention is directed to compound 61A.

Another embodiment of this invention is directed to compound 62A.

Another embodiment of this invention is directed to compound 63A.

Another embodiment of this invention is directed to compound 64A.

Another embodiment of this invention is directed to compound 65A.

Another embodiment of this invention is directed to compound 66A.

Another embodiment of this invention is directed to compound 67A.

Another embodiment of this invention is directed to compound 68A.

Another embodiment of this invention is directed to compound 69A.

Another embodiment of this invention is directed to compound 70A.

Another embodiment of this invention is directed to compound 71A.

Another embodiment of this invention is directed to compound 72A.

Another embodiment of this invention is directed to compound 73A.

Another embodiment of this invention is directed to compound 74A.

Another embodiment of this invention is directed to compound 75A.

Another embodiment of this invention is directed to compound 76A.

Another embodiment of this invention is directed to compound 77A.

Another embodiment of this invention is directed to compound 78A.

Another embodiment of this invention is directed to compound 79A.

Another embodiment of this invention is directed to compound 82A.

Another embodiment of this invention is directed to compound 83A.

Another embodiment of this invention is directed to compound 84A.

Another embodiment of this invention is directed to compound 85A.

Another embodiment of this invention is directed to compound 86A.

Another embodiment of this invention is directed to compound 87A.

Another embodiment of this invention is directed to compound 88A.

Another embodiment of this invention is directed to compound 91A.

Another embodiment of this invention is directed to compound 92A.

Another embodiment of this invention is directed to compound 93A.

Another embodiment of this invention is directed to compound 94A.

Another embodiment of this invention is directed to compound 95A.

Another embodiment of this invention is directed to compound 96A.

Another embodiment of this invention is directed to compound 97A.

Another embodiment of this invention is directed to compound 100A.

Another embodiment of this invention is directed to compound 101A.

In the embodiments below Groups A, B, C, D and E are as defined as follows:
(1) Group A: compounds B2, B3, B5-B9, B11, and B13-B35;
(2) Group B: compounds B45 to B49, and B52 to B74;
(3) Group C: compounds B45.1 to B49.1 and B52.1 to B74.1;
(4) Group D: compounds B75 to B77; and
(5) Group E: compounds 1 to 162 (identified below).

Another embodiment of this invention is directed to a compound of formula (I).

Another embodiment of this invention is directed to a pharmaceutically acceptable salt of a compound of formula (I). And in one example the salt is a salt of a compound selected from the group consisting of Group A. And in another example the salt is a salt of a compound selected from the group consisting of Group B. And in another example the salt is a salt of a compound selected from the group consisting of Group C. And in another example the salt is a salt of a compound selected from the group consisting of Group D. And in another example the salt is a salt of a compound selected from the group consisting of Group E.

Another embodiment of this invention is directed to a pharmaceutically acceptable ester of a compound of formula (I). And in one example the ester is an ester of a compound selected from the group consisting of Group A. And in another example the ester is an ester of a compound selected from the group consisting of Group B. And in another example the ester is an ester of a compound selected from the group consisting of Group C. And in another example the ester is an ester of a compound selected from the group consisting of Group D. And in another example the ester is an ester of a compound selected from the group consisting of Group E.

Another embodiment of this invention is directed to a solvate of a compound of formula (I). And in one example the solvate is a solvate of a compound selected from the group consisting of Group A. And in another example the solvate is a solvate of a compound selected from the group consisting of Group B. And in another example the solvate is a solvate of a compound selected from the group consisting of Group C. And in another example the solvate is a solvate of a compound selected from the group consisting of Group D. And in another example the solvate is a solvate of a compound selected from the group consisting of Group E.

Another embodiment of this invention is directed to a compound of formula (I) in isolated form. And in one example the compound of formula (I) is selected from the group consisting of Group A. And in one example the compound of formula (I) is selected from the group consisting of Group D. And in one example the compound of formula (I) is selected from the group consisting of Group E.

Another embodiment of this invention is directed to a compound of formula (I) in pure form. And in one example the compound of formula (I) is selected from the group consisting of Group A. And in one example the compound of formula (I) is selected from the group consisting of Group D. And in one example the compound of formula (I) is selected from the group consisting of Group E.

Another embodiment of this invention is directed to a compound of formula (I) in pure and isolated form. And in one example the compound of formula (I) is selected from the group consisting of Group A. And in one example the compound of formula (I) is selected from the group consisting of Group D. And in one example the compound of formula (I) is selected from the group consisting of Group E.

Another embodiment of this invention is directed to a pharmaceutical composition comprising an effective amount of one or more (e.g., one) compounds of Formula (I), or a pharmaceutically acceptable salt, solvate, or ester thereof, and one or more (e.g., one) pharmaceutically acceptable carriers.

Another embodiment is directed to a pharmaceutical composition comprising an effective amount of one or more (e.g., one) compounds of formula (I) and a pharmaceutically acceptable carrier.

Another embodiment is directed to a pharmaceutical composition comprising an effective amount of a pharmaceutically acceptable salt of one or more (e.g., one) compounds of formula (I) and a pharmaceutically acceptable carrier.

Another embodiment is directed to a pharmaceutical composition comprising an effective amount of a pharmaceutically acceptable ester of one or more (e.g., one) compounds of formula (I) and a pharmaceutically acceptable carrier.

Another embodiment is directed to a pharmaceutical composition comprising an effective amount of a solvate of one or more (e.g., one) compounds of formula (I) and a pharmaceutically acceptable carrier.

Another embodiment of this invention is directed to a pharmaceutical composition comprising an effective amount of one or more (e.g., one) compounds of formula (I), and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising a therapeutically effective amount of one or more (e.g. one) compounds of Formula (I), or a pharmaceutically acceptable salt, solvate, or ester thereof, and one or more (e.g., one) pharmaceutically acceptable carriers, and an effective amount of one or more compounds selected from the group consisting of cholinesterase inhibitors, Aβ antibody inhibitors, gamma secretase inhibitors and beta secretase inhibitors.

Another embodiment of this invention is directed to a pharmaceutic composition comprising an effective amount of one or more (e.g., one) compounds of formula (I), and effective amount of one or more BACE inhibitors, and a pharmaceutically acceptable carrier.

Another embodiment of this invention is directed to a pharmaceutical composition comprising an effective amount of one or more (e.g., one) compounds of formula (I), and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds of formula (I).

Another embodiment of this invention is directed to a pharmaceutical composition comprising an effective amount of one or more (e.g., one) compounds of formula (I), and effective amount of one or more muscarinic antagonists (e.g., $m_1$ agonist or $m_2$ antagonists), and a pharmaceutically acceptable carrier.

Another embodiment of this invention is directed to a pharmaceutical composition comprising an effective amount of one or more (e.g., one) compounds of formula (I), and effective amount of Exelon (rivastigmine), and a pharmaceutically acceptable carrier.

Another embodiment of this invention is directed to a pharmaceutical composition comprising an effective amount of one or more (e.g., one) compounds of formula (I), and effective amount of Cognex (tacrine), and a pharmaceutically acceptable carrier.

Another embodiment of this invention is directed to a pharmaceutical composition comprising an effective amount of one or more (e.g., one) compounds of formula (I), and effective amount of a Tau kinase inhibitor, and a pharmaceutically acceptable carrier.

Another embodiment of this invention is directed to a pharmaceutical composition comprising an effective amount of one or more (e.g., one) compounds of formula (I), and effective amount of one or more Tau kinase inhibitor (e.g., GSK3beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds of formula (I), and effective amount of one anti-Abeta vaccine (active immunization), and a pharmaceutically acceptable carrier.

Another embodiment of this invention is directed to a pharmaceutical composition comprising an effective amount of one or more (e.g., one) compounds of formula (I), and effective amount of one or more APP ligands, and a pharmaceutically acceptable carrier.

Another embodiment of this invention is directed to a pharmaceutical composition comprising an effective amount of one or more (e.g., one) compounds of formula (I), and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds of formula (I), and effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds of formula (I), and effective amount of one or more fibrates (for example, clofibrate, Clofibride, Etofibrate, Aluminium Clofibrate), and a pharmaceutically acceptable carrier Another embodiment of this invention is directed to a pharmaceutical composition comprising an effective amount of one or more (e.g., one) compounds of formula (I), and effective amount of one or more LXR agonists, and a pharmaceutically acceptable carrier.

Another embodiment of this invention is directed to a pharmaceutical composition comprising an effective amount of one or more (e.g., one) compounds of formula (I), and effective amount of one or more LRP mimics, and a pharmaceutically acceptable carrier.

Another embodiment of this invention is directed to a pharmaceutical composition comprising an effective amount of one or more (e.g., one) compounds of formula (I), and effective amount of one or more 5-HT6 receptor antagonists, and a pharmaceutically acceptable carrier.

Another embodiment of this invention is directed to a pharmaceutical composition comprising an effective amount of one or more (e.g., one) compounds of formula (I), and effective amount of one or more nicotinic receptor agonists, and a pharmaceutically acceptable carrier.

Another embodiment of this invention is directed to a pharmaceutical composition comprising an effective amount of one or more (e.g., one) compounds of formula (I), and effective amount of one or more H3 receptor antagonists, and a pharmaceutically acceptable carrier.

Another embodiment of this invention is directed to a pharmaceutical composition comprising an effective amount of one or more (e.g., one) compounds of formula (I), and effective amount of one or more histone deacetylase inhibitors, and a pharmaceutically acceptable carrier.

Another embodiment of this invention is directed to a pharmaceutical composition comprising an effective amount of one or more (e.g., one) compounds of formula (I), and effective amount of one or more hsp90 inhibitors, and a pharmaceutically acceptable carrier.

Another embodiment of this invention is directed to a pharmaceutical composition comprising an effective amount of one or more (e.g., one) compounds of formula (I), and effective amount of one or more m1 muscarinic receptor agonists, and a pharmaceutically acceptable carrier.

Another embodiment of this invention is directed to combinations, i.e., a pharmaceutical composition, comprising a pharmaceutically acceptable carrier, an effective (i.e., therapeutically effective) amount of one or more compounds of formula (I), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors.

Another embodiment of this invention is directed to a pharmaceutical composition comprising an effective amount of one or more (e.g., one) compounds of formula (I), and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds of formula (I), and effective amount of one or more one mGluR2/3 antagonists, and a pharmaceutically acceptable carrier.

Another embodiment of this invention is directed to a pharmaceutical composition comprising an effective amount of one or more (e.g., one) compounds of formula (I), and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds of formula (I), and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds of formula (I), and effective amount of one or more PAl-1 inhibitors, and a pharmaceutically acceptable carrier.

Another embodiment of this invention is directed to a pharmaceutical composition comprising an effective amount of one or more (e.g., one) compounds of formula (I), and effective amount of one or more agents that can induce Abeta efflux such as gelsolin, and a pharmaceutically acceptable carrier.

Other embodiments of this invention are directed to any one of the above embodiments directed to pharmaceutical compositions wherein the compound of formula (I) is selected from the group consisting of IA.1, IA, IB.1, IB, IC, ID.1, ID, IE.1, and IE.

Other embodiments of this invention are directed to any one of the above embodiments directed to pharmaceutical compositions wherein the compound of formula (I) is selected from the group consisting of Group A.

Other embodiments of this invention are directed to any one of the above embodiments directed to pharmaceutical compositions wherein the compound of formula (I) is selected from the group consisting of Group B.

Other embodiments of this invention are directed to any one of the above embodiments directed to pharmaceutical compositions wherein the compound of formula (I) is selected from the group consisting of Group C.

Other embodiments of this invention are directed to any one of the above embodiments directed to pharmaceutical compositions wherein the compound of formula (I) is selected from the group consisting of Group D.

Other embodiments of this invention are directed to any one of the above embodiments directed to pharmaceutical compositions wherein the compound of formula (I) is selected from the group consisting of Group E.

The compounds of formula (I) can be useful as gamma secretase modulators and can be useful in the treatment and prevention of diseases such as, for example, central nervous system disorders (such as Alzheimers disease and Downs Syndrome), mild cognitive impairment, glaucoma, cerebral amyloid angiopathy, stroke, dementia, microgliosis, brain inflammation, and olfactory function loss.

Another embodiment of this invention is directed to a method of treating a central nervous system disorder comprising administering a therapeutically effective amount of at least one compound of formula (I) to a patient in need of such treatment.

Another embodiment of this invention is directed to a method of treating a central nervous system disorder comprising administering a therapeutically effective amount of a pharmaceutical composition comprising a therapeutically effective amount of at least one compound of formula (I), or a pharmaceutically acceptable salt, solvate, or ester thereof, and at least one pharmaceutically acceptable carrier.

Another embodiment of this invention is directed to a method of treating a central nervous system disorder comprising administering a therapeutically effective amount of a pharmaceutical composition comprising a therapeutically effective amount of at least one compound of formula (I), or a pharmaceutically acceptable salt, solvate, or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Thus, another embodiment of this invention is directed to a method for modulating (including inhibiting, antagonizing and the like) gamma-secretase comprising administering an effective (i.e., therapeutically effective) amount of one or more (e.g. one) compounds of formula (I) to a patient in need of such treatment.

Another embodiment of this invention is directed to a method for modulating (including inhibiting, antagonizing and the like) gamma-secretase, comprising administering an effective (i.e., therapeutically effective) amount of a compound of formula (I) to a patient in need of treatment.

Another embodiment of this invention is directed to a method of treating one or more neurodegenerative diseases, comprising administering an effective (i.e., therapeutically effective) amount of one or more (e.g., one) compounds of formula (I) to a patient in need of treatment.

Another embodiment of this invention is directed to a method of treating one or more neurodegenerative diseases, comprising administering an effective (i.e., therapeutically effective) amount of a compound of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound of formula (I) to a patient in need of treatment.

Another embodiment of this invention is directed to a method of treating Alzheimer's disease, comprising administering an effective (i.e., therapeutically effective) amount of one or more (e.g., one) compounds of formula (I) to a patient in need of treatment.

Another embodiment of this invention is directed to a method of treating Alzheimer's disease, comprising administering an effective (i.e., therapeutically effective) amount of a compound of formula (I) to a patient in need of treatment.

Another embodiment of this invention is directed to a method of treating Alzheimer's disease, comprising administering an effective (i.e., therapeutically effective) amount of a compound of formula (I) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds of formula (I) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound of formula (I) to a patient in need of treatment.

Another embodiment of this invention is directed to a method of treating mild cognitive impairment, comprising administering an effective amount of one or more (e.g., one) compounds of formula (I) to a patient in need of treatment.

Another embodiment of this invention is directed to a method of treating glaucoma, comprising administering an effective amount of one or more (e.g., one) compounds of formula (I) to a patient in need of treatment.

Another embodiment of this invention is directed to a method of treating cerebral amyloid angiopathy, comprising administering an effective amount of one or more (e.g., one) compounds of formula (I) to a patient in need of treatment.

Another embodiment of this invention is directed to a method of treating stroke, comprising administering an effective amount of one or more (e.g., one) compounds of formula (I) to a patient in need of treatment.

Another embodiment of this invention is directed to a method of treating dementia, comprising administering an effective amount of one or more (e.g., one) compounds of formula (I) to a patient in need of treatment.

Another embodiment of this invention is directed to a method of treating microgliosis, comprising administering an effective amount of one or more (e.g., one) compounds of formula (I) to a patient in need of treatment.

Another embodiment of this invention is directed to a method of treating brain inflammation, comprising administering an effective amount of one or more (e.g., one) compounds of formula (I) to a patient in need of treatment.

Another embodiment of this invention is directed to a method of treating olfactory function loss, comprising administering an effective amount of one or more (e.g.; one) compounds of formula (I) to a patient in need of treatment.

Another embodiment of this invention is directed to a method of treating Downs syndrome, comprising administering an effective amount of one or more (e.g., one) compounds of formula (I) to a patient in need of treatment.

Another embodiment of this invention is directed to a method of treating Downs syndrome, comprising administering an effective amount of a compound of formula (I) to a patient in need of treatment.

Other embodiments of this invention are directed to any one of the above embodiments directed to methods of treating wherein the compound of formula (I) is selected from the group consisting of wherein the compound of formula (I) is selected from the group consisting of IA.1, IA, IB.1, IB, IC, IC.1, ID, IE.1, and IE.

Other embodiments of this invention are directed to any one of the above embodiments directed to methods of treating wherein the compound of formula (I) is selected from the group consisting of Group A.

Other embodiments of this invention are directed to any one of the above embodiments directed to methods of treating wherein the compound of formula (I) is selected from the group consisting of Group B.

Other embodiments of this invention are directed to any one of the above embodiments directed to methods of treating wherein the compound of formula (I) is selected from the group consisting of Group C.

Other embodiments of this invention are directed to any one of the above embodiments directed to methods of treating wherein the compound of formula (I) is selected from the group consisting of Group D.

Other embodiments of this invention are directed to any one of the above embodiments directed to methods of treating wherein the compound of formula (I) is selected from the group consisting of Group E.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (I) and the administration of one or more (e.g., one) other pharmaceutical active ingredients (e.g., drugs). The compounds of formula (I) and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein an effective amount of the compound of formula (I) is used in combination with an effective amount of one or more other pharmaceutically active ingredients (e.g., drugs). The other pharmaceutically active ingredients drugs) are selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mauRl; mGluR5; positive allosteric modulators or agonists; mGluR2/3 antagonists; anti-inflammatory agents that can reduce neuroinflammation; Prostaglandin EP2 receptor antagonists; PAl-1 inhibitors; and agents that can induce Abeta efflux such as gelsolin.

Other embodiments of this invention are directed to any one of the methods of treatment, or methods of inhibiting, described herein, wherein the compound of formula (I) is used in combination with an effective amount of one or more other pharmaceutically active ingredients selected from the group consisting of: BACE inhibitors (beta secretase inhibitors), muscarinic antagonists (e.g., $m_1$ agonist or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Another embodiment of this invention is directed to a method of treating Alzheimer's disease, comprising administering an effective (i.e., therapeutically effective) amount of one or more (e.g., one) compounds of formula (I), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of a compound of formula (I), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of one or more (e.g., one) compounds of formula (I), in combination with an effective (i.e., therapeutically effective) amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective (i.e., therapeutically effective) amount of one or more (e.g., one) compounds of formula (I), in combination with an effective (i.e., therapeutically effective) amount of one or more BACE inhibitors.

Another embodiment of this invention is directed to a method of treating Alzheimer's disease, comprising administering an effective amount of one or more compounds of formula (I), in combination with an effective amount of Exelon (rivastigmine).

Another embodiment of this invention is directed to a method of treating Alzheimer's disease, comprising administering an effective amount of one or more compounds of formula (I), in combination with an effective amount of Cognex (tacrine).

Another embodiment of this invention is directed to a method of treating Alzheimer's disease, comprising administering an effective amount of one or more compounds of formula (I), in combination with an effective amount of a Tau kinase inhibitor.

Another embodiment of this invention is directed to a method of treating Alzheimer's disease, comprising administering an effective amount of one or more compounds of formula (I), in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds of formula (I), in combination with an effective amount of one anti-Abeta vaccination (active immunization).

Another embodiment of this invention is directed to a method of treating Alzheimer's disease, comprising administering an effective amount of one or more compounds of formula (I), in combination with an effective amount of one or more APP ligands.

Another embodiment of this invention is directed to a method of treating Alzheimer's disease, comprising administering an effective amount of one or more compounds of formula (I), in combination with an effective amount of one or more agents that upregulate insulin degrading enzyme and/or neprilysin.

Another embodiment of this invention is directed to a method of treating Alzheimer's disease, comprising administering an effective amount of one or more compounds of formula (I), in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds of formula (I), in combination with an effective amount of one or more fibrates (for example, clofibrate, Clabride, Etofibrate, Aluminium Clofibrate).

Another embodiment of this invention is directed to a method of treating Alzheimer's disease, comprising administering an effective amount of one or more compounds of formula (I), in combination with an effective amount of one or more LXR agonists.

Another embodiment of this invention is directed to a method of treating Alzheimer's disease, comprising administering an effective amount of one or more compounds of formula (I), in combination with an effective amount of one or more LRP mimics.

Another embodiment of this invention is directed to a method of treating Alzheimer's disease, comprising administering an effective amount of one or more compounds of formula (I), in combination with an effective amount of one or more 5-HT6 receptor antagonists.

Another embodiment of this invention is directed to a method of treating Alzheimer's disease, comprising administering an effective amount of one or more compounds of formula (I), in combination with an effective amount of one or more nicotinic receptor agonists.

Another embodiment of this invention is directed to a method of treating Alzheimer's disease, comprising administering an effective amount of one or more compounds of formula (I), in combination with an effective amount of one or more H3 receptor antagonists.

This invention also provides a method of treating Alzheimer's disease, comprising administering an effective amount of one or more compounds of formula (I), in combination with an effective amount of one or more histone deacetylase inhibitors.

Another embodiment of this invention is directed to a method of treating Alzheimer's disease, comprising administering an effective amount of one or more compounds of formula (I), in combination with an effective amount of one or more hsp90 inhibitors.

Another embodiment of this invention is directed to a method of treating Alzheimer's disease, comprising administering an effective amount of one or more compounds of formula (I), in combination with an effective amount of one or more m1 muscarinic receptor agonists.

Another embodiment of this invention is directed to a method of treating Alzheimer's disease, comprising administering an effective amount of one or more compounds of formula (I), in combination with an effective amount of one or more 5-HT6 receptor antagonists mGluR1 or mGluR5 positive allosteric modulators or agonists.

Another embodiment of this invention is directed to a method of treating Alzheimer's disease, comprising administering an effective amount of one or more compounds of formula (I), in combination with an effective amount of one or more mGluR2/3 antagonists.

Another embodiment of this invention is directed to a method of treating Alzheimer's disease, comprising administering an effective amount of one or more compounds of formula (I), in combination with an effective amount of one or more anti-inflammatory agents that can reduce neuroinflammation.

Another embodiment of this invention is directed to a method of treating Alzheimer's disease, comprising administering an effective amount of one or more compounds of formula (I), in combination with an effective amount of one or more Prostaglandin EP2 receptor antagonists.

Another embodiment of this invention is directed to a method of treating Alzheimer's disease, comprising administering an effective amount of one or more compounds of formula (I), in combination with an effective amount of one or more PAl-1 inhibitors.

Another embodiment of this invention is directed to a method of treating Alzheimer's disease, comprising administering an effective amount of one or more compounds of formula (I), in combination with an effective amount of one or more agents that can induce Abeta efflux such as gelsolin.

Another embodiment of this invention is directed to a method of treating Downs syndrome, comprising administering an effective (i.e., therapeutically effective) amount of one or more (e.g., one) compounds of formula (I) to a patient in need of treatment.

Another embodiment of this invention is directed to a method of treating Downs syndrome, comprising administering an effective (i.e., therapeutically effective) amount of a compound of formula (I) to a patient in need of treatment.

Another embodiment of this invention is directed to a method of treating Downs syndrome, comprising administering an effective (i.e., therapeutically effective) amount of one or more (e.g., one) compounds of formula (I), in combination with an effective (i.e., therapeutically effective) amount of one or more cholinesterase inhibitors (such as, for example, (±)-2 ,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective (i.e., therapeutically effective) amount of a compound of formula (I), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl] methyl]-1H-inden-1-one hydrochloride, i.e., donepezil hydrochloride, available as the Aricept® brand of donepezil hydrochloride), to a patient in need of treatment.

Another embodiment of this invention is directed to combinations (i.e., pharmaceutical compositions) comprising an effective (i.e., therapeutically effective) amount of one or more (e.g., one) compounds of formula (I), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of IA.1, IA, IB.1, IB, IC, IC.1, ID, IE.1, and IE.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group A.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group B.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group C.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group D.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group E.

Another embodiment of this invention is directed to a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase, or (e) mild cognitive impairment, or (f) glaucoma, or (g) cerebral amyloid angiopathy, or (h) stroke, or (i) dementia, or (j) microgliosis, or (k) brain inflammation, or (l) olfactory function loss.

Another embodiment of this invention is directed to a kit comprising, in separate containers, in a single package, pharmaceutical compositions for use in combination, wherein one container comprises an effective amount of one or more (e.g., one) compounds of formula (I) in a pharmaceutically acceptable carrier, and another container (i.e., a second container) comprises an effective amount of another pharmaceutically active ingredient (as described above), the combined quantities of the compounds of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment of this invention is directed to a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Other embodiments of this invention are directed to any one of the above embodiments directed to kits wherein the compound of formula (I) is selected from the group consisting of IA.1, IA, IB.1, IB, IC, ID.1, ID, IE.1, and IE.

Other embodiments of this invention are directed to any one of the above embodiments directed to kits wherein the compound of formula (I) is selected from the group consisting of Group A.

Other embodiments of this invention are directed to any one of the above embodiments directed to kits wherein the compound of formula (I) is selected from the group consisting of Group B.

Other embodiments of this invention are directed to any one of the above embodiments directed to kits wherein the compound of formula (I) is selected from the group consisting of Group C.

Other embodiments of this invention are directed to any one of the above embodiments directed to kits wherein the compound of formula (I) is selected from the group consisting of Group D.

Other embodiments of this invention are directed to any one of the above embodiments directed to kits wherein the compound of formula (I) is selected from the group consisting of Group E.

Another embodiment is directed to a pharmaceutical composition comprising an effective amount of one or more (e.g., one) compounds selected from the group consisting of formulas (IA), (IB), (IC), (ID) and (IE) and a pharmaceutically acceptable carrier.

Another embodiment is directed to a pharmaceutical composition comprising an effective amount of a pharmaceutically acceptable salt of one or more (e.g., one) compounds selected from the group consisting of formulas (IA), (IB), (IC), (ID) and (IE) and a pharmaceutically acceptable carrier.

Another embodiment is directed to a pharmaceutical composition comprising an effective amount of a pharmaceutically acceptable ester of one or more (e.g., one) compounds selected from the group consisting of formulas (IA), (IB), (IC), (ID) and (IE) and a pharmaceutically acceptable carrier.

Another embodiment is directed to a pharmaceutical composition comprising an effective amount of a solvate of one or more (e.g., one) compounds selected from the group consisting of formulas (IA), (IB), (IC), (ID) and (IE) and a pharmaceutically acceptable carrier.

Another embodiment of this invention is directed to a pharmaceutical composition comprising an effective amount of one or more (e.g., one) compounds selected from the group consisting of formulas (IA), (IB), (IC), (ID) and (IE), and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g. one) compounds selected from the group consisting of formulas (IA), (IB), (IC), (ID) and (IE), and effective amount of one or more BACE inhibitors, and a pharmaceutically acceptable carrier.

Another embodiment of this invention is directed to a pharmaceutical composition comprising an effective amount of one or more (e.g., one) compounds selected from the group consisting of formulas (IA), (IB), (IC), (ID) and (IE), and effective amount of one or more cholinesterase inhibitors (e.g., acetyl- and/or butyrylchlolinesterase inhibitors), and a pharmaceutically acceptable carrier.

Another embodiment of this invention is directed to a method for modulating (including inhibiting, antagonizing and the like) gamma-secretase, comprising administering an effective (i.e., therapeutically effective) amount of a compound selected from the group consisting of formulas (IA), (IB), (IC), (ID) and (IE) to a patient in need of treatment.

Another embodiment of this invention is directed to a method of treating one or more neurodegenerative diseases, comprising administering an effective (i.e., therapeutically effective) amount of one or more (e.g., one) compounds of formula (I) to a patient in need of treatment, said compound of formula (I) being selected from the group consisting of: compounds of formulas (IA), (IB), (IC), (ID) and (IE).

Another embodiment of this invention is directed to a method of treating Alzheimer's disease, comprising administering an effective (i.e., therapeutically effective) amount of one or more (e.g., one) compounds selected from the group consisting of formulas (IA), (IB), (IC), (ID) and (IE) to a patient in need of treatment.

Examples of cholinesterase inhibitors are tacrine, donepezil, rivastigmine, galantamine, pyridostigmine and neostigmine, with tacrine, donepezil, rivastigmine and galantamine being preferred.

Examples of agonist are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636;

5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 24, 2005), US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published May 3, 200 (see also WO2007/050721 published May 3, 2007), WO2007/053506 published May 10, 2007 (see also US2007/099875 published May 3, 2007), U.S. application Ser. No. 11/759,336 filed Jun. 7, 2007, U.S. Application Ser. No. 60/874,362 filed Dec. 12, 2006, and U.S. APPLICATION Ser. No. 60/874,419 filed Dec. 12, 2006, the disclosures of each being incorporated herein by reference thereto.

As used above, and throughout this disclosure, the following terms, unless otherwise indicated, shall be understood to have the following meanings:

"ADDP" means 1,1'-(azodicarbonyl)dipiperidine.

"BEMP" means 2-tert-butylimino-2-diethylamino-1,3-dimethyl-perhydro-1,3,2-diazaphosphorine.

"DAST" means diethylaminosulphurtrifluoride.

"DCM" means dichloromethane.

"DMP" means Dess-Martin Periodinane.

"DPPA" means Diphenyl phosphoryl azide.

"DMF" means dimethylformamide.

"m-CPBA" means meta-Chloroperoxybenzoic acid.

"OTBDMS" means tert-butyl dimethylsilyloxy.

"PDC" means pyridium dichromate.

"PTLC" means Preparative Thin Layer Chromatography.

"RT" (or r.t.) means room temperature.

"TBAF" means tetra-N-butylammonium fluoride.

"Tol" means toluene.

"Patient" includes both human and animals,

"Mammal" means humans and other mammalian animals.

"One or more" means that there is at least one and there can be more than one, and examples include 1, 2 or 3, or 1 and 2, or 1.

"At least one" means there is at least one and there can be more than one, and examples include 1, 2 or 3, or 1 and 2, or 1.

It is noted that the carbons of formula (I) and other formulas herein may be replaced with 1 to 3 silicon atoms so long as all valency requirements are satisfied.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl.aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloakenylalkyls include cyclopentenylmethyl, cyclohexenylmethyl and the like.

"Halogen" means fluorine, chlorine, bromine, or iodine. Preferred are fluorine, chlorine and bromine. "Halo" refers to fluoro, chloro, bromo or iodo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

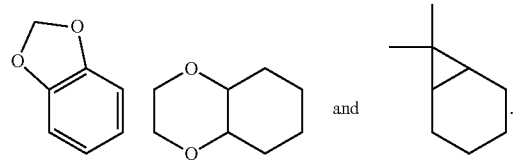

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituent" which may be the same or different, and are as defined herein. The nitrogen or sulfur atom of the heterocyclyl can be optionally oxidized to the corresponding N-oxide, S-oxide or SS-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

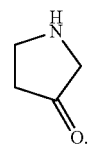

"Heterocyclylalkyl" (or heterocycloalkylalkyl) means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" (or heterocycloalkenyl) means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[22.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

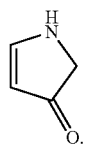

"Heterocyclenylalkyl" (or heterocycloalkenylalkyl) means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

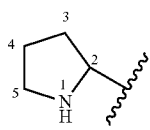

there is no —OH attached directly to carbons marked 2 and 5.

It should also be noted that tautomeric forms such as, for example, the moieties:

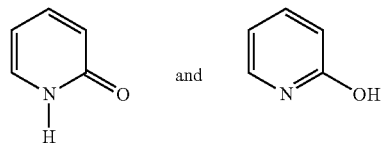 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl —O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R$^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, $C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, atylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, C(OY$^2$)Y$^3$ wherein Y$^2$ is ($C_1$-$C_4$) alkyl and Y$^3$ is ($C_1$-$C_6$)alkyl, carboxy($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid, "Solvate" encompasses both solution-phase and isolatable solvates.

Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula (I), and salts, solvates, esters and prodrugs thereof, may exist in their tautomeric form (for example, as an amide, enol, keto or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopicaliy labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula (I), and of the salts, solvates, esters and prodrugs of the compounds of Formula (I), are intended to be included in the present invention.

The compounds according to the invention can have pharmacological properties; in particular, the compounds of Formula (I) can be modulators of gamma secretase (including inhibitors, antagonists and the like).

More specifically, the compounds of Formula (I) can be useful in the treatment of a variety of disorders of the central nervous system including, for example, including, but not limited to, Alzheimer's disease, AIDS-related dementia, Parkinson's disease, amyotrophic lateral sclerosis, retinitis pigmentosa, spinal muscular atrophy and cerebellar degeneration and the like.

Another aspect of this invention is a method of treating a mammal (e.g., human) having a disease or condition of the central nervous system by administering a therapeutically effective amount of at least one compound of Formula (I), or a pharmaceutically acceptable salt, solvate, ester or prodrug of said compound to the mammal.

A preferred dosage is about 0.001 to 500 mg/kg of body weight/day of the compound of Formula (I). An especially preferred dosage is about 0.01 to 25 mg/kg of body weight/day of a compound of Formula (I), or a pharmaceutically acceptable salt or solvate of said compound.

The compounds of this invention may also be useful in combination (administered together or sequentially) with one or more additional agents listed above.

The compounds of this invention may also be useful in combination (administered together or sequentially) with one or more compounds selected from the group consisting of Aβ antibody inhibitors, gamma secretase inhibitors and beta secretase inhibitors.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of Formula (I), or a pharmaceutically acceptable salt, solvate, ester or prodrug thereof, and an amount of one or more additional agents listed above wherein the amounts of the compounds/treatments result in desired therapeutic effect.

The pharmacological properties of the compounds of this invention may be confirmed by a number of pharmacological assays. Certain assays are exemplified later in this document.

This invention is also directed to pharmaceutical compositions which comprise at least one compound of Formula (I), or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18<sup>th</sup> Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form, in such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula (I), or a pharmaceutically acceptable salt, solvate, ester or prodrug of said compound and a pharmaceutically acceptable carrier, vehicle or diluent.

Yet another aspect of this invention is a kit comprising an amount of at least one compound of Formula (I), or a pharmaceutically acceptable salt, solvate, ester or prodrug of said compound and an amount of at least one additional agent listed above, wherein the amounts of the two or more ingredients result in desired therapeutic effect.

The invention disclosed herein is exemplified by the following illustrative processes which should not be construed to limit the scope of the invention. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz, Bruker 400) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm 10; gradient flow: 0 min-10% CH$_3$CN, 5 min-95% CH$_3$CN, 7 min-95% CH$_3$CN, 7.5 min-10% CH$_3$CN, 9 min-stop. The observed parent ion is given.

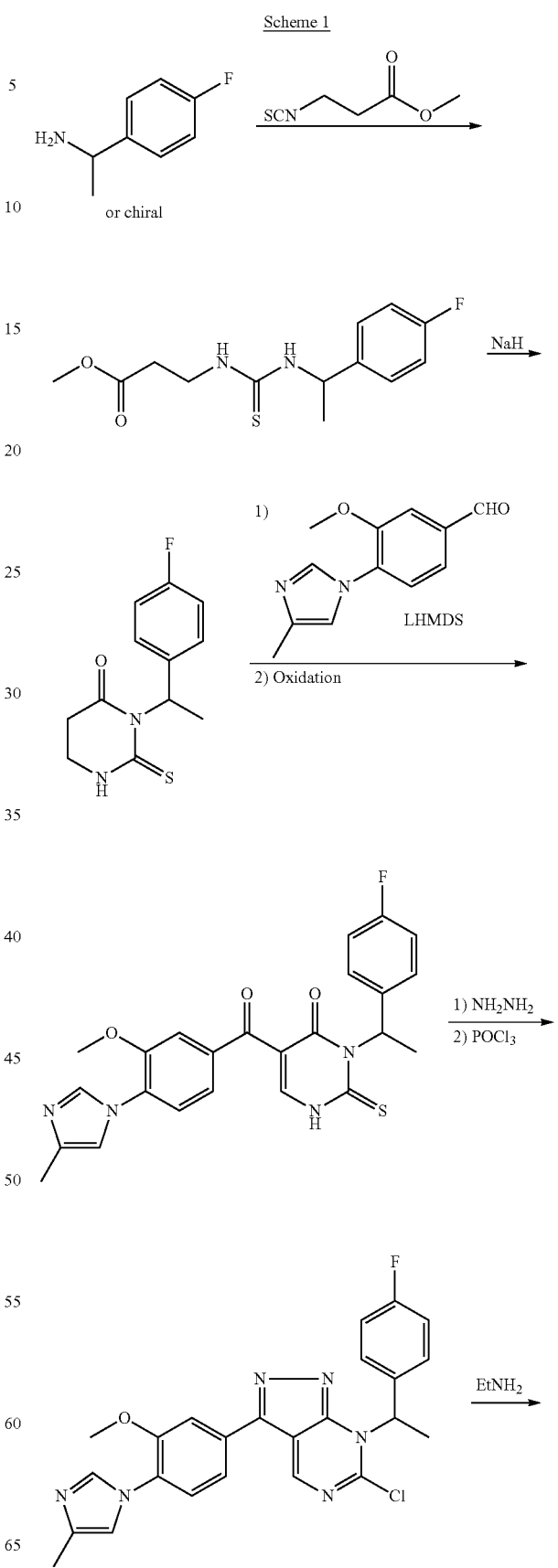

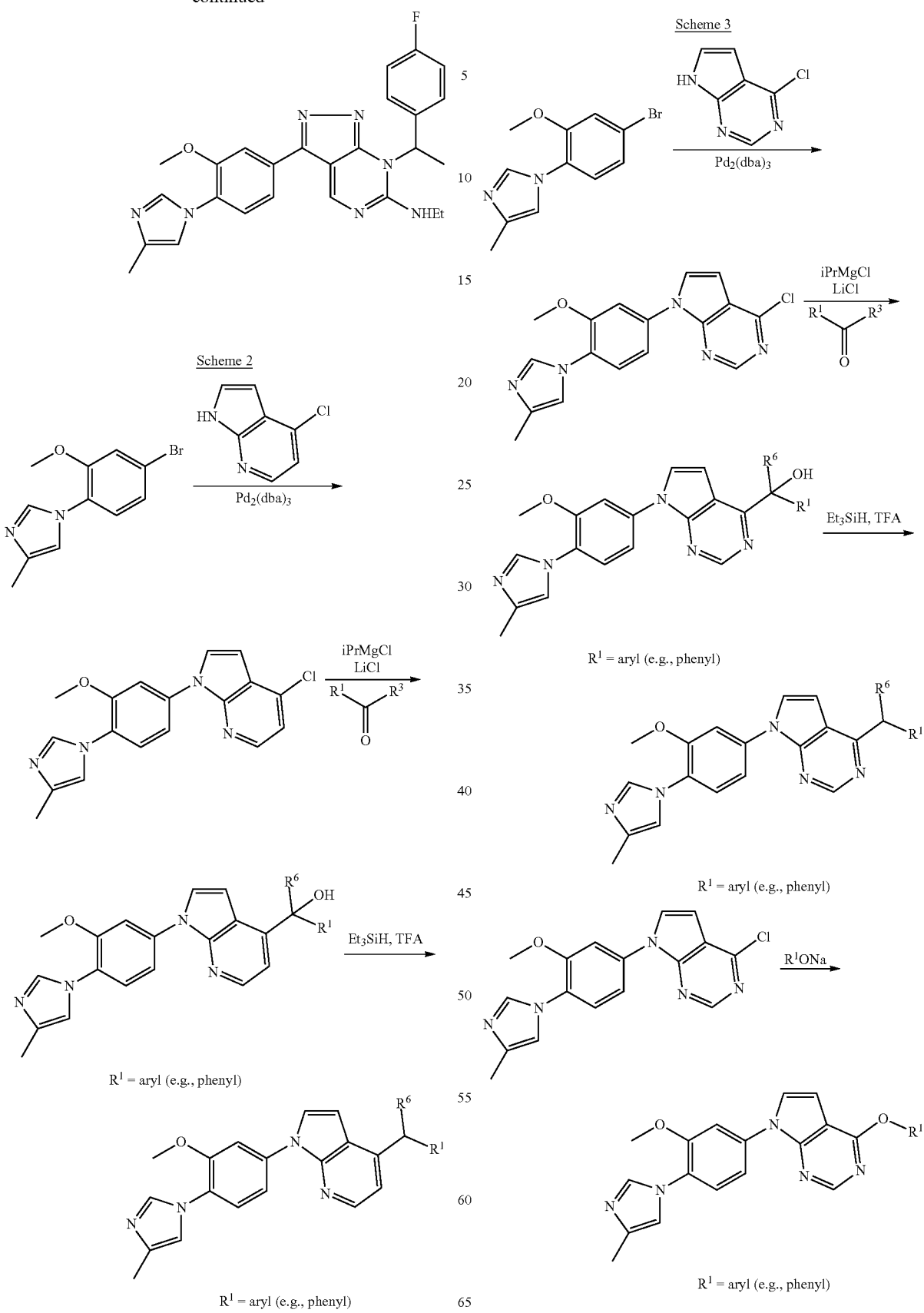

151
Scheme 4
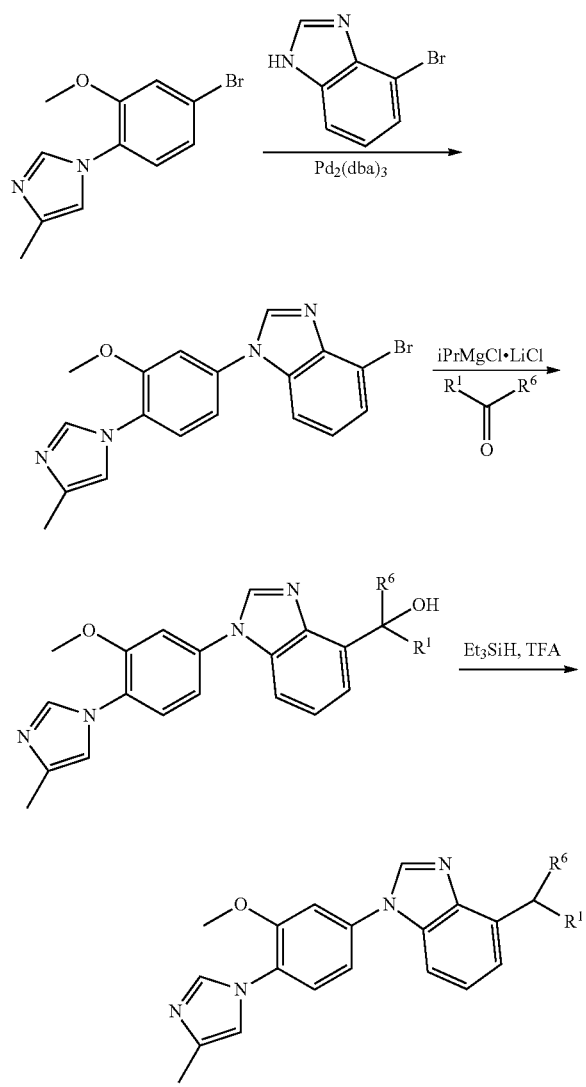
152
Scheme 5
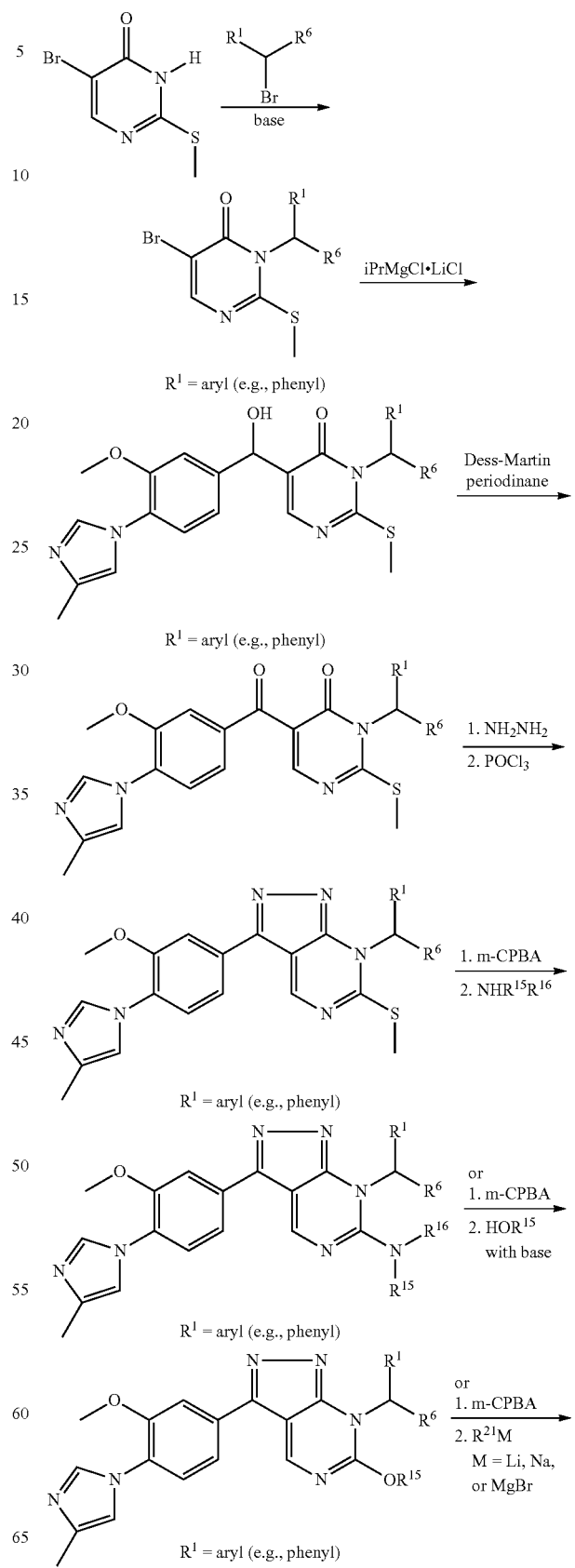

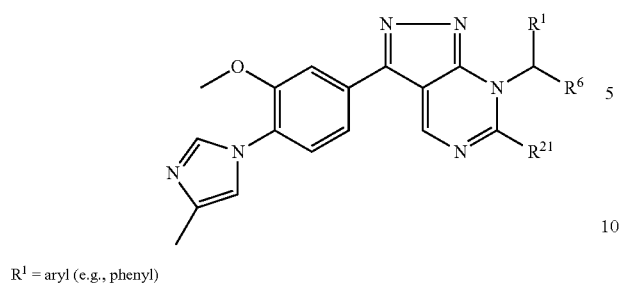
R¹ = aryl (e.g., phenyl)
Scheme 6
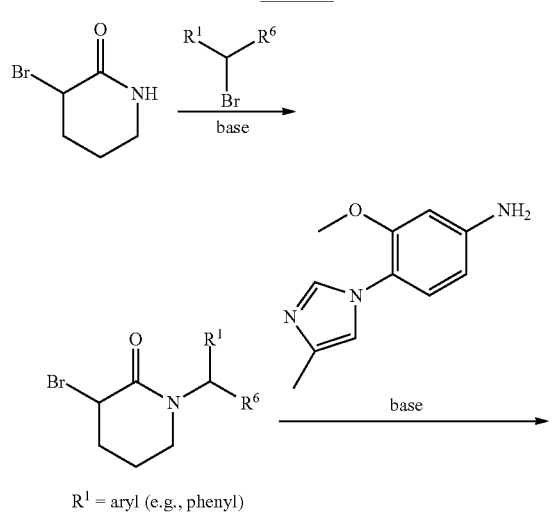
R¹ = aryl (e.g., phenyl)
R¹ = aryl (e.g., phenyl)
R¹ = aryl (e.g., phenyl)
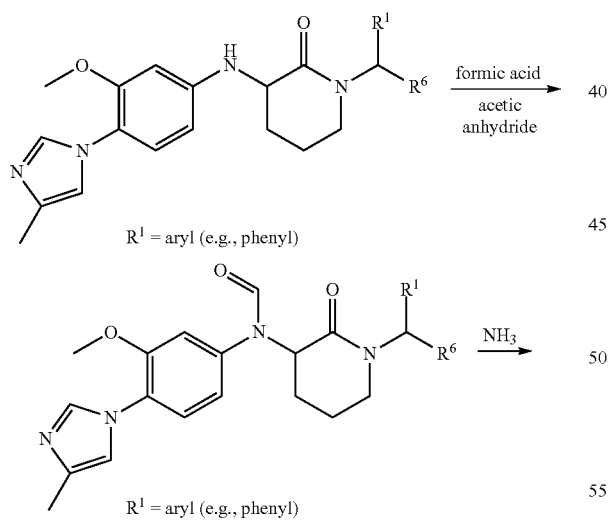
Scheme 7
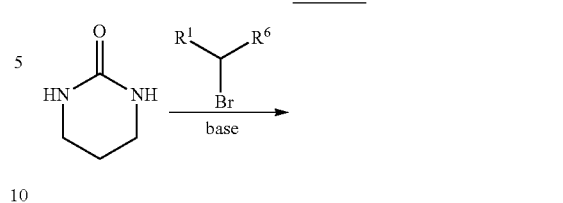
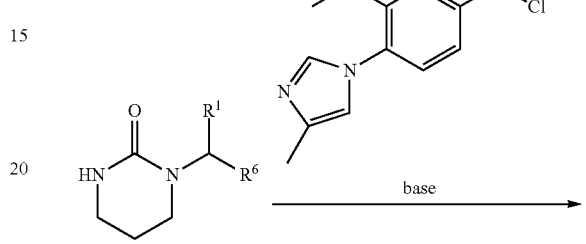
R¹ = aryl (e.g., phenyl)
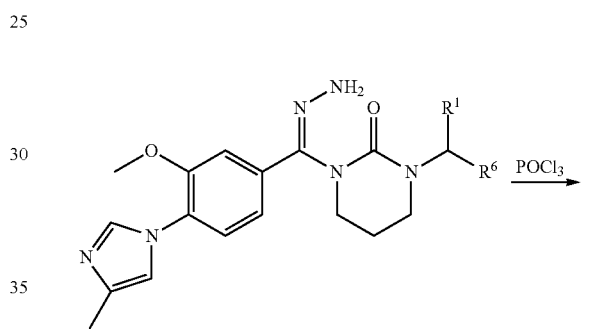
R¹ = aryl (e.g., phenyl)
Scheme 8
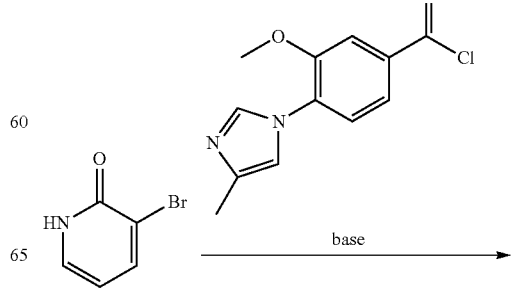

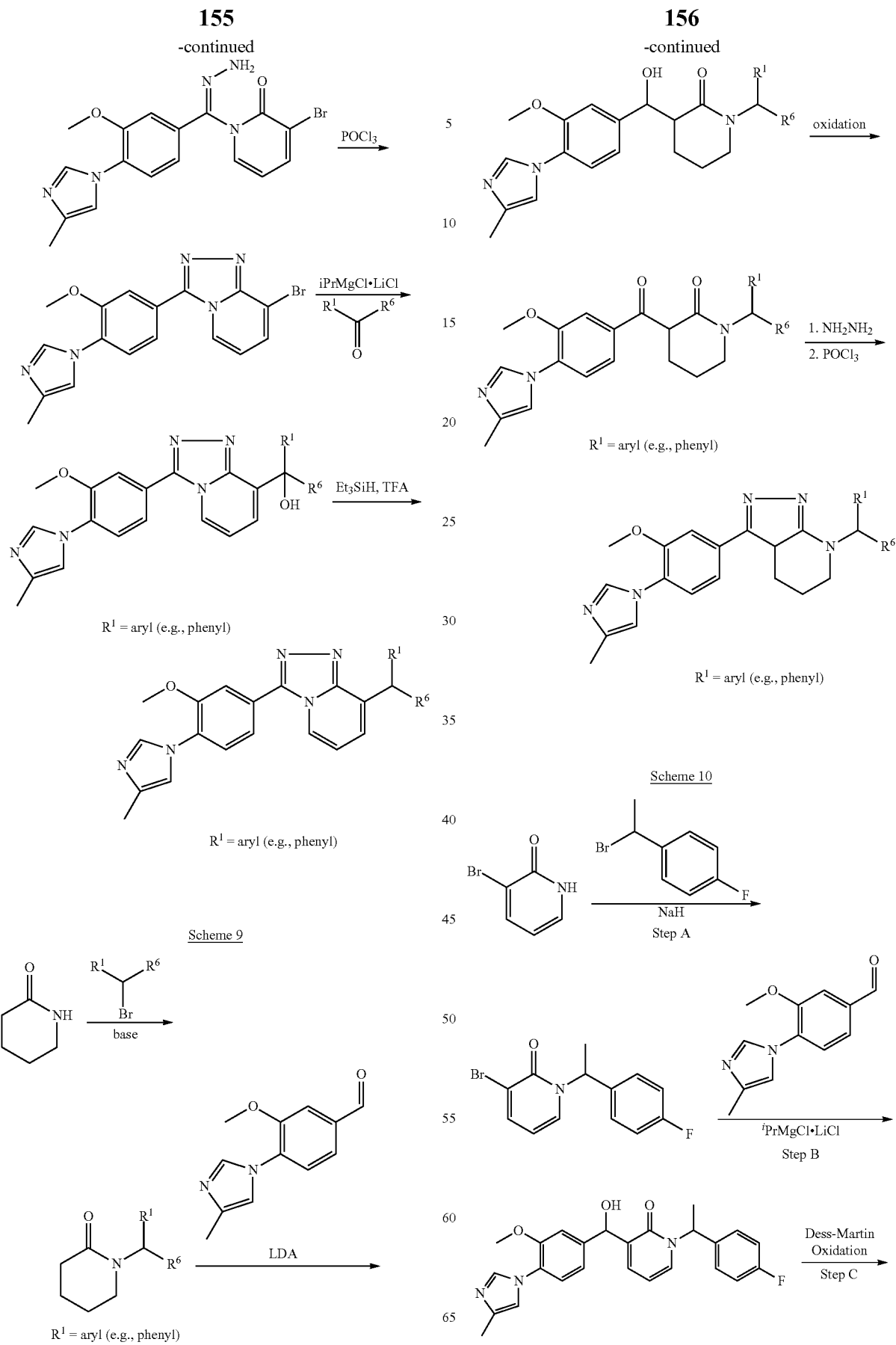

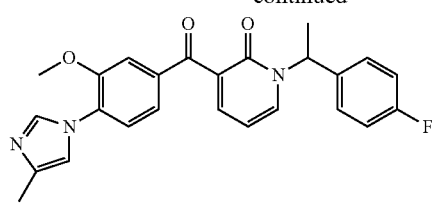
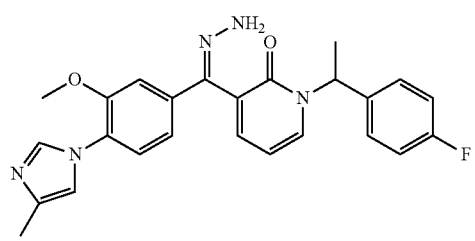
1
Scheme 11
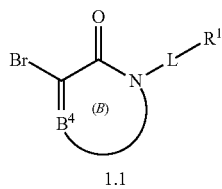
1.1
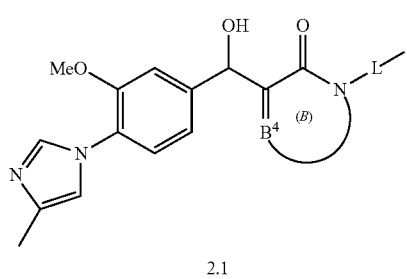
2.1
2.1 →(Dess-Martin Periodinane)
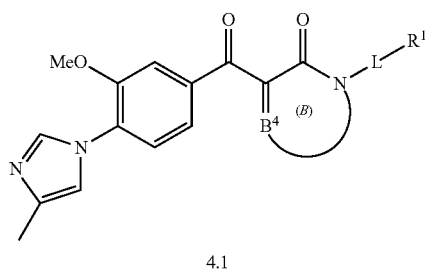
4.1
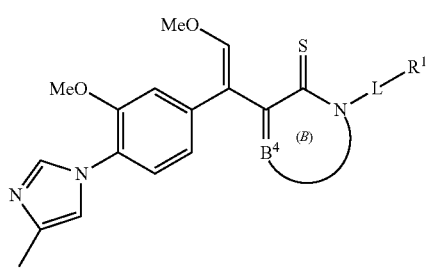
5.1
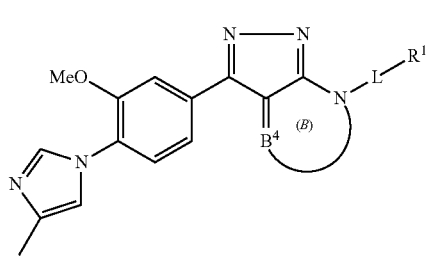
7.1
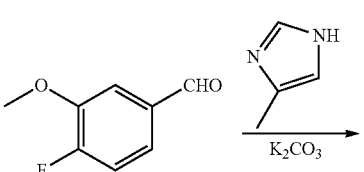
6.1
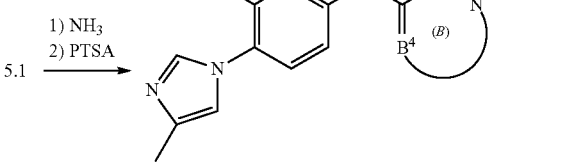
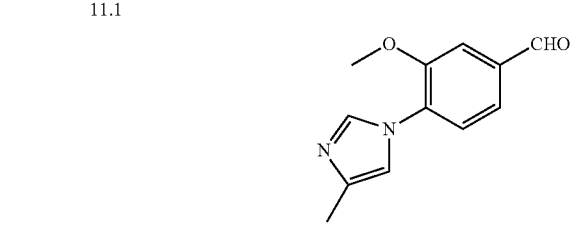
12.1
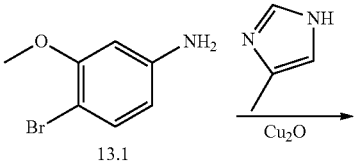
13.1

-continued
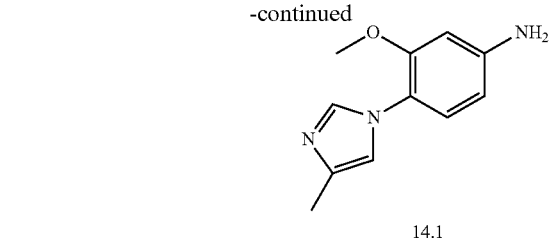
14.1
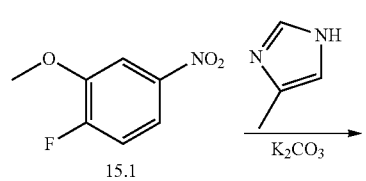
15.1
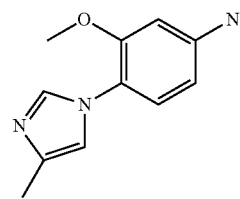
16.1
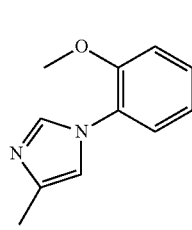
14.1
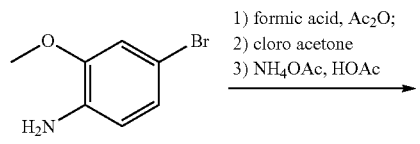
commercially available
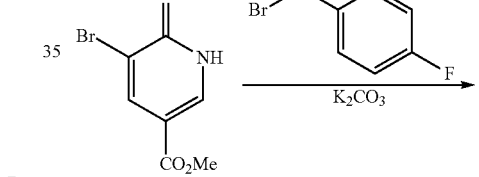
17.1
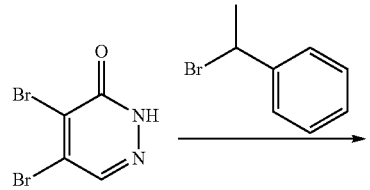
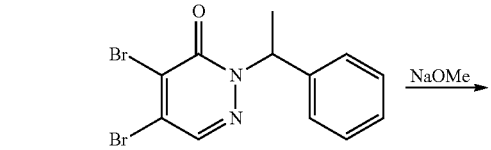
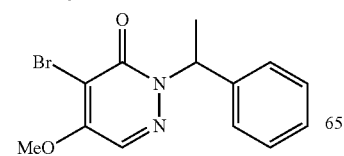
-continued
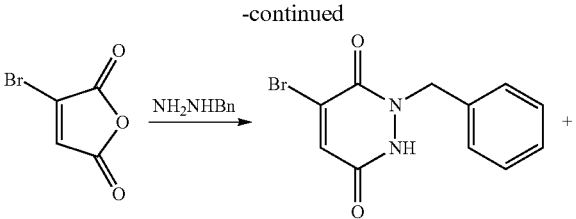
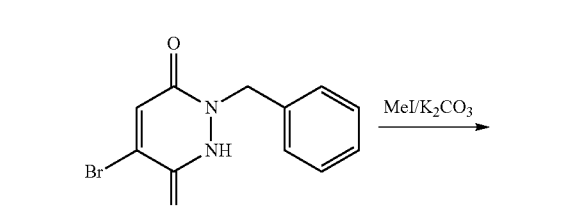
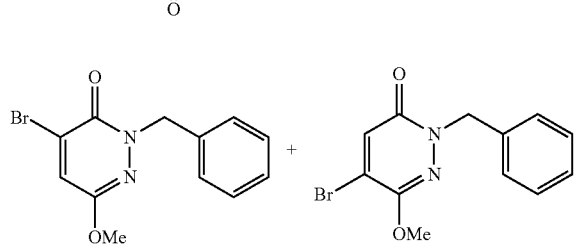
Separation by silica gel column
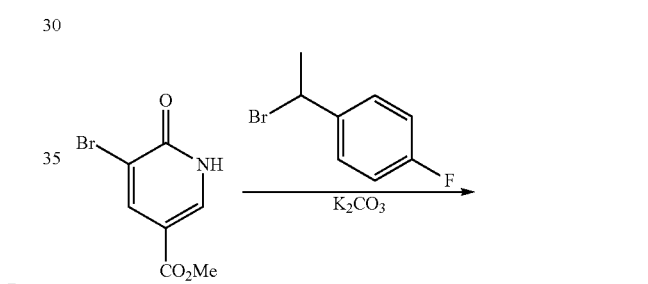
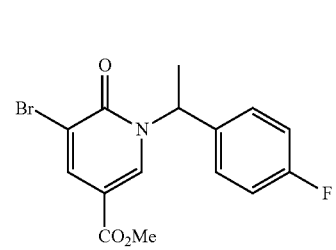
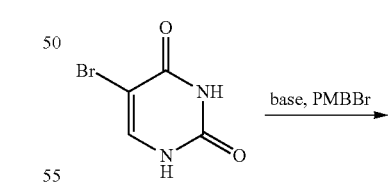
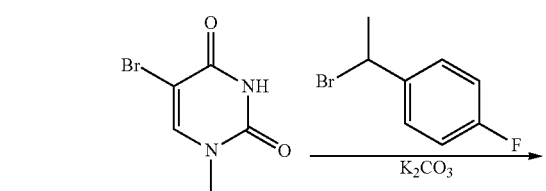

161
-continued
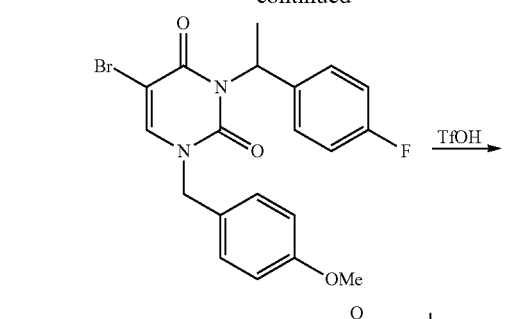
TfOH →
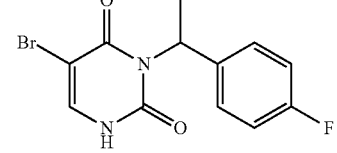
MeI, base →
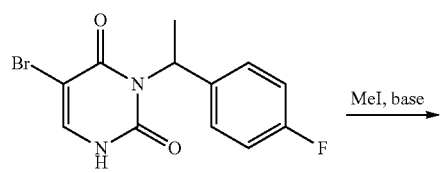
+
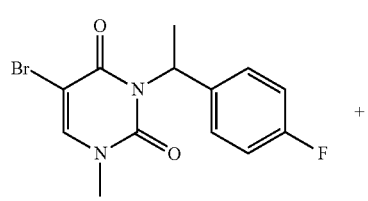
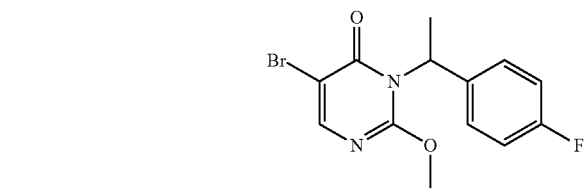
POCl₃ →
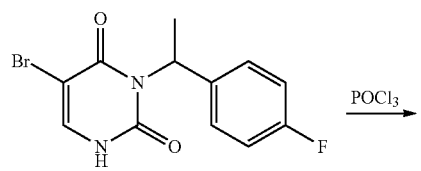
BnNH₂ →
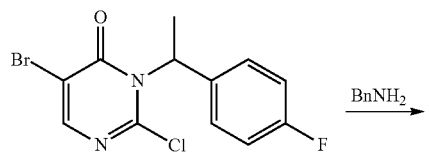
MeI, base →
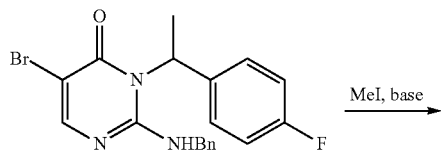
+
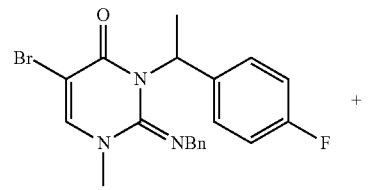
162
-continued
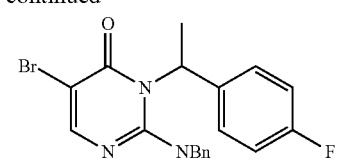
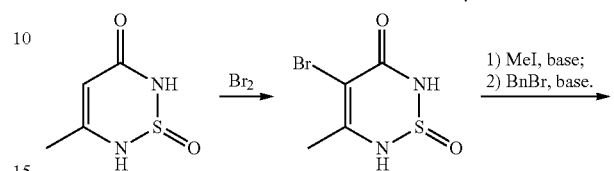
Br₂ →
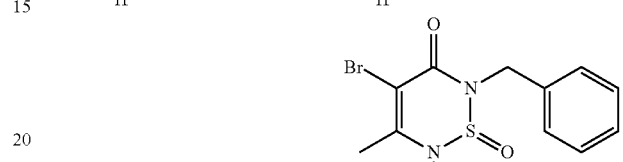
1) MeI, base;
2) BnBr, base.
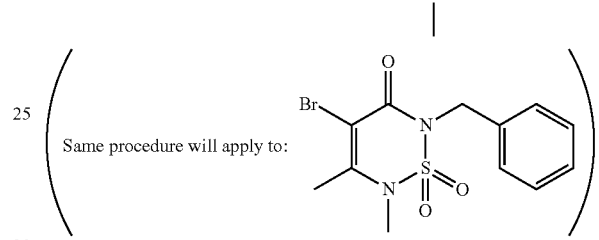
(Same procedure will apply to:
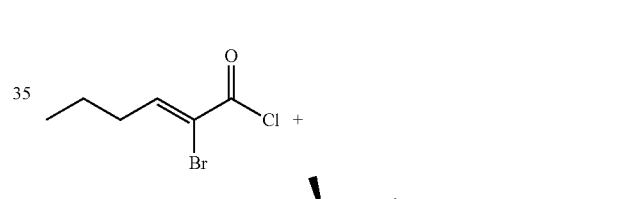
)
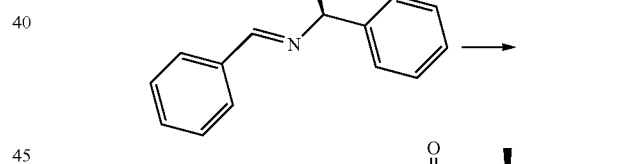
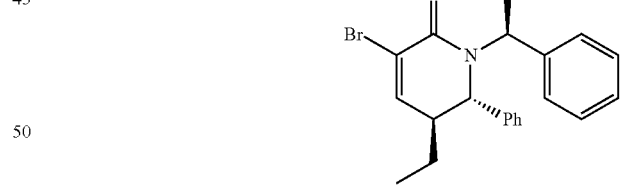
CARDILLO, G.; FABBRONI, S.; GENTILUCCI, L.; PERCIACCANTE, R.;
PICCINELLI, F.; TOLOMELLI, A.; Tetrahedron 2004, 60 (23), 5031-5040.
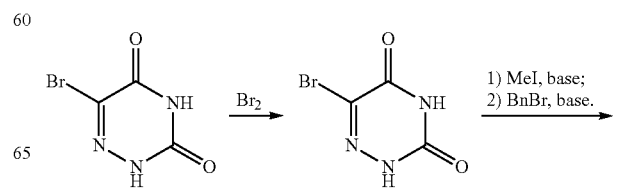
Br₂ →
1) MeI, base;
2) BnBr, base.

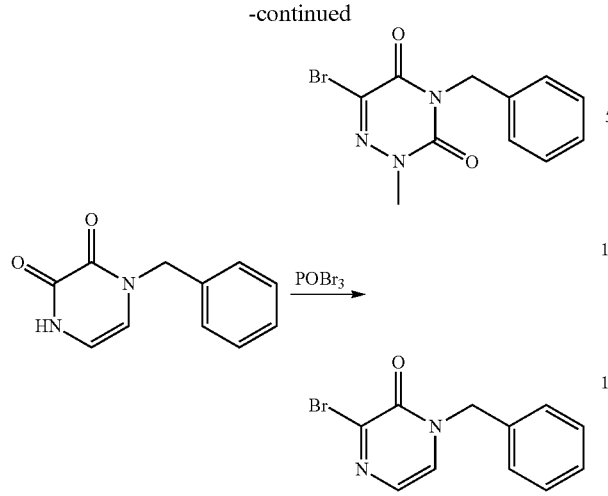

FLEITZ, F. J.; LYLE, T. A.; ZHENG, N.; ARMSTRONG, J. D. III;
VOLANTE, R. P.; Synth Commun 2000, 30 (17), 3171-3180.

Scheme 12

Preparation of aldehyde E4:

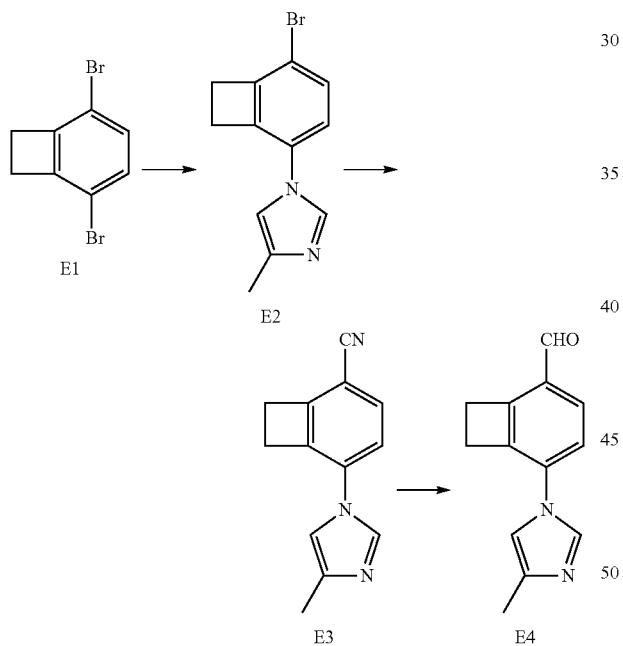

Compound E1 is obtained using a literature method by K. Walker, L., Markoski and J. Moore *Synthesis*, 1992, 1265.

Step A:

To a solution of E1 (0.11 mmol) in dry 0.5 mL will be added 4-methyl imidazole (5 eq, 0.546 mmol, 44 mg), $Cu_2O$ (0.4 equiv, 0.044 mmol, 6 mg), 4,7-dimethoxyl-1,8-phenanthracene (0.4 equiv, 0.044 mmol, 10 mg), $Cu_2CO_3$ (1.4 equiv, 0.154 mmol, 50 mg) and PEG (40 mg). The resulting solution will be degassed and heated at 110° C. for 40 h to give compound E1 after purification.

Step B:

A procedure from P. Schirch and V. Bockclheide is adapted (*J. Amer. Chem. Soc.* 1981, 103, 6873). To a solution of E2 (1.5 g) will be added 5.0 eq of cuprous cyanide in 100 ml of N-methyl-2-pyrrolidinone. The mixture will be heated at 115° C. with stirring under nitrogen to give E3 after workup and purification.

Step C:

To a 140 mg of E3 in ether will be added 1 eq of DiBAL in hexane. After 1 h, 5 mL of MeOH will be added and the mixture will be poured into ice water followed by acidification with 10% HCl and extraction with ether. The organic layers will be combined and solvent evaporated to give a residue which will be chromatographed to give compound E4.

The following intermediates will be synthesized using methods similar to

Scheme 12:

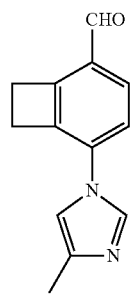

E5

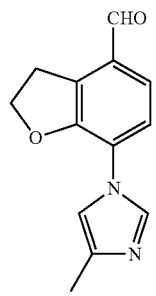

E6

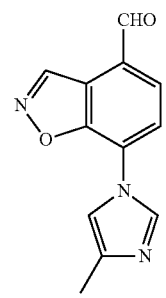

E7

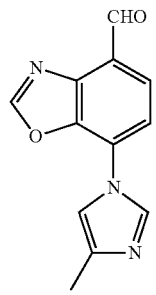

E8

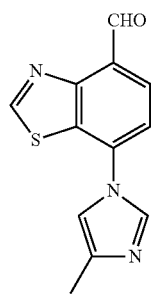 E9
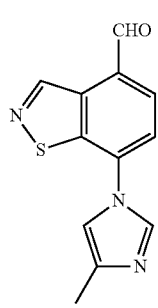 E10
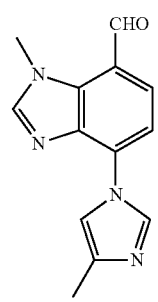 E11
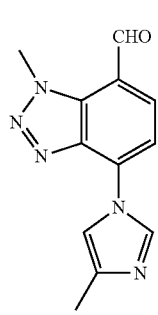 E12
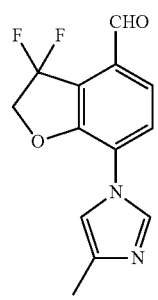 E13
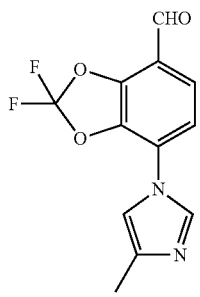 E14
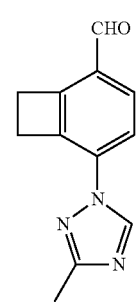 E15
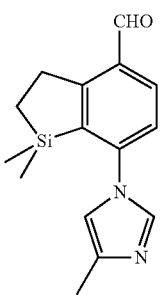 E16
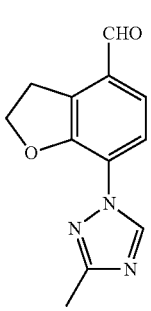 E17
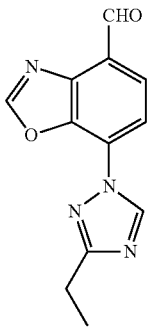 E18

E19 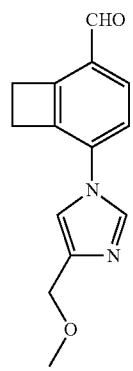
E20 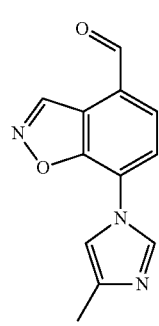
E21 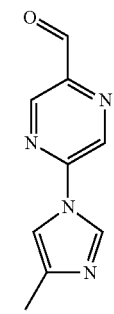
E22 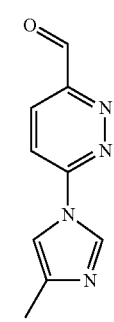
E23 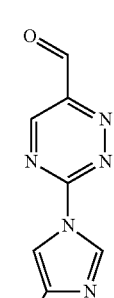
E24 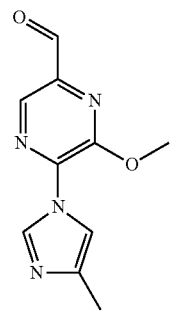
E25 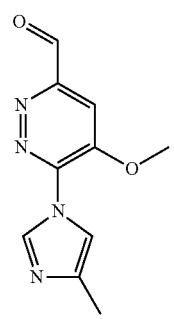
E26 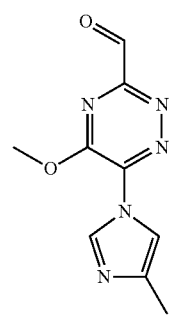
E27 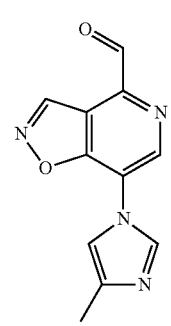
E28 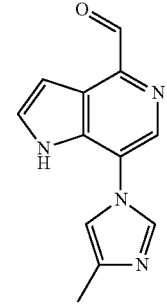

-continued

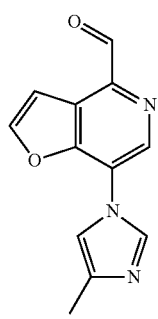

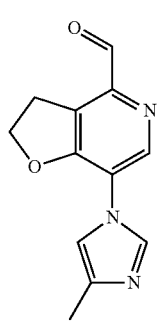

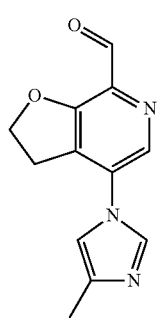

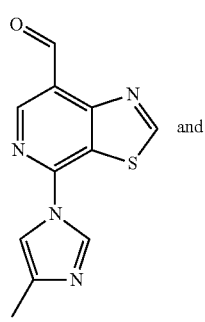 and

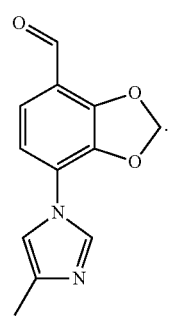

Example 1

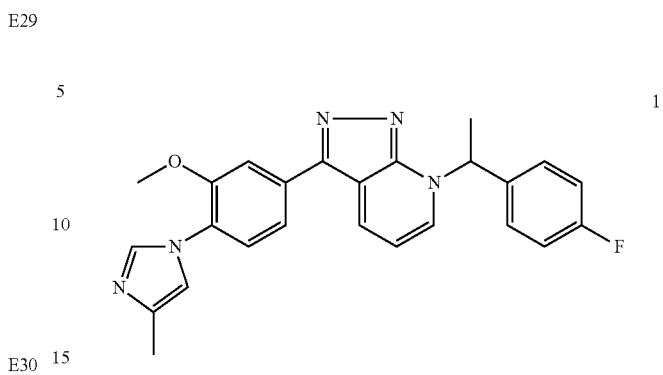

Step A:

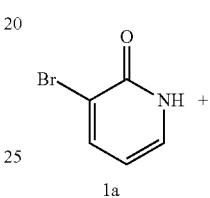

1a

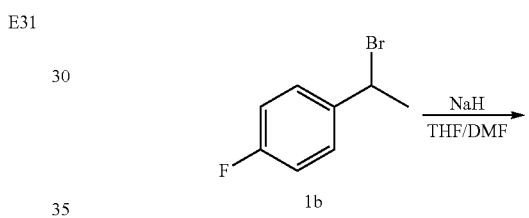

1b

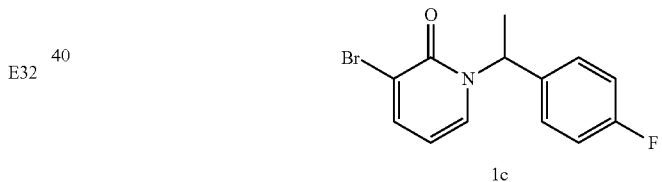

1c

To a solution of 1a (4.0 g, 22.98 mmol) in THF/DMF (20/20 ml) was added NaH (60%, 1.10 g, 27.6 mmol) at 0° C. and stirred for 10 min, followed with addition of 1b (5.57 g, 27.6 mmol). The resulting mixture was stirred overnight, then quenched with saturated aqueous NH₄Cl, extracted with EtOAc (3×). The combination of organic layers was washed with brine, dried (Na₂SO₄), concentrated and purified by flash chromatography to afford product 1c as colorless oil (4.0 g, 59%).

Step B:

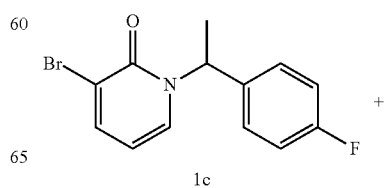

1c

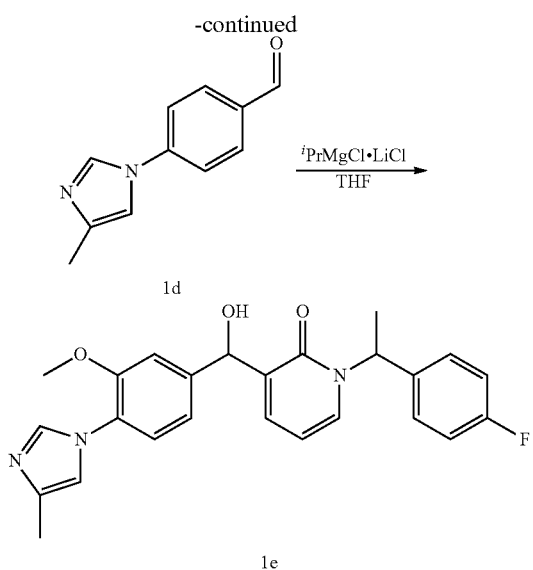

1d

1e

To a solution of 1c (300 mg, 1.01 mmol) in THF (5 ml) was added ⁱPrMgCl·LiCl (1M in THF, 1.3 ml, 1.3 mmol) and stirred at room temperature for 10 min, followed with addition of 1d (216 mg, 1.01 mmol). The resulting mixture was stirred overnight, then quenched with saturated aqueous NH$_4$Cl, extracted with EtOAc (3×). The combination of organic layers was washed with brine, dried (Na$_2$SO$_4$), concentrated and purified by flash chromatography to afford product 1e as colorless oil (210 mg, 48%). $^1$H NMR (CDCl$_3$, ppm): 7.39-7.36 (m, 1H), 7.31-7.25 (m, 3H), 7.20-7.10 (m, 2H), 7.09-7.02 (m, 4H), 6.44-6.35 (m, 1H), 6.28-6.20 (m, 1H), 5.85 (d, 1H), 3.89 (d, 3H), 2.47 (s, 3H), 1.75-1.70 (m, 3H); MS (ES-LCMS, M+1) 434.2. Retention time: 2.55 min.
Step C:

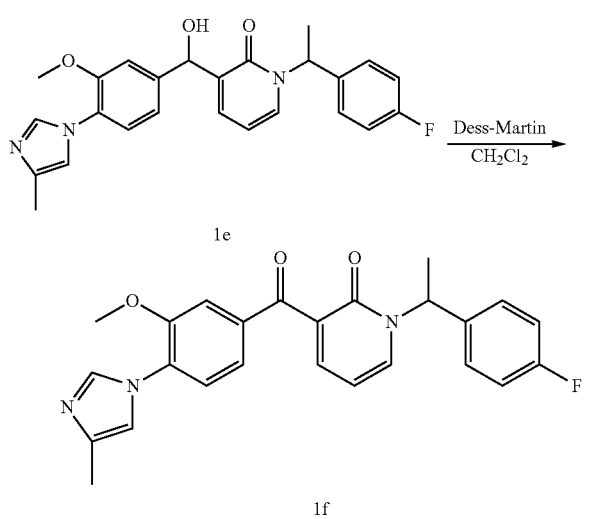

1e

1f

To a solution of 1e (300 mg, 0.69 mmol) in CH$_2$Cl$_2$ (5 ml) was added Dess-Martin Periodinane (440 mg, 1.04 mmol) and stirred overnight. Then it was diluted with CH$_2$Cl$_2$, washed with saturated aqueous NaHCO$_3$, dried (Na$_2$SO$_4$), concentrated and purified by flash chromatography to afford product it as colorless oil (200 mg, 67%). $^1$H NMR (CDCl$_3$, ppm): 7.82 (d, 1H), 7.59 (s, 1H), 7.51-7.47 (m, 1H), 7.46-7.39 (m, 2H), 7.34-7.28 (m, 21-), 7.14 (s, 1H), 7.10-7.03 (m, 2H), 6.42-6.37 (m, 1H), 6.37-6.30 (m, 1H), 3.91 (s, 3H), 2.47 (s, 3H), 1.75 (d, 3H); MS (ES-LCMS, M+1) 432.2. Retention time: 2.48 min.
Step D:

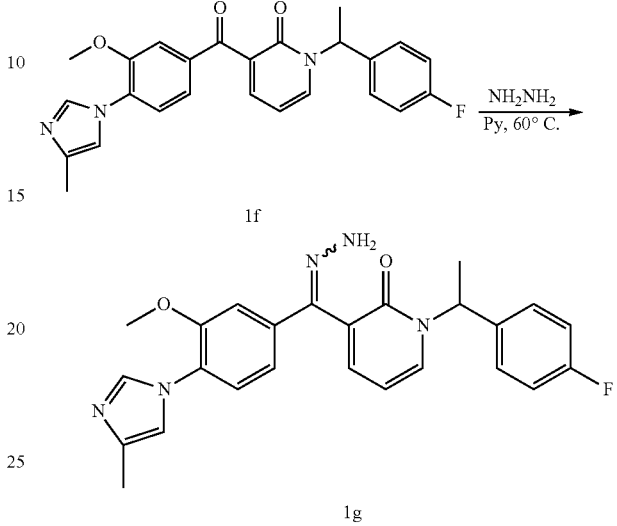

1f

1g

A mixture of 1f (150 mg, 0.35 mmol) and NH$_2$NH$_2$ (111 mg, 3.4 mmol) in pyridine (1.5 ml) was heated at 60° C. overnight. Then it was concentrated under vacuum to remove pyridine and the residue was purified by flash chromatography to afford product 1g as colorless oil (70 mg, 45%). $^1$H NMR (CDCf$_3$, ppm): 7.50 (s, 1H), 7.40-7.37 (d, 1H), 7.36-7.32 (m, 3H), 7.16-7.02 (m, 3H), 6.93-6.84 (m, 2H), 6.53-6.46 (m, 1H), 6.34-6.30 (m, 1H), 5.94 (s, 2H), 3.86 (s, 3H), 2.29 (s, 3H), 1.78 (d, 3H); MS (ES-LCMS, M+1) 446.2. Retention time: 2.52 min.
Step E:

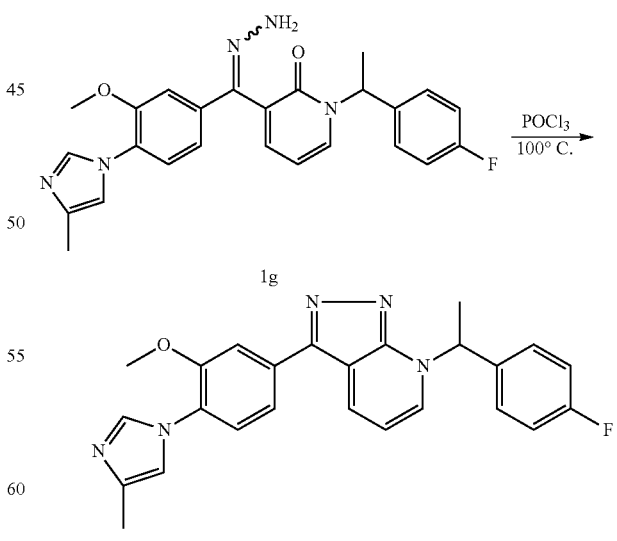

1g

1

A mixture of 1g (25 mg, 0.056 mmol) and POCl$_3$ (1.5 ml) was heated at 100° C. for 3 hrs, then concentrated to provide a crude product residue, which was purified by reverse phase HPLC (H₂O:CH₃CN: TFA) to afford 20 mg product 1 as yellow oil (83%). ¹H NMR (CD₃OD, ppm): 9.27-9.23 (m, 1H), 9.20-9.16 (m, 1H), 7.90-7.77 (m, 4H), 7.69-7.61 (m, 3H), 7.23-7.15 (m, 2H), 6.82-6.74 (m, 1H), 4.08 (s, 3H), 2.45 (s, 3H), 2.22 (d, 3H); (ES-LCMS, M+1) 428.2. Retention time: 1.88 min.

Compounds 4.7, 8, 12-14, 16-22, 24-34, 42, 47, 48, 51, 57, 58, 63, 90, 98, 111, 112, 125, 131, and 157 were prepared using a similar procedure as that of Example 1 starting from corresponding bromide.

Examples 5 & 6

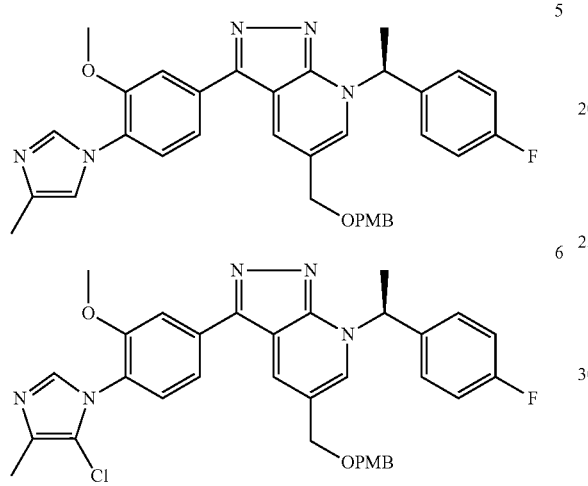

Step A:

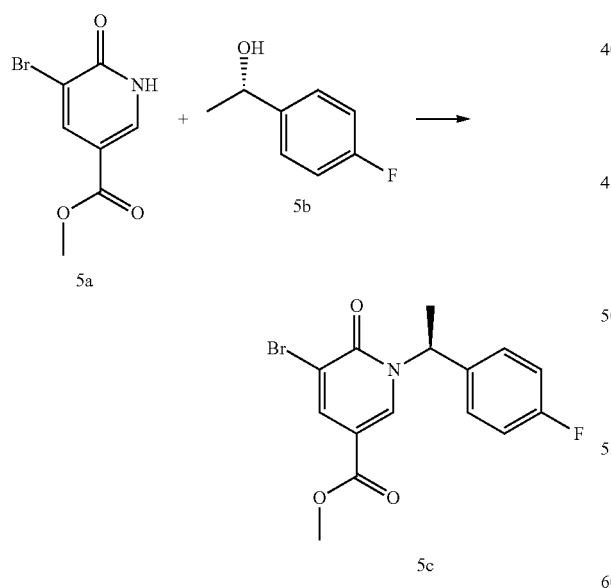

The mixture of 5a (11.0 g, 48 mmol) and 5b (5.6 g, 40 mmol) in THF (100 ml) was stirring at 0° C., PBu₃ (20 ml, 80 mmol) was added dropwise to the mixture, the mixture was stirring at 0° C. for 0.5 h before the addition of ADDP (20 g, 80 mmol). The resultant mixture was kept stirring at 0° C. for 0.5 h, the slowly warmed up to 80° C., and kept stirring at 80° C. for 48 h. The mixture was cooled to RT, the white precipitate was filtered off, the filtrate was concentrated and purified via ISCO (EtOAc-Hexane=1:6) to obtain 5c as a light orange liquid. (7.6 g). MH⁺ 356/354

Step B:

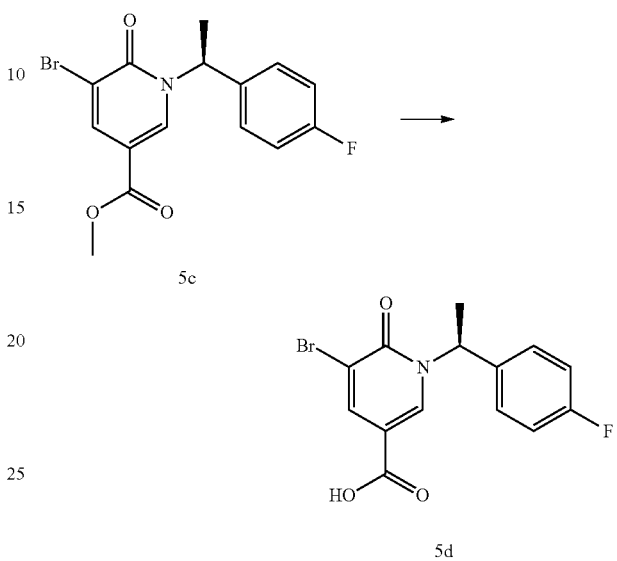

To the solution of 5c (7.6 g, 21 mmol) in MeOH (42 ml) at RT was added 2N NaOH (21 ml). The resultant mixture was kept stirring at RT for 16 h. The organic solvent was removed via rotavapor, the aqueous layer was extracted with EtOAc (50 ml) once, then the aqueous layer was acidified with 2N HCl pH 2~3. White precipitate formed. Collected the solid, washed with H₂O, dried; obtain 5d as a white powder (5.86 g). MH⁺ . 342/340

Step C:

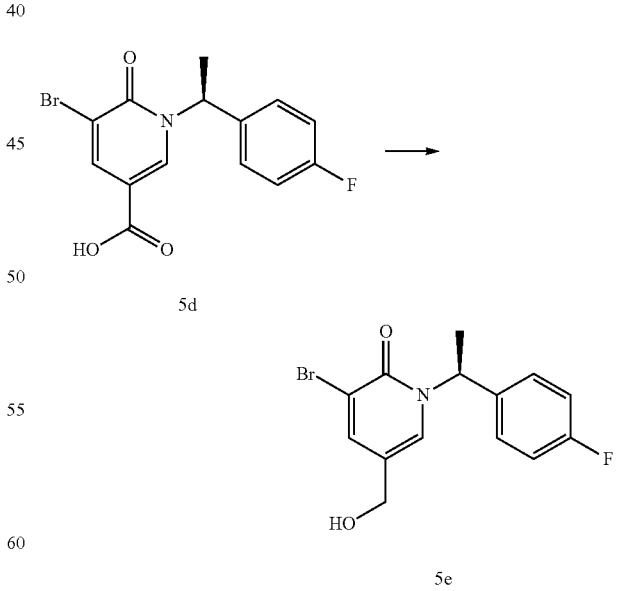

The solution of 5d (5.80 g, 17.0 mmol) in DCM (150 ml) and Pyridine (1.32 mL, 17.0 mmol) was cooled in an ice-salt bath, Cyanuric fluoride (1.60 mL, 34.0 mmol) was added dropwise, and the mixture was kept stirring at 0° C. for 1 h. ice water was added to the mixture, the aqueous was extracted once more with DCM (100 ml), the combined organic was washed with ice water (50 ml), dried over anhydrous MgSO$_4$, and concentrated. The residue was taken up in DCM (150 ml), NaBH$_4$ (1.30 g, 34 mmol) was added, followed by the addition of MeOH (40 ml). The mixture was kept stirring at RT for 16 h. 1N H$_2$SO$_4$ was added to neutralize the mixture, extracted with DCM (100 ml×2), the combined organic was washed with 1N H$_2$SO$_4$, dried over anhydrous MgSO$_4$, and concentrated. The residue was purified via Biotage (EtOAc-Hexane=2:1), obtained 5e as a white solid (4.83 g). MH$^+$ 328/326

Step D:

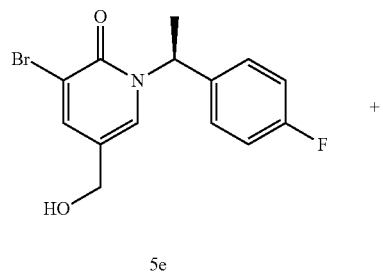

5e

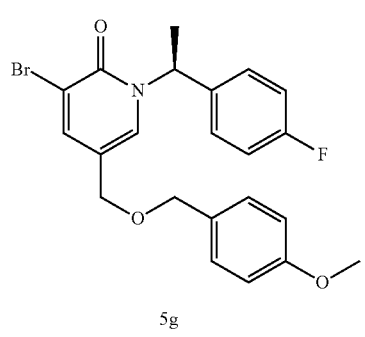

5f

To the mixture of 5e (4.7 g, 14.4 mmol) in THF (40 ml) was added solid NaH (864 mg, 21.6 mmol), after stirring at R.T. for 30 min, 5f (2.5 ml, 17.3 mmol) was added, the resultant mixture was kept stirring at R.T. for 4 h. EtOAc (150 ml) and H$_2$O (50 ml) were added, the aqueous was extracted once more with EtOAc (6 ml). The combined organic was dried over anhydrous MgSO$_4$, and concentrated. The residue was purified via ISCO to obtain 5g as yellow foam (5.85 g). MH$^+$ 448/446

Step E:

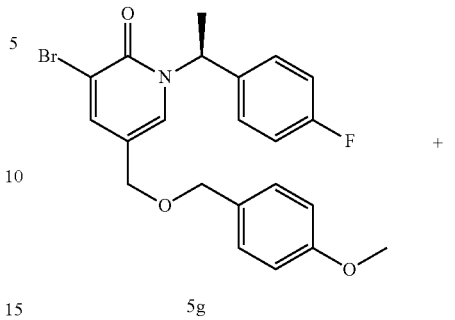

5g

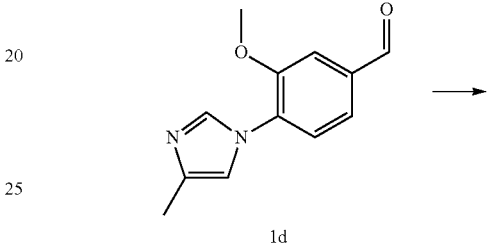

1d

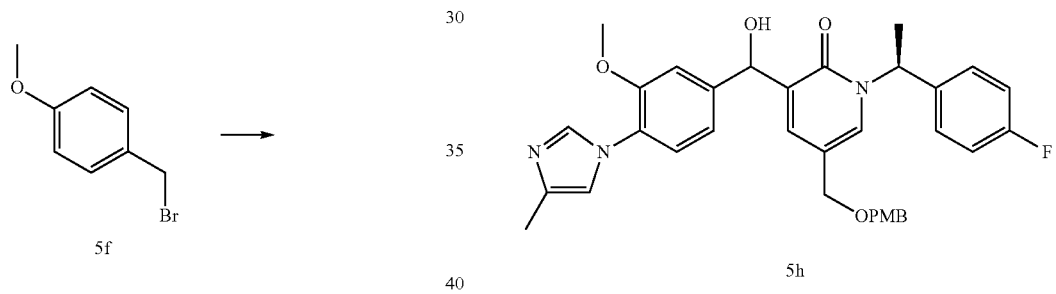

5h

The solution of 5g (130 mg, 0.291 mmol) in THF (3 ml) in ice-H$_2$O bath was added IprMgCl LiCl (1.3M in THF) solution (336 μl, 0.437 mmol), the mixture was kept stirring for 30 min at 0° C. before the addition of compound 1d (75 mg, 0.350 mmol), the resultant mixture was kept stirring at 0° C. for 2 h. EtOAc (10 ml) and NH$_4$Cl (6 ml) were added, the aqueous was extracted once more with EtOAc (6 ml). The combined organic was washed with brine (6 ml), dried over anhydrous MgSO$_4$, and concentrated. The residue was purified via ISCO (DCM/MeOH (2N NH$_3$)=25:1) to 5h as a yellow solid (132 mg). MH$^+$ 584

Step F:

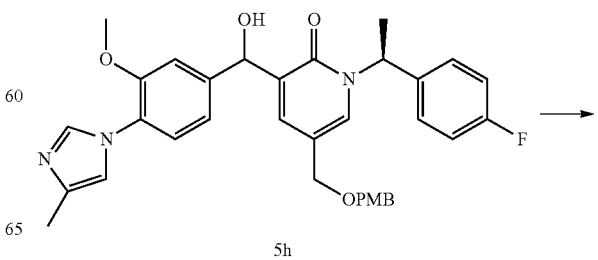

5h

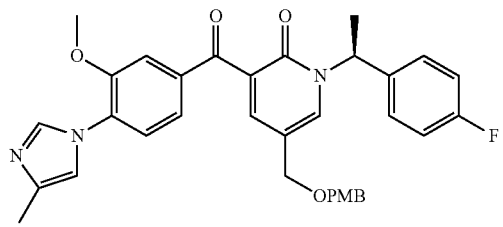

5i

+

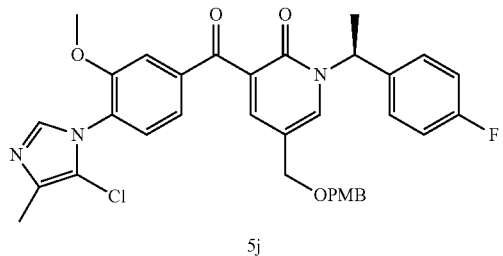

5j

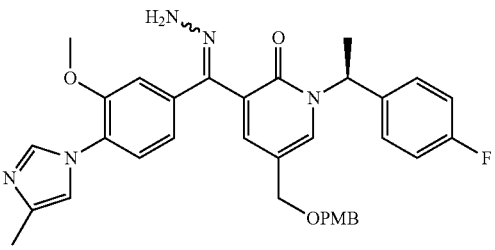

5k

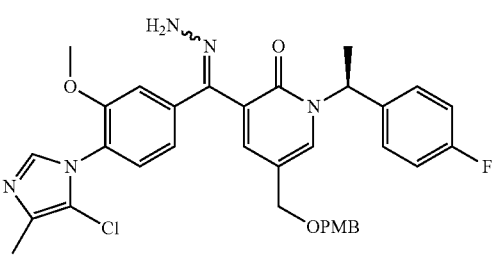

5l

Dess-Martin Periodinane (5.21 g, 24.6 mmol) was added to the solution of 5h (7.2 g, 12.3 mmol) in DCM (100 ml), the resultant mixture was kept stirring at R.T. for 16 h. DCM (10 ml) and NH$_4$Cl (60 ml) were added, the aqueous was extracted once more with DCM (60 ml). The combined organic was washed with brine (60 ml), dried over anhydrous MgSO$_4$, and concentrated. The residue was purified via ISCO (DCM/MeOH (2N NH$_3$)=25:1) to obtain a yellow foam (7.21 g), of which 60 mg was taken for PTLC (DCM/MeOH (2N NH$_3$)=12:1) to obtain 5i MH$^+$ 582 and 5j, MH$^+$ 616.

Step G:

Hydrazine hydrate (1.25 ml, 64%, 25.8 mmol) was added to the solution of 5i and 5j (1.5 g, 2.58 mmol) in EtOH (20 ml), the resultant mixture was kept stirring at 80° C. for 2 h. The organic solvent was removed, the residue was partitioned between DCM (10 ml) and H$_2$O (6 ml) were added, the aqueous was extracted once more with DCM (10 ml). The combined organic was washed with brine (6 ml), dried over anhydrous MgSO$_4$, and concentrated. The residue was purified via ISCO (DCM/MeOH (2N NH$_3$)=30:1) to obtain a yellow foam (0.83 g), which is a mixture of 2 compounds 5k and 5l.

Step H:

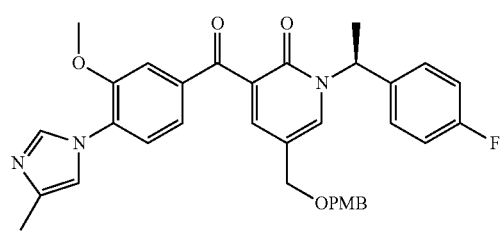

5i

+

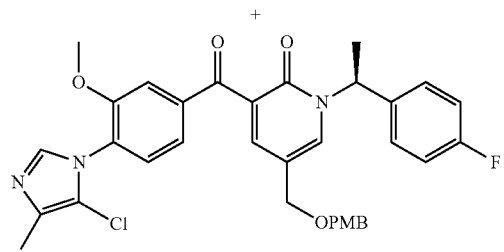

5j

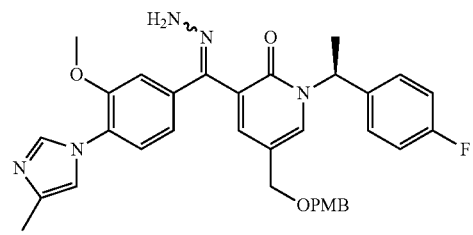

5k

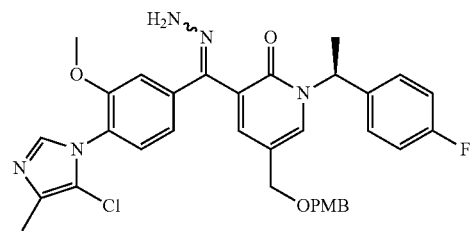

5l

-continued

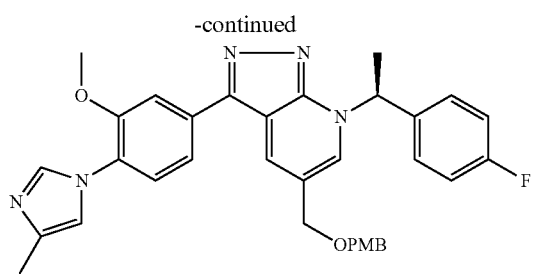
5

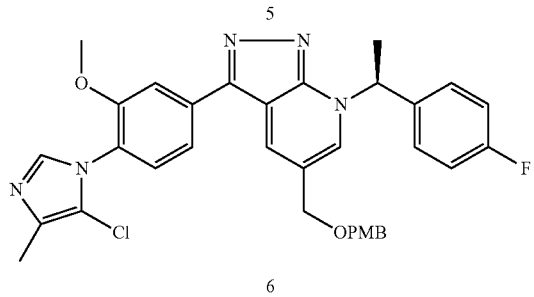
6

POCl₃ (1.2 ml) was added to the solution of 5k and 5l (820 g, 1.38 mmol) in Pyridine (6 ml), the resultant mixture was kept stirring at 50° C. for 2 h. The organic solvent was removed, the residue was partitioned between DCM (40 ml) and NaHCO₃ (Sat. 16 ml) were added, the aqueous was extracted once more with DCM (15 ml). The combined organic was washed with brine (10 ml), dried over anhydrous MgSO₄, and concentrated. The residue was purified via ISCO (DCM/MeOH (2N NH₃)=50:1->20:1) to obtain red solids 5 (50 mg) MH⁺ 612, 6 (73 mg) MH⁺ 578, and the mixture of two.

Examples 9 and 10

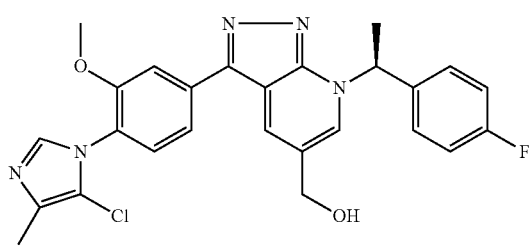
9

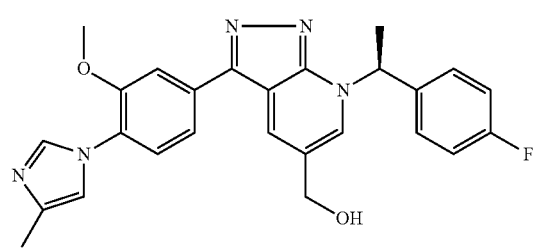
10

Step A:

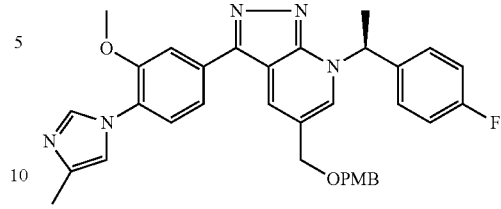
5

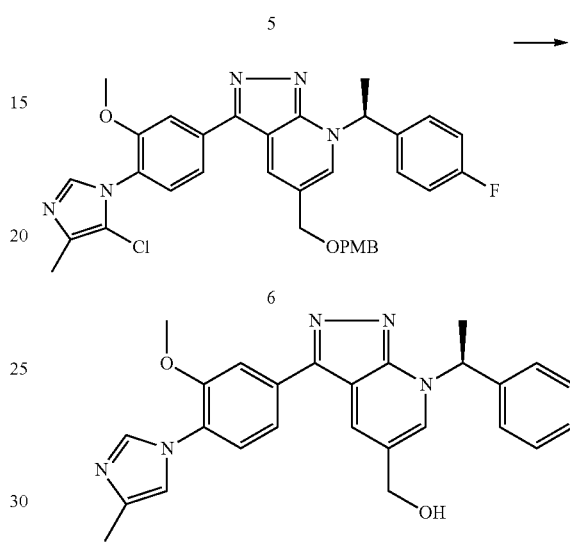
6

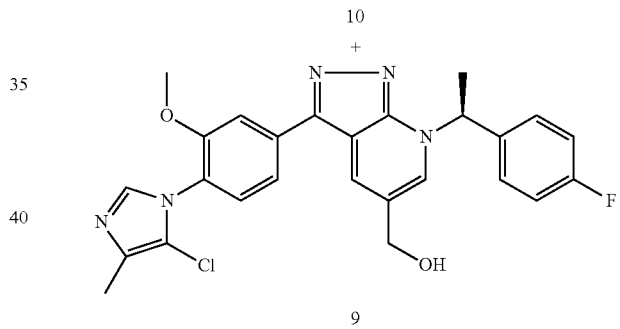
9

Ammonium cerium(IV) nitrate (88 mg, 0.16 mmol) was added to the solution of 5 and 6 (50 mg, 0.081 mmol) in mixed solvent of CH₃CN—H₂O (9:1, 2 ml), the resultant mixture was kept stirring at R.T. for 16 h. The mixture was concentrated, coevaporated with toluene (3 ml×2). The residue was purified via PTLC (DCM/MeOH (2N NH₃)=12:1) to obtain the title compounds 9. MH⁺ 492 and 10, MH⁺ 458.

Example 11

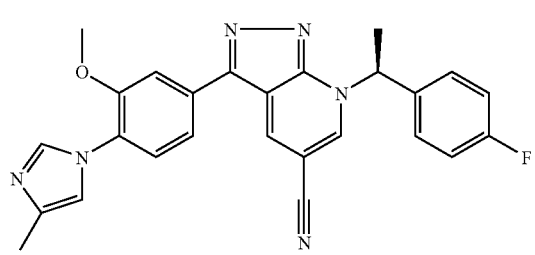
11

Step A:

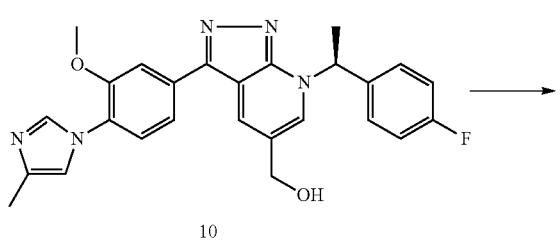

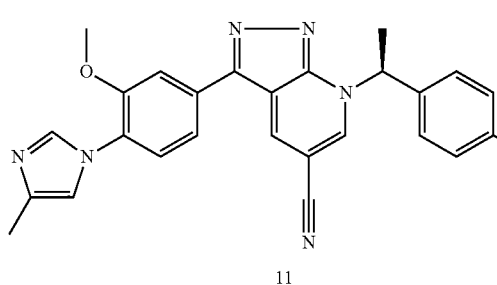

I₂ (31 mg, 0.122 mmol) was added to the solution of 10 (28 mg, 0.061 mmol) in NH₄OH (1 ml). The resultant mixture was kept stirring at 60° C. for 16 h. Na₂SO₃ (Sat.) was added, extracted with EtOAc (10 ml×2), the organic was washed with H₂O (6 ml), dried over anhydrous MgSO₄, and concentrated. The residue was purified PTLC (DCM/MeOH (2N NH₃)=20:1), obtained 11 as a red colored solid. MH⁺ 453

Example 15

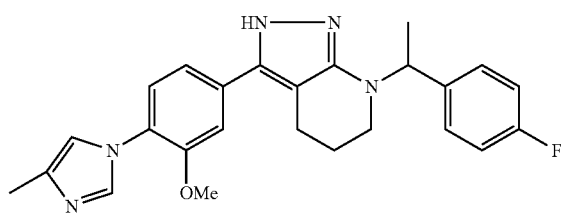

Step A:

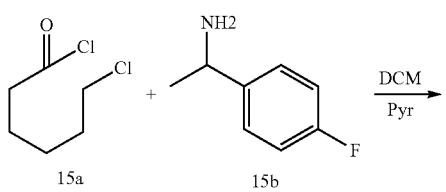

-continued

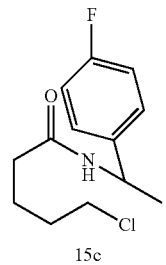

To a solution of 1-(4-fluorophenyl)ethanamine 15b (5.0 g, 35.9 mmol) in a mixture of 10 mL of DCM and 14.5 mL of pyridine, with ice cooling, was added dropwise a solution of 6-chlorohexanoyl chloride 15a in 20 mL of DCM. After the addition was compete, cooling was removed and the resulting precipitate was stirred overnight. The reaction mixture was diluted with 100 mL of ther and washed with 100 mL of 1M HCl. The organic phase was dried over MgSO₄ and concentrated to furnish 9.2 g of crude 5-chloro-N-(1-(4-fluorophenyl)ethyl)pentanamide 15c which was used in the next step without purification.

Step B:

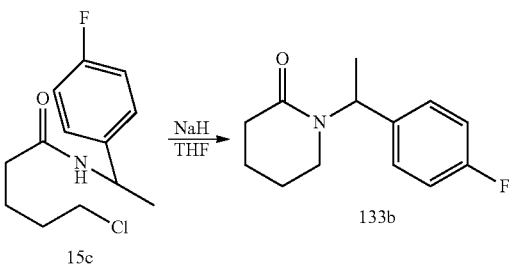

To a solution of crude 5-chloro-N-(1-(4-fluorophenyl)ethyl)pentanamide 15c (900 mg, 3.5 mmol) in 15 mL of THF at 0° C. was added 154 mg (3.85 mmol) of 60% suspension of NaH in mineral oil. Stirred the mixture 1 hr at room temperature, then at reflux overnight. The reaction mixture was cooled to room temperature, taken up in ether and washed with water. The organic phase was dried over MgSO₄, concentrated, and the residue was chromatographed over 12 g of silica gel using a gradient from hexanes to 50% of ethyl acetate in hexanes, providint 400 mg of lactam 133b.

Step C:

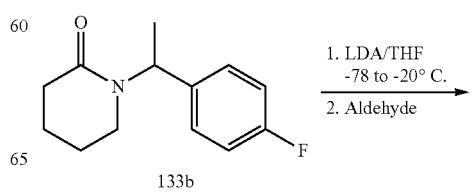

-continued

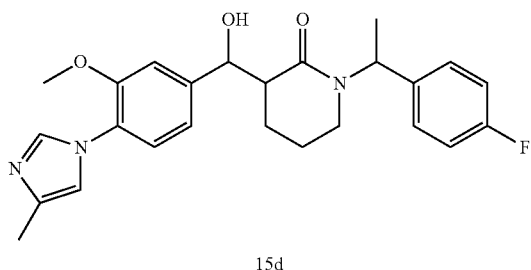

15d

To a solution of lactam 133b (110 mg, 0.497 mmol) in THF (2 ml) at −78° C. was added LDA (2M in THF/Heptane, 0.62 ml, 1.244 mmol). The reaction was stirred for 30 min. at −78° C., another 30 min. at −20° C. Re-cooled to −78° C. 3-methoxy-4-(4-methyl-1H-imidazol-1-yl)benzaldehyde was added as solid. The reaction mixture was stirred for 30 min. The reaction was quenched with sat. NaHCO₃, extracted with EtOAc (2×), washed with brine (2×). Dried (MgSO₄) and concentrated. The crude product was purified by flash chromatograph (7% MeOH/DCM) to afford compound 15d (110 mg, 50.6%).

Step D:

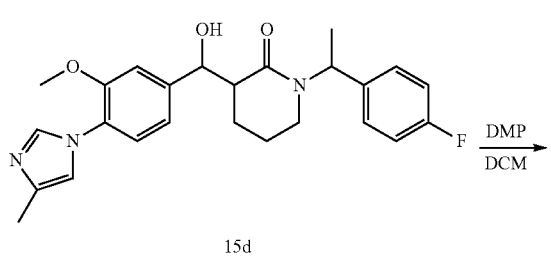

15d

To a solution of compound 15d (345 mg, 0.789 mmol) in DCM (15 ml) at RT was added Dess-Martin periodinane (402 mg, 0.947 mmol) and NaHCO₃ (99.5 mg, 1.15 mmol). The reaction was stirred over night. The mixture was quenched with Na₂S₂O₃ in sat. NaHCO₃, extracted with DCM (2×), washed with brine. Dried (MgSO₄) and concentrated. The crude product was purified by flash chromatography (7% MeOH/DCM) to afford compound 15e (310 mg, 90.3%).

Step E:

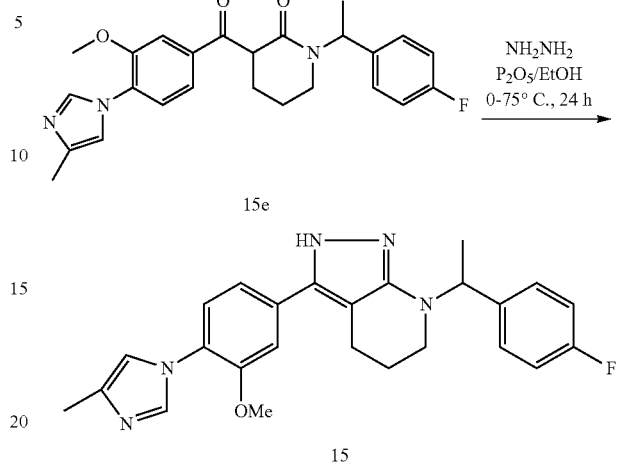

To a mixture of compound 15e (114 mg, 0.262 mmol) and P₂O₅ (743.6 mg, 5.24 mmol) at 0° C., was added absolute EtOH (2 ml) slowly. Stirred for a few minutes, hydrazine (84 mg, 2.62 mmol) was added. The reaction mixture was heated to 70° C. for 24 h. The solvent was removed. The residue was extracted with DCM (3×), washed with brine, dried (MgSO4) and concentrated. The crude product was purified by flash chromatograph or prepare TLC (10% MeOH/DCM) to afford 15 (9.0 mg, 9%). LCMS m/z=432.2 (M+H⁺), ret. time 2.52 min.

Compounds 95 and 102 were prepared following a similar procedure as Example 15 starting from the corresponding lactam.

Example 23

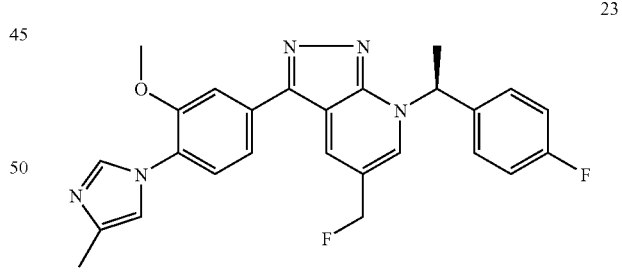

23

Step A:

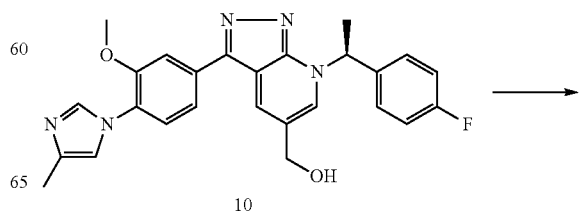

10

-continued

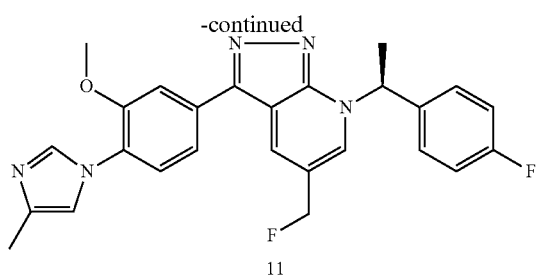
11

DAST (11 μL, 0.090 mmol) was added to the solution of 10 (20 mg, 0.044 mmol) in DCM (4 ml), and the resultant mixture was kept stirring at RT for 16 h. The mixture was washed with H$_2$O (2 ml), NaHCO$_3$ (Sat. 6 ml), respectively, dried over anhydrous MgSO$_4$, and concentrated. The residue was purified via PTLC (DCM/MeOH (2N NH$_3$)=20:1), obtained 23 as a red colored solid, MH$^+$ 460

Example 41

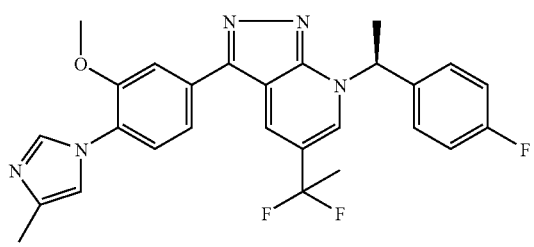
41

Step A:

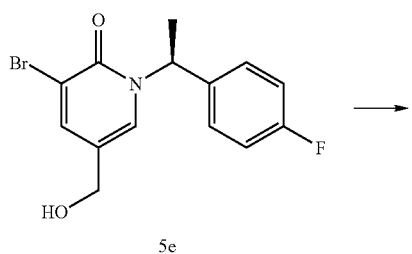
5e

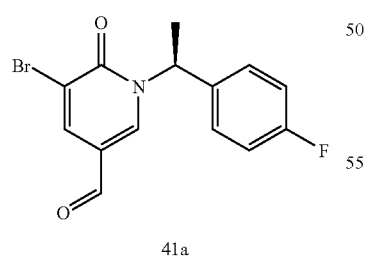
41a

PDC (4.16 g, 11.0 mmol) was added to the solution of 5e (2.4 g, 7.36 mmol) in DCM (40 ml), and the resultant mixture was kept stirring at RT for 6 h. Celite was added to the mixture and stirred at RT for 5 minutes, the solid was filtered and the filtrate was concentrated. The residue was purified via ISCO (EtOAc-Hexane=1:4) to obtain 41a as a clear syrup (1.8 g). MH$^+$ 325

Step B:

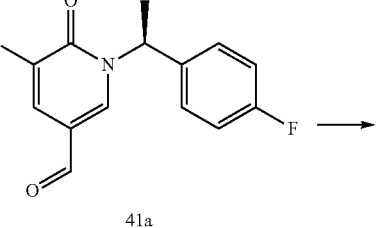
41a

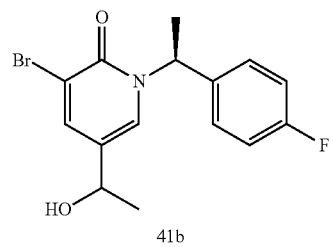
41b

The solution of 41a (1.2 g, 3.70 mmol), and Et$_3$N (1.7 ml, 12.2 mmol) in THF (12 ml) was cooled in an acetone-dry ice bath, CH$_3$MgBr (1.96 ml, 6.08 mmol) was added dropwise, and the reaction was kept stirring at −78° C. for 4 h. EtOAc (30 ml) and NH$_4$Cl (sat. 20 ml) were added, and the aqueous layer was extracted once more with EtOAc (20 ml), the combined organic was dried over anhydrous MgSO$_4$, and concentrated. The residue was purified ISCO (EtOAc-Hexane=1:1) to obtain 41b as a clear syrup, MH$^+$ 342/340

Step C:

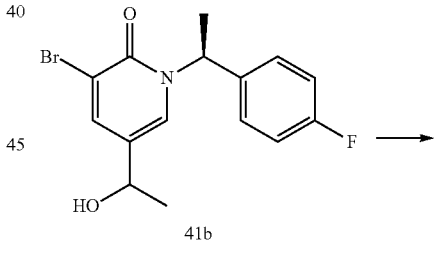
41b

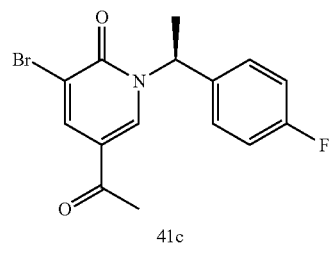
41c

PDC (1.88 g, 5 mmol) was added to the solution of 41b (850 mg, 2.5 mmol) in DCM (20 ml), and the resultant mixture was kept stirring at RT for 16 h. Celite was added to the mixture and stirred at RT for 5 minutes, the solid was filtered and the filtrate was concentrated. The residue was purified via ISCO (EtOAc-Hexane=1:1) to obtain 41c as a white foam (876 mg). MH$^+$ 340/338

Step D:

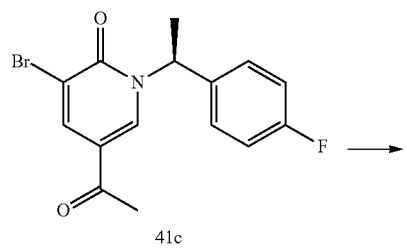

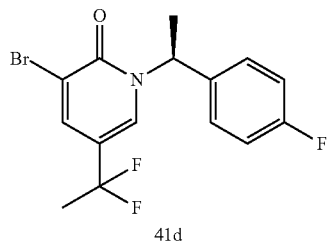

Deoxy-fluor (3.8 ml, 50% in THF, 8.64 mmol) was mixed with 41c (730 mg, 2.16 mmol) in a sealed tube, and the resultant mixture was kept stirring at 80° C. for 16 h. The cooled mixture was poured into ice, basified with NaHCO$_3$ (Sat.) to pH ~9, extracted with DCM (30 ml×2). The combined organic was washed with brine (30 mL), dried over anhydrous MgSO$_4$, and concentrated. The residue was purified ISCO (EtOAc-Hexane=1:3) to obtain 41d (362 mg) as a clear syrup. MH$^+$ 362/360

Compound 41d was converted to the title compound 41 using a similar procedure as for Example 5 (steps E-H);

Example 52

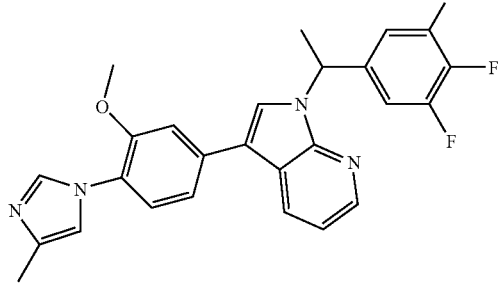

Step A:

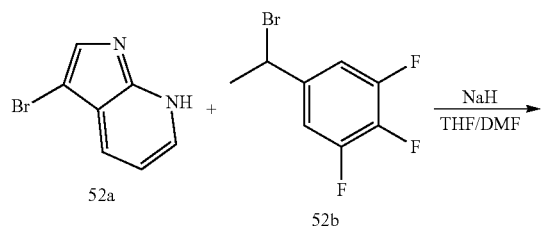

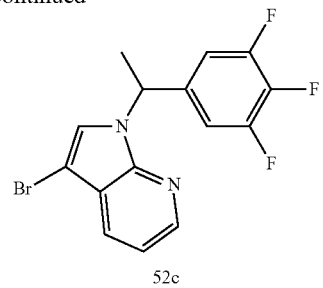

To a solution of 52a (1.0 g, 5.07 mmol) in DMF (25 ml/25 ml) was added NaH (60%, 300 mg, 7.6 mmol) at 0° C. and stirred for 30 min, followed with addition of 52b (1.80 g, 7.6 mmol). The resulting mixture was stirred overnight, then quenched with saturated aqueous NH$_4$Cl, extracted with EtOAc (3×). The combination of organic layers was washed with brine, dried (Na$_2$SO$_4$), concentrated and purified by flash chromatography to afford product 52c as colorless oil (1.2 g, 67%).

Step B:

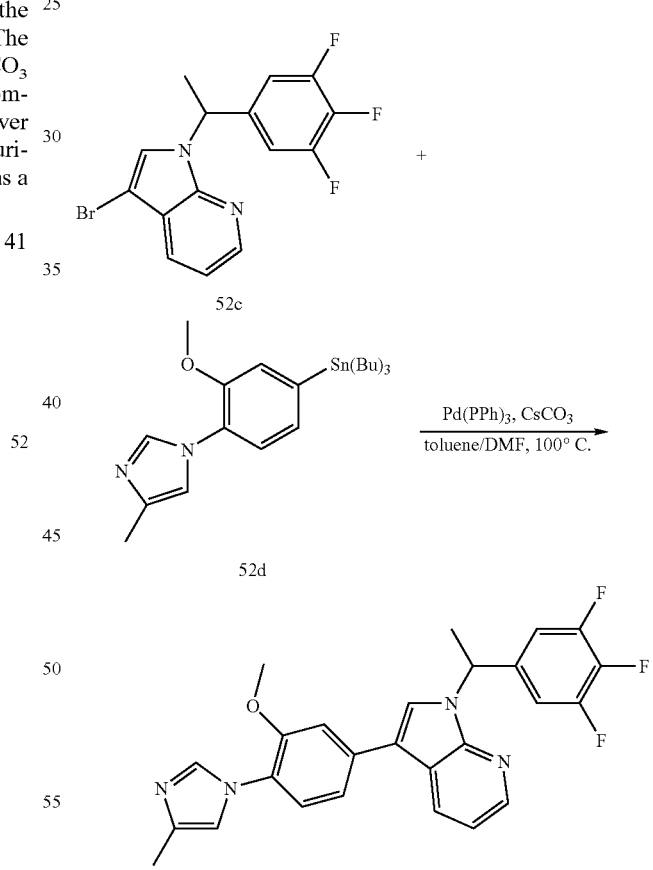

To a solution of 52c (289 mg, 0.81 mmol) and 52d (388 mg, 0.81 mmol) in toluene/DMF (3 ml/3 ml) was added Pd(PPh$_3$)$_4$ (94 mg, 0.081 mmol) and CsCO$_3$ (1.32 g, 4.05 mmol). The resulting mixture was heated at 120° C. overnight, then quenched with saturated aqueous NH$_4$Cl, extracted with EtOAc (3×). The combination of organic layers was washed with brine, dried (Na$_2$SO$_4$), concentrated and purified by flash chromatography to afford product 52 as white solid (40 mg, 11%). ¹H NMR (CDCl₃, ppm): 8.49 (d, 1H), 8.28 (d, 1H), 7.56 (s, 1H), 7.48-7.28 (m, 5H), 7.15 (s, 1H), 7.02-6.93 (m, 2H), 6.40-6.33 (m, 1H), 4.04 (s, 3H), 2.55 (s, 3H), 2.02 (d, 3H); (ES-LCMS, M+1) 464.3. Retention time: 3.73 min.

Compounds 55, 56, 65, and 68 were prepared using a similar procedure procedure as Example 52 starting from corresponding bromide.

Example 53

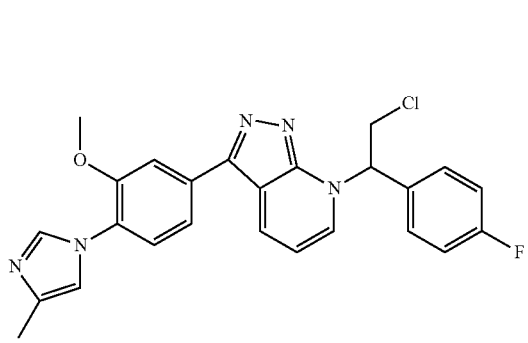

Step A:

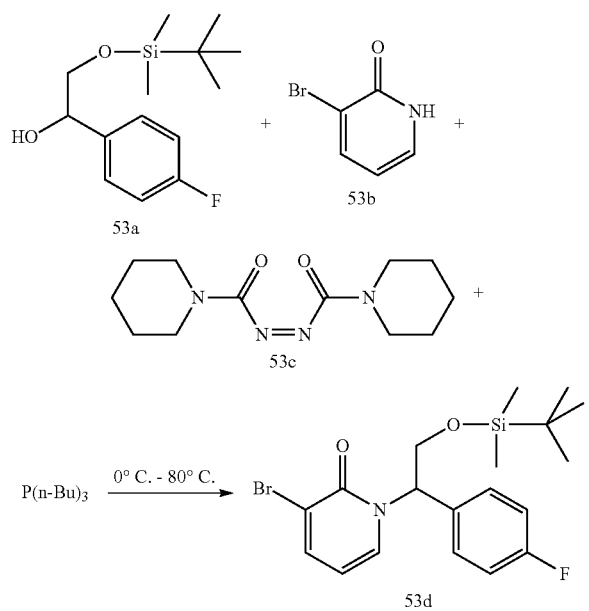

To the solution of 53a (7.24 g, 26.8 mmol) in 54 ml of THF was added 53b (5.76 g, 32.1 mmol). This mixture was allowed to stir at 0° C. for 30 minutes, followed by the addition of P(n-Bu)₃ (10.8 g, 53.6 mmol) and 53c (13.6 g, 53.6 mmol). This mixture was allowed to stir at 0° C. for another 30 minutes. Now the reaction mixture was warmed to room temperature and then allowed to reflux at 80° C. overnight. The reaction mixture was cooled to room temperature and filtered until no solid was observed in the filtrate. The filtrate was concentrated and purified by silica gel chromatography using ethyl acetate/hexanes to afford 3.20 g of 53d.

Step B:

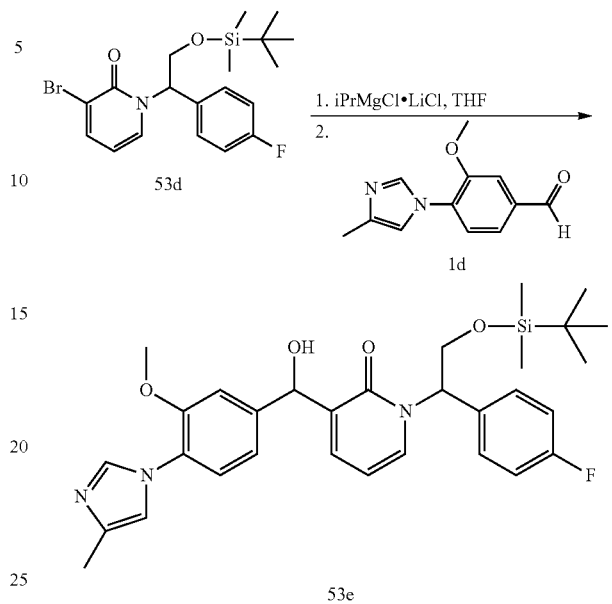

To the solution of 53d (3.20 g, 7.5 mmol) in 25 ml THF was added, iPrMgCl.LiCl (9.27 ml, 8.96 mmol). This mixture was allowed to stir for 30 minutes followed by the addition of 1d (1.79 g, 8.2 mmol). The reaction mixture was allowed to stir overnight. It was quenched with aq. NH₄Cl solution, extracted three times with ethyl acetate. The combined organic layer was dried with Na₂SO₄. It was then filtered and concentrated. The residue was purified by silica gel chromatography using (0-5) % MeOH/CH₂Cl₂ to give 3.41 g of 53e.

Step C:

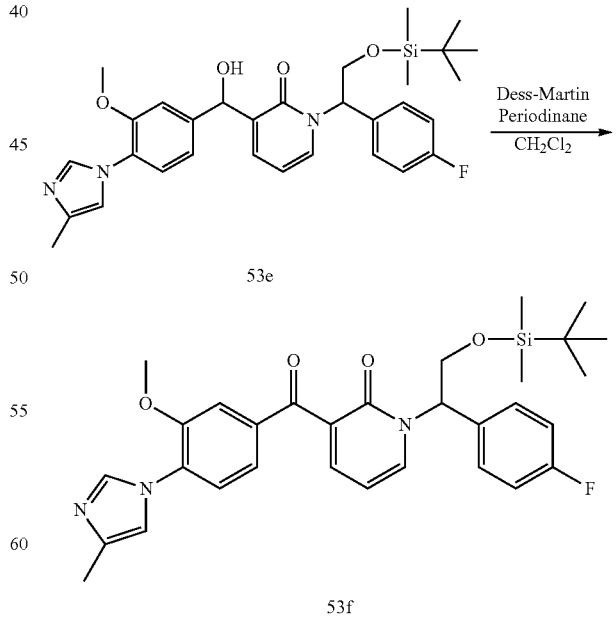

To the solution of 53e (3.41 g, 6.0 mmol) in 20 ml of CH₂Cl₂ was added dess-martin periodinane (5.3 g, 12.1 mmol). The reaction mixture was allowed to stir overnight.

The reaction mixture was concentrated and then diluted with ethyl acetate. It was then quenched with aq. NaHCO₃ solution and extracted three times with ethyl acetate while continuously removing solids from both layers. The combined organic layer was dried with Na₂SO₄ and then filtered. The filtrate was concentrated and the residue was purified by silica gel chromatography using (0-5) % MeOH/CH₂Cl₂ to give 1.78 g of 53f.

Step D:

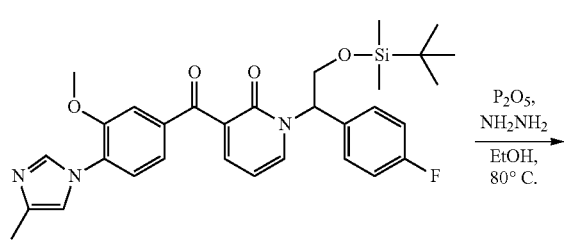

53f

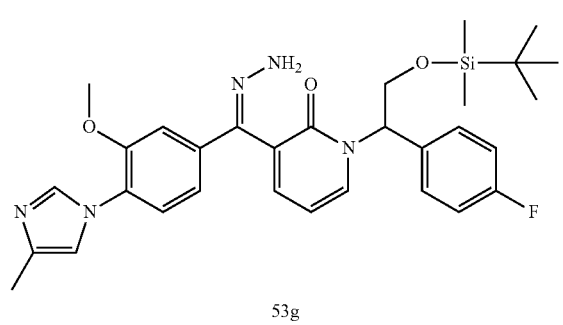

53g

To the solution of 53f (1.78 g, 3.17 mmol) in 12 ml ethanol was added P₂O₅ (1.80 g, 12.7 mmol) followed by NH₂NH₂ (1.01 ml, 31.7 mmol). The reaction mixture was allowed to reflux at 80° C. for overnight. The reaction mixture was cooled to room temperature and diluted with ethyl acetate. This was then washed with aq. NaHCO₃ solution. The extracted organic layer was dried with Na₂SO₄ and then filtered. The filtrate was concentrated and the residue was purified by silica gel chromatography using (0-5) % (2N NH₃/MeOH)/CH₂Cl₂ to give 880 mg of 53g.

Step E:

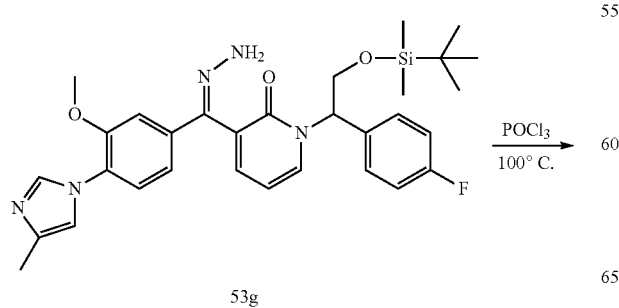

53g

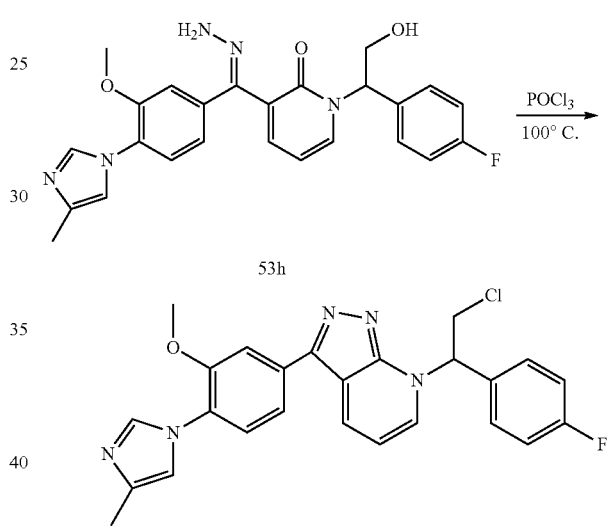

53h

53

The solution of 53g (880 mg, 1.5 mmol) in 15 ml of POCl₃ was stirred at 100° C. for 90 minutes. The reaction mixture was cooled to room temperature and concentrated to get rid of POCl₃. The residue was purified by silica gel chromatography using (0-5) % (2N NH₃/MeOH)/CH₂Cl₂ to give 324 mg of 53h.

Step F:

The solution of 53h (100 mg, 022 mmol) in 2 ml of POCl₃ was stirred at 100° C. for 90 minutes. The reaction mixture was cooled to room temperature and 2N HCl in Diethyl ether was added. The mixture was stirred at room temperature and was filtered to obtain 27 mg of 53.

Example 54

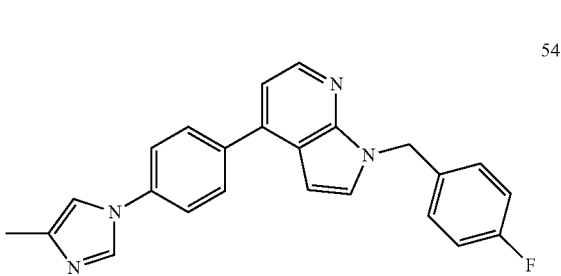 [SMILES: Cc1cn(-c2ccc(-c3ccnc4c3ccn4Cc3ccc(F)cc3)cc2)cn1]

54

Step A: 4-chloro-1-(4-fluorobenzyl)-1H-pyrrolo[2,3-b]pyridine

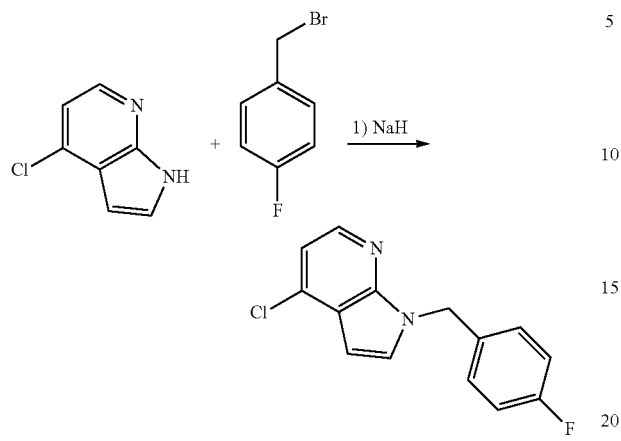

To 4-chloro-1H-pyrrolo[2,3-b]pyridine (300 mg, 2.00 mmol) in 5 ml DMF was added 4-Fluorobenzylbromide (0.27 ml, 2.2 mmol) then add NaH (80 mg, 2.0 mmol) and stir at room temperature overnight. Work up by adding water and EtOAc and extract three times with EtOAc. Pool all organics and wash one time with brine then dry over sodium sulfate, filter and concentrate to dryness. The residue was purified by chromatography over silica gel (eluted with Hexanes/EtOAc 99:1 to 50:50) to provide 400 mg (77%) of product.

Step B: 1-(4-fluorobenzyl)-4-(4-(4-methyl-1H-imidazol-1-yl)phenyl)-1H-pyrrolo[2,3-b]pyridine

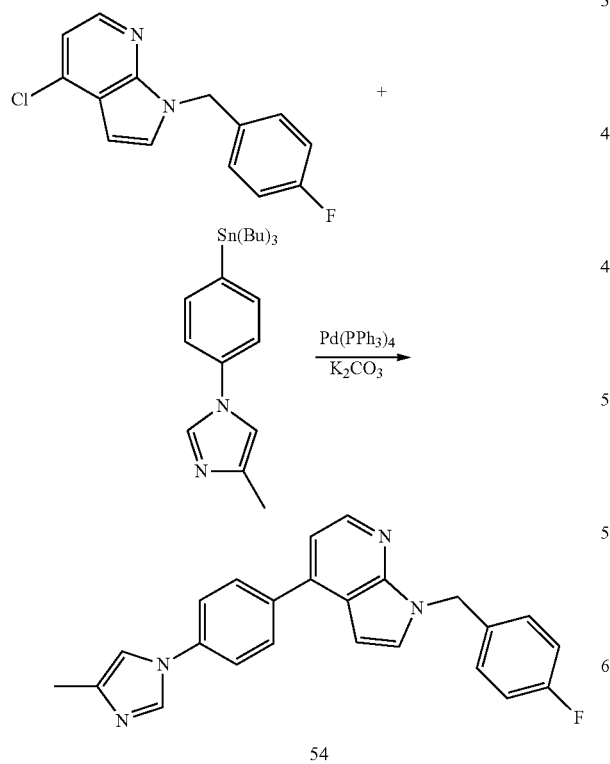

To 4-chloro-1-(4-fluorobenzyl)-1H-pyrrolo[2,3-b]pyridine (36 mg, 0.14 mmol), 4-methyl-1-(4-(tributylstannyl) phenyl)-1H-imidazole (100 mg, 0.21 mmol) and Potassium carbonate (100 mg, 0.7 mmol) was added 3 ml Toluene followed by Pd(PPh$_3$)$_4$ (20 mg, 0.014 mmol) then heat to 120 C for 2 hrs. The reaction was worked up by cooling to RT then adding water and DCM. Extract aqueous layer 3×DCM, then dry over sodium sulfate and filter and concentrate to dryess. The residue was purified by chromatography over silica gel (eluted with DCM/MeOH 99:1 to 90:10) to provide 5.8 mg (10%) of product. $^1$H NMR (CDCl$_3$ 400 MHz): 8.4 (d, 1H), 8.01 (s, 2H), 7.78-7.8 (m, 1H), 7.4 (s, 2H), 7.26-7.27 (m, 3H), 6.95-7.02 (m, 3H), 6.65-6.72 (m, 1H), 5.53 (s, 1H), 3.93 (s, 3H), 2.33 (s, 3H). LCMS (MH$^+$)=413; retention time=3.19 min.

Following procedures similar to those in Example 54, all other compounds in the table below with this core

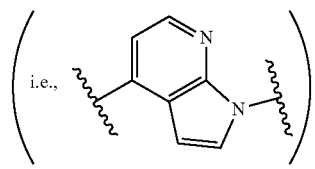

were prepared.

Example 61

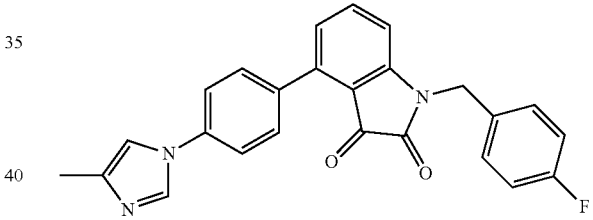

Step A: 4-bromo-1-(4-fluorobenzyl)indoline-2,3-dione

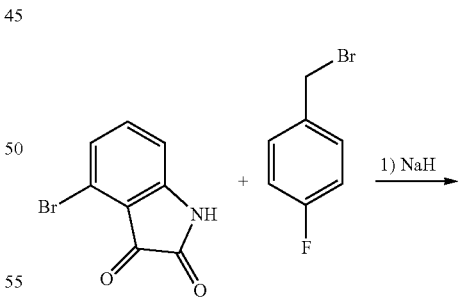

To 4-bromoindoline-2,3-dione (200 mg, 0.89 mmol) in 5 ml DMF was added 4-Fluorobenzylbromide (0.120 ml, 0.98 mmol) then add NaH (35 mg, 0.89 mmol) and stir at room temperature overnight. Work up by adding water and EtOAc and extract three times with EtOAc. Pool all organics and wash one time with brine then dry over sodium sulfate, filter and concentrate to dryness. The residue was purified by chromatography over silica gel (eluted with Hexanes/EtOAc 99:1 to 50:50) to provide 270 mg (90%) of product.

Step B: 1-(4-fluorobenzyl)-4-(4-(4-mthyl-1H-imidazol-1-yl) phenyl) indoline-2,3-dione

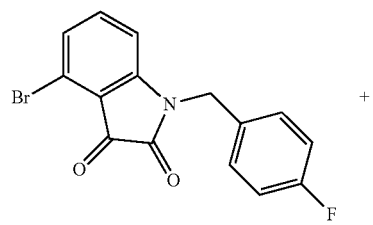

+

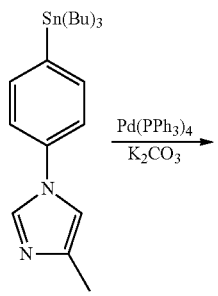

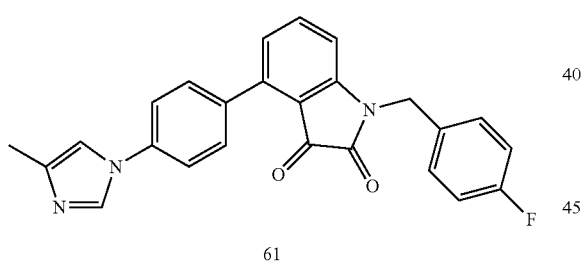

61

To 4-bromo-1-(4-fluorobenzyl)indoline-2,3-dione (60 mg, 0.18 mmol), 4-methyl-1-(4-(tributylstannyl)phenyl)-1H-imidazole (130 mg, 0.27 mmol) and Potassium carbonate (125 mg, 0.9 mmol) was added 3 ml Toluene followed by Pd(PPh3)4 (20 mg, 0.018 mmol) then heat to 120 C for 2 hrs. The reaction was worked up by cooling to RT then adding water and DCM. Extract aqueous layer 3×DCM, then dry over sodium sulfate and filter and concentrate to dryess. The residue was purified by chromatography over silica gel (eluted with DCM/MeOH 99:1 to 90:10) to provide 33.0 mg (42%) of product 61. $^1$H NMR (CDCl$_3$ 400 MHz): 7.78 (s, 1H), 7.50-7.61 (t, 1H), 7.34-7.38 (m, 2H), 7.32 (s, 1H), 7.28 (s, 1H), 7.26 (s, 1H), 7.06-7.15 (m, 3H), 6.78-6.80 (d, 2H), 4.95 (s, 2H), 3.91 (s, 3H), 2.31 (s, 3H), LCMS (MH$^+$) 442; retention time=1.980 min.

Following procedures similar to those in Example 61, all other compounds in the table below with this core

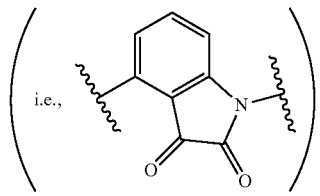

were prepared.

Example 62

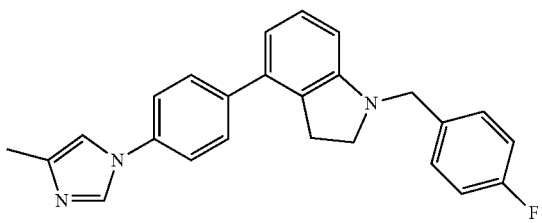

62

Step A: 4-bromo-1-(4-fluorobenzyl)indoline

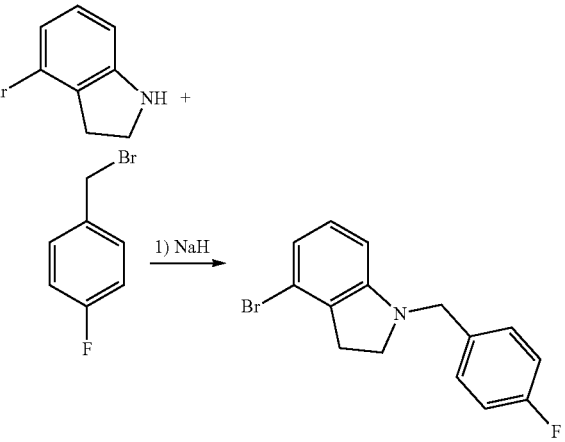

To 4-bromoindoline (200 mg, 1.00 mmol) in 5 ml DMF was added 4-Fluorobenzylbromide (0.14 ml, 1.1 mmol) then add NaH (40 mg, 1.0 mmol) and stir at room temperature overnight. Work up by adding water and EtOAc and extract three times with EtOAc. Pool all organics and wash one time with brine then dry over sodium sulfate, filter and concentrate to dryness. The residue was purified by chromatography over silica gel (eluted with Hexanes/EtOAc 99:1 to 50:50) to provide 280 mg (92%) of product.

Step B: 1-(4-fluorobenzyl)-4-(4-(4-methyl-1H-imidazol-1-yl)phenyl)indoline

Step A: 4-chloro-1-(4-fluorobenzyl)-1H-pyrrolo[3,2-c]pyridine

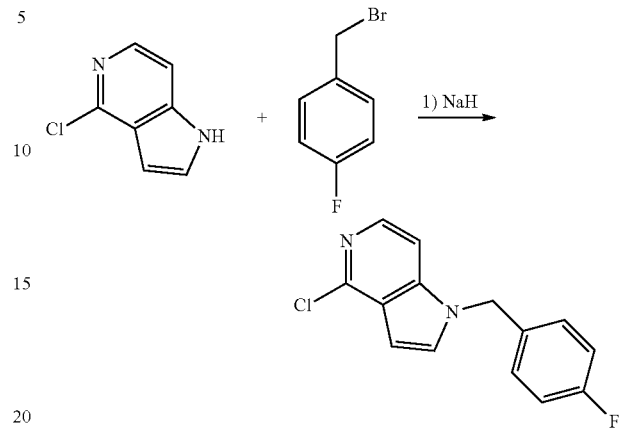

To 4-Chloro-5-azaindole (120 mg, 079 mmol) in 5 ml DMF was added 4-Fluorobenzylbromide (0.120 ml, 0.95 mmol) then add NaH (32 mg, 0.79 mmol) and stir at room temperature overnight. Work up reaction by adding water and EtOAc then extract three times with EtOAc. Pool all organics and wash one time with brine then dry over sodium sulfate, filter and concentrate to dryness. The residue was purified by chromatography over silica gel (eluted with Hexanes/EtOAc 99:1 to 50:50) to provide 100 mg (50%) of product.

Step B: 1-(4-fluorobenzyl)-4-(4-(4-methyl-1H-imidazol-1-yl)phenyl)-1H-pyrrolo[3,2-c]pyridine

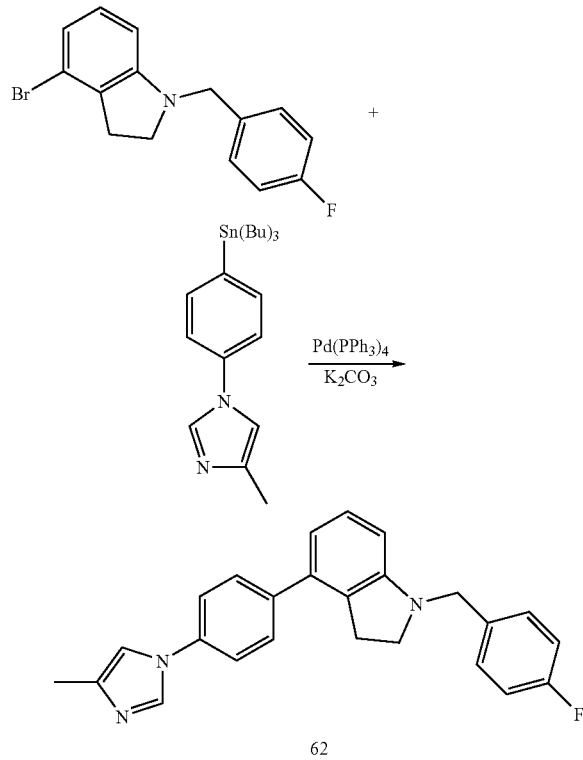

62

To 4-bromo-1-(4-fluorobenzyl)indoline (60 mg, 0.20 mmol), 4-methyl-1-(4-(tributylstannyl)phenyl)-1H-imidazole (143 mg, 0.30 mmol) and Potassium carbonate (140 mg, 1.00 mmol) was added 3 ml Toluene followed by Pd(PPh3)4 (30 mg, 0.020 mmol) then heat to 120 C for 2 hrs. The reaction was worked up by cooling to RT then adding water and DCM. Extract aqueous layer 3×DCM, then dry over sodium sulfate and filter and concentrate to dryess. The residue was purified by chromatography over silica gel (eluted with DCM/MeOH 99:1 to 90:10) to provide 5.8 mg (7%) of product 62. $^1$H NMR (CDCl$_3$ 400 MHz): 7.6-7.7 (m, 2H), 7.40-7.5 (m, 1H), 7.3-7.4 (m, 2H), 7.21-7.3 (m, 1H), 7.1-7.21 (m, 2H), 7.0-7.18 (m, 2H), 6.78-6.8 (d, 1H), 6.50-6.58 (d, 1H), 4.26 (s, 2H), 3.87 (s, 3H), 3.33 (m, 2H), 3.06 (m, 2H). LCMS (MH$^+$)=414; retention time=2.14 min.

Following procedures similar to those in Example 62, compound 66 in the table below was prepared.

Example 67

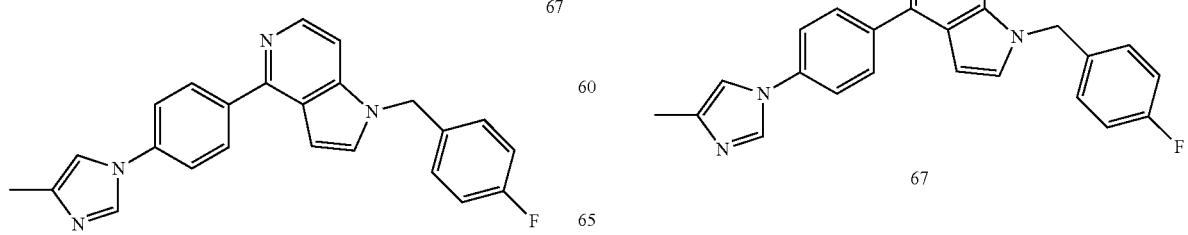

67

To 4-chloro-1-(4-fluorobenzyl)-1H-pyrrolo[3,2-c]pyridine (100 mg, 0.38 mmol), 4-methyl-1-(4-(tributylstannyl)

phenyl)-1H-imidazole (277 mg, 0.58 mmol) and Potassium carbonate (262 mg, 1.9 mmol) was added 2 ml Toluene followed by Pd(PPh3)4 (44 mg, 0.038 mmol) then heat to 120 C for 2 hrs. The reaction was worked up by cooling to RT then adding water and DCM. Extract aqueous layer 3×DCM, then dry over sodium sulfate and filter and concentrate to dryness. The residue was purified by chromatography over silica gel (eluted with DCM/MeOH 99:1 to 90:10) to provide 10.9 mg (8%) of product 67. $^1$H NMR (CDCl$_3$ 400 MHz): 8.42-8.43 (d, 1H), 7.78 (s, 1H), 7.73 (s, 1H), 7.64-7.66 (d, 1H), 7.38-7.40 (d, 1H), 7.13-7.22 (m, 2H), 7.00-712 (m, 3H), 6.86-6.87 (d, 2H), 5.34 (s, 2H), 3.97 (s, 3H), 2.32 (s, 3H). LCMS (MH$^+$)=413; retention time 1.763 min.

Following procedures similar to those in Example 67, compounds 69, 70, 83, 108, 109, and 119 in the table below were prepared.

Example 71

71

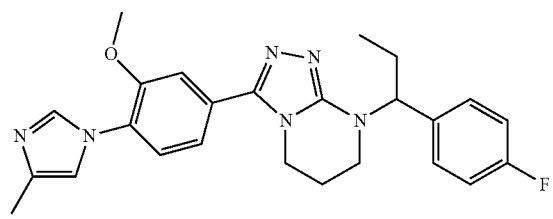

Step A:

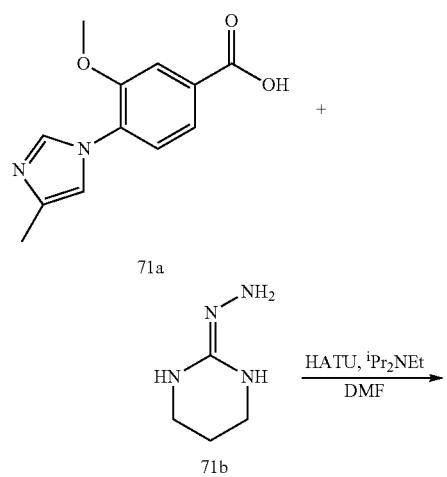

A solution of 71a (1.80 g, 7.72 mmol) in DMF (30 ml) was added 71b (1.50 g, 7.72 mmol), HATU (4.40 g, 11.6 mmol) and $^i$Pr$_2$NEt (4.04 ml, 23.76 mmol). The resulting mixture was stirred at room temperature overnight, then concentrated to remove most of the solvent. The resulting crude product was purified by flash chromatography (CH$_2$Cl$_2$:MeOH:NH$_3$) to afford product 71c as off-white solid (2.0 g, 79%).

Step B:

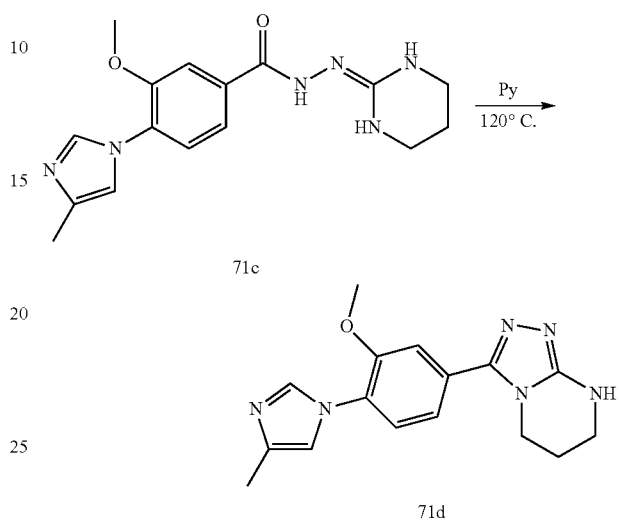

A solution of 71c (1.80 g, 5.48 mmol) in Pyridine (25 ml) was heated at 120° C. overnight. Then it was concentrated to remove pyridine and the residue was purified by flash chromatography (CH$_2$Cl$_2$:MeOH:NH$_3$) to afford product 71d as off-white solid (500.0 mg, 29%).

Step C:

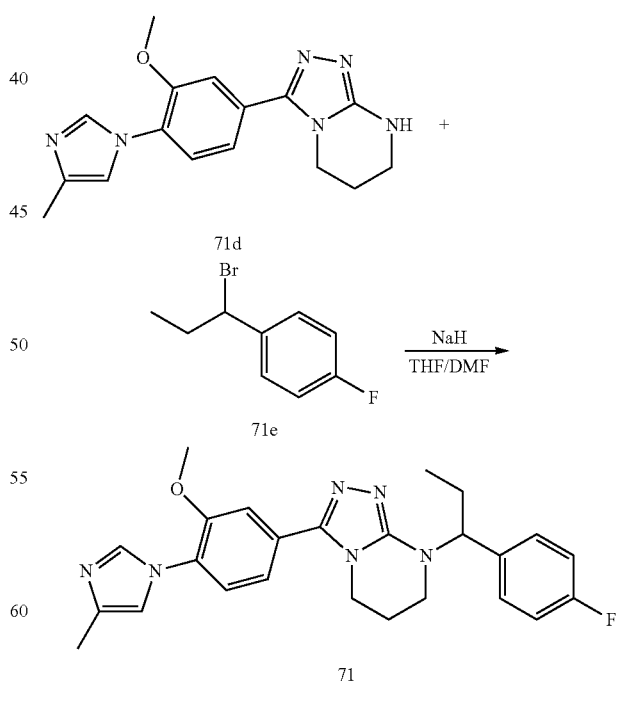

To a solution of 71d (50 mg, 0.16 mmol) in DMF/THF (2 ml/2 ml) was added NaH (60%, 15 mg, 0.375 mmol) and 71e (100 mg, 0.46 mmol). The resulting mixture was stirred at room temperature overnight, then quenched with saturated aqueous NH₄Cl, extracted with EtOAc (3×). The combination of organic layers was washed with brine, dried (Na₂SO₄), concentrated and purified by reverse phase HPLC (H₂O: CH₃CN) to afford product 71 as colorless oil (25 mg, 34%). ¹H NMR (CDCl₃, ppm): 7.62 (s, 1H), 7.52-7.47 (m, 2H), 7.37 (d, 1H), 7.22 (d, 1H), 7.12-7.02 (m, 3H), 5.65-5.58 (m. 1H), 4.10-3.95 (m, 5H), 3.38-3.28 (m, 1H), 3.06-2.99 (m, 1H), 2.40 (s, 3H), 2.18-1.94 (m, 4H), 1.10 (m, 3H); (ES-LCMS, M+1) 447.2. Retention time: 2.31 min.

Compounds 72, 84, 85, 92, 97, 99, 103, 104, 106, 107, 113-118, 121-123, 138, 143, and 144 were prepared following a similar procedure as that of Example 71 using different alkylating agents.

Example 74

74

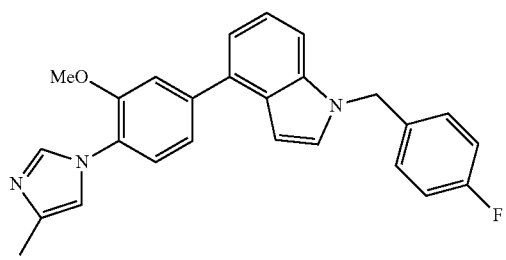

Step A:

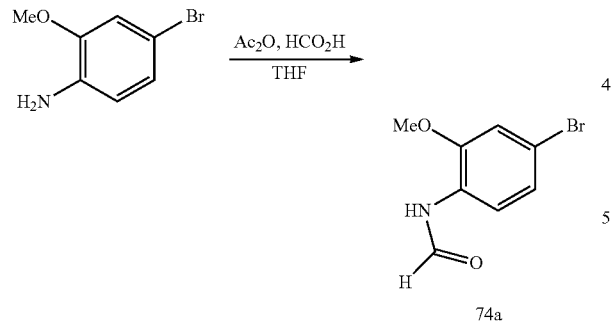

To a round bottom flask at r.t. containing formic acid (85%, 27 mL, 624.4 mmol) was added acetic anhydride (16 mL, 169.5 mmol) dropwise. The reaction stirred for 45 min. followed by the dropwise addition of a solution of 4-bromo-2-methoxyaniline (9.01 g, 44.6 mmol) in THF (56 mL). The reaction mixture was quenched with ice-water after 23 h and the resulting precipitate was filtered to afford compound 74a (9.20 g, 90%) as a brown solid. ¹HNMR (CDCl₃, 400 MHz) 8.45 (d, 1H), 8.26 (d, 1H), 732 (s, 1H), 7.11-7.01 (m, 2H), 3.89 (s, 3H); MS (M-NHCOH+1)⁺ m/z calcd for C₇H₆BrO⁺= 187.0. found m/z=187.1.

Step B:

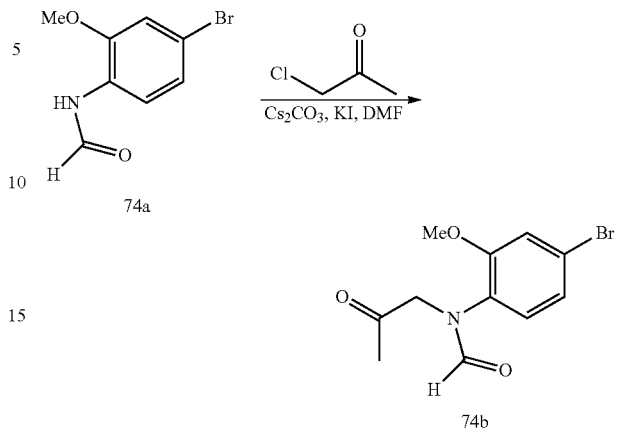

To a round bottom flask at rt, containing a mixture of compound 74a (9.20 g, 39.9 mmol), cesium carbonate (26.05 g, 79.9 mmol), and potassium iodide (0.66 g, 3.9 mmol) in DMF (40 mL) was added chloroacetone (6.7 mL, 79.9 mmol) dropwise. The reaction stirred for 3 h followed by addition of cesium carbonate (13.02 g, 39.9 mmol) and chloroacetone (3.35 mL, 39.9 mmol). After 19 h the reaction was diluted with water, extracted with 75% ethyl acetate/hexanes, washed with brine, dried over Na₂SO₄, and concentrated in vacuo. The crude material was purified by silica gel chromatography with ethyl acetate/DCM to afford compound 74b (10.94 g, 96%) as a beige solid. ¹HNMR(CDCl₃, 400 MHz) 8.22 (s, 1H), 7.19-7.08 (m, 3H), 4.43 (s, 2H), 3.84 (s, 3H); MS (M+1)⁺ m/z calcd for C₁₇H₁₂BrNO₃⁺=286.0. found m/z=286.2.

Step C:

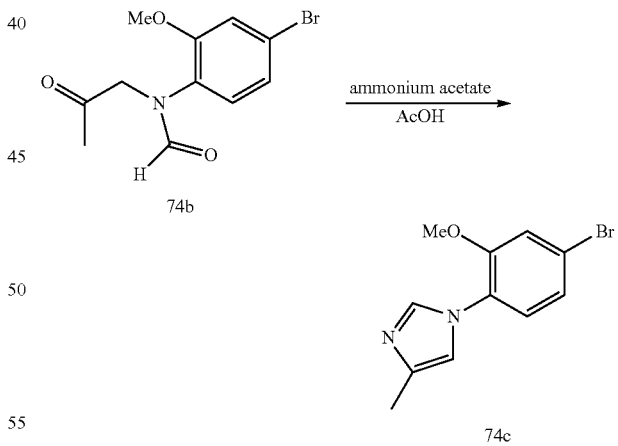

A round bottom flask at r.t. containing a mixture of compound 74b (10.94 g, 38.24 mmol), ammonium acetate (14.74 g, 191.2 mmol), and acetic acid (22 mL, 382.4 mmol) was heated to 140° C. The reaction stirred for 1 h and then was poured over ice-water. Ammonium hydroxide (60 mL) was added to the mixture, extracted with ethyl acetate, dried over Na₂SO₄, and concentrated in vacuo. The crude material was purified by silica gel chromatography with acetone/ammonium hydroxide/DCM to afford compound 74c (7.57 g, 74%) as a brown/orange solid. ¹HNMR (CDCl₃, 400 MHz) 7.64 (s, 1H), 7.17-7.10 (m, 3H), 7.87 (s, 1H), 3.85 (s, 3H), 2.29 (s, 3H); MS (M+1)+ m/z calcd for $C_{11}H_{11}BrN_2C^+$=267.0. found m/z=267.1.

Step D:

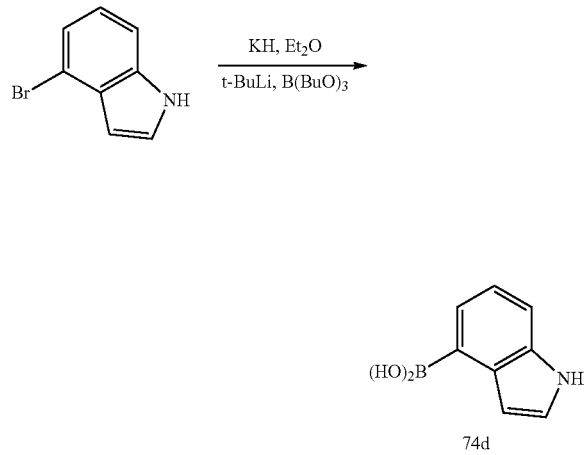

To a round bottom flask at 0° C. containing a mixture of potassium hydride (35 wt, % dispersion in mineral oil, 4.5 g, 39.3 mmol) and ether (105 mL) was added a solution of 4-bromo-1H-indole (7.0 g, 35.7 mmol) in ether (35 mL) dropwise. The reaction was transferred to a −78° C. bath and stirred for 45 min followed by addition of a −78° C. solution of t-BuLi (1.7 M in pentane, 46.2 mL, 78.5 mmol) via cannulation. To this slurry at −78° C. was added tributyl borate (29 mL, 107.1 mmol). The reaction warmed to r.t. over 21 h and then was placed in a 0° C. bath followed by addition of a solution of $H_3PO_4$ (350 mL, 1 M). The mixture was stirred for 30 min., extracted with ether, dried over $Na_2SO_4$, and concentrated in vacuo to afford 74d (4.01 g, 70%) as a beige solid. 1HNMR (($CD_3)_2$CO/15% $D_2O$, 400 MHz) 5.37-5.33 (m, 2H), 5.13 (s, 1H), 4.90 (t, 1H), 4.76 (s, 1H), 1.27 (s, 3H); MS (M+1)+ m/z calcd for $C_8H_8BNO_2^+$=161.0, found m/z=not found.

Step E:

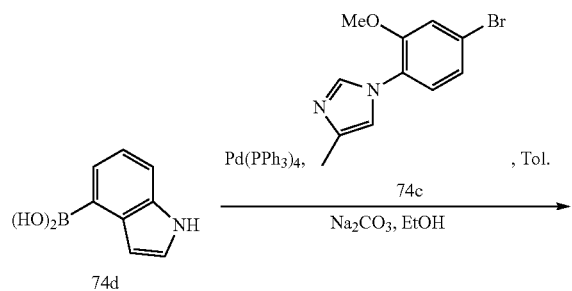

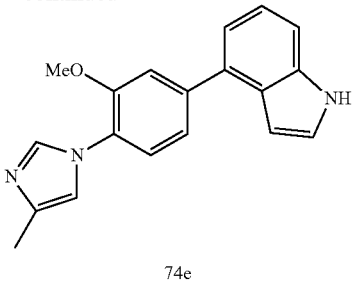

To an oven-dried round bottom flask under Ar at r.t. containing a solution of compound 74c (0.107 g, 0.40 mmol) in toluene (8 mL) was added $Pd(PPh_3)_4$ (2.2 mg, 0.019 mmol). The reaction stirred for 1.3 h followed by addition of a solution of compound 74d (0.05 g, 0.31 mmol) in ethanol (1.5 mL) and $Na_2CO_3$ (2 M water). The reaction was then transferred to a 105° C. bath and stirred for 21 h and was quenched with brine, extracted with toluene, dried over $Na_2SO_4$, and concentrated in vacuo. The crude material was purified by silica gel chromatography with methanol/ammonium hydroxide/DCM to afford compound 74e (0.019 g, 20%) as oily solid. 1HNMR(CDCl3, 400 Mz) 9.35 (s, 1H), 8.17 (d, 1H), 7.52 (d, 1H), 7.37 (d, 1H), 7.33 (t, 1H), 7.28-7.26 (m, 2H), 7.18 (d, 2H), 7.04 (m, 1H), 6.62 (m, 1H), 3.88 (s, 3H), 2.47 (s, 3H); MS (M+1)+ m/z calcd for $C_{19}H_{17}N_3O^+$=304.1. found m/z=304.2.

Step F:

To a round bottom flask at r.t. containing a mixture of sodium hydride (60% dispersion, 0.008 g, 0.198 mmol) in toluene (2 mL) was added compound 74e (0.050 g, 0.165 mmol) followed 1-(chloromethyl)-4-fluorobenzene (22 uL, 0.181 mmol). The reaction was heated to 60° C. and stirred for 1.5 h, quenched with water, extracted with ethyl acetate, dried over $Na_2SO_4$, and concentrated in vacuo. The crude material was purified by silica gel chromatography with methanol/ ammonium hydroxide/DCM to afford compound 74 (0.024 g, 35%). ¹HNMR (CDCl₃, 400 MHz) 8.77 (s, 1H), 7.44 (m, 3H), 7.35-7.21 (m, 4H), 7.15-7.11 (m, 3H), 7.01 (t, 2H), 6.69 (m, 1H), 5.36 (s, 2H) 3.95 (s, 3H), 2.50 (s, 3H); MS (M+1)⁺ m/z calcd for $C_{26}H_{22}FN_3O^+$=412.1. found m/z=412.2.

Analogues 75-82, 86, and 91 (see table below) of 74 were made in a similar manner with various benzyl and benzoyl halides.

Example 94

94

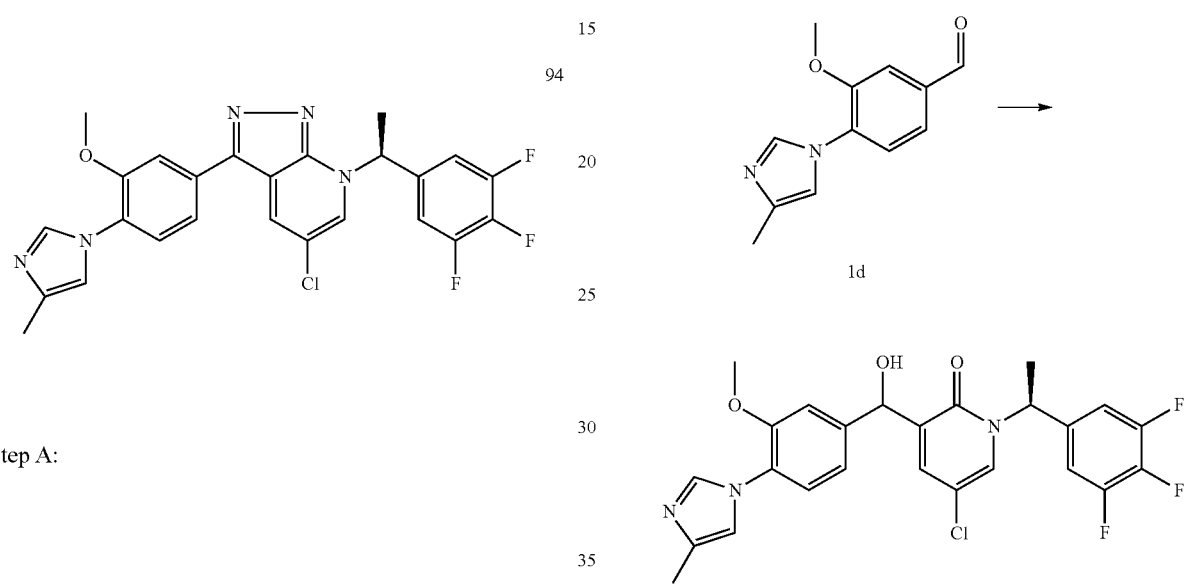

Step A:

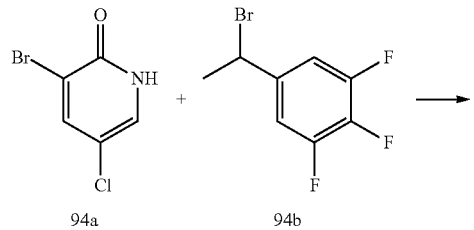

The mixture of 94a (2.08 g, 10 mmol) and K₂CO₃ (2.76 g, 20 mmol) in DMF was added bromide 94b (2.63 g, 11 mmol), the mixture was stirring at R.T. for 16 h, EtOAc (20 ml) and H₂O (20 ml) were added, and the aqueous layer was extracted once more with EtOAc (20 ml), the combined organic was washed with brine (20 ml), dried over anhydrous MgSO₄, and concentrated. The residue was purified ISCO (EtOAc-Hexane=1:5) to obtain 94c as a light yellow solid. MH⁺ 368/366

Step B:

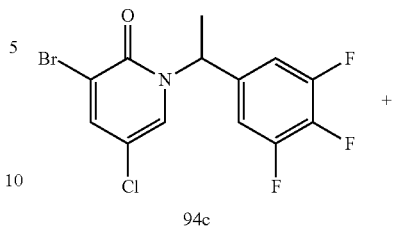

+

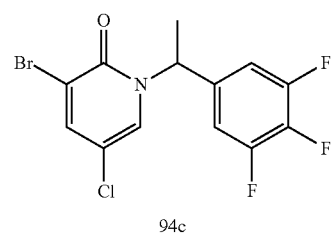

The solution of 94c (1.72 g, 4.57 mmol) in THF (20 ml) in ice-H₂O bath was added IprMgCl LiCl (1.3M in THF) solution (4.57 ml, 5.94 mmol), the mixture was kept stirring for 30 min at 0° C. before the addition of compound 1d (1.03 g, 4.80 mmol), the resultant mixture was kept stirring at 0° C. for 2 h, EtOAc (30 ml) and NH₄Cl (10 ml) were added, the aqueous was extracted once more with EtOAc (15 ml). The combined organic was washed with brine (15 ml), dried over anhydrous MgSO₄, and concentrated. The residue was purified via ISCO (DCM/MeOH (2N NH₃)=40:1->25:1) to 94b as a yellow solid (1.21 g), MH⁺ 504

Step C:

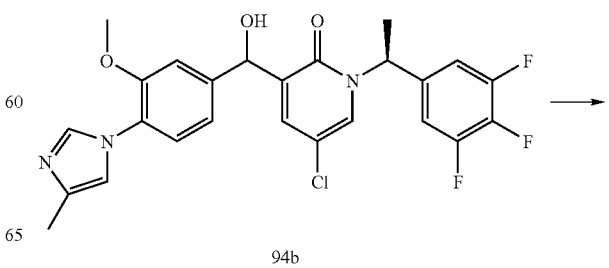

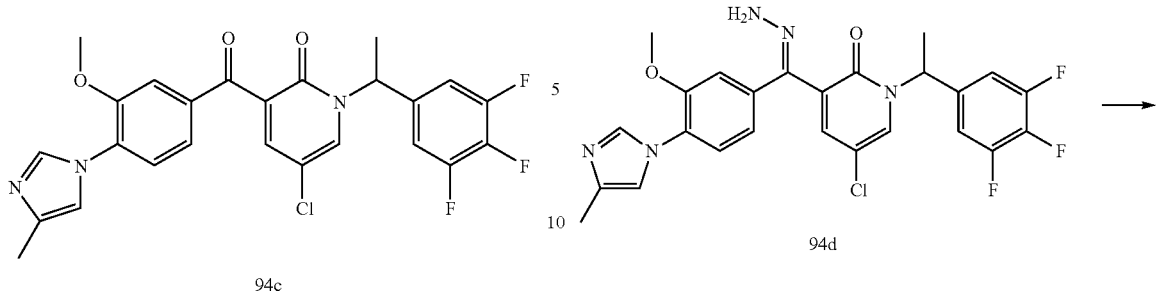

Dess-Martin Periodinane (2.02 g, 4.76 mmol) was added to the solution of 94b (1.2 g, 2.38 mmol) in DCM (20 ml), the resultant mixture was kept stirring at R.T. for 16 h. DCM (20 ml) and Na$_2$S$_2$O$_3$ (sat. 20 ml) were added, the aqueous was extracted once more with DCM (20 ml). The combined organic was washed with NaHCO$_3$ (sat. 3×20 ml), dried over anhydrous MgSO$_4$, and concentrated. The residue, 94c (1.23 g) MH$^+$ 502, a yellow foam was used directly into the next step.

Step D:

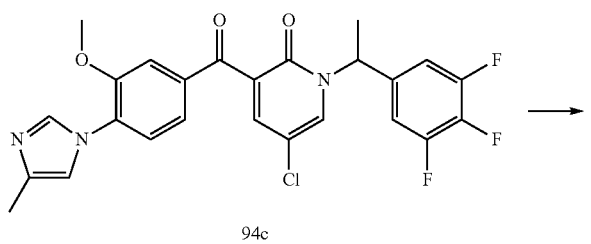

94c

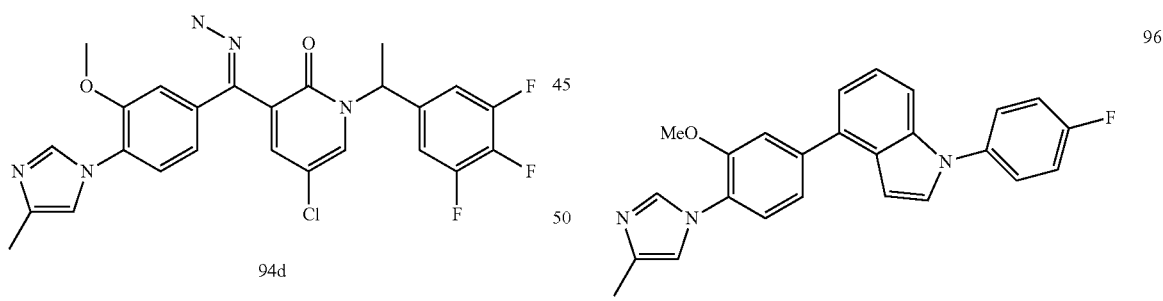

The solution of 94c (1.23 g, 2.46 mmol) in EtOH (8 ml) was added to the solid P$_2$O$_5$ (1.40 g, 9.82 mmol), the resultant mixture was kept stirring at R.T. for 10 min before the addition of anhydrous hydrazine (787 □l, 24.6 mmol), and the mixture was kept stirring at 80° C. for 2 h. The organic solvent was removed, the residue was partitioned between EtOAc (40 ml) and NaHCO$_3$ (20 ml) were added, the aqueous was extracted once more with EtOAc (10 ml). The combined organic was washed with brine (16 ml), dried over anhydrous MgSO$_4$, and concentrated. The residue, 94d (1.16 g) MH$^+$ 516, a yellow foam was used directly into the next step.

POCl$_3$ (1.4 ml) was added to the solution of 94d (1.160 g, 2.25 mmol) in Pyridine (7 ml), the resultant mixture was kept stirring at 50° C. for 2 h. The organic solvent was removed, the residue was partitioned between DCM (40 ml) and NaHCO$_3$ (Sat. 16 ml) were added, the aqueous was extracted once more with DCM (15 ml). The combined organic was washed with brine (10 ml), dried over anhydrous MgSO$_4$, and concentrated. The residue was purified via ISCO (DCM/MeOH (2N NH$_3$)=20:1->10:1) to obtain red solids 94e (362 mg) MH$^+$ 498. 94e was then separated by Chiral OD (Hexane-IPA=4:1) to obtain 93 and 94.

EXAMPLE 96

To an oven-dried test tube under Ar containing Pd$_2$(dba)$_3$ (0.002 g, 0.004 mmol), DavePhos (0.005 g, 0.012 mmol), compound 74e (0.050 g, 0.165 mmol) and NaOt-Bu (0.017 g, 0.178 mmol) was added toluene (2 mL) and 1-bromo-4-fluorobenzene (18 □L, 0.162 mmol). The reaction was heated to 100° C. and stirred for 6 d. The reaction was concentrated in vacuo and purified by silica gel chromatography with methanol/ammonium hydroxide/DCM to afford compound 96 (0.017 g, 27%). $^1$HNMR (CDCl$_3$, 400 MHz) 8.80 (s, 1H), 7.51-7.46 (m, 6H), 7.39-7.26 (m, 5H), 7.15 (s, 1H), 6.81 (d, 1H). 3.97 (s, 3H), 2.51 (s, 3H); MS (M+1)$^+$ m/z calcd for C$_{25}$H$_{20}$FN$_3$O$^+$=398.1. found m/z =398.2.

EXAMPLE 100

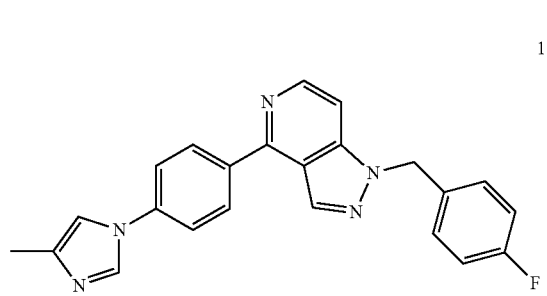

Step A: 4-chloro-1-(4-fluorobenzyl)-1H-pyrazolo[4,3-c]pyridine

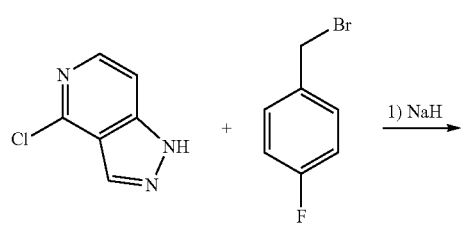

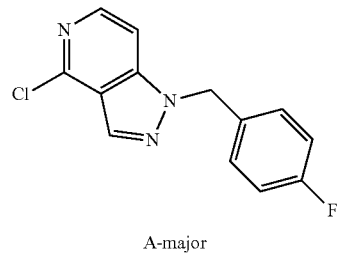

A-major

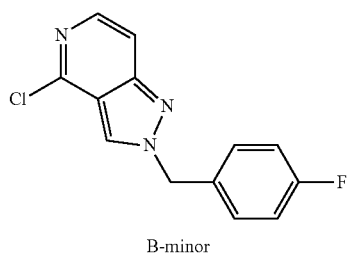

B-minor

To 4-chloro-1H-pyrazolo[4,3-c]pyridine (60 mg, 0.40 mmol) in 2 ml DMF was added 4-Fluorobenzylbromide (0.060 ml, 0.48 mmol) then add NaH (20 mg, 0.4 mmol) and stir at room temperature overnight. Work up by adding water and EtOAc and extract three times with EtOAc. Pool all organics and wash one time with brine then dry over sodium sulfate, filter and concentrate to dryness. The residue was purified by chromatography over silica gel (eluted with Hexanes/EtOAc 99:1 to 50:50) to provide 38 mg of major isomer A and 15 mg of minor isomer B.

Step B: 1-(4-fluorobenzyl)-4-(4-(4-methyl-1H-imidazol-1-yl)phenyl)-1H-pyrrolo[2,3-b]pyridine

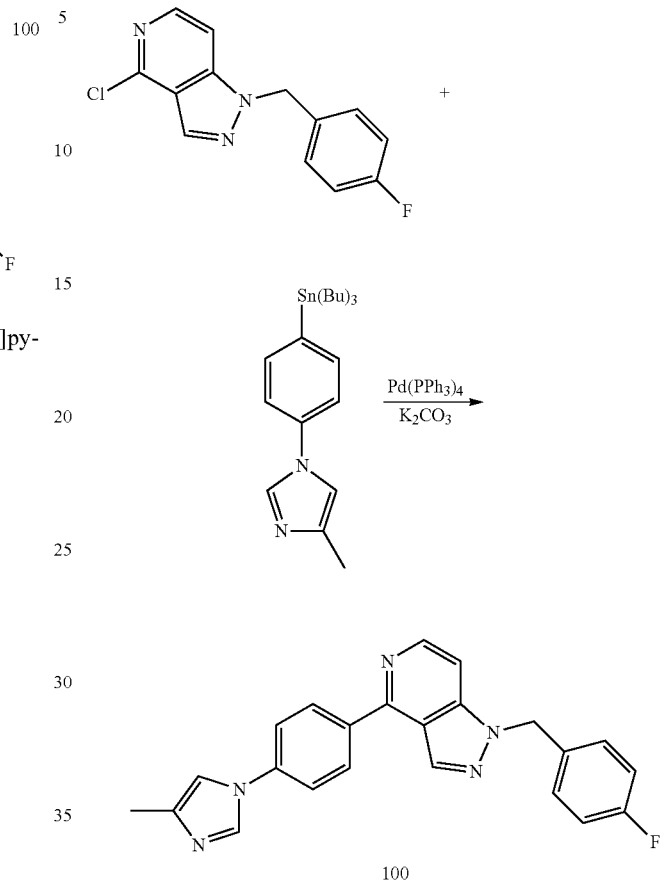

To 4-chloro-1-(4-fluorobenzyl)-1H-pyrazolo[4,3-c]pyridine, isomer A-major; (33 mg, 0.15 mmol), 4-methyl-1-(4-(tributylstannyl)phenyl)-1H-imidazole (100 mg, 021 mmol) and Potassium carbonate (100 mg, 0.7 mmol) was added 3 ml Toluene followed by Pd(PPh3)4 (20 mg, 0.014 mmol) then heat to 120 C for 2 hrs. The reaction was worked up by cooling to RT then adding water and DCM. Extract aqueous layer 3×DCM, then dry over sodium sulfate and filter and concentrate to dryess. The residue was purified by chromatography over silica gel (eluted with DCM/MeOH 99:1 to 90:10) to provide 5.8 mg (10%) of product 100. $^1$H NMR (CDCl$_3$ 400 MHz): 8.49-8.50 (d, 1H), 8.35 (s, 1H), 7.80 (s, 1H), 7.76 (s, 1H), 7.67-7.68 (d, 1H), 7.42-7.44 (d, 2H), 7.24-7.26 (m, 3H), 7.00-7.22 (m, 3H), 5.60 (s, 2H), 3.97 (s, 3H), 2.32 (s, 3H). LCMS (MH$^+$)=414; retention time=1.76 min.

Following procedures similar to those in Example 100, all other compounds in the table below with this core

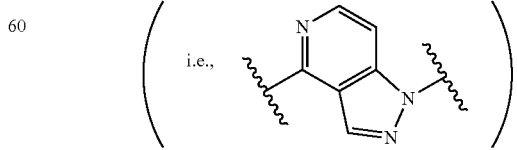

were prepared.

EXAMPLE 101

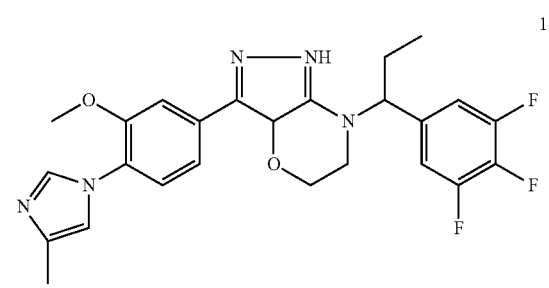

Step A:

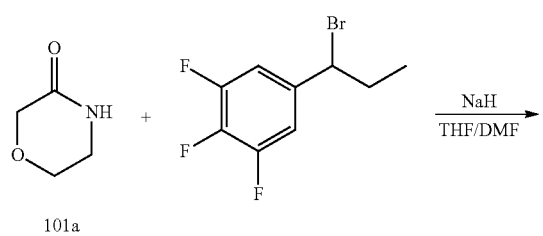

To a solution of 101a (1 g, 9.89 mmol) in THF/DMF (20/5 ml) was added NaH (60%, 0.435 g, 10.88 mmol) at 0° C. and stirred for 10 min, followed with addition of 3,4,5-trifluoro alpha-methyl benzyl bromide (3.1 g, 12.36 mmol). The resulting mixture was stirred overnight, then quenched with saturated aqueous NH₄Cl, extracted with EtOAc (3×). The combination of organic layers was washed with brine, dried (Na₂SO₄), concentrated and purified by flash chromatography to afford product 101b as colorless oil (2.15 g).

Step B:

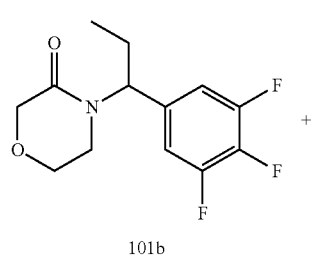

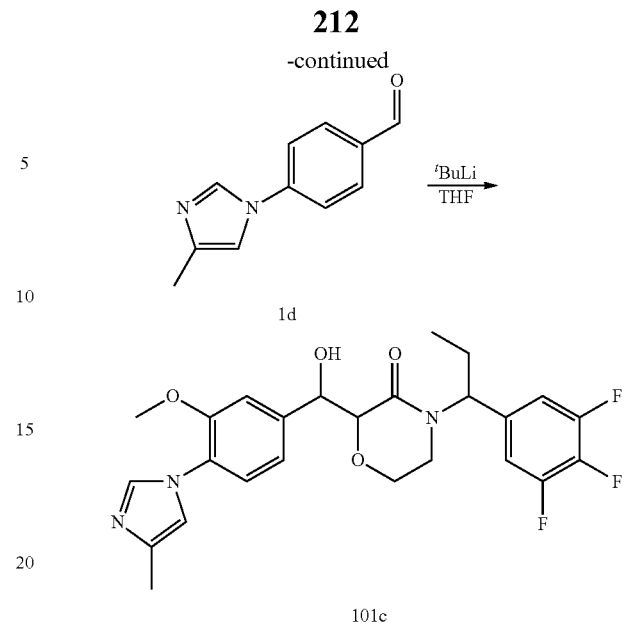

To a solution of 101b (1.0 g, 3.66 mmol) in THF (12 ml) was added ᵗBuLi (1.7M in THF, 13.23 ml, 22.5 mmol) at −78° C. and stirred for 45 min, followed with addition of 1d (0.816 g, 3.84 mmol). The resulting mixture was stirred overnight, then quenched with saturated aqueous NH₄Cl, extracted with EtOAc (3×). The combination of organic layers was washed with brine, dried (Na₂SO₄), concentrated and purified by flash chromatography to afford product 101c as colorless oil (1.15 g).

Step C:

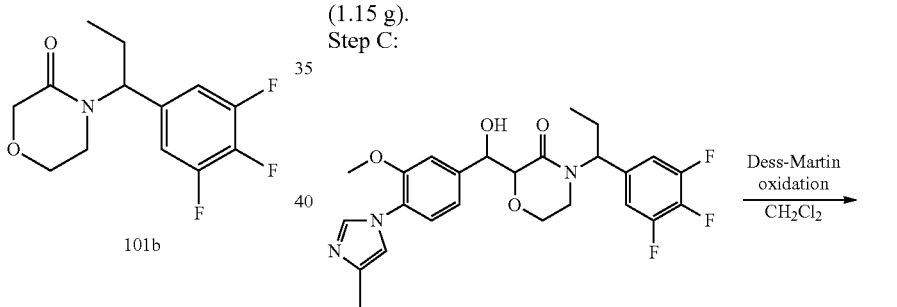

To a solution of 101c (0.5 g, 1.02 mmol) in CH₂Cl₂ (10 ml) was added Dess-Martin periodinane (0.605 g, 1.43 mmol) at room temperature. The resulting mixture was stirred for 2 hours at room temperature. The mixture was diluted with saturated aqueous Na₂S₂O₃ and EtOAc. The organic phase was washed with NaHCO₃ solution. The combination of organic layers was washed with brine, dried (Na₂SO₄), concentrated and purified by flash chromatography to afford product 101d as off-white solid (0.45 g).

Step D:

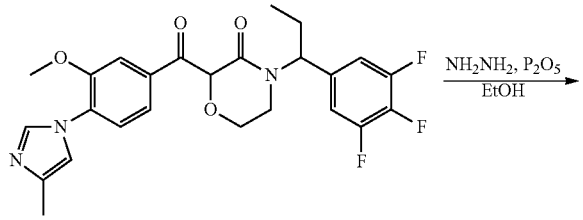
101d

NH$_2$NH$_2$, P$_2$O$_5$
———————→
EtOH

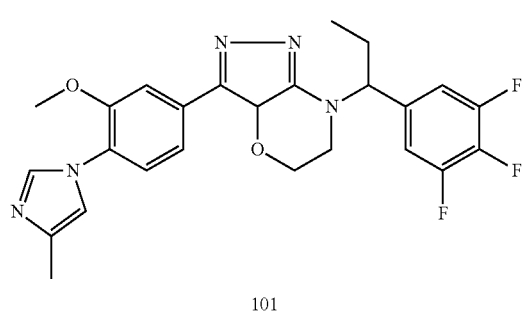
101

A mixture of 101d (0.45 g), P$_2$O$_5$ (2.6 g) in EtOH (10 ml) was heated at 80° C. overnight. Then it was concentrated under vacuum and the residue was taken into CH$_2$Cl$_2$ and washed by 10% NaOH, brine, and dried (Na$_2$SO$_4$), concentrated and purified by flash chromatography (CH$_2$Cl$_2$:MeOH) to afford product 101 as colorless oil. ES-LCMS (M+1): 484.3.

EXAMPLE 120

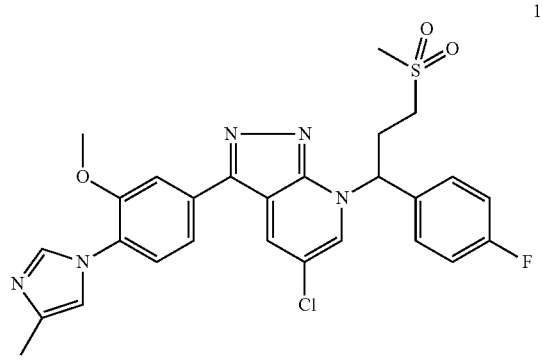
120

Step A:

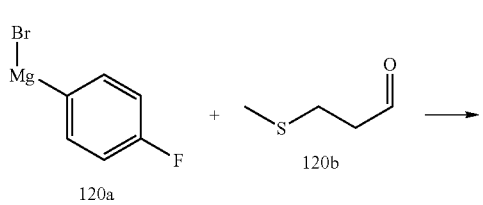
120a    120b

-continued

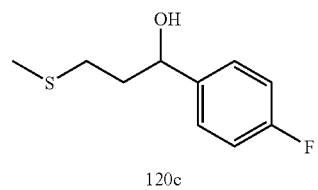
120c

The solution of 120b (4.16 g, 40.0 mmol) in THF (12 ml) was cooled in an ice bath, Grignard solution 120a (1M in THF, 48 ml, 48 mmol) was added dropwise, and the reaction was kept stirring at 0° C. for 2 h, EtOAc (150 ml) and NH$_4$Cl (sat. 80 ml) were added, and the aqueous layer was extracted once more with EtOAc (80 ml), the combined organic was washed with brine (80 ml) dried over anhydrous MgSO$_4$, and concentrated. The residue was purified ISCO (EtOAc-Hexane=1:5) to obtain 120c as a clear liquid.

Step B:

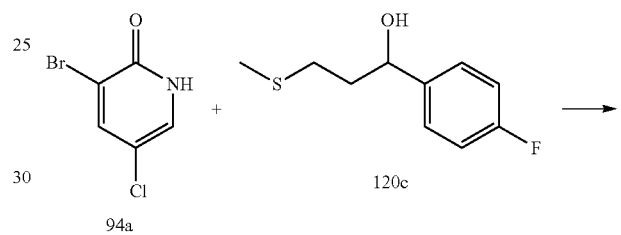
94a    120c

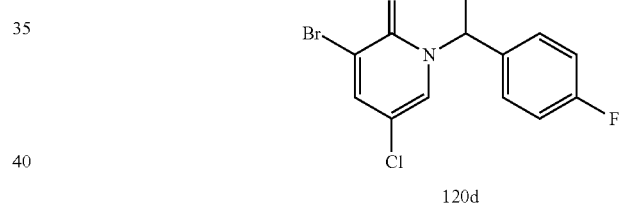
120d

The mixture of 94a (4.53 g, 218 mmol) and 120c (3.63 g, 18.1 mmol) in THF (70 ml) was stirring at 0° C., PBu$_3$ (6.3 ml, 27.2 mmol) was added dropwise to the mixture, the mixture was stirring at 0° C. for 0.5 h before the addition of ADDP (6.3 g, 27.2 mmol). The resultant mixture was kept stirring at 0° C. for 0.5 h, the slowly warmed up to 80° C., and kept stirring at 80° C. for 48 h. The mixture was cooled to RT, the white precipitate was filtered off, the filtrate was concentrated and purified via ISCO (EtOAc-Hexane=1:6) to obtain 120d as a light yellow syrup. (2.21 g). MH$^+$392/390

Step C:

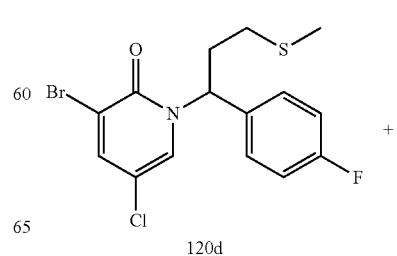
120d

+

-continued

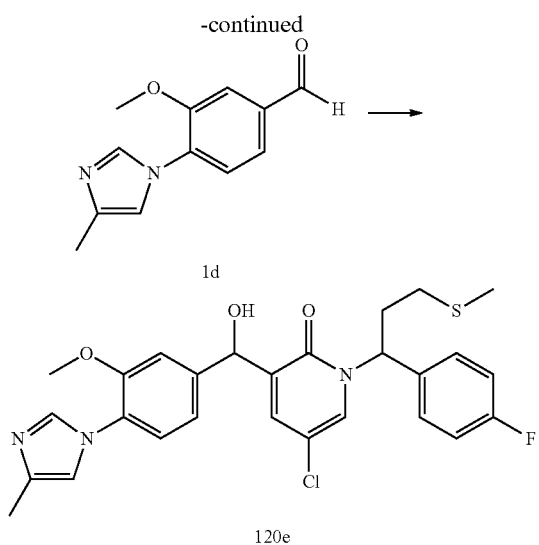

The solution of 120d (2.20 g, 5.64 mmol) in THF (20 ml) in ice-H$_2$O bath was added IprMgCl LiCl (1.3M in THF) solution (5.64 ml, 7.73 mmol), the mixture was kept stirring for 30 min at 0° C. before the addition of compound 1d (1.34 g, 6.20 mmol), the resultant mixture was kept stirring at 0° C. for 2 h. EtOAc (30 ml) and NH$_4$Cl (10 ml) were added, the aqueous was extracted once more with EtOAc (15 ml). The combined organic was washed with brine (15 ml), dried over anhydrous MgSO$_4$, and concentrated. The residue was purified via ISCO (DCM/MeOH (2N NH$_3$)=50:1->25:1) to 120e as a yellow solid (1.41 g). MH$^+$ 529

Step D:

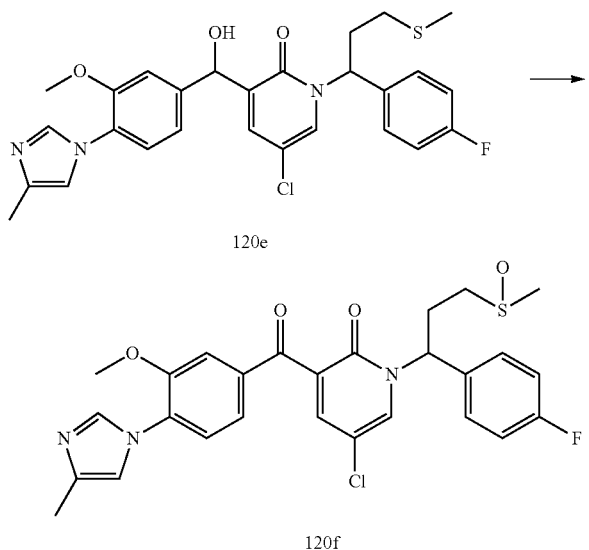

Dess-Martin Periodinane (120 mg, 0.284 mmol) was added to the solution of 120e (100 mg, 0.190 mmol) in DCM (4 ml), the resultant mixture was kept stirring at R.T. for 16 h. DCM (10 ml) and Na$_2$S$_2$O$_3$ (sat. 10 ml) were added, the aqueous was extracted once more with DCM (20 ml). The combined organic was washed with NaHCO$_3$ (sat. 3×10 ml), dried over anhydrous MgSO$_4$, and concentrated. The residue was purified via ISCO (DCM/MeOH (2N NH$_3$)=50:1->25:1) to obtain 120f as a yellow foam, MH$^+$ 542.

Step E:

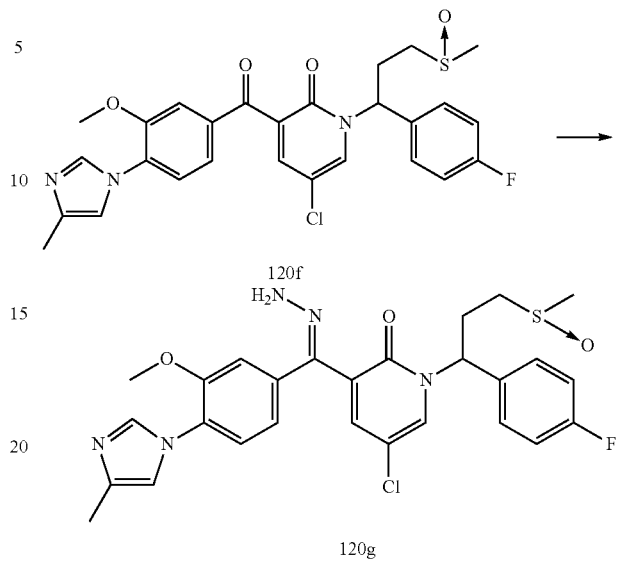

The solution of 120f (870 mg, 1.60 mmol) in EtOH (8 ml) was added to the solid P$_2$O$_5$ (910 mg, 6.42 mmol), the resultant mixture was kept stirring at R.T. for 10 min before the addition of anhydrous hydrazine (512 µl, 16.0 mmol), and the mixture was kept stirring at 80° C. for 2 h. The organic solvent was removed, the residue was partitioned between EtOAc (50 ml) and NaHCO$_3$ (30 ml) were added, the aqueous was extracted once more with EtOAc (40 ml). The combined organic was dried over anhydrous MgSO$_4$, and concentrated. The residue, 120g (900 g) MH$^+$ 557, a yellow foam was used directly into the next step.

Step F:

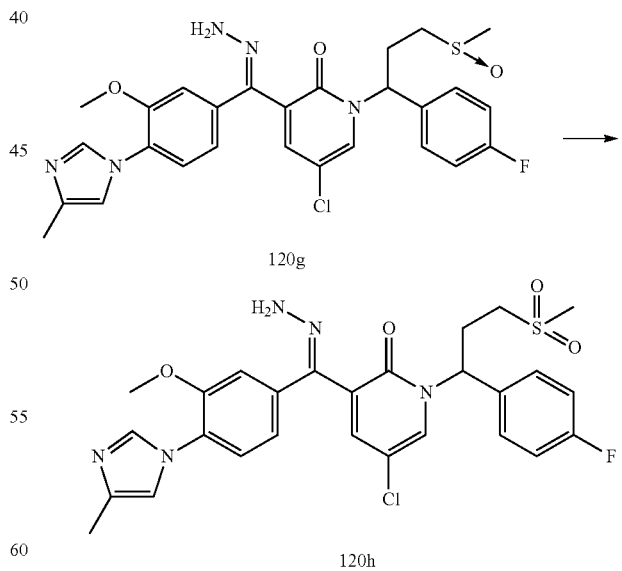

m-CPBA (76 mg, 0.368 mmol) was added to the solution of 120g (85 mg, 0.153 mmol) in DCM (1 ml), and the mixture was kept stirring at RT for 2 h. (CH$_3$)$_2$S (1 ml) was added, the solvent was removed, diluted with DCM (3 ml), washed with NaHCO$_3$ (sat. 2 ml) and brine (2 ml), respectively, dried over anhydrous MgSO₄, and concentrated. The residue was purified via ISCO (DCM/MeOH (2N NH₃)=50:1->25:1) to obtain 120h (82 mg) as a yellow foam, MH⁺ 559.
Step G:
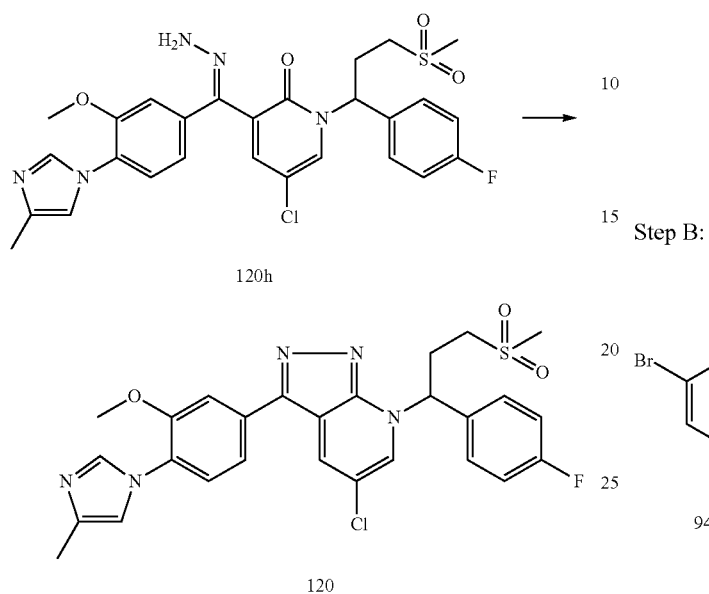
Compound 120h was converted to title compound 120 using a similar procedure as for Example 94, Step E.
EXAMPLE 126
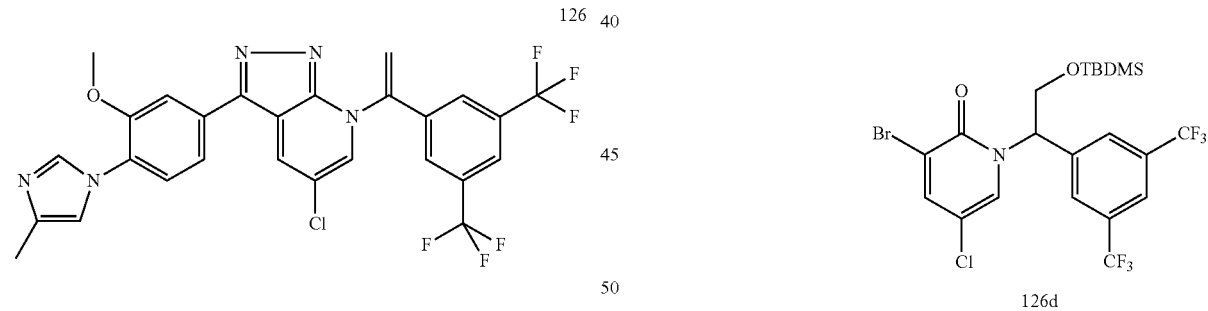
Steps A-D: were similar to the procedure for Example 120, Steps A-D.
Step A:
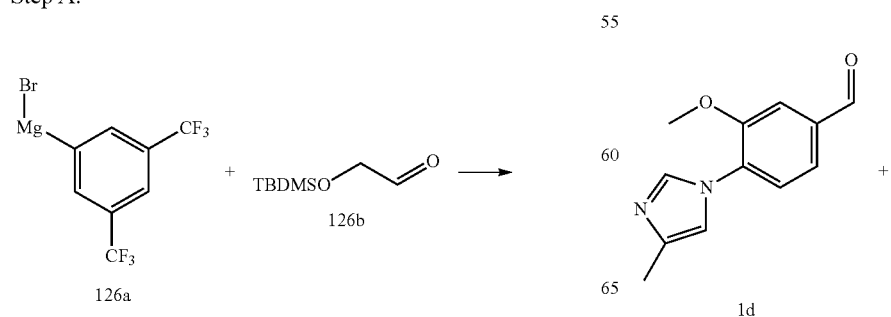
Step B:
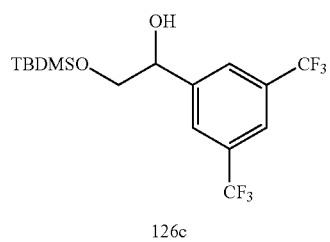
Step C:

-continued
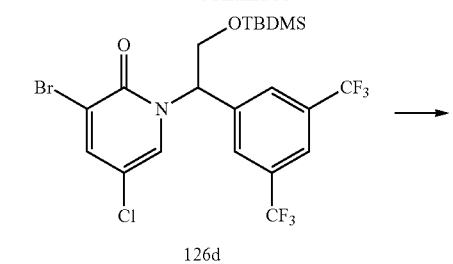
126d
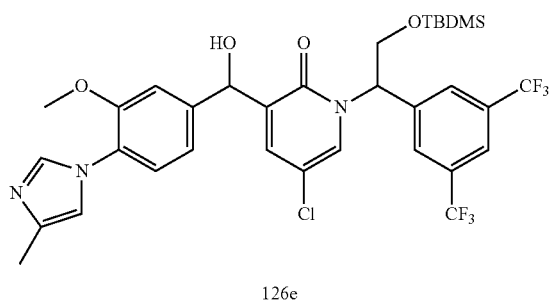
126e
Step D:
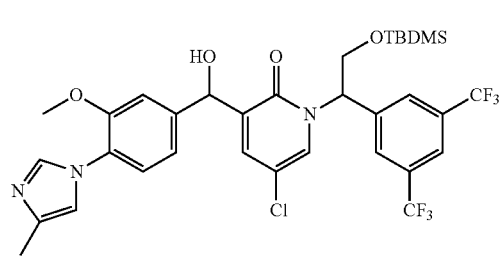
126e
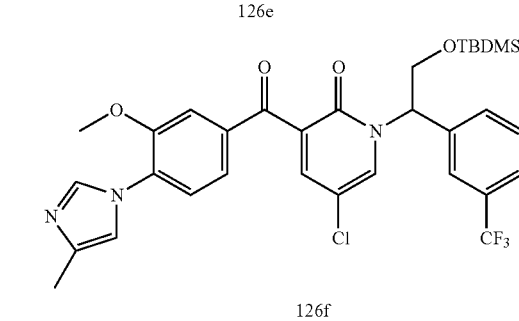
126f
Step E
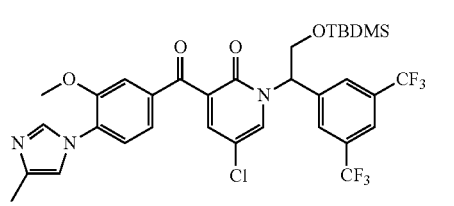
126f
-continued
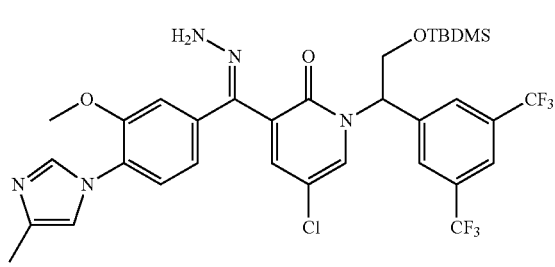
126g
+
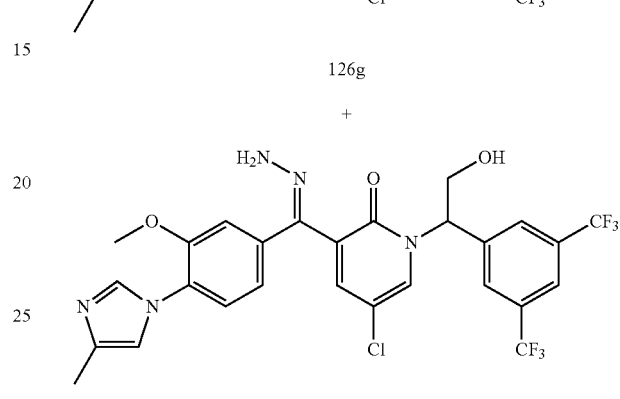
126h
Step E was a similar procedure as for Example 94, step D.
Step F:
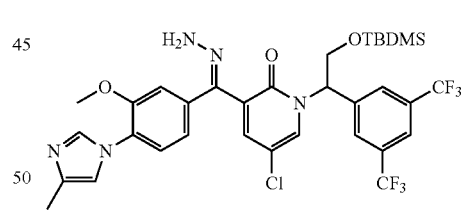
126g
+
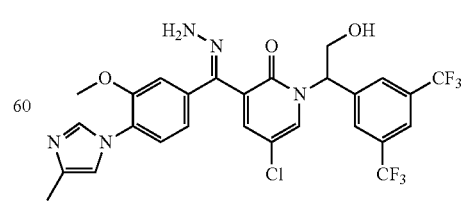
126h

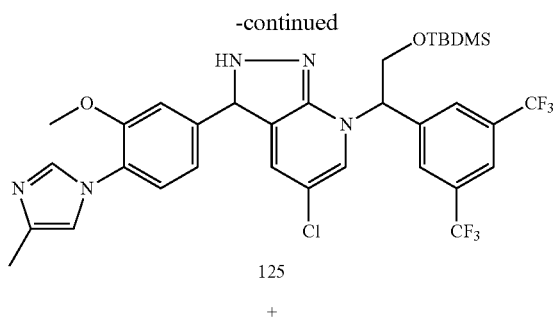

125

+

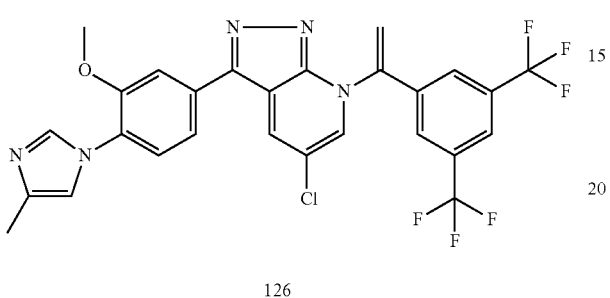

126

The mixture of 126g and 126h was converted to corresponding 125 (MH+ 711) and title compound 126 (MH+ 578), using a similar procedure as for Example 94, Step E.

Compounds 124, 155, and 156 were prepared in a similar manner as that of Example 126.

Compounds 64, 127, 132, and 158 were synthesized from compounds 63, 125, 131, and 157 by desilylation with TBAF, respectively.

EXAMPLE 128

Step A:

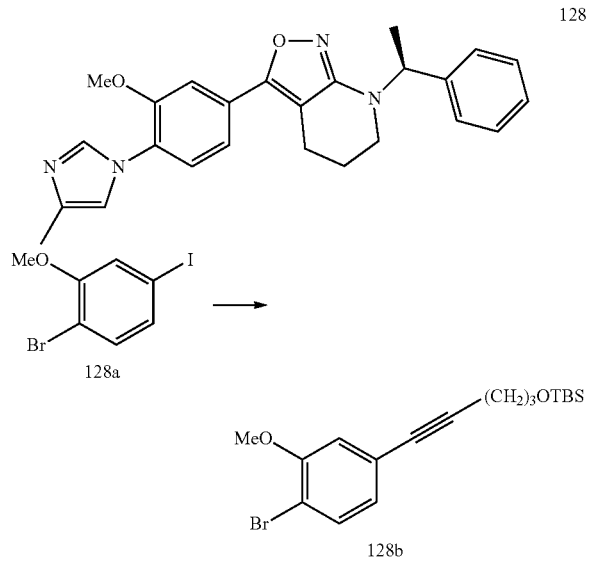

To a solution of 128a (31.5 gm, 101 mmol) in 100 mL THF were added 4-pentyn-1-ol (1.1 equiv., 111.4 mmol, 10.3 mL), PdCl$_2$(PPh$_3$)$_2$ (0.02 equiv., 2 mmol, 1.4 gm), CuI (0.04 equiv., 4 mmol, 0.769 gm), DIEA (4 equiv., 404.8 mmol, 70 mL), and the resulting solution was degassed and stirred at room for 12 hours or until the reaction completed. The reaction mixture was filtered through a pad of celite and evaporated to dryness. To this crude reaction product in 100 mL dichloromethane were added 18 gm of TBSCl and 10.3 gm of imidazole at 0° C. The ice bath was removed and the resulting solution was stirred for 2 hours at room temperature. Upon completion of the reaction, the reaction mixture was evaporated to dryness and loaded into column and purified using ethyl acetate in hexanes to obtain the 40 gm of 128b in 99% yield. $^1$H NMR: 7.43 (d, J=8 Hz, 1H), 6.88-6.83 (m, 2H), 3.85 (s, 3H), 3.73 (t, J=5.9 Hz, 2H), 2.46 (t, J=7 Hz, 2H), 1.78 (m, 2H), 0.89 (s, 9H), 0.08 (s, 6H).

Step B:

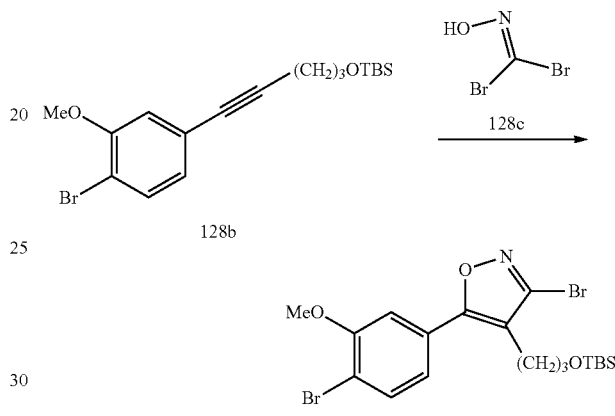

To a solution of alkyne 128b (40 gm, 104 mmol) in 100 CH$_2$Cl$_2$ were added 21 gm of 128c (1 equiv., 104 mmol) and NaHCO$_3$ (2 equiv., 17 gm). The resulting solution was heated at 50° C. for 24 hours. TLC indicated presence of starting material. Additional 21 gm of 3 and 17 gm of NaHCO$_3$ were added and the resulting mixture was heated for additional 48 hours at 50° C. The reaction mixture was evaporated to dryness. Purification using dichloromethane in hexanes followed by recrystallization from hexanes provided compound 128d in 30% yield. $^1$H NMR: 7.61 (d, J=8.38 Hz, 1H), 7.18 (m, 2H), 3.94 (s, 3 H), 3.67 (t, J=6 Hz, 2H), 2.69 (m, 2H), 1.77 (m, 2H), 0.88 (s, 9H), 0.039 (s, 6H).

Step C:

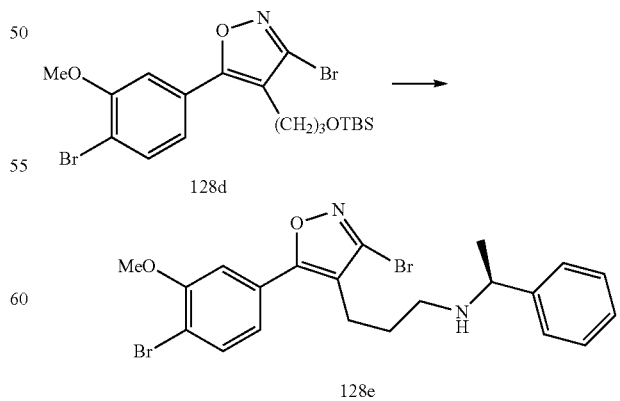

To a solution of 128d (1.7 gm, 3.51 mmol) in 10 mL THF was added 2 mL HF-pyridine (70%) at 0° C. After 30 minutes the TLC indicated the completion of the reaction. Excess of triethyl amine was added and the reaction mixture was evaporated to dryness and loaded into column and purified by ethyl in hexanes to yield the corresponding alcohol in 99% yield. This alcohol was taken for swern oxidation in next step.

To a solution of (COCl)$_2$ (2 equiv., 0.091 mL, 1.08 mmol) in 2 mL dichloromethane was added a solution of DMSO (4 equiv., 0.151 mL, 2.16 mmol) in 0.5 mL dichloromethane at −78° C. The resulting solution was stirred at −78° C. for 5 minutes. Then a solution of alcohol (1 equiv., 0.2 gm, 0.542 mmol) in 0.5 mL dichloromethane was added slowly into the reaction mixture. The resulting solution was stirred for 30 minutes at that temperature before addition of triethyl amine (10 equiv., 0.754 mL, 5.42 mmol). After the addition of triethyl amine the reaction mixture was stirred for 10 minutes at −78° C., then warmed to 0° C. and stirred for additional 10 minutes and finally warned to room temperature and stirred for another 10 minutes. At this moment the reaction mixture was diluted with water and extracted with ether, and the organic layer was dried with MgSO$_4$, evaporated and taken to the next step directly without further purification.

To this aldehyde (170 mg, 0.463 mmol) in 2 mL dichloromethane were added α-methyl benzyl amine (1.1 equiv., 0.064 mL, 0.509 mL) and MgSO$_4$ (0.55 gm) and the resulting reaction mixture was stirred at room temperature for 3 hours or until the reaction completed. Upon completion of the reaction, the reaction mixture was filtered, and the filtrate was evaporated to yield the crude imine. This crude imine was taken directly for the next step.

To this solution of imine in 2 mL methanol was added 17 mg of NaBH$_4$ at 0° C. The resulting solution was stirred at 0° C. for 30 minutes or until the reaction completed. Water was added and then the reaction mixture was stirred for another 10 minutes. The resulting solution was evaporated to dryness and load into column and purified using methanol in dichloromethane to provide the amine 128e in 80% yield. $^1$H NMR: 7.61, 1H, 7.32, 2H, 7.26, 2H, 7.24, 1H, 7.19, 1H, 7.15, 1H, 3.91, 3H, 3.71, 1H, 2.69, 1H, 2.57, 2H, 2.47, 1H, 1.73, 2H, 1.33, 3H)

Step D:

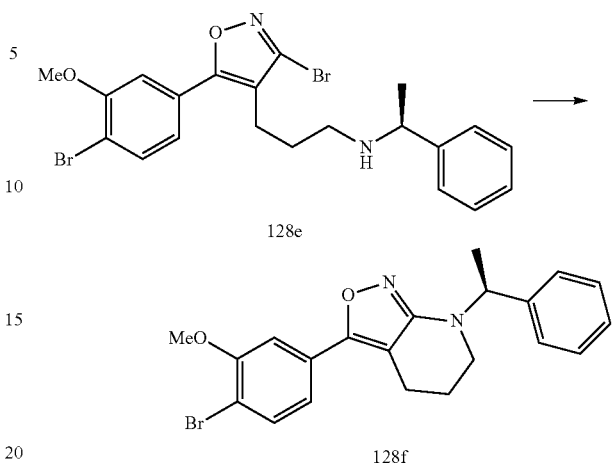

To a solution of 128e in 5 mL CH$_3$CN was added 0.227 mL BEMP and the resulting solution was heated at 180° C. for 4 hours in microware. The resulting solution was evaporated to dryness and purified using ethyl acetate in hexanes to yield 128f in 15% yield. $^1$H NMR: 7.57 (d, J=7.94, 1H), 7.40-7.24 (m, 6H), 7.07 (dd, J=8.1 Hz, J=1.84 Hz), 5.36 (q, J=6.9 Hz, 1H), 3.92 (s, 3H), 3.05 (m, 1H), 2.86 (m, 1H), 2.71 (m, 2H), 1.85 (m, 2H), 1.59 (d, J=7.2 Hz, 3H).

Step E:

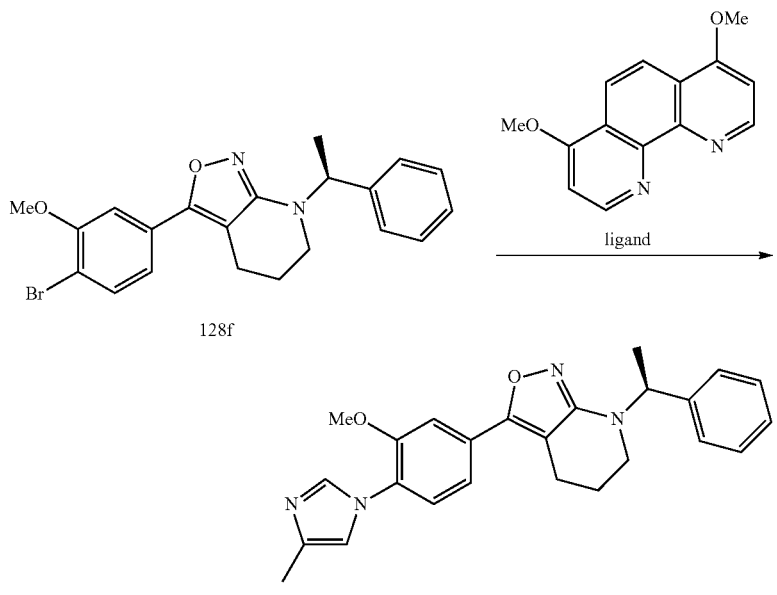

To a solution of 128f (15 mg, 0.036 mmol) in 0.2 ml butyronitrile were added 4-methyl imidazole (3.5 mg), Cu$_2$O (2.4 mg), Cs$_2$CO$_3$ (16 mg), ligand (4 mg) PEG (10 μg) and the resulting mixture were heated at 110° C. for 40 hours. At this time, the reaction mixture was evaporated to dryness and purified using ethyl acetate in hexanes to provide the 128 in 30% yield. $^1$H NMR: 8.74 (br, 1H), 7.48 (s, 1H), 7.40-7.26 (m, 7 Hz), 7.09 (s, 1H), 5.36 (q, J=6.9 Hz, 1H), 3.94 (s, 3H), 3.14 (m, 1H), 2.90 (m, 1H), 2.75 (m, 2H), 2.46 (s, 3H), 1.88 (2H), 1.61 (d, J=6.9 Hz, 3H).

EXAMPLE 137

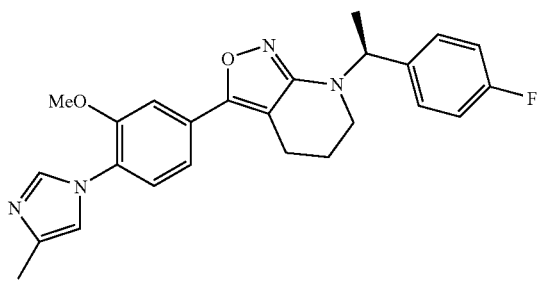

137

Compound 137 was made following the similar sets of reaction procedure as described for Example 128. $^1$H NMR: 7.78 (s, 1H), 7.41-7.24 (m, 5H), 7.03-6.94 (m, 3H), 5.33 (q, J=6.5 Hz, 1H), 3.89 (s, 3H), 3.10 (m, 1H), 2.87-2.73 (m, 3H), 2.29 (s, 3H), 1.85 (m, 2H), 1.58 (d, J=6.9 Hz, 3H).

EXAMPLE 134

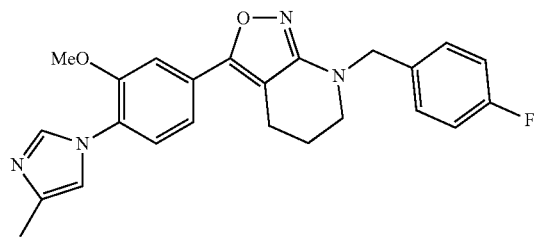

134

Step A:

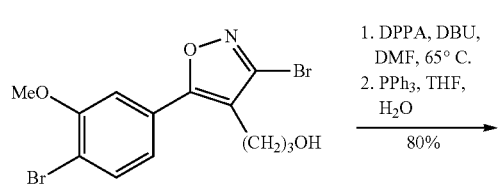

134a

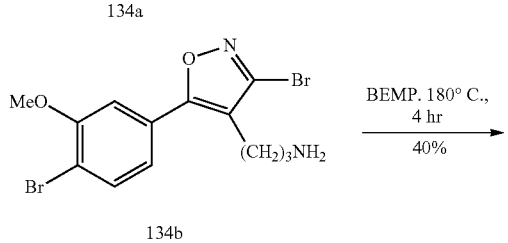

134b

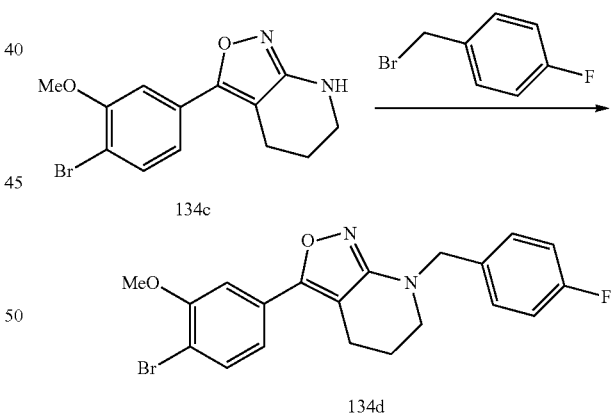

To a solution of alcohol 134a (377 mg, 0.97 mmol, 1 equiv.,) in 2 mL DMF were added DPPA (1.2 equiv., 1.16 mmol, 0.251 mL) and DBU (1.2 equiv., 1.16 mmol, 0.174 mL) and the resulting solution was heated at 65° C. for 3 hour. Upon completion of the reaction the reaction mixture was diluted with ether, the organic layer was washed with water, dried with MgSO$_4$, concentrated, evaporated and purified using ethyl acetate in hexanes to yield the azide. To this azide in 2 mL THF was added triphenyl phosphine and stirred at room temperature until the starting material disappeared. Then, 0.2 mL water was added and heated at 70° C. until the imine hydrolysis was complete. The reaction mixture was evaporated to dryness and purified using methanol in dichloromethane to provide the amine 134b in 80% yield. $^1$H NMR: 7.63 (d, J=8.5 Hz, 1H), 7.15 (m, 2H), 3.94 (s, 3H), 2.74 (t, J=6.72 Hz, 2H), 2.66 (t, J=7.7 Hz, 2H), 1.69 (m, 2H). To this amine (0.77 mol) in 2 mL butyronitrile was added BEMP (1.2 equiv., 0.92 mmol) and the resulting solution was heated at 180° C. for 4 hours in microwave. The reaction mixture was evaporated to dryness and purified using ethyl acetate in hexanes to provide 134c in 40% yield. $^1$H NMR: 7.58 (d, J=8.14 Hz, 1H), 7.25 (d, 1.8 Hz, 1H), 7.08 (dd, J=8.1 Hz, J=1.8 Hz, 1H), 4.42 (br-s), 3.93 (s, 3H), 3.32 (m, 2H), 2.79 (t, J=7.52 Hz, 2H), 1.95 (m, 2H).

Step B:

To a solution of 11 in 4.5 mL, THF was added KHMDS (0.5 M. 1.2 equiv., 0.845 mmol, 1.69 mL) at 0° C. The resulting solution was stirred at 0° C. for 45 minutes. Then the ice bath was removed and the resulting solution was stirred at room temperature for 15 minutes before cooling down to 0° C. At this moment a solution of p-fluoro benzyl bromide in 1 mL THF was added slowly through the side of the wall. The resulting solution was stirred over 12 hours with slowly warming up to room temperature. Saturated NH$_4$Cl (2 mL) was added, resulting solution was extracted with ethyl acetate, dried with MgSO$_4$, concentrated, evaporated and purified using ethyl acetate in hexanes to provide 12 in 60% yield. ¹H NMR 7.56 (d, J=7.9 Hz, 1H), 7.33-7.24 (m, 3H), 7.0-6.9 (m, 3H), 4.48 (s, 2H), 3.92 (s, 3H), 3.09 (m, 2H), 2.74 (t, J=6.6 Hz, 2H), 1.94 (m, 2H).

Step C:

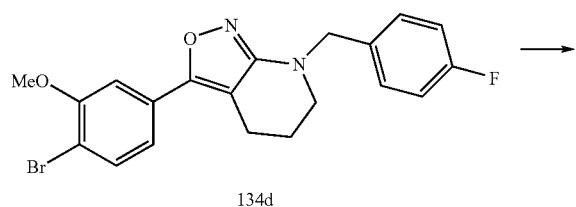

134d

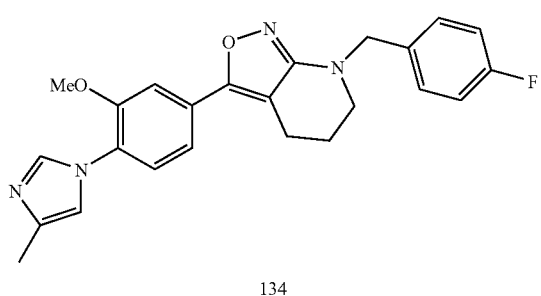

134

Compound 134 was made following the similar procedure as described for Compound 128 (step E). ¹H NMR: 7.74 (s, 1H), 7.41 (m, 1H), 7.37-7.24 (m, 4H), 7.02-6.92 (m, 3H), 4.5 (s, 2H), 3.89 (s, 3H), 3.11 (m, 2H), 2.79 (t, J=6.6 Hz), 2.28 (s, 3H), 1.96 (m, 2H).

Compound 146 in the table below was prepared using a similar sequence as 134.

Example 133

133

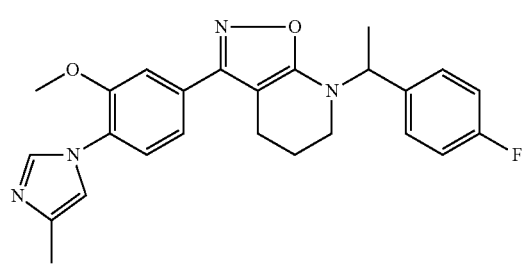

Step A:

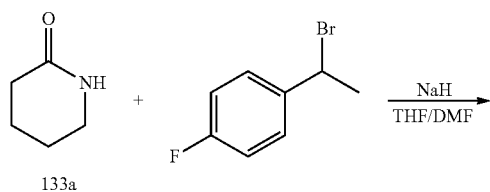

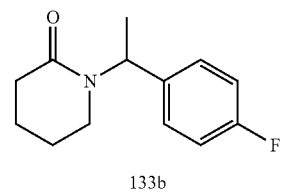

133b

To a solution of 133a (3.25 g, 32.80 mmol) in THF/DMF (25/25 ml) was added NaH (60%, 1.95 g, 49.25 mmol) at 0° C. and stirred for 10 min, followed with addition of 4-fluoro alpha-methyl benzyl bromide (10.00 g, 49.25 mmol). The resulting mixture was stirred overnight, then quenched with saturated aqueous NH₄Cl, extracted with EtOAc (3×). The combination of organic layers was washed with brine, dried (Na₂SO₄), concentrated and purified by flash chromatography to afford product 133b as colorless oil (4.1 g, 56.6%).

Step B:

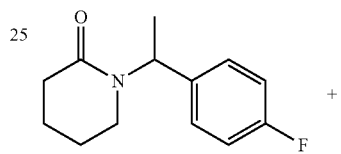

133b

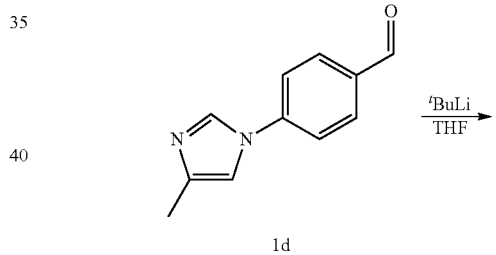

1d

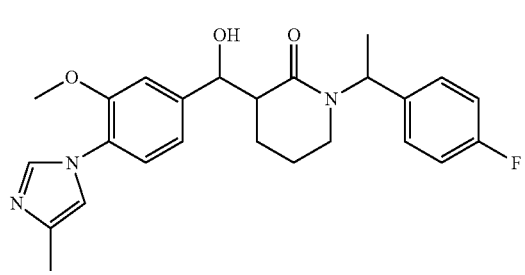

133c

To a solution of 133b (4.15 g, 18.80 mmol) in THF (50 ml) was added ᵗBuLi (1.7M in THF, 13.23 ml, 22.5 mmol) at −78° C. and stirred for 30 min, followed with addition of id (4.87 g, 22.50 mmol). The resulting mixture was stirred overnight, then quenched with saturated aqueous NH₄Cl, extracted with EtOAc (3×). The combination of organic layers was washed with brine, dried (Na₂SO₄), concentrated and purified by flash chromatography to afford product 133c as colorless oil (4.1 g, 49.9%).

Step C:

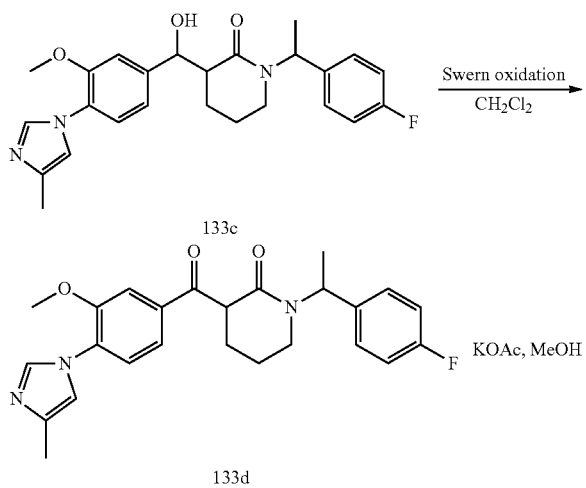

To a solution of DMSO (1.42 ml, 20.0 mmol) in CH₂Cl₂ (60 ml) was added (COCl)₂ (1.71 ml, 20 mmol) at −78° C. and stirred for 30 min, followed with addition of a solution of 133c (3.50 g, 8.0 mmol) in CH₂Cl₂ (10 ml). The resulting mixture was stirred for 50 min at 78° C., then quenched by Et₃N (6.68 ml, 48 mmol). The mixture was then stirred overnight and allowed to warm up to room temperature. Then it was quenched with saturated aqueous NH₄Cl, extracted with EtOAc (3×). The combination of organic layers was washed with brine, dried (Na₂SO₄), concentrated and purified by flash chromatography to afford product 133d as off-white solid (3.5 g, 94.6%).

Step D:

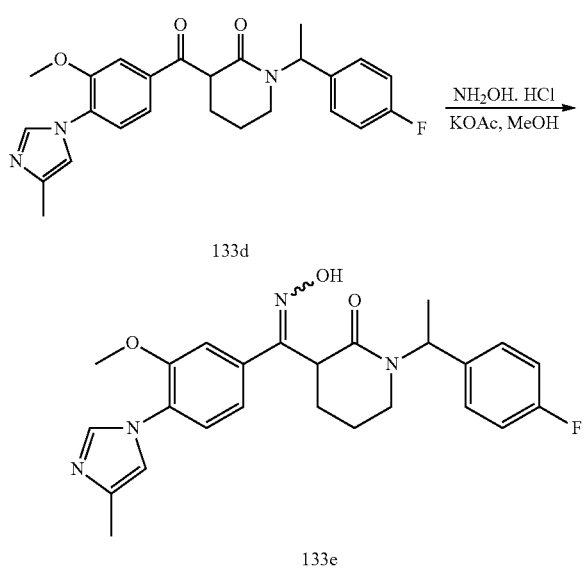

A mixture of 133d (200 mg, 0.46 mmol), NH₂OH·HCl (96 mg, 1.38 mmol) and KOAc (136 mg, 1.38 mmol) in MeOH (4.0 ml) was stirred at room temperature overnight. Then it was filtered to remove the solid and the filtrate was concentrated under vacuum and the residue was purified by flash chromatography to afford product 133e as off-white solid (150 mg, 72.5%).

Step E:

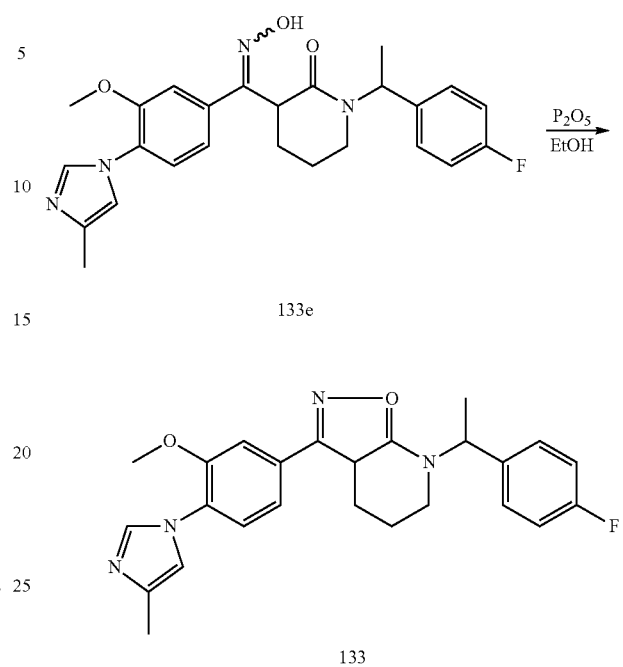

A mixture of 133e (1.0 g, 2.22 mmol), P₂O₅ (3.15 g, 22.2 mmol) in EtOH (25 ml) was heated at 80° C. overnight. Then it was concentrated under vacuum and the residue was taken into CH₂Cl₂ and washed by 10% NaOH, brine, and dried (Na₂SO₄), concentrated and purified by flash chromatography (CH₂Cl₂:MeOH) to afford product 133 as colorless oil (280 mg, 29%). ¹H NMR (CDCl₃, ppm): 7.54 (s, 1H), 7.43-7.33 (m, 4H), 7.12-7.06 (m, 2H), 7.02 (s, 1H), 5.39-5.30 (m, 1H), 3.96 (s, 3H), 3.30-3.19 (m, 1H), 3.06-2.96 (m, 1H), 2.75-2.65 (m, 2H), 2.37 (s, 3H), 2.04-1.84 (m, 2H), 1.70 (d, 3H); (ES-LCMS, M+1) 433.2. Retention time: 3.49 min.

Compounds 147 and 148 in the table below were prepared using a similar sequence as Example 133.

Compounds 2, 3, 35-40, 43-46, 49, 50, 59, 60, 87, 88, 93, 129, 130, 135, 136, 139-142, 149-154, and 159-162 in the table below were prepared from chiral HPLC resolution of their corresponding racemic products.

EXAMPLE 161

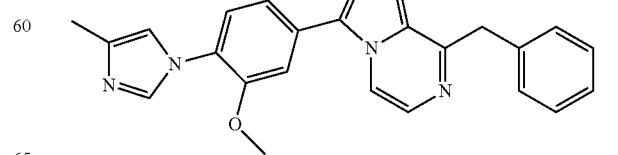

Step A:

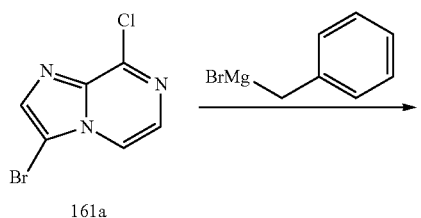

If one were to add 0.8 eq of benzylmagnesium bromide, in ether at −78 C with 5% Palladium tetrakistriphenylphosphine under Nitrogen, to compound 161a then one would obtain compound 161b after workup using techniques known in the art.

Step B:

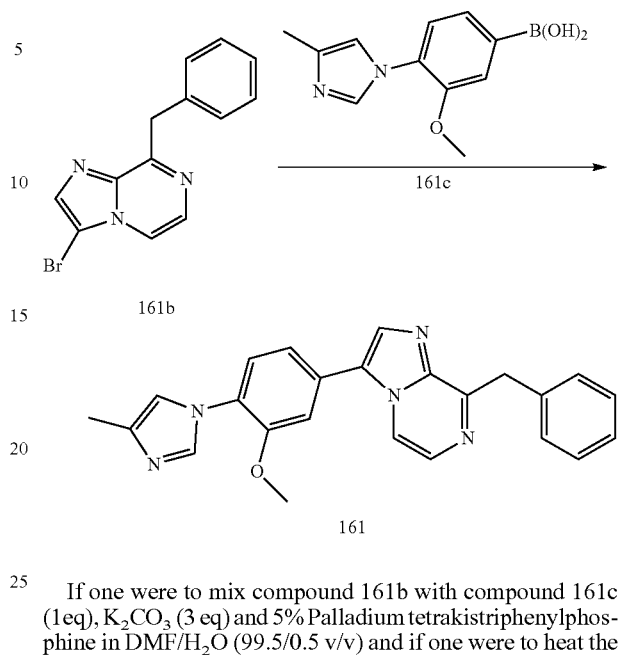

If one were to mix compound 161b with compound 161c (1eq), $K_2CO_3$ (3 eq) and 5% Palladium tetrakistriphenylphosphine in DMF/$H_2O$ (99.5/0.5 v/v) and if one were to heat the solution to 100° C. under microwave then one would obtain compound 161 after purification using techniques known in the art.

The table below gives observed LCMS data for compounds of the invention which compounds are obtained by the above methods. In the table "Cmpd" stands for "Compound", and "Obs" stands for "Observed".

| Cmpd | Structure | Obs LCMS |
|---|---|---|
| 1 | 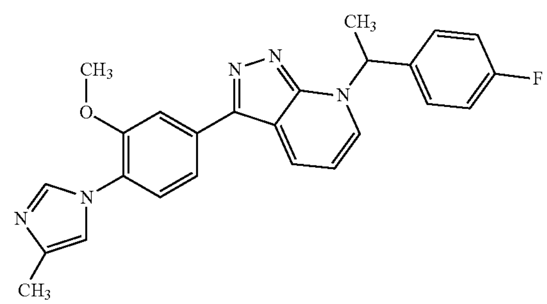 [SMILES: COc1cc(-c2nnc3n(C(C)c4ccc(F)cc4)cccc2-3)ccc1-n1cnc(C)c1] | 428.2 |
| 2 | 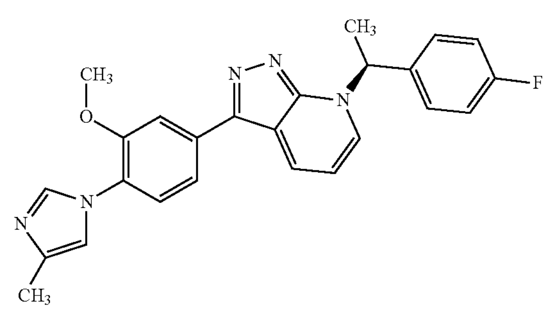 [SMILES: COc1cc(-c2nnc3n([C@@H](C)c4ccc(F)cc4)cccc2-3)ccc1-n1cnc(C)c1] | 428.2 |

-continued

| Cmpd | Structure | Obs LCMS |
|---|---|---|
| 3 | 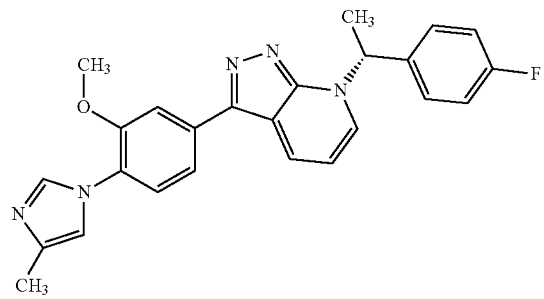 [SMILES: COc1cc(-c2nnc3n([C@H](C)c4ccc(F)cc4)cccc2-3)ccc1-n1cnc(C)c1] | 428.2 |
| 4 | 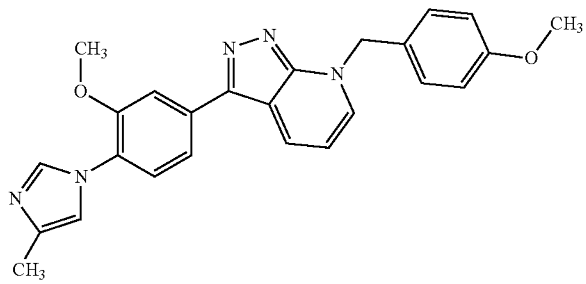 [SMILES: COc1ccc(Cn2cccc3c(-c4ccc(-n5cnc(C)c5)c(OC)c4)nnc2-3)cc1] | 426.2 |
| 5 | 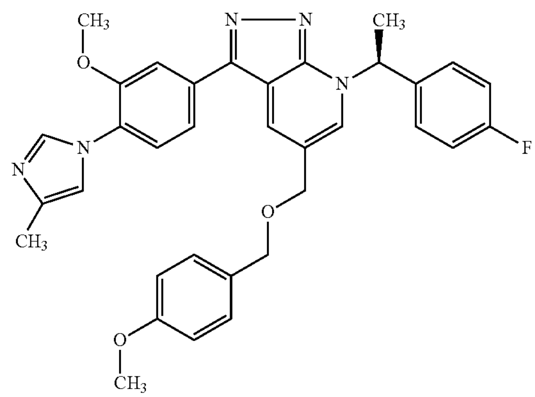 [SMILES: COc1ccc(COCc2cc3c(-c4ccc(-n5cnc(C)c5)c(OC)c4)nnc-3n([C@@H](C)c3ccc(F)cc3)c2)cc1] | 578.3 |
| 6 | 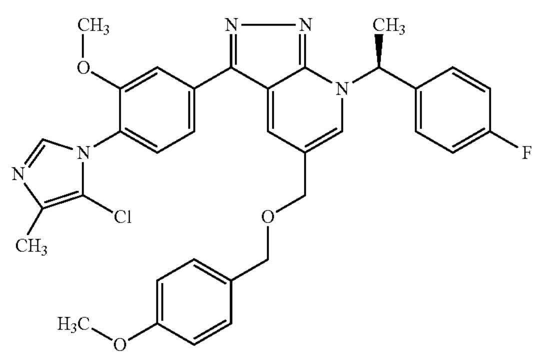 [SMILES: COc1ccc(COCc2cc3c(-c4ccc(-n5cnc(C)c5Cl)c(OC)c4)nnc-3n([C@@H](C)c3ccc(F)cc3)c2)cc1] | 612.3 |
| 7 | 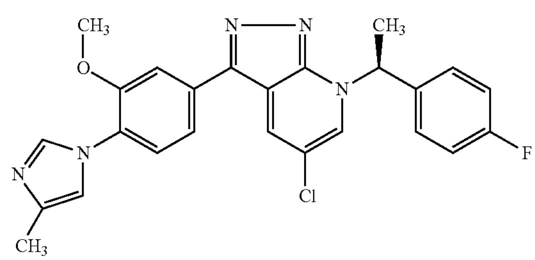 | 462.3 |

-continued

| Cmpd | Structure | Obs LCMS |
|---|---|---|
| 8 | 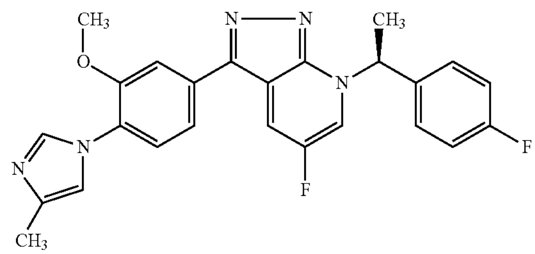 | 446.2 |
| 9 | 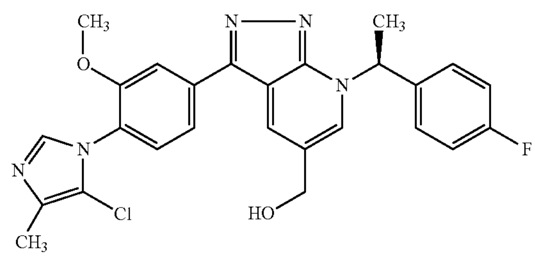 [SMILES: COc1cc(-c2nnc3n([C@@H](C)c4ccc(F)cc4)cc(CO)cc2-3)ccc1-n1cnc(C)c1Cl] | 492.3 |
| 10 | 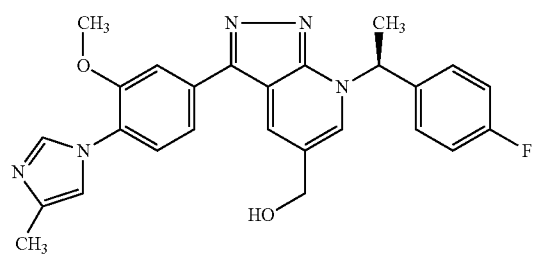 [SMILES: COc1cc(-c2nnc3n([C@@H](C)c4ccc(F)cc4)cc(CO)cc2-3)ccc1-n1cnc(C)c1] | 458.2 |
| 11 | 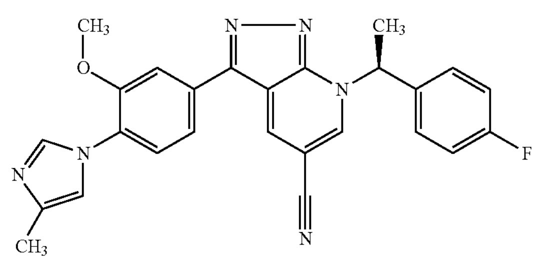 [SMILES: COc1cc(-c2nnc3n([C@@H](C)c4ccc(F)cc4)cc(C#N)cc2-3)ccc1-n1cnc(C)c1] | 453.2 |
| 12 | 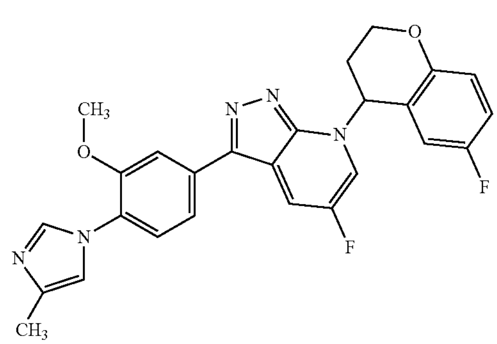 [SMILES: COc1cc(-c2nnc3n(C4CCOc5ccc(F)cc54)cc(F)cc2-3)ccc1-n1cnc(C)c1] | 474.3 |

| Cmpd | Structure | Obs LCMS |
|---|---|---|
| 13 | 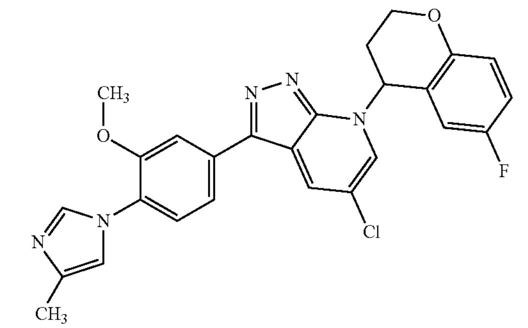 [SMILES: COc1cc(-c2nnc3n(C4CCOc5ccc(F)cc54)cc(Cl)cc2-3)ccc1-n1cnc(C)c1] | 490.3 |
| 14 | 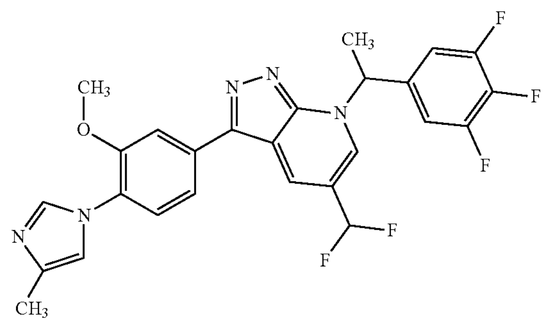 [SMILES: COc1cc(-c2nnc3n(C(C)c4cc(F)c(F)c(F)c4)cc(C(F)F)cc2-3)ccc1-n1cnc(C)c1] | 514.3 |
| 15 | 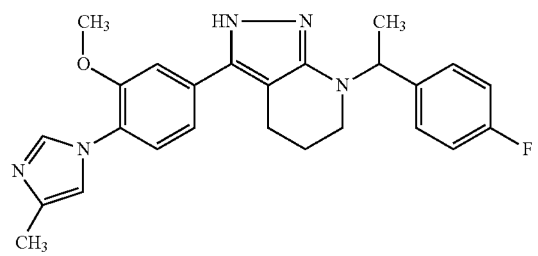 [SMILES: COc1cc(-c2[nH]nc3c2CCCN3C(C)c2ccc(F)cc2)ccc1-n1cnc(C)c1] | 432.2 |
| 16 | 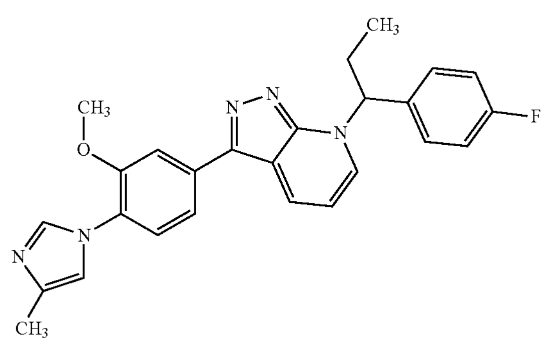 [SMILES: CCC(c1ccc(F)cc1)n1cccc2c(-c3ccc(-n4cnc(C)c4)c(OC)c3)nnc1-2] | 442.2 |
| 17 | 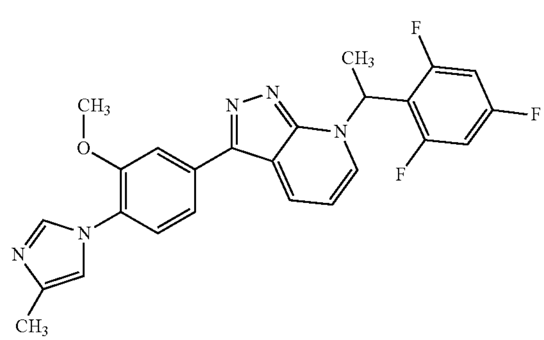 [SMILES: COc1cc(-c2nnc3n(C(C)c4c(F)cc(F)cc4F)cccc2-3)ccc1-n1cnc(C)c1] | 464.3 |

-continued

| Cmpd | Structure | Obs LCMS |
|---|---|---|
| 18 | 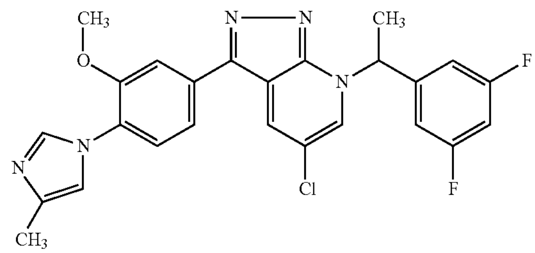 | 480.3 |
| 19 | 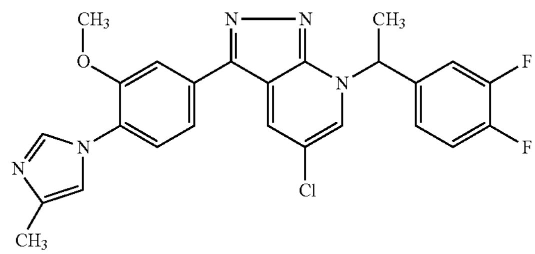 [SMILES: COc1cc(-c2nnc3n(C(C)c4ccc(F)c(F)c4)cc(Cl)cc2-3)ccc1-n1cnc(C)c1] | 480.3 |
| 20 | 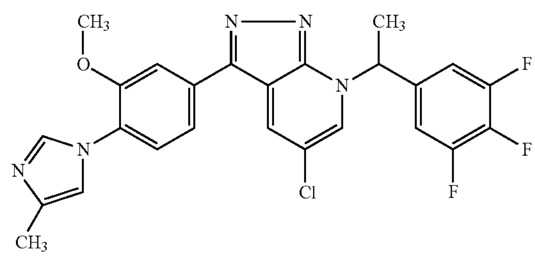 | 498.3 |
| 21 | 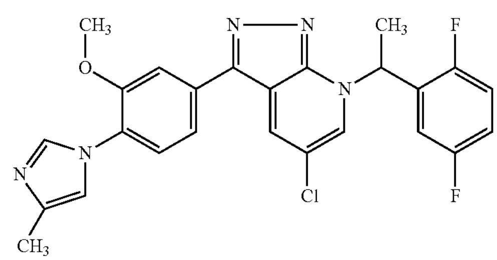 | 480.3 |
| 22 | 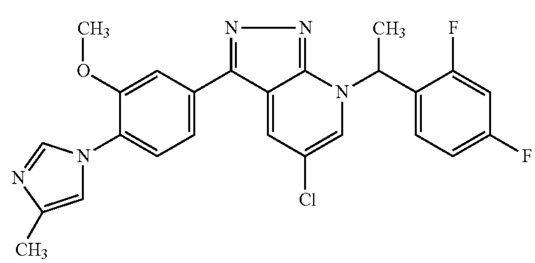 | 480.3 |
| 23 | 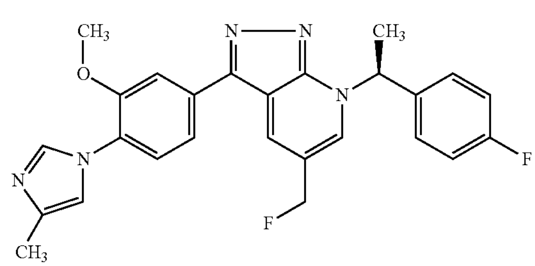 | 460.3 |

-continued
| Cmpd | Structure | Obs LCMS |
|---|---|---|
| 24 | 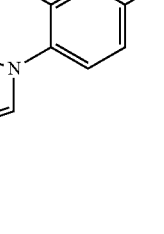 | 442.2 |
| 25 | 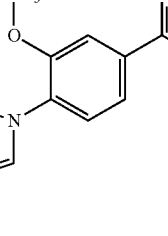 | 478.3 |
| 26 | 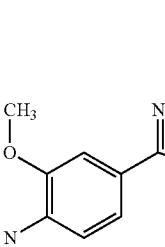 | 464.3 |
| 27 | 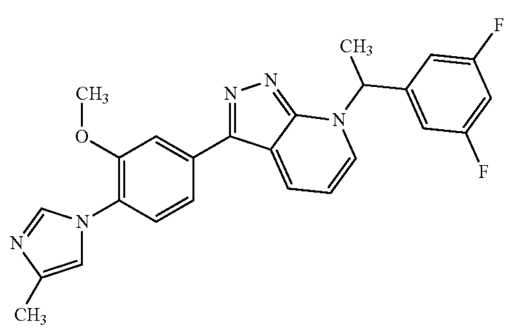 [SMILES: COc1cc(-c2nnc3n(C(C)c4cc(F)cc(F)c4)cccc2-3)ccc1-n1cnc(C)c1] | 446.2 |
| 28 | 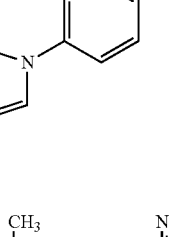 | 496.3 |

| Cmpd | Structure | Obs LCMS |
|---|---|---|
| 29 | 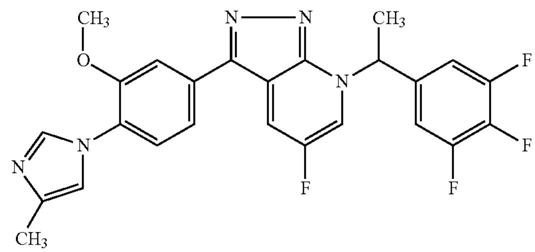 | 482.3 |
| 30 | 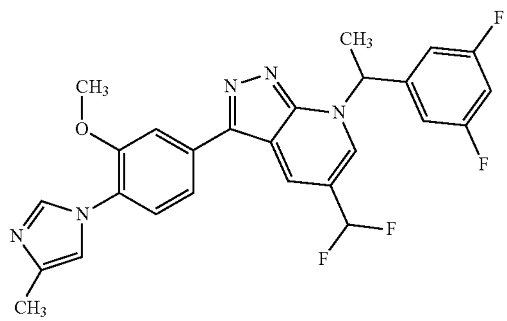 [SMILES: COc1cc(-c2nnc3n(C(C)c4cc(F)cc(F)c4)cc(C(F)F)cc2-3)ccc1-n1cnc(C)c1] | 496.3 |
| 31 | 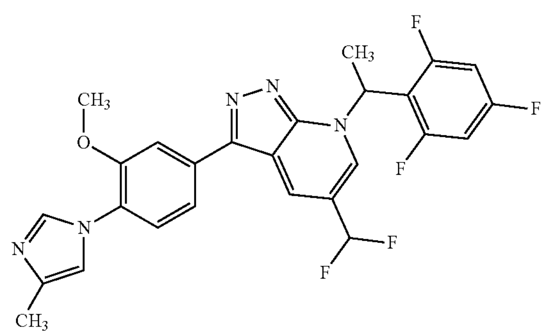 [SMILES: COc1cc(-c2nnc3n(C(C)c4c(F)cc(F)cc4F)cc(C(F)F)cc2-3)ccc1-n1cnc(C)c1] | 514.2 |
| 32 | 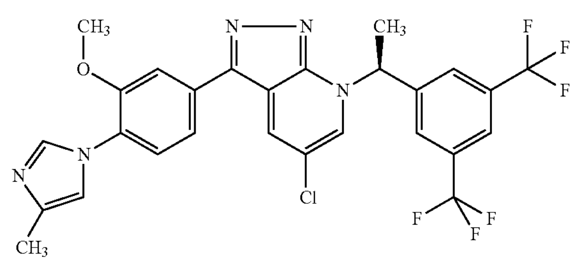 | 580.3 |
| 33 | 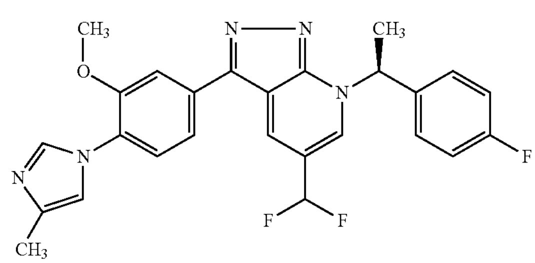 [SMILES: COc1cc(-c2nnc3n([C@@H](C)c4ccc(F)cc4)cc(C(F)F)cc2-3)ccc1-n1cnc(C)c1] | 478.3 |

-continued

| Cmpd | Structure | Obs LCMS |
|---|---|---|
| 34 | 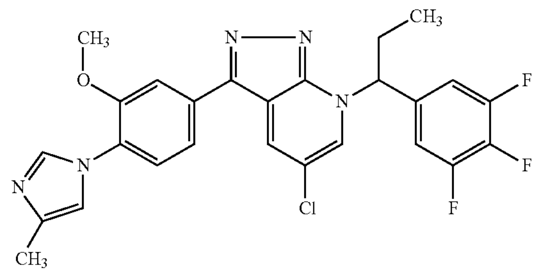 | 512.3 |
| 35 | 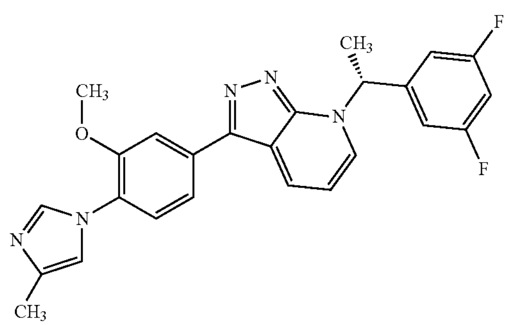 [SMILES: COc1cc(-c2nnc3n([C@H](C)c4cc(F)cc(F)c4)cccc2-3)ccc1-n1cnc(C)c1] | 446.2 |
| 36 | 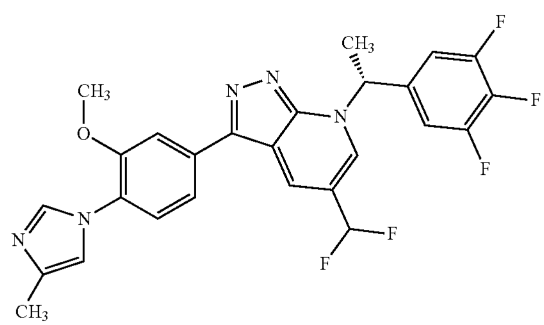 [SMILES: COc1cc(-c2nnc3n([C@H](C)c4cc(F)c(F)c(F)c4)cc(C(F)F)cc2-3)ccc1-n1cnc(C)c1] | 514.3 |
| 37 | 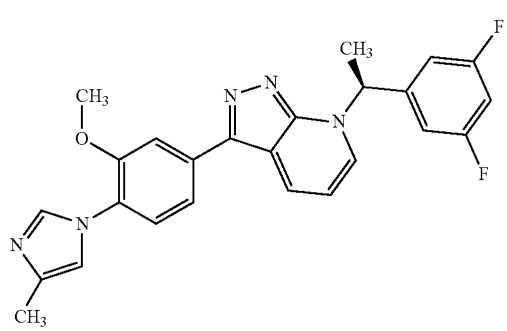 [SMILES: COc1cc(-c2nnc3n([C@@H](C)c4cc(F)cc(F)c4)cccc2-3)ccc1-n1cnc(C)c1] | 446.2 |
| 38 | 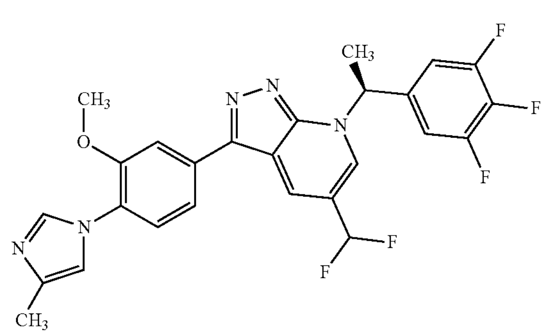 [SMILES: COc1cc(-c2nnc3n([C@@H](C)c4cc(F)c(F)c(F)c4)cc(C(F)F)cc2-3)ccc1-n1cnc(C)c1] | 514.3 |

-continued

| Cmpd | Structure | Obs LCMS |
|---|---|---|
| 39 | 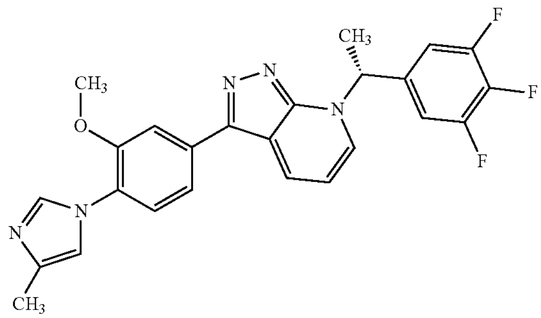 [SMILES: COc1cc(-c2nnc3n([C@H](C)c4cc(F)c(F)c(F)c4)cccc2-3)ccc1-n1cnc(C)c1] | 464.3 |
| 40 | 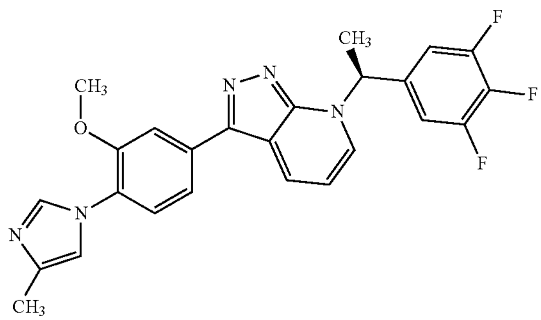 [SMILES: COc1cc(-c2nnc3n([C@@H](C)c4cc(F)c(F)c(F)c4)cccc2-3)ccc1-n1cnc(C)c1] | 464.3 |
| 41 | 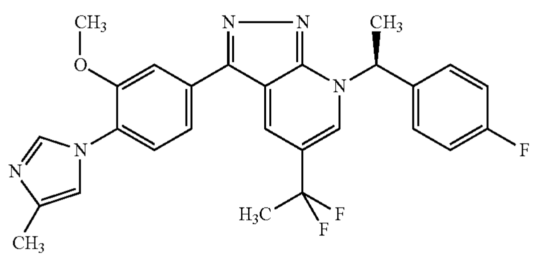 [SMILES: COc1cc(-c2nnc3n([C@@H](C)c4ccc(F)cc4)cc(C(C)(F)F)cc2-3)ccc1-n1cnc(C)c1] | 492.3 |
| 42 | 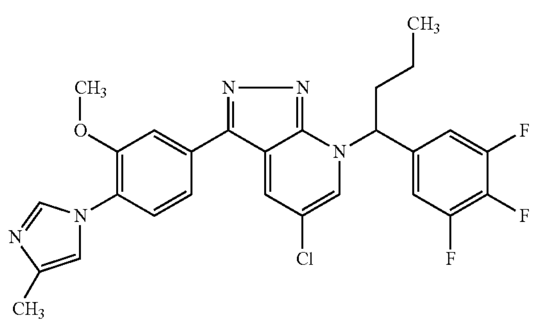 [SMILES: CCCC(c1cc(F)c(F)c(F)c1)n1cc(Cl)cc2c(-c3ccc(-n4cnc(C)c4)c(OC)c3)nnc1-2] | 526.3 |
| 43 | 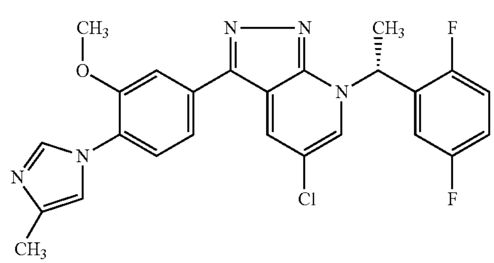 [SMILES: COc1cc(-c2nnc3n([C@H](C)c4cc(F)ccc4F)cc(Cl)cc2-3)ccc1-n1cnc(C)c1] | 480.3 |

-continued

| Cmpd | Structure | Obs LCMS |
|---|---|---|
| 44 | 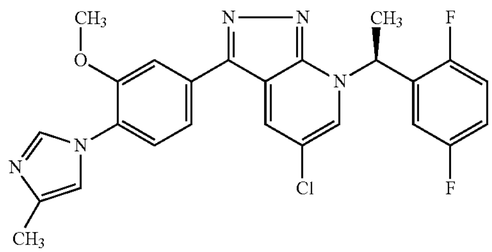 [SMILES: COc1cc(-c2nnc3n([C@@H](C)c4cc(F)ccc4F)cc(Cl)cc2-3)ccc1-n1cnc(C)c1] | 480.3 |
| 45 | 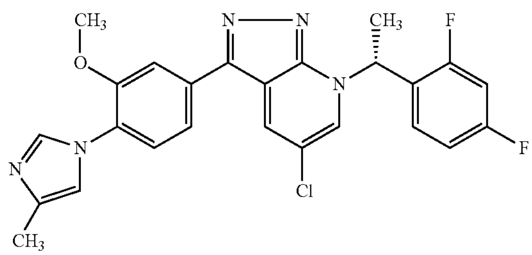 [SMILES: COc1cc(-c2nnc3n([C@H](C)c4ccc(F)cc4F)cc(Cl)cc2-3)ccc1-n1cnc(C)c1] | 480.3 |
| 46 | 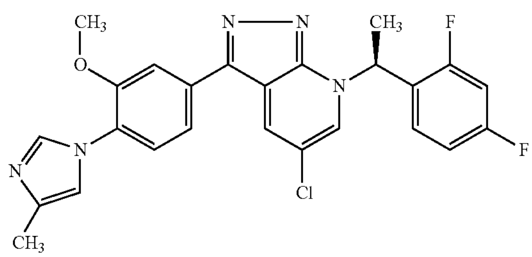 | 480.3 |
| 47 | 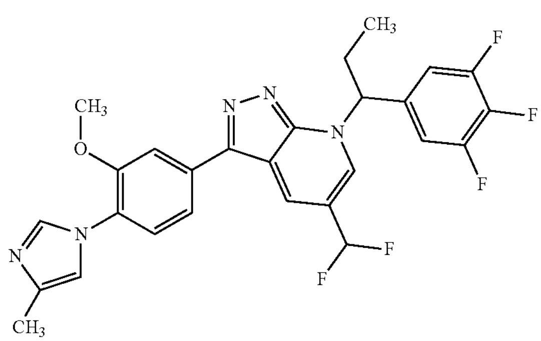 [SMILES: CCC(c1cc(F)c(F)c(F)c1)n1cc(C(F)F)cc2c(-c3ccc(-n4cnc(C)c4)c(OC)c3)nnc1-2] | 528.3 |
| 48 | 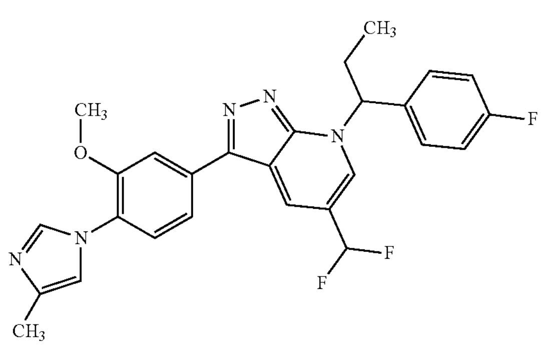 [SMILES: CCC(c1ccc(F)cc1)n1cc(C(F)F)cc2c(-c3ccc(-n4cnc(C)c4)c(OC)c3)nnc1-2] | 492.3 |

-continued

| Cmpd | Structure | Obs LCMS |
|---|---|---|
| 49 | 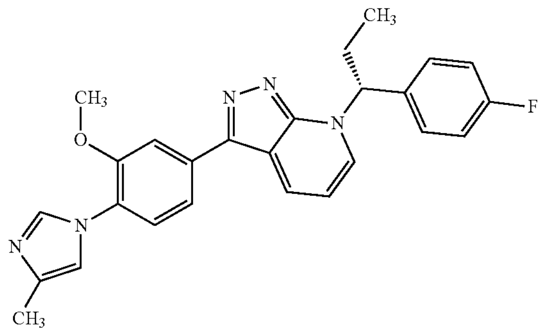 [SMILES: CC[C@H](c1ccc(F)cc1)n1cccc2c(-c3ccc(-n4cnc(C)c4)c(OC)c3)nnc1-2] | 442.3 |
| 50 | 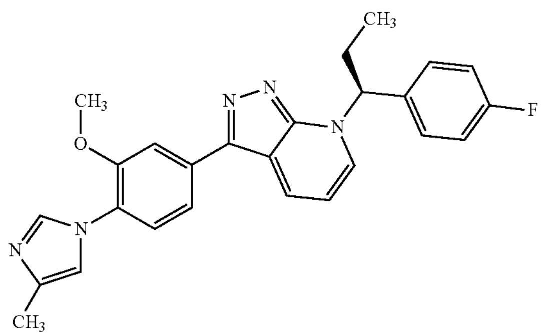 [SMILES: CC[C@@H](c1ccc(F)cc1)n1cccc2c(-c3ccc(-n4cnc(C)c4)c(OC)c3)nnc1-2] | 442.2 |
| 51 | 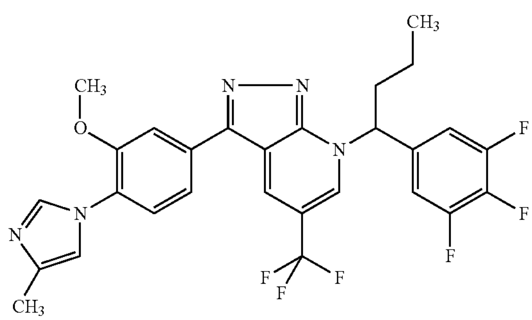 [SMILES: CCCC(c1cc(F)c(F)c(F)c1)n1cc(C(F)(F)F)cc2c(-c3ccc(-n4cnc(C)c4)c(OC)c3)nnc1-2] | 560.3 |
| 52 | 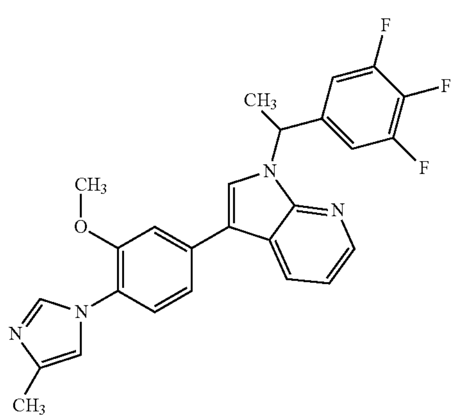 [SMILES: COc1cc(-c2cn(C(C)c3cc(F)c(F)c(F)c3)c3ncccc23)ccc1-n1cnc(C)c1] | 464.3 |

-continued

| Cmpd | Structure | Obs LCMS |
|---|---|---|
| 53 | 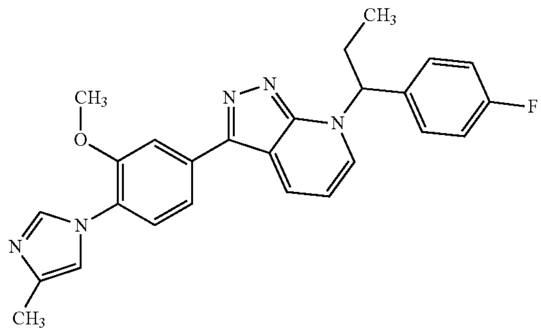 [SMILES: CCC(c1ccc(F)cc1)n1cccc2c(-c3ccc(-n4cnc(C)c4)c(OC)c3)nnc1-2] | 462.3 |
| 54 | 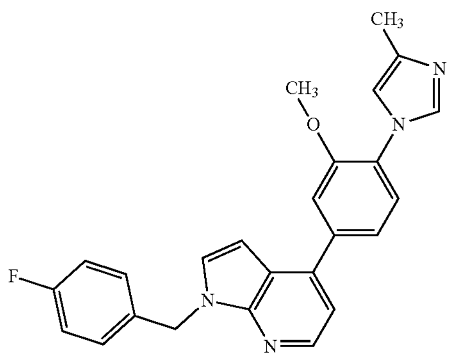 [SMILES: COc1cc(-c2ccnc3c2ccn3Cc2ccc(F)cc2)ccc1-n1cnc(C)c1] | 413.2 |
| 55 | 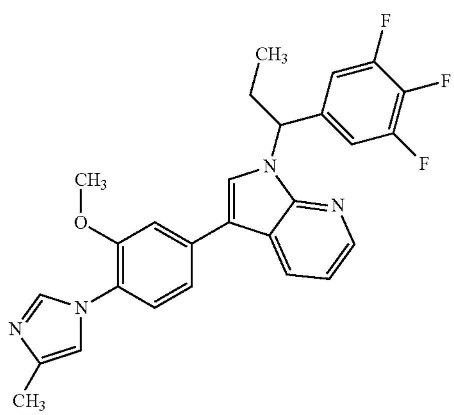 [SMILES: CCC(c1cc(F)c(F)c(F)c1)n1cc(-c2ccc(-n3cnc(C)c3)c(OC)c2)c2cccnc21] | 477.3 |
| 56 | 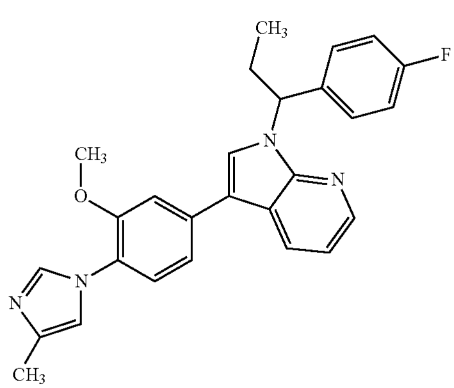 [SMILES: CCC(c1ccc(F)cc1)n1cc(-c2ccc(-n3cnc(C)c3)c(OC)c2)c2cccnc21] | 441.2 |

-continued

| Cmpd | Structure | Obs LCMS |
|---|---|---|
| 57 | 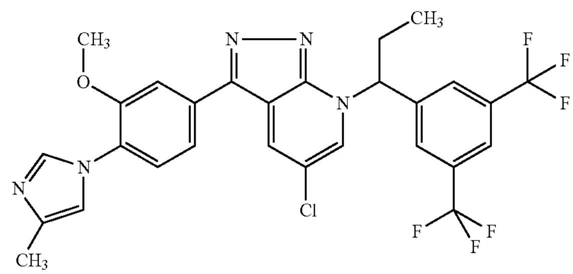 | 594.3 |
| 58 | 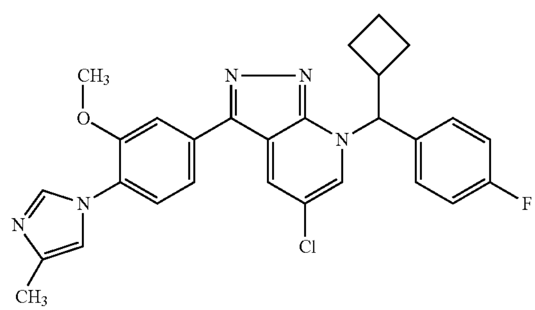 [SMILES: COc1cc(-c2nnc3n(C(c4ccc(F)cc4)C4CCC4)cc(Cl)cc2-3)ccc1-n1cnc(C)c1] | 502.3 |
| 59 | 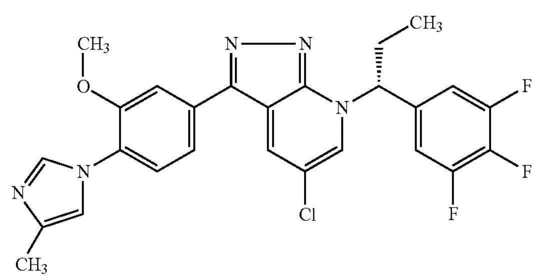 | 512.3 |
| 60 | 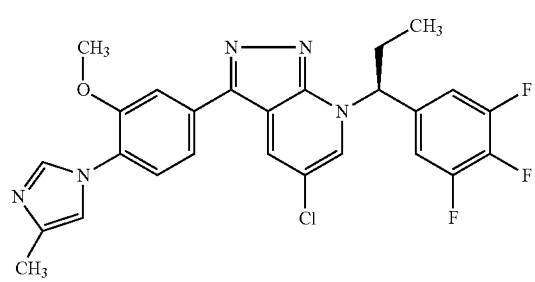 | 512.3 |
| 61 | 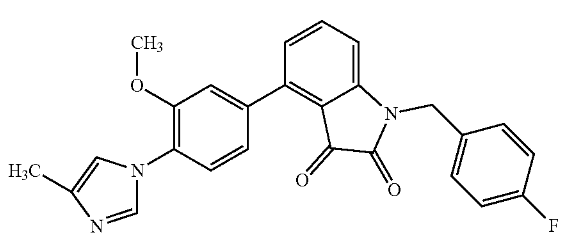 [SMILES: COc1cc(-c2cccc3c2C(=O)C(=O)N3Cc2ccc(F)cc2)ccc1-n1cnc(C)c1] | 442.2 |

| Cmpd | Structure | Obs LCMS |
|---|---|---|
| 62 | 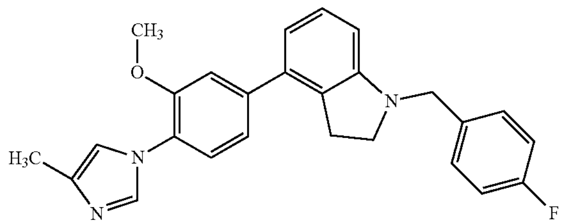 [SMILES: COc1cc(-c2cccc3c2CCN3Cc2ccc(F)cc2)ccc1-n1cnc(C)c1] | 414.2 |
| 63 | 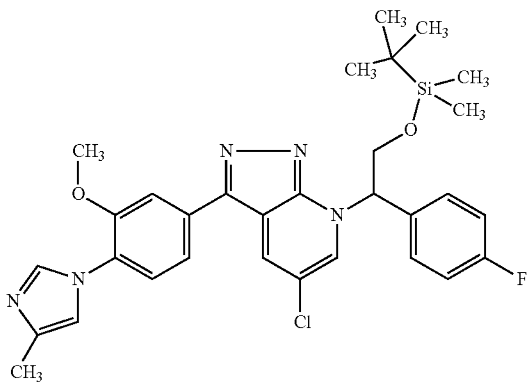 [SMILES: COc1cc(-c2nnc3n(C(CO[Si](C)(C)C(C)(C)C)c4ccc(F)cc4)cc(Cl)cc2-3)ccc1-n1cnc(C)c1] | 592.3 |
| 64 | 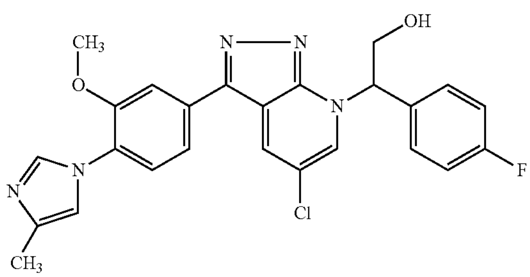 | 478.3 |
| 65 | 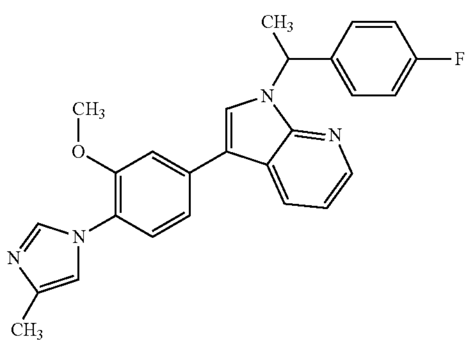 [SMILES: COc1cc(-c2cn(C(C)c3ccc(F)cc3)c3ncccc23)ccc1-n1cnc(C)c1] | 427.2 |
| 66 | 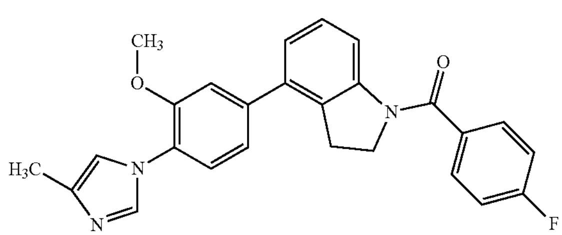 [SMILES: COc1cc(-c2cccc3c2CCN3C(=O)c2ccc(F)cc2)ccc1-n1cnc(C)c1] | 428.2 |

259
-continued

260

| Cmpd | Structure | Obs LCMS |
|------|-----------|----------|
| 67 | 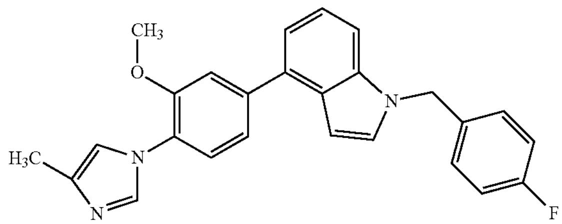 [SMILES: COc1cc(-c2cccc3c2ccn3Cc2ccc(F)cc2)ccc1-n1cnc(C)c1] | 413.2 |
| 68 | 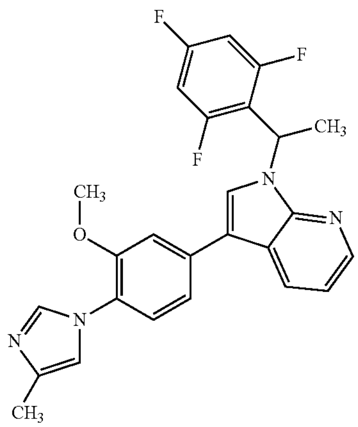 [SMILES: COc1cc(-c2cn(C(C)c3c(F)cc(F)cc3F)c3ncccc23)ccc1-n1cnc(C)c1] | 463.2 |
| 69 | 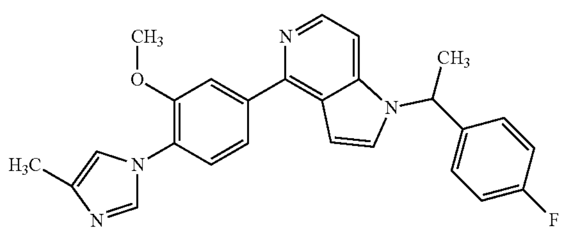 [SMILES: COc1cc(-c2nccc3c2ccn3C(C)c2ccc(F)cc2)ccc1-n1cnc(C)c1] | 427.2 |
| 70 | 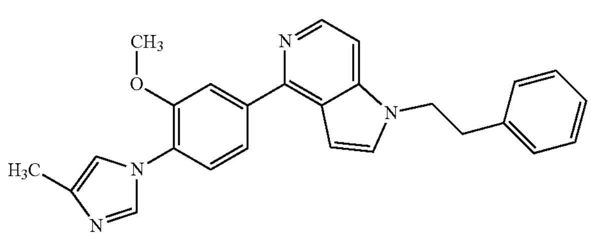 [SMILES: COc1cc(-c2nccc3c2ccn3CCc2ccccc2)ccc1-n1cnc(C)c1] | 409.2 |
| 71 | 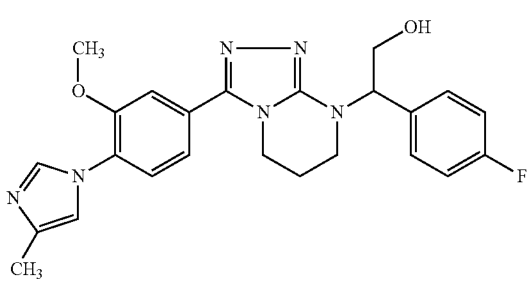 [SMILES: COc1cc(-c2nnc3n2CCCN3C(CO)c2ccc(F)cc2)ccc1-n1cnc(C)c1] | 447.2 |

-continued
| Cmpd | Structure | Obs LCMS |
|---|---|---|
| 72 | 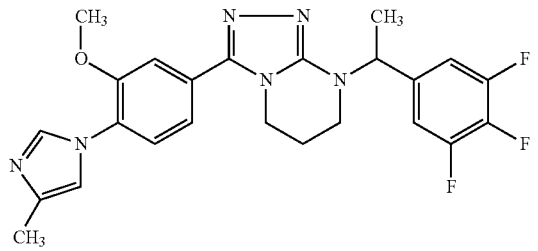 [SMILES: COc1cc(-c2nnc3n2CCCN3C(C)c2cc(F)c(F)c(F)c2)ccc1-n1cnc(C)c1] | 469.3 |
| 73 | 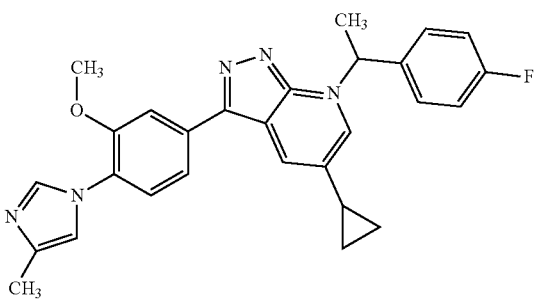 | 468.3 |
| 74 | 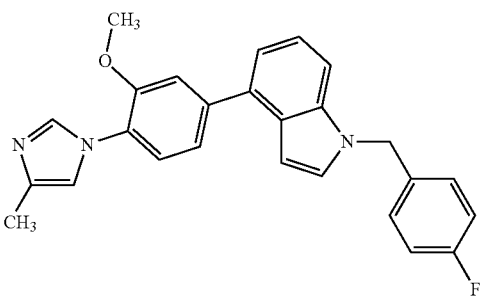 [SMILES: COc1cc(-c2cccc3c2ccn3Cc2ccc(F)cc2)ccc1-n1cnc(C)c1] | 412.2 |
| 75 | 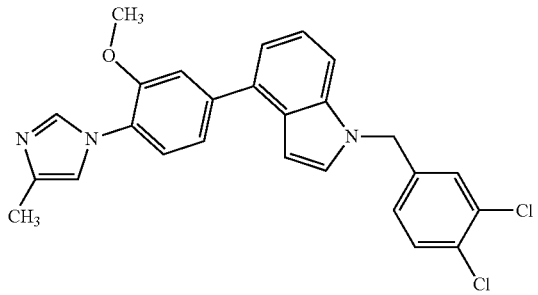 [SMILES: COc1cc(-c2cccc3c2ccn3Cc2ccc(Cl)c(Cl)c2)ccc1-n1cnc(C)c1] | 462.3 |
| 76 | 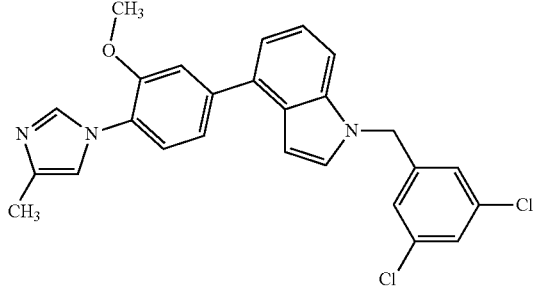 [SMILES: COc1cc(-c2cccc3c2ccn3Cc2cc(Cl)cc(Cl)c2)ccc1-n1cnc(C)c1] | 462.3 |

| Cmpd | Structure | Obs LCMS |
|---|---|---|
| 77 | 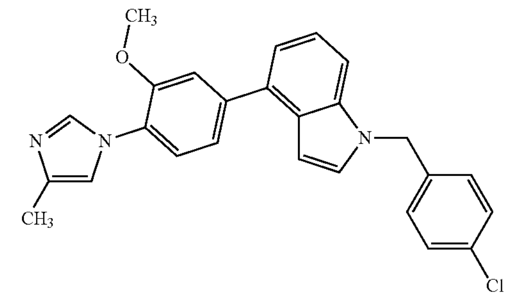 [SMILES: COc1cc(-c2cccc3c2ccn3Cc2ccc(Cl)cc2)ccc1-n1cnc(C)c1] | 428.2 |
| 78 | 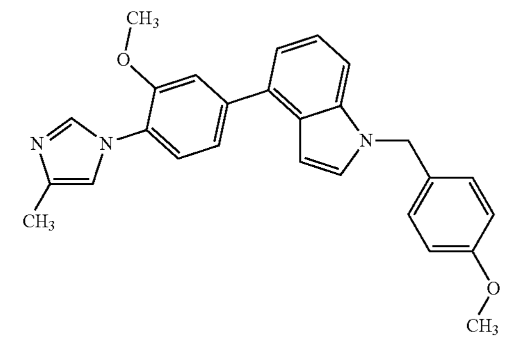 [SMILES: COc1ccc(Cn2ccc3c(-c4ccc(-n5cnc(C)c5)c(OC)c4)cccc32)cc1] | 424.2 |
| 79 | 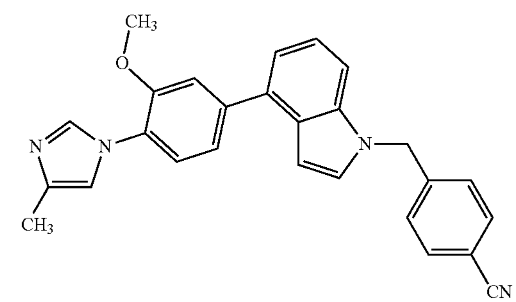 [SMILES: COc1cc(-c2cccc3c2ccn3Cc2ccc(C#N)cc2)ccc1-n1cnc(C)c1] | 419.2 |
| 80 | 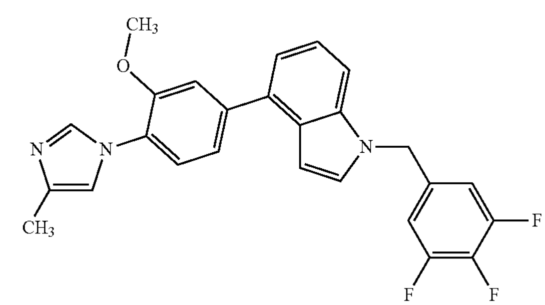 [SMILES: COc1cc(-c2cccc3c2ccn3Cc2cc(F)c(F)c(F)c2)ccc1-n1cnc(C)c1] | 448.2 |
| 81 | 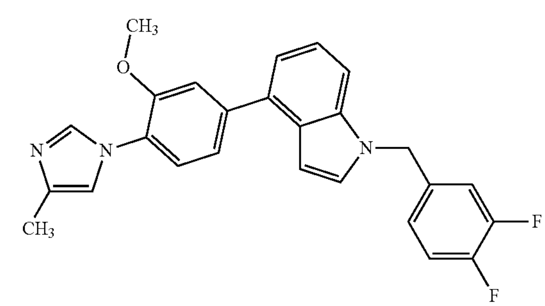 [SMILES: COc1cc(-c2cccc3c2ccn3Cc2ccc(F)c(F)c2)ccc1-n1cnc(C)c1] | 430.2 |

-continued
| Cmpd | Structure | Obs LCMS |
|---|---|---|
| 82 | 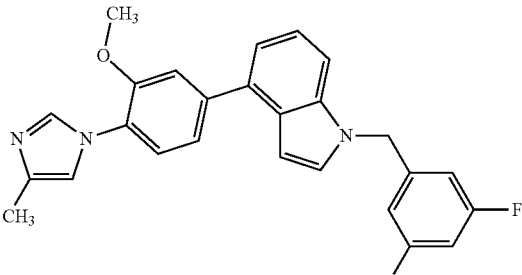 | 430.2 |
| 83 | 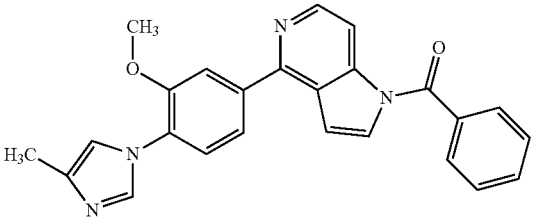 [SMILES: COc1cc(-c2nccc3c2ccn3C(=O)c2ccccc2)ccc1-n1cnc(C)c1] | 409.2 |
| 84 | 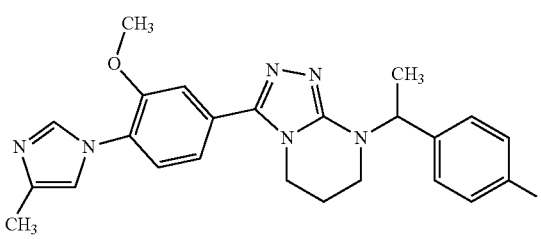 | 433.2 |
| 85 | 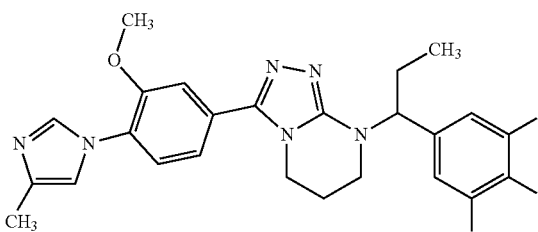 | 483.3 |
| 86 | 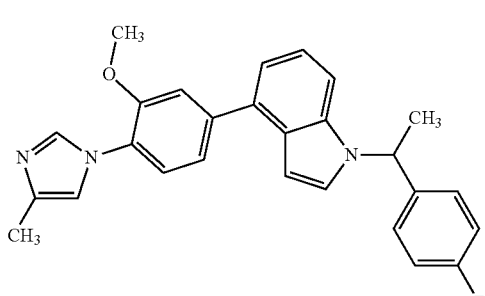 | 426.2 |
| 87 | 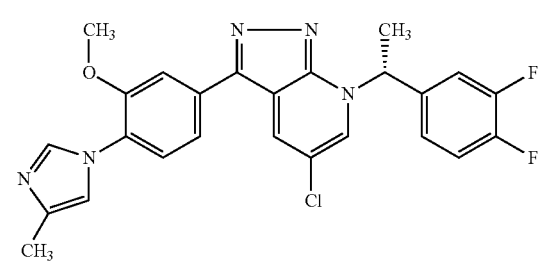 | 480.3 |

| Cmpd | Structure | Obs LCMS |
|---|---|---|
| 88 | 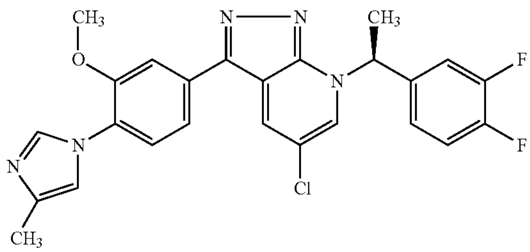 [SMILES: COc1cc(-c2nnc3n([C@@H](C)c4ccc(F)c(F)c4)cc(Cl)cc2-3)ccc1-n1cnc(C)c1] | 480.3 |
| 89 | 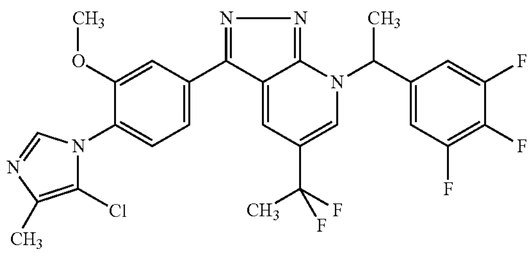 [SMILES: COc1cc(-c2nnc3n(C(C)c4cc(F)c(F)c(F)c4)cc(C(C)(F)F)cc2-3)ccc1-n1cnc(C)c1Cl] | 562.3 |
| 90 | 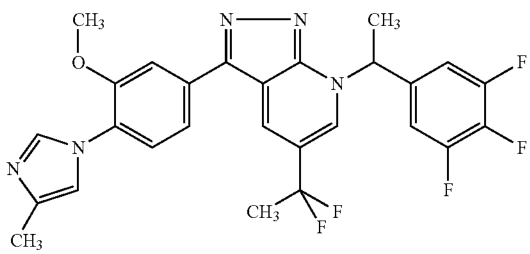 [SMILES: COc1cc(-c2nnc3n(C(C)c4cc(F)c(F)c(F)c4)cc(C(C)(F)F)cc2-3)ccc1-n1cnc(C)c1] | 528.3 |
| 91 | 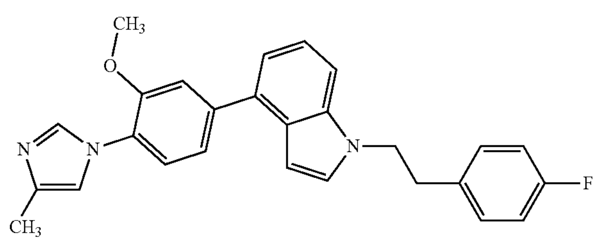 [SMILES: COc1cc(-c2cccc3c2ccn3CCc2ccc(F)cc2)ccc1-n1cnc(C)c1] | 426.2 |
| 92 | 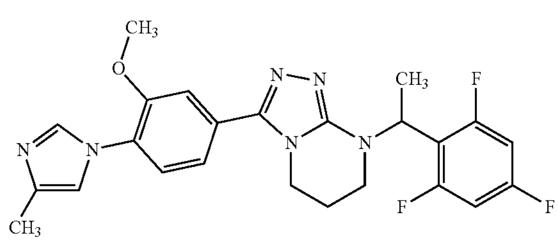 [SMILES: COc1cc(-c2nnc3n2CCCN3C(C)c2c(F)cc(F)cc2F)ccc1-n1cnc(C)c1] | 469.3 |
| 93 | 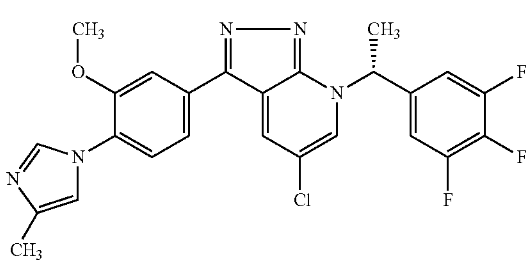 [SMILES: COc1cc(-c2nnc3n([C@H](C)c4cc(F)c(F)c(F)c4)cc(Cl)cc2-3)ccc1-n1cnc(C)c1] | 498.3 |

-continued

| Cmpd | Structure | Obs LCMS |
|---|---|---|
| 94 | 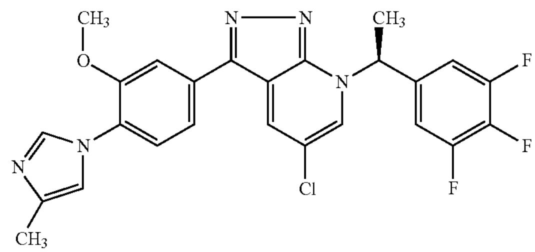 [SMILES: COc1cc(-c2nnc3n([C@@H](C)c4cc(F)c(F)c(F)c4)cc(Cl)cc2-3)ccc1-n1cnc(C)c1] | 498.3 |
| 95 | 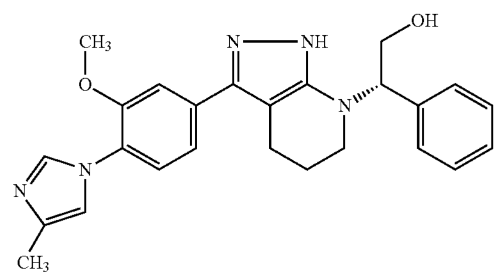 [SMILES: COc1cc(-c2n[nH]c3c2CCCN3[C@H](CO)c2ccccc2)ccc1-n1cnc(C)c1] | 430.2 |
| 96 | 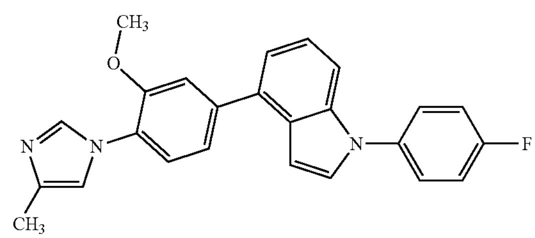 [SMILES: COc1cc(-c2cccc3c2ccn3-c2ccc(F)cc2)ccc1-n1cnc(C)c1] | 398.2 |
| 97 | 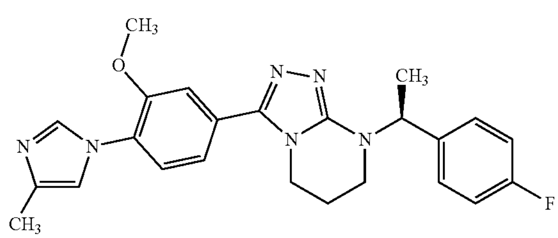 [SMILES: COc1cc(-c2nnc3n2CCCN3[C@@H](C)c2ccc(F)cc2)ccc1-n1cnc(C)c1] | 433.2 |
| 98 | 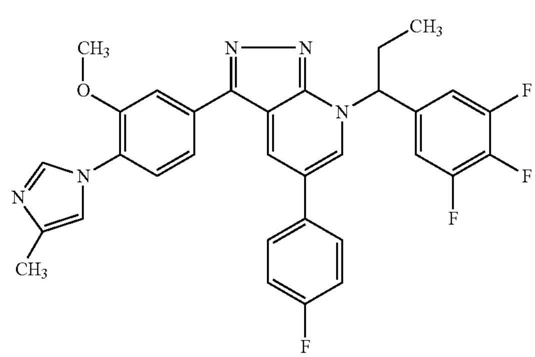 [SMILES: CCC(c1cc(F)c(F)c(F)c1)n1cc(-c2ccc(F)cc2)cc2c(-c3ccc(-n4cnc(C)c4)c(OC)c3)nnc1-2] | 572.3 |

-continued

| Cmpd | Structure | Obs LCMS |
|---|---|---|
| 99 | 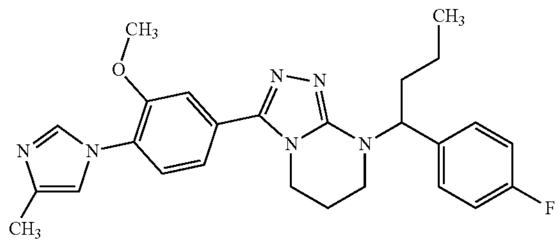 [SMILES: CCCC(c1ccc(F)cc1)N1CCCn2c(-c3ccc(-n4cnc(C)c4)c(OC)c3)nnc21] | 461.3 |
| 100 | 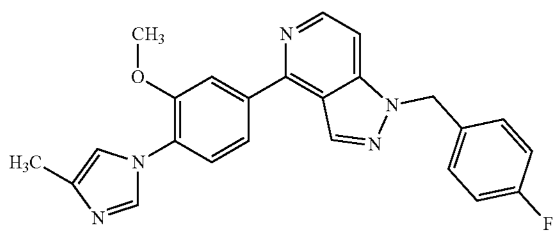 [SMILES: COc1cc(-c2nccc3c2cnn3Cc2ccc(F)cc2)ccc1-n1cnc(C)c1] | 414.2 |
| 101 | 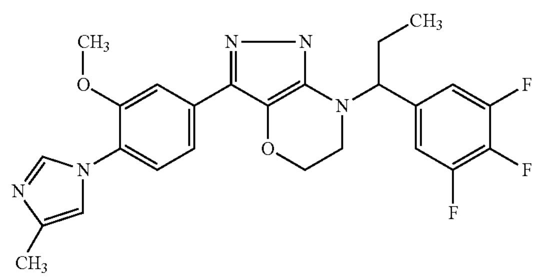 [SMILES: CCC(c1cc(F)c(F)c(F)c1)N1CCOc2c(-c3ccc(-n4cnc(C)c4)c(OC)c3)n[nH]c21] | 484.3 |
| 102 | 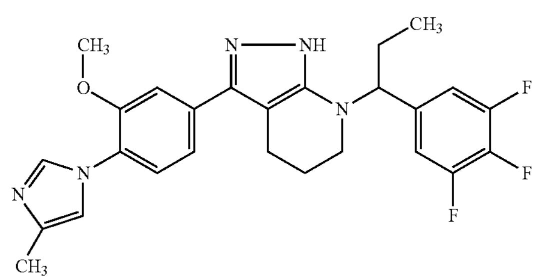 [SMILES: CCC(c1cc(F)c(F)c(F)c1)N1CCCc2c(-c3ccc(-n4cnc(C)c4)c(OC)c3)n[nH]c21] | 482.3 |
| 103 | 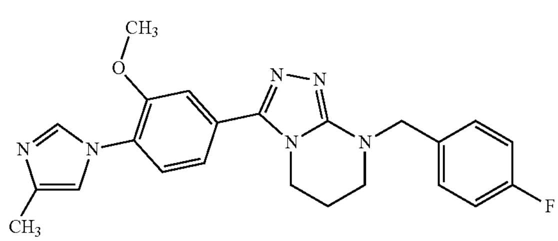 [SMILES: COc1cc(-c2nnc3n2CCCN3Cc2ccc(F)cc2)ccc1-n1cnc(C)c1] | 419.2 |
| 104 | 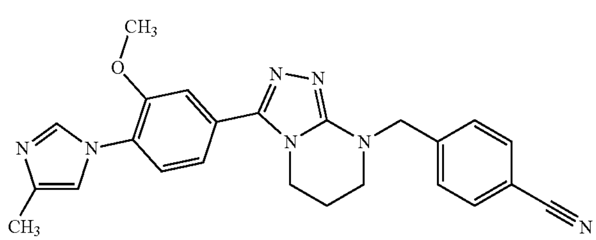 [SMILES: COc1cc(-c2nnc3n2CCCN3Cc2ccc(C#N)cc2)ccc1-n1cnc(C)c1] | 426.2 |

-continued
| Cmpd | Structure | Obs LCMS |
|---|---|---|
| 105 | 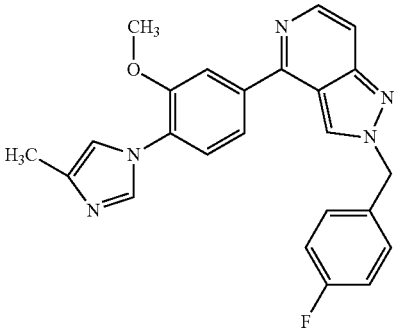 [SMILES: COc1cc(-c2nccc3nn(Cc4ccc(F)cc4)cc23)ccc1-n1cnc(C)c1] | 414.2 |
| 106 | 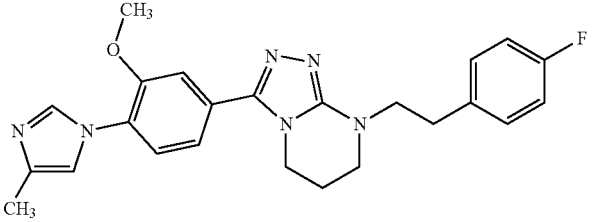 [SMILES: COc1cc(-c2nnc3n2CCCN3CCc2ccc(F)cc2)ccc1-n1cnc(C)c1] | 433.2 |
| 107 | 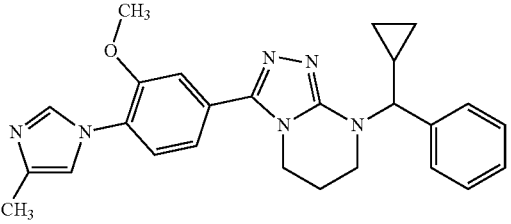 [SMILES: COc1cc(-c2nnc3n2CCCN3C(c2ccccc2)C2CC2)ccc1-n1cnc(C)c1] | 441.2 |
| 108 | 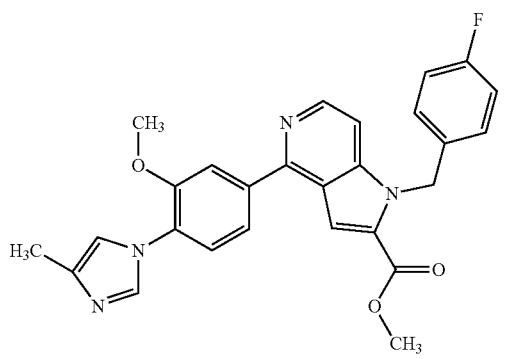 [SMILES: COC(=O)c1cc2c(-c3ccc(-n4cnc(C)c4)c(OC)c3)nccc2n1Cc1ccc(F)cc1] | 471.2 |
| 109 | 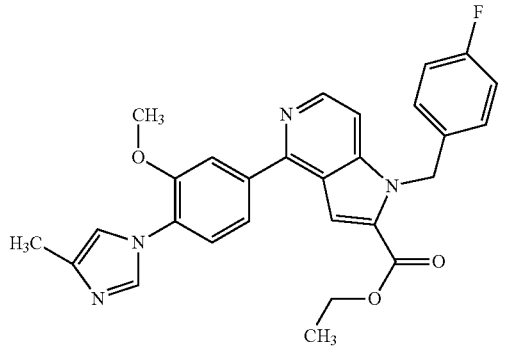 [SMILES: CCOC(=O)c1cc2c(-c3ccc(-n4cnc(C)c4)c(OC)c3)nccc2n1Cc1ccc(F)cc1] | 485.2 |

-continued

| Cmpd | Structure | Obs LCMS |
|---|---|---|
| 110 | 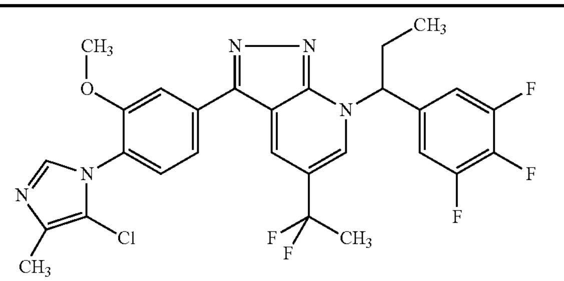 | 576.3 |
| 111 | 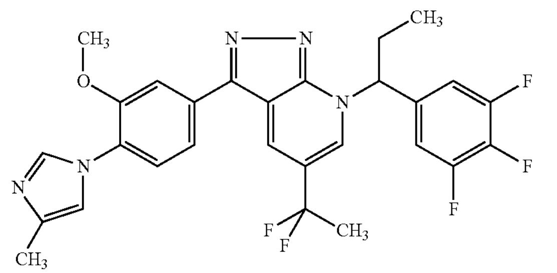 [SMILES: CCC(c1cc(F)c(F)c(F)c1)n1cc(C(C)(F)F)cc2c(-c3ccc(-n4cnc(C)c4)c(OC)c3)nnc1-2] | 542.3 |
| 112 | 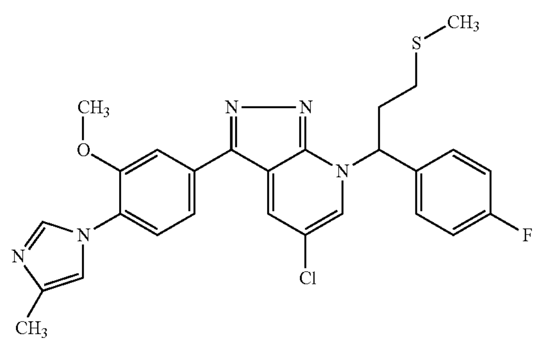 [SMILES: COc1cc(-c2nnc3n(C(CCSC)c4ccc(F)cc4)cc(Cl)cc2-3)ccc1-n1cnc(C)c1] | 522.3 |
| 113 | 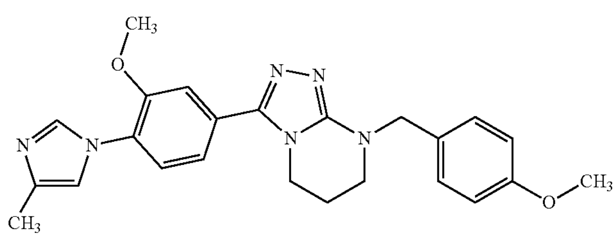 | 431.2 |
| 114 | 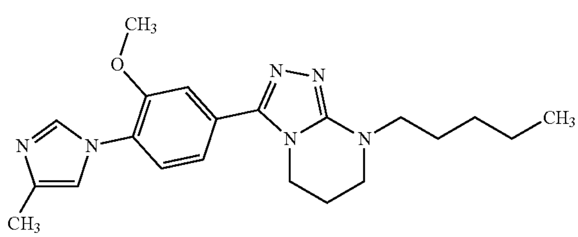 [SMILES: CCCCCN1CCCn2c(-c3ccc(-n4cnc(C)c4)c(OC)c3)nnc21] | 381.2 |
| 115 | 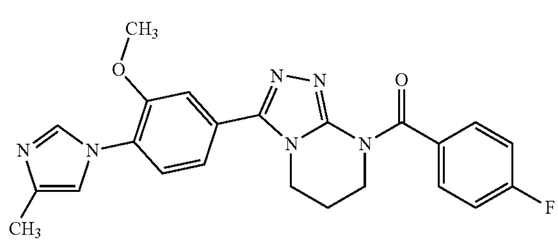 [SMILES: COc1cc(-c2nnc3n2CCCN3C(=O)c2ccc(F)cc2)ccc1-n1cnc(C)c1] | 433.2 |

-continued

| Cmpd | Structure | Obs LCMS |
|---|---|---|
| 116 | 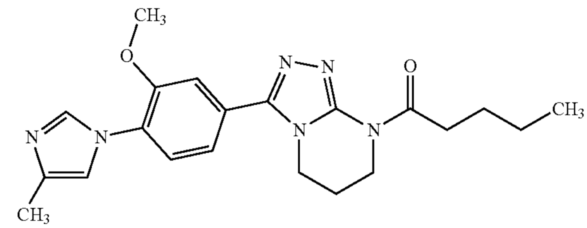 [SMILES: CCCCC(=O)N1CCCn2c(-c3ccc(-n4cnc(C)c4)c(OC)c3)nnc21] | 395.2 |
| 117 | 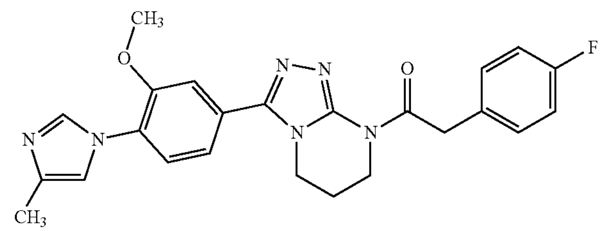 [SMILES: COc1cc(-c2nnc3n2CCCN3C(=O)Cc2ccc(F)cc2)ccc1-n1cnc(C)c1] | 447.2 |
| 118 | 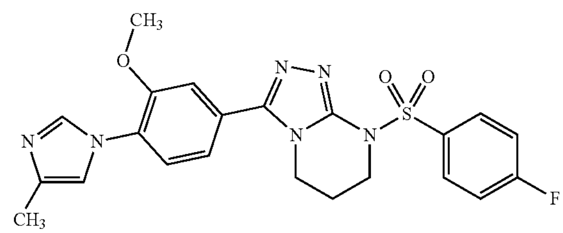 [SMILES: COc1cc(-c2nnc3n2CCCN3S(=O)(=O)c2ccc(F)cc2)ccc1-n1cnc(C)c1] | 469.3 |
| 119 | 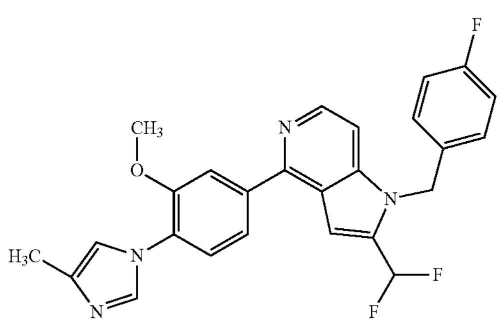 [SMILES: COc1cc(-c2nccc3c2cc(C(F)F)n3Cc2ccc(F)cc2)ccc1-n1cnc(C)c1] | 463.2 |
| 120 | 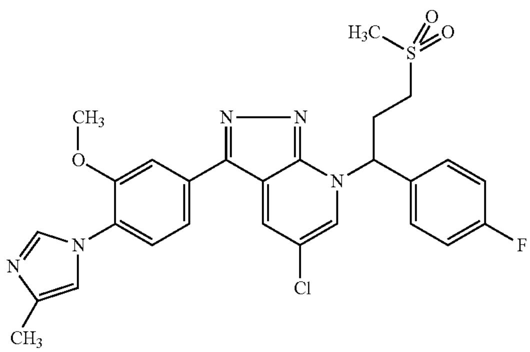 [SMILES: COc1cc(-c2nnc3n(C(CCS(C)(=O)=O)c4ccc(F)cc4)cc(Cl)cc2-3)ccc1-n1cnc(C)c1] | 554.3 |

| Cmpd | Structure | Obs LCMS |
|---|---|---|
| 121 | 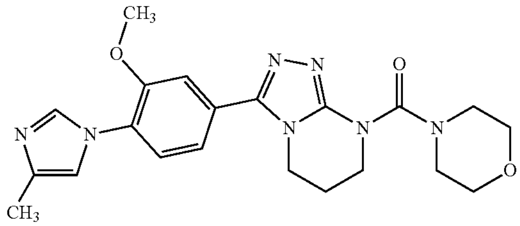 [SMILES: COc1cc(-c2nnc3n2CCCN3C(=O)N2CCOCC2)ccc1-n1cnc(C)c1] | 424.2 |
| 122 | 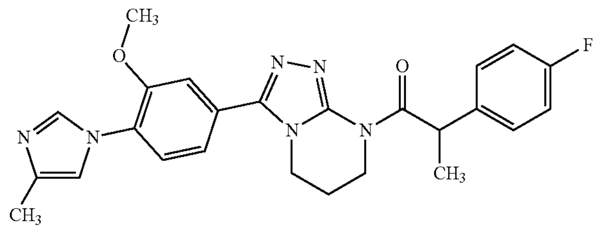 [SMILES: COc1cc(-c2nnc3n2CCCN3C(=O)C(C)c2ccc(F)cc2)ccc1-n1cnc(C)c1] | 461.3 |
| 123 | 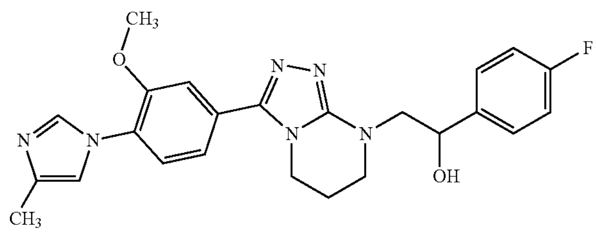 [SMILES: COc1cc(-c2nnc3n2CCCN3CC(O)c2ccc(F)cc2)ccc1-n1cnc(C)c1] | 449.2 |
| 124 | 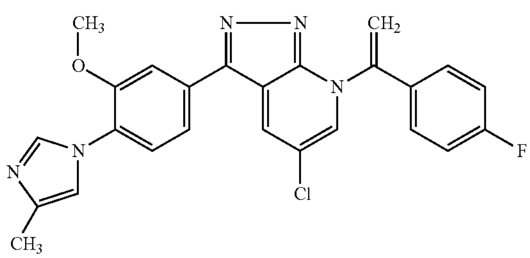 [SMILES: C=C(c1ccc(F)cc1)n1cc(Cl)cc2c(-c3ccc(-n4cnc(C)c4)c(OC)c3)nnc1-2] | 460.3 |
| 125 | 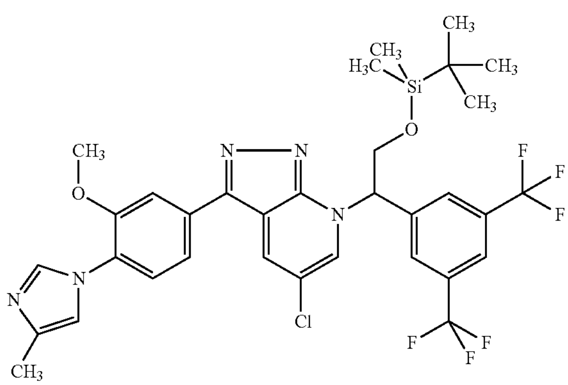 [SMILES: COc1cc(-c2nnc3n(C(CO[Si](C)(C)C(C)(C)C)c4cc(C(F)(F)F)cc(C(F)(F)F)c4)cc(Cl)cc2-3)ccc1-n1cnc(C)c1] | 710.4 |
| 126 | 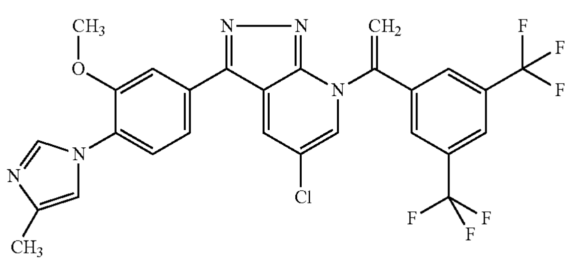 [SMILES: C=C(c1cc(C(F)(F)F)cc(C(F)(F)F)c1)n1cc(Cl)cc2c(-c3ccc(-n4cnc(C)c4)c(OC)c3)nnc1-2] | 578.3 |

| Cmpd | Structure | Obs LCMS |
|---|---|---|
| 127 | 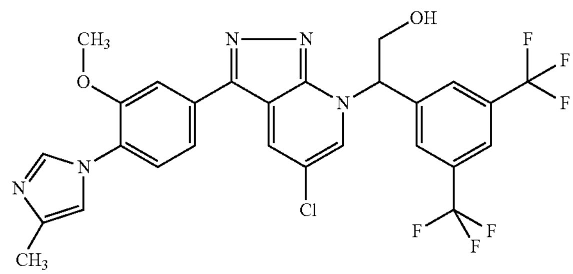 [SMILES: COc1cc(-c2nnc3n(C(CO)c4cc(C(F)(F)F)cc(C(F)(F)F)c4)cc(Cl)cc2-3)ccc1-n1cnc(C)c1] | 596.3 |
| 128 | 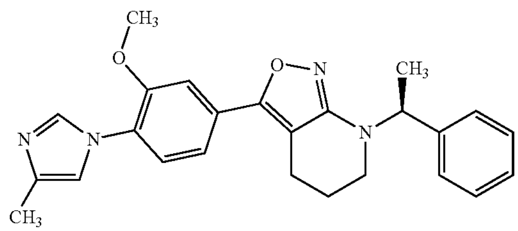 [SMILES: COc1cc(-c2onc3c2CCCN3[C@@H](C)c2ccccc2)ccc1-n1cnc(C)c1] | 415.2 |
| 129 | 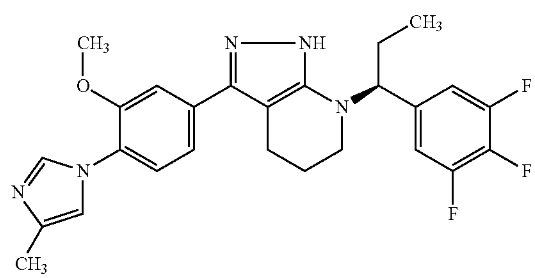 [SMILES: CC[C@@H](c1cc(F)c(F)c(F)c1)N1CCCc2c(-c3ccc(-n4cnc(C)c4)c(OC)c3)n[nH]c21] | 482.3 |
| 130 | 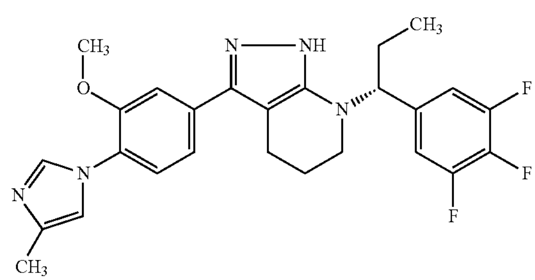 [SMILES: CC[C@H](c1cc(F)c(F)c(F)c1)N1CCCc2c(-c3ccc(-n4cnc(C)c4)c(OC)c3)n[nH]c21] | 482.3 |
| 131 | 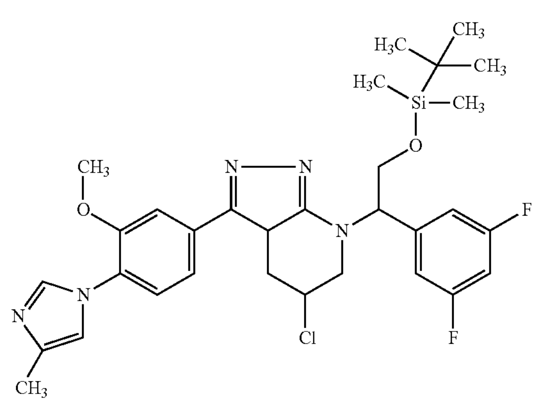 [SMILES: COc1cc(C2=NN=C3C2CC(Cl)CN3C(CO[Si](C)(C)C(C)(C)C)c2cc(F)cc(F)c2)ccc1-n1cnc(C)c1] | 610.3 |

-continued

| Cmpd | Structure | Obs LCMS |
|---|---|---|
| 132 | 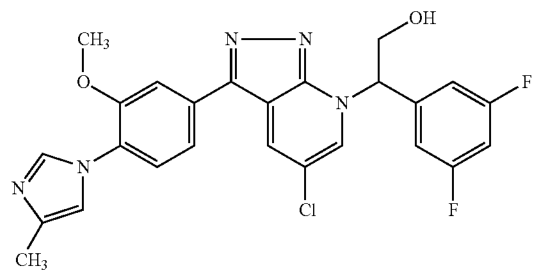 [SMILES: COc1cc(-c2nnc3n(C(CO)c4cc(F)cc(F)c4)cc(Cl)cc2-3)ccc1-n1cnc(C)c1] | 496.3 |
| 133 | 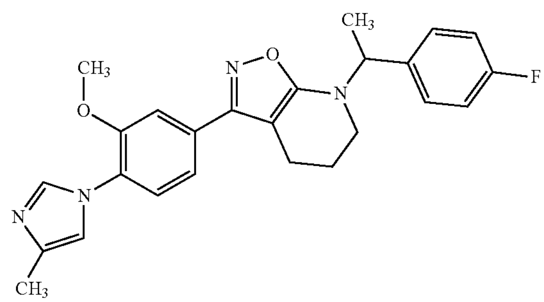 [SMILES: COc1cc(-c2noc3c2CCCN3C(C)c2ccc(F)cc2)ccc1-n1cnc(C)c1] | 433.2 |
| 134 | 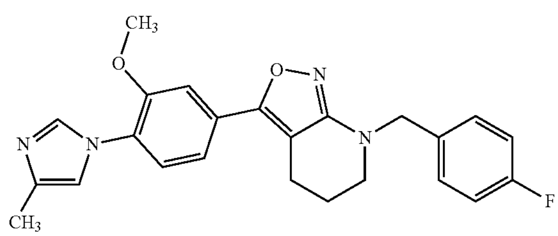 [SMILES: COc1cc(-c2onc3c2CCCN3Cc2ccc(F)cc2)ccc1-n1cnc(C)c1] | 419.2 |
| 135 | 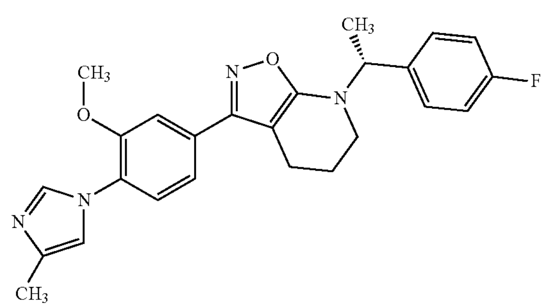 [SMILES: COc1cc(-c2noc3c2CCCN3[C@H](C)c2ccc(F)cc2)ccc1-n1cnc(C)c1] | 433.2 |
| 136 | 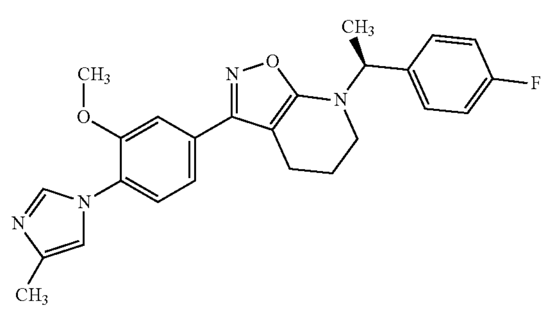 [SMILES: COc1cc(-c2noc3c2CCCN3[C@@H](C)c2ccc(F)cc2)ccc1-n1cnc(C)c1] | 433.2 |

-continued

| Cmpd | Structure | Obs LCMS |
|---|---|---|
| 137 | 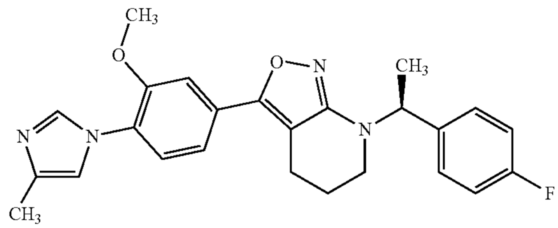 [SMILES: COc1cc(-c2onc3c2CCCN3[C@@H](C)c2ccc(F)cc2)ccc1-n1cnc(C)c1] | 433.2 |
| 138 | 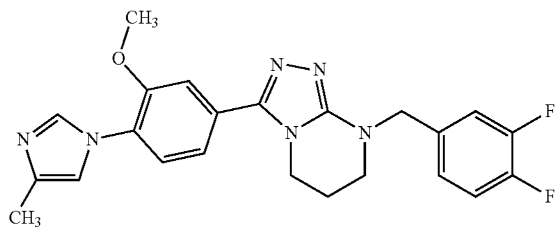 [SMILES: COc1cc(-c2nnc3n2CCCN3Cc2ccc(F)c(F)c2)ccc1-n1cnc(C)c1] | 437.2 |
| 139 | 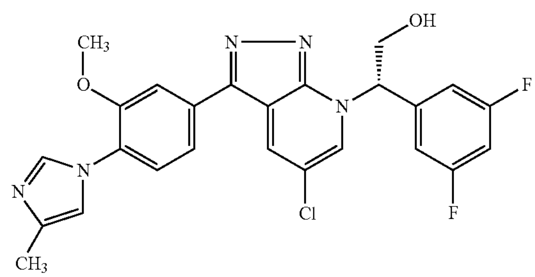 [SMILES: COc1cc(-c2nnc3n([C@H](CO)c4cc(F)cc(F)c4)cc(Cl)cc2-3)ccc1-n1cnc(C)c1] | 496.3 |
| 140 | 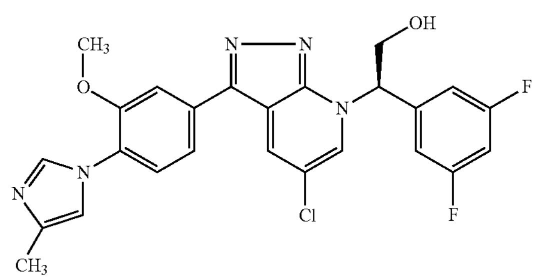 [SMILES: COc1cc(-c2nnc3n([C@@H](CO)c4cc(F)cc(F)c4)cc(Cl)cc2-3)ccc1-n1cnc(C)c1] | 496.3 |
| 141 | 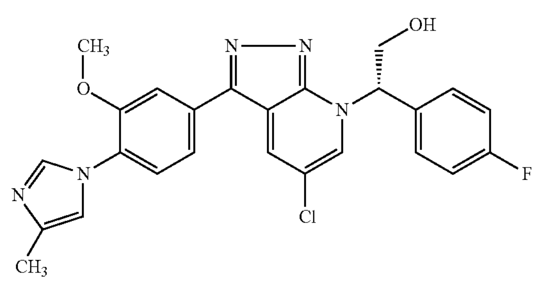 [SMILES: COc1cc(-c2nnc3n([C@H](CO)c4ccc(F)cc4)cc(Cl)cc2-3)ccc1-n1cnc(C)c1] | 478.3 |
| 142 | 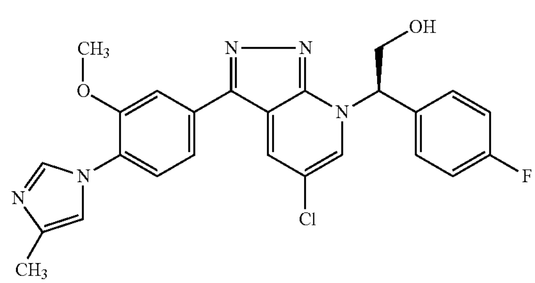 [SMILES: COc1cc(-c2nnc3n([C@@H](CO)c4ccc(F)cc4)cc(Cl)cc2-3)ccc1-n1cnc(C)c1] | 478.3 |

| Cmpd | Structure | Obs LCMS |
|---|---|---|
| 143 | 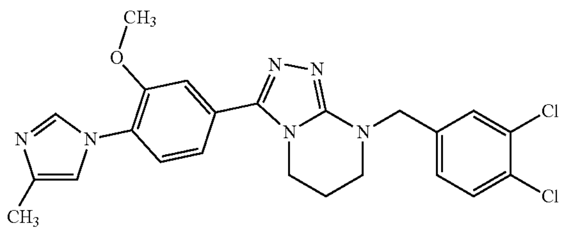 [SMILES: COc1cc(-c2nnc3n2CCCN3Cc2ccc(Cl)c(Cl)c2)ccc1-n1cnc(C)c1] | 469.3 |
| 144 | 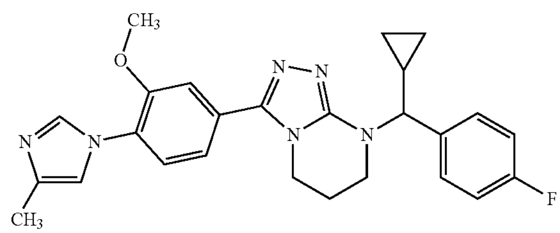 [SMILES: COc1cc(-c2nnc3n2CCCN3C(c2ccc(F)cc2)C2CC2)ccc1-n1cnc(C)c1] | 459.3 |
| 145 | 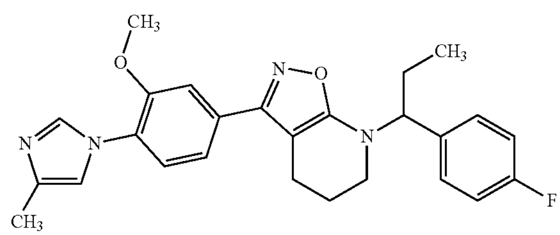 [SMILES: CCC(c1ccc(F)cc1)N1CCCc2c(-c3ccc(-n4cnc(C)c4)c(OC)c3)noc21] | 447.2 |
| 146 | 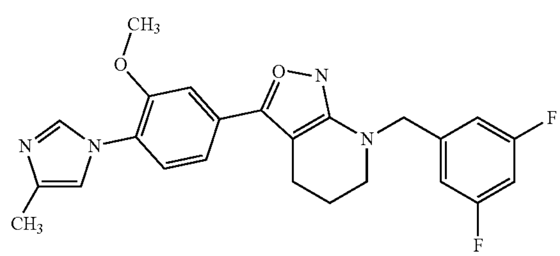 | 437.2 |
| 147 | 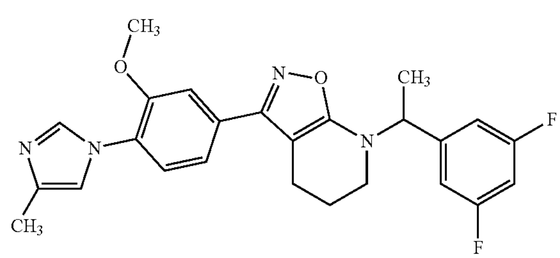 [SMILES: COc1cc(-c2noc3c2CCCN3C(C)c2cc(F)cc(F)c2)ccc1-n1cnc(C)c1] | 451.2 |
| 148 | 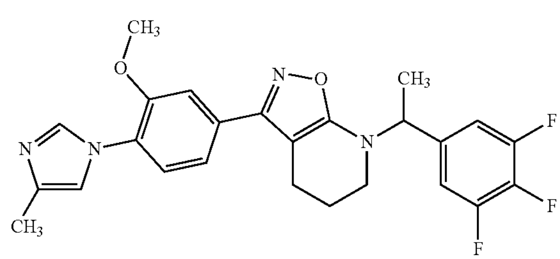 [SMILES: COc1cc(-c2noc3c2CCCN3C(C)c2cc(F)c(F)c(F)c2)ccc1-n1cnc(C)c1] | 469.3 |

| Cmpd | Structure | Obs LCMS |
|---|---|---|
| 149 | 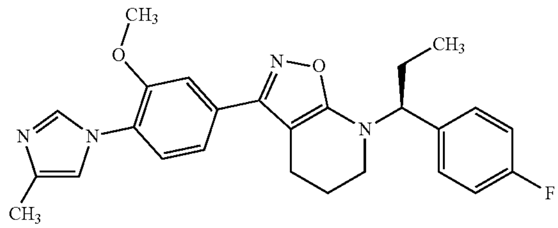 [SMILES: CC[C@@H](c1ccc(F)cc1)N1CCCc2c(-c3ccc(-n4cnc(C)c4)c(OC)c3)noc21] | 447.2 |
| 150 | 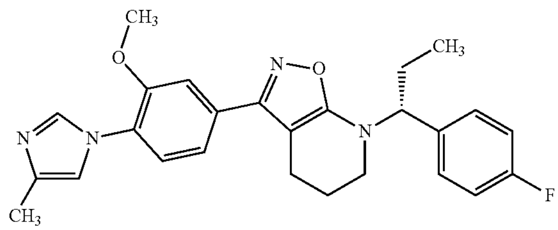 [SMILES: CC[C@H](c1ccc(F)cc1)N1CCCc2c(-c3ccc(-n4cnc(C)c4)c(OC)c3)noc21] | 447.2 |
| 151 | 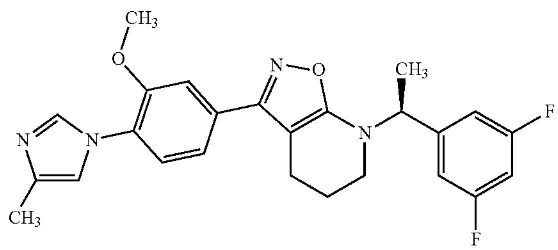 [SMILES: COc1cc(-c2noc3c2CCCN3[C@@H](C)c2cc(F)cc(F)c2)ccc1-n1cnc(C)c1] | 451.2 |
| 152 | 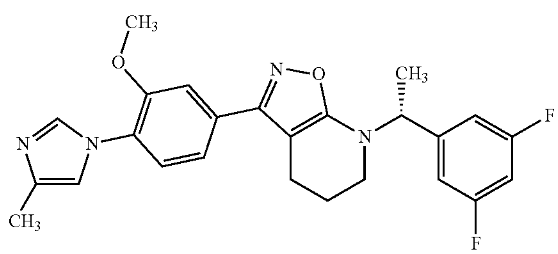 [SMILES: COc1cc(-c2noc3c2CCCN3[C@H](C)c2cc(F)cc(F)c2)ccc1-n1cnc(C)c1] | 451.2 |
| 153 | 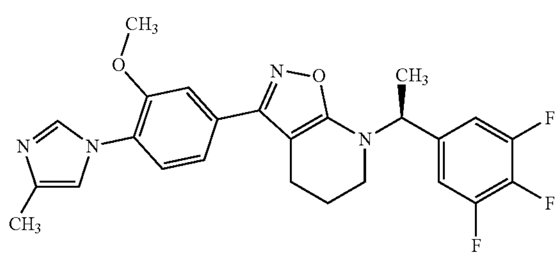 [SMILES: COc1cc(-c2noc3c2CCCN3[C@@H](C)c2cc(F)c(F)c(F)c2)ccc1-n1cnc(C)c1] | 469.3 |
| 154 | 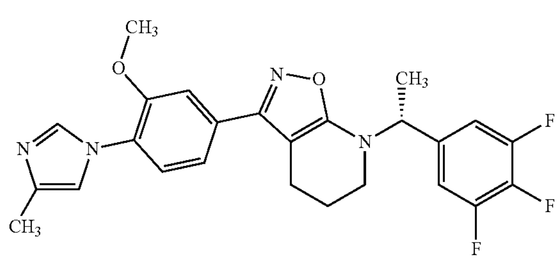 [SMILES: COc1cc(-c2noc3c2CCCN3[C@H](C)c2cc(F)c(F)c(F)c2)ccc1-n1cnc(C)c1] | 469.3 |

| Cmpd | Structure | Obs LCMS |
|---|---|---|
| 155 | 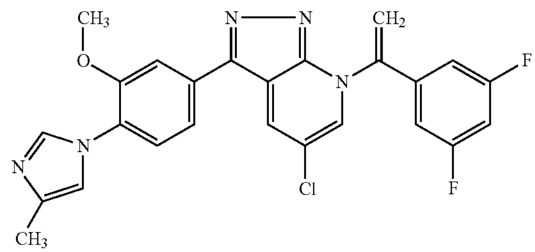 [SMILES: C=C(c1cc(F)cc(F)c1)n1cc(Cl)cc2c(-c3ccc(-n4cnc(C)c4)c(OC)c3)nnc1-2] | 478.3 |
| 156 | 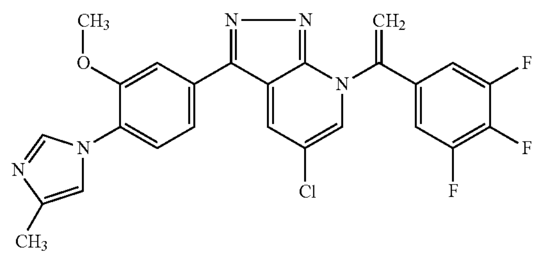 [SMILES: C=C(c1cc(F)c(F)c(F)c1)n1cc(Cl)cc2c(-c3ccc(-n4cnc(C)c4)c(OC)c3)nnc1-2] | 496.3 |
| 157 | 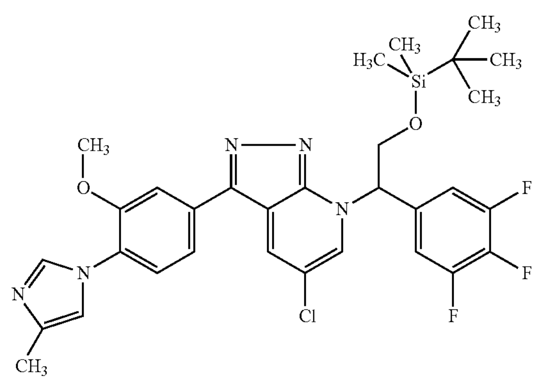 [SMILES: COc1cc(-c2nnc3n(C(CO[Si](C)(C)C(C)(C)C)c4cc(F)c(F)c(F)c4)cc(Cl)cc2-3)ccc1-n1cnc(C)c1] | 628.3 |
| 158 | 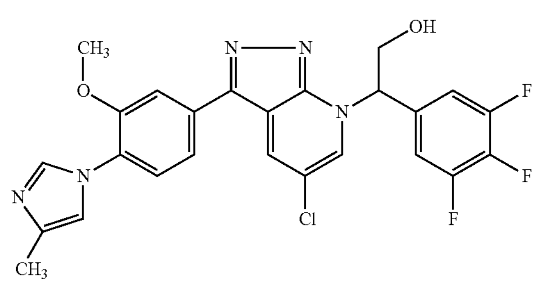 [SMILES: COc1cc(-c2nnc3n(C(CO)c4cc(F)c(F)c(F)c4)cc(Cl)cc2-3)ccc1-n1cnc(C)c1] | 514.3 |
| 159 | 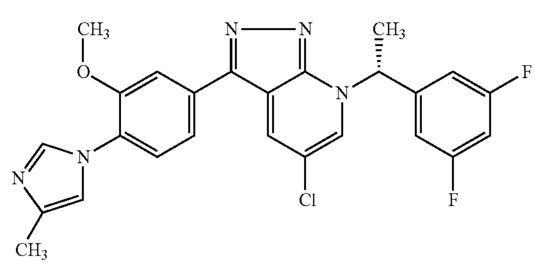 [SMILES: COc1cc(-c2nnc3n([C@H](C)c4cc(F)cc(F)c4)cc(Cl)cc2-3)ccc1-n1cnc(C)c1] | 480.3 |

| Cmpd | Structure | Obs LCMS |
|---|---|---|
| 160 | 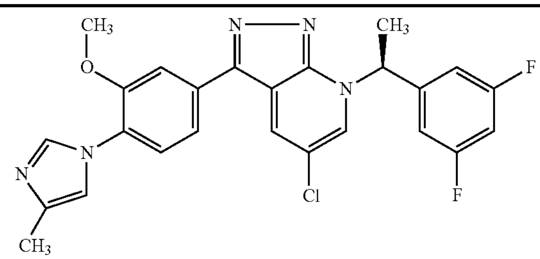 | 480.3 |
| 161 | 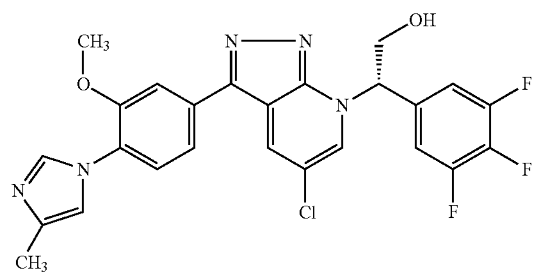 [SMILES: COc1cc(-c2nnc3n([C@H](CO)c4cc(F)c(F)c(F)c4)cc(Cl)cc2-3)ccc1-n1cnc(C)c1] | 514.3 |
| 162 | 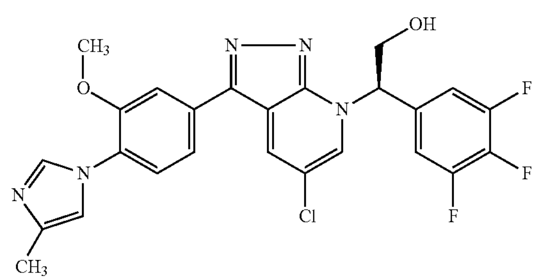 [SMILES: COc1cc(-c2nnc3n([C@@H](CO)c4cc(F)c(F)c(F)c4)cc(Cl)cc2-3)ccc1-n1cnc(C)c1] | 514.3 |

Assay:

Secretase Reaction and Aβ Analysis in Whole Cells: HEK293 cells overexpressing APP with Swedish and London mutations were treated with the specified compounds for 5 hour at 37° C. in 100 ml of DMEM medium containing 10% fetal bovine serum. At the end of the incubation, total Aβ, Aβ40 and Aβ42 were measured using electrochemiluminescence (ECL) based sandwich immunoassays. Total Aβ was determined using a pair of antibodies TAG-W02 and biotin-4G8, Aβ40 was identified with antibody pairs TAG-G2-10 and biotin-4G8, while Aβ42 was identified with TAG-G2-11 and biotin-4G8. The ECL signal was measured using Sector Imager 2400 (Meso Scale Discovery).

MS Analysis of Aβ Profile: Aβ profile in conditioned media was determined using surface enhanced laser desorption/ionization (SELDI) mass spectrometry. Conditioned media was incubated with antibody W02 coated PS20 ProteinChip array.

Mass spectra of Aβ captured on the array was read on SELDI ProteinChip Reader (Bio-Rad) according to manufacturer's instructions.

CSF Aβ Analysis: Aβ in rat CSF was determined using MSD technology as described above. Aβ40 was measured using antibody pair Tag-G2-10 and biotin-4G8, while Aβ42 was measured using Tag-anti Aβ42 (Mesa Scale Discovery) and biotin-4G8. The ECL signal was measured using Sector Imager 2400 (Meso Scale Discovery).

Matrix-assisted laser desorption/ionization mass spectrometric (MALDI MS) analysis of Aβ was performed on a Voyager-DE STR mass spectrometer (ABI, Framingham, Mass.). The instrument is equipped with a pulsed nitrogen laser (337 nm). Mass spectra was acquired in the linear mode with an acceleration voltage of 20 kV. Each spectrum presented in this work represents an average of 256 laser shots. To prepare the sample-matrix solution, 1 μL of immunoprecipitated Aβ sample was mixed with 3 of saturated α-cyano-4-hydroxycinnamic acid solution in 0.1% TFA/acetonitrile. The sample-matrix solution was then applied to the sample plate and dried at ambient temperature prior to mass spectrometric analysis. All the spectra are externally calibrated with a mixture of bovine insulin and ACTH (18-39 clip).

Certain compounds of the invention had an Ab42 $IC_{50}$ within the range of about 31 nM to about 20000 nM. Certain compounds of the invention had an Ab42 $IC_{50}$ within the range of about 31 nM to about 1808 nM. Certain compounds of the invention had an Ab42 $IC_{50}$ within the range of about 31 nM to about 107 nM.

Certain compounds of the invention had Abtotal/Ab42 ratio within the range of about 1 to about 516. Certain compounds of the invention had Abtotal/Ab42 ratio within the range of about 323 to about 516.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula (I):

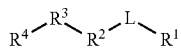

or a pharmaceutically acceptable salt thereof, wherein:

$R^1$ is a phenyl ring optionally substituted by a halogen, alkoxy or haloalkyl group;

L is selected from the group consisting of: L is a direct bond, —O—, —N($R^5$)—, —C($R^6$)($R^7$)—, —(C=O)—, —(C=N$R^{21A}$)—, —S—, —S(O)—, and —S(O)$_2$—;

$R^2$ is the fused bicyclic ring:

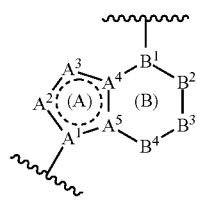

wherein:
(1) Ring (A) is a five membered heteroaryl ring comprising atoms $A^1$ to $A^5$, wherein the dashed circle in Ring A represent a sufficient number of bonds for Ring (A) to be a heteroaryl ring:
   (a) $A^1$, $A^4$, and $A^5$ are each C,
   (b) $A^2$ and $A^3$ are each N wherein each substitutable N is optionally substituted with one $R^{21A}$ group and each $R^{21A}$ for each N is independently selected,
(2) Ring (B) (which comprises atoms $A^4$, $A^5$, and $B^1$ to $B^4$) is a heterocycloalkenyl ring, wherein
$A^4$ and $A^5$ are as defined for Ring (A) above,
$B^1$ is N;
$B^2$ to $B^4$ is C;
wherein each substitutable $A^4$, $A^5$, and $B^2$ to $B^4$ is optionally substituted with 1 or 2 independently selected $R^{21B}$ groups,
and wherein said heterocycloalkenyl Ring (B) comprises two double bonds;

$R^3$ is an alkoxy substituted phenyl ring;

$R^4$ is an imidazol-1-yl ring optionally substituted with an alkyl group or an alkyl and halo group;

$R^5$ is selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$); or $R^5$ taken together with $R^1$ and the nitrogen to which they are bound form a heterocycloalkyl or heterocycloalkenyl ring fused to said $R^1$ ring said fused ring is optionally substituted with 1 to 5 independently selected $R^{21}$ groups;

$R^6$ and $R^7$ are each independently selected from the group consisting of: H, alkyl, alkenyl, alkynyl, aryl, arylalkyl-, alkylaryl-, cycloalkyl, cycloalkylalkyl-, heteroarylalkyl-, heterocyclyl and heterocyclylalkyl-, wherein independently each of said alkyl, alkenyl and alkynyl, aryl, arylalkyl-, alkylaryl-, cycloalkyl, cycloalkylalkyl-, heteroaryl, heteroarylalkyl-, heterocyclyl and heterocyclylalkyl- is optionally substituted with 1 to 5 independently selected $R^{21}$ groups; or $R^6$ taken together with $R^1$ and the carbon to which they are bound form a cycloalkyl, cycloalkenyl, heterocycloalkyl or heterocycloalkenyl ring fused to said $R^1$ ring, said fused ring is optionally substituted with 1 to 5 independently selected $R^{21}$ groups; or $R^6$ and $R^7$ taken together with the carbon to which they are bound form a spirocycloalkyl ring, a spirocycloalkenyl ring, a spiroheterocycloalkyl ring, or a spiroheterocycloalkenyl ring, and wherein the spiro ring is optionally substituted with 1-5 independently selected $R^{21}$ groups;

$R^{15A}$ and $R^{16A}$ are independently selected from the group consisting of alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, ($R^{18}$)$_q$-alkyl, ($R^{18}$)$_q$-cycloalkyl, ($R^{18}$)$_q$-cycloalkylalkyl, ($R^{18}$)$_q$-heterocyclyl, ($R^{18}$)$_q$-heterocyclylalkyl, ($R^{18}$)$_q$-aryl, ($R^{18}$)$_q$-arylalkyl, ($R^{18}$)$_q$-heteroaryl and ($R^{18}$)$_q$ heteroarylalkyl, wherein q is 1 to 5;

$R^{15}$, $R^{16}$ and $R^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, ($R^{18}$)$_q$-alkyl, ($R^{18}$)$_q$-cycloalkyl, ($R^{18}$)$_q$-cycloalkylalkyl, ($R^{18}$)$_q$-heterocyclyl, ($R^{18}$)$_q$-heterocyclylalkyl, ($R^{18}$)$_q$-aryl, ($R^{18}$)$_q$-arylalkyl, ($R^{18}$)$_q$-heteroaryl and ($R^{18}$)$_q$ heteroarylalkyl, wherein q is 1 to 5 and each $R^{18}$ is independently selected (and those skilled in the art will appreciate that the $R^{18}$ moieties can be bound to any available substitutable atom);

each $R^{18}$ is independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)$R^{19}$, —C(O)OH, —C(O)O$R^{19}$, —C(O)NH$R^{20}$, —C(O)NH$_2$, —C(O)NH$_2$—C(O)N(alkyl)$_2$, —C(O)N(alkyl)(aryl), —C(O)N(alkyl)(heteroaryl), —S$R^{19}$, —S(O)$_2$$R^{20}$, —S(O)NH$_2$, —S(O)NH(alkyl), —S(O)N(alkyl)(alkyl), —S(O)NH(aryl), —S(O)$_2$NH$_2$, —S(O)$_2$NH$R^{19}$, —S(O)$_2$NH(heterocyclyl), —S(O)$_2$N(alkyl)$_2$, —S(O)$_2$N(alkyl)(aryl), —OCF$_3$, —OH, —O$R^{20}$, —O-heterocyclyl, —O-cycloalkylalkyl, —O-heterocyclylalkyl, —NH$_2$, —NH$R^{20}$, —N(alkyl)$_2$, —N(arylalkyl)$_2$, —N(arylalkyl)-(heteroarylalkyl), —NHC(O)$R^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$$R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl); or alternately, two $R^{18}$ moieties on adjacent carbons can be linked together to form:

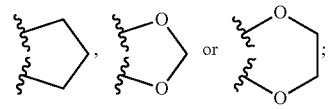

$R^{19}$ is alkyl, cycloalkyl, aryl, arylalkyl or heteroarylalkyl;
$R^{20}$ is alkyl, cycloalkyl, aryl, halo substituted aryl, arylalkyl, heteroaryl or heteroarylalkyl;

each R²¹ group is independently selected from the group consisting of alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, halo, —CN, —OR¹⁵, —C(O)R¹⁵, —C(O)OR¹⁵, —C(O)N(R¹⁵)(R¹⁶), —P(O)(CH₃)₂, —SO(=NR¹⁵)R¹⁶—, —SF₅, —OSF₅, —Si(R¹⁵ᴬ)₃ wherein each R¹⁵ᴬ is independently selected, —SR¹⁵, —S(O)N(R¹⁵)(R¹⁶), —CH(R¹⁵)(R¹⁶), —S(O)₂N(R¹⁵)(R¹⁶), —C(=NOR¹⁵)R¹⁶, —P(O)(OR¹⁵)(OR¹⁶), —N(R¹⁵)(R¹⁶), -alkyl-N(R¹⁵)(R¹⁶), —N(R¹⁵)C(O)R¹⁶, —CH₂—N(R¹⁵)C(O)R¹⁶, —CH₂—N(R¹⁵)C(O)N(R¹⁶)(R¹⁷), —CH₂—R¹⁵, —CH₂N(R¹⁵)(R¹⁶), —N(R¹⁵)S(O)R¹⁶ᴬ, —N(R¹⁵)S(O)₂R¹⁶ᴬ, —CH₂—N(R¹⁵)S(O)₂R¹⁶ᴬ, —N(R¹⁵)S(O)₂N(R¹⁶)(R¹⁷), —N(R¹⁵)S(O)N(R¹⁶)(R¹⁷), —N(R¹⁵)C(O)N(R¹⁶)(R¹⁷), —CH₂—N(R¹⁵)C(O)N(R¹⁶)(R¹⁷), —N(R¹⁵)C(O)OR¹⁶, —CH₂—N(R¹⁵)C(O)OR¹⁶, —S(O)R¹⁵ᴬ, =NOR¹⁵, —N₃, —NO₂, —S(O)₂R¹⁵ᴬ, —O—N=C(R¹⁵)₂ (wherein each R¹⁵ is independently selected), and —O—N=C(R¹⁵)₂ wherein said R¹⁵ groups are taken together with the carbon atom to which they are bound to form a 5 to 10 membered ring and wherein said ring optionally contains 1 to 3 heteroatoms independently selected from the group consisting of —O—, —O—, —S(O)—, —S(O)₂—, and —NR²¹ᴬ;

each R²¹ᴬ is independently selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, halo, —OR¹⁵, —CN, -alkyl-(R¹⁵)(R¹⁶), —CH(R¹⁵)(R¹⁶), —CH₂—N(R¹⁵)C(O)R¹⁶, —CH₂—N(R¹⁵)C(O)N(R¹⁶)(R¹⁷), —CH₂—R¹⁵; —CH₂N(R¹⁵)(R¹⁶), —C(O)R¹⁵, —C(O)OR¹⁵, —C(O)N(R¹⁵)(R¹⁶), —C(=NOR¹⁵)R¹⁶, —CH₂—N(R¹⁵)S(O)₂R¹⁶ᴬ, —CH₂—N(R¹⁵)C(O)N(R¹⁶)(R¹⁷), —CH₂—N(R¹⁵)C(O)OR¹⁶, —C(R¹⁵)=NOR¹⁶, —S(O)R¹⁵ᴬ; —S(O)(OR¹⁵), —S(O)₂(O R¹⁵), —S(O)₂R¹⁵ᴬ, —S(O)N(R¹⁵)(R¹⁶), —S(O)₂N(R¹⁵)(R¹⁶), —P(O)(OR¹⁵)(OR¹⁶), —N(R¹⁵)(R¹⁶), —N(R¹⁵)C(O)R¹⁶, —N(R¹⁵)S(O)R¹⁶ᴬ, —N(R¹⁵)S(O)₂R¹⁶ᴬ, —N(R¹⁵)S(O)₂N(R¹⁶)(R¹⁷), —N(R¹⁵)S(O)N(R¹⁶)(R¹⁷), —N(R¹⁵)C(O)N(R¹⁶)(R¹⁷), —N(R¹⁵)C(O)OR¹⁶, —N₃, —NO₂, —P(O)(CH₃)₂, —SO(=NR¹⁵)R¹⁶—, —SF₅, and —OSF₅;

each R²¹ᴮ group is independently selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, halo, —OR¹⁵, —CN, -alkyl-(R¹⁵)(R¹⁶), —CH(R¹⁵)(R¹⁶), —CH₂—N(R¹⁵)C(O)R¹⁶, —CH₂—N(R¹⁵)C(O)N(R¹⁶)(R¹⁷), —CH₂—R¹⁵, —CH₂N(R¹⁵)(R¹⁶), —C(O)R¹⁵, —C(O)OR¹⁵, —C(O)N(R¹⁵)(R¹⁶), —C(=NOR¹⁵)R¹⁶, —CH₂—N(R¹⁵)S(O)₂R¹⁶ᴬ, —CH₂—N(R¹⁵)C(O)N(R¹⁶)(R¹⁷), —CH₂—N(R¹⁵)C(O)OR¹⁶, —C(R¹⁵)=NOR¹⁶, —SR¹⁵; —S(O)R¹⁵ᴬ; —S(O)(OR¹⁵), —S(O)₂(OR¹⁵), —S(O)₂R¹⁵ᴬ, —S(O)N(R¹⁵)(R¹⁶), —S(O)₂N(R¹⁵)(R¹⁶), —P(O)(OR¹⁵)(OR¹⁶), —N(R¹⁵)(R¹⁶), —N(R¹⁵)C(O)R¹⁶, —N(R¹⁵)S(O)R¹⁶ᴬ, —N(R¹⁵)S(O)₂R¹⁶ᴬ, —N(R¹⁵)S(O)₂N(R¹⁶)(R¹⁷), —N(R¹⁵)S(O)N(R¹⁶)(R¹⁷), —N(R¹⁵)C(O)N(R¹⁶)(R¹⁷), —N(R¹⁵)C(O)OR¹⁶, —N₃, —NO₂, —P(O)(CH₃)₂, —SO(=NR¹⁵)R¹⁶—, —SF₅, —OSF₅, and —Si(R¹⁵ᴬ)₃ wherein each R¹⁵ᴬ is independently selected; and wherein each alkyl, cycloalkenyl, cycloalkyl, cycloalkylalkyl, heterocyclyl, heterocyclylalkyl, aryl, arylalkyl, heteroaryl, heteroarylalkyl, alkenyl and alkynyl R²¹, R²¹ᴬ, and R²¹ᴮ group is optionally substituted by 1 to 5 independently selected R²² groups wherein each R²² group is independently selected from the group consisting of alkyl, cycloalkyl, cycloalkenyl, heterocyclyl, aryl, heteroaryl, halo, —CF₃, —CN, —OR¹⁵, —C(O)R¹⁵, —C(O)OR¹⁵, -alkyl-C(O)OR¹⁵, C(O)N(R¹⁵)(R¹⁶), —SR¹⁵, —S(O)N(R¹⁵)(R¹⁶), —S(O)₂N(R¹⁵)(R¹⁶), —C(=NOR¹⁵)R¹⁶, —P(O)(OR¹⁵)(OR¹⁶), —N(R¹⁵)(R¹⁶), -alkyl-N(R¹⁵)(R¹⁶), —N(R¹⁵)C(O)R¹⁶, —CH₂—N(R¹⁵)C(O)R¹⁶, —N(R¹⁵)S(O)R¹⁶, —N(R¹⁵)S(O)₂R¹⁶, —CH₂—N(R¹⁵)S(O)₂R¹⁶, —N(R¹⁵)S(O)₂N(R¹⁶)(R¹⁷), —N(R¹⁵)S(O)N(R¹⁶)(R¹⁷), —N(R¹⁵)C(O)N(R¹⁶)(R¹⁷), —CH₂—N(R¹⁵)C(O)N(R¹⁶)(R¹⁷), —N(R¹⁵)C(O)OR¹⁶, —CH₂—N(R¹⁵)C(O)OR¹⁶, —N₃, =NOR¹⁵, —NO₂, —S(O)R¹⁵ᴬ and —S(O)₂R¹⁵A.

2. The compound of claim 1 or a pharmaceutically acceptable salt thereof, wherein R¹ is selected from the group consisting of:

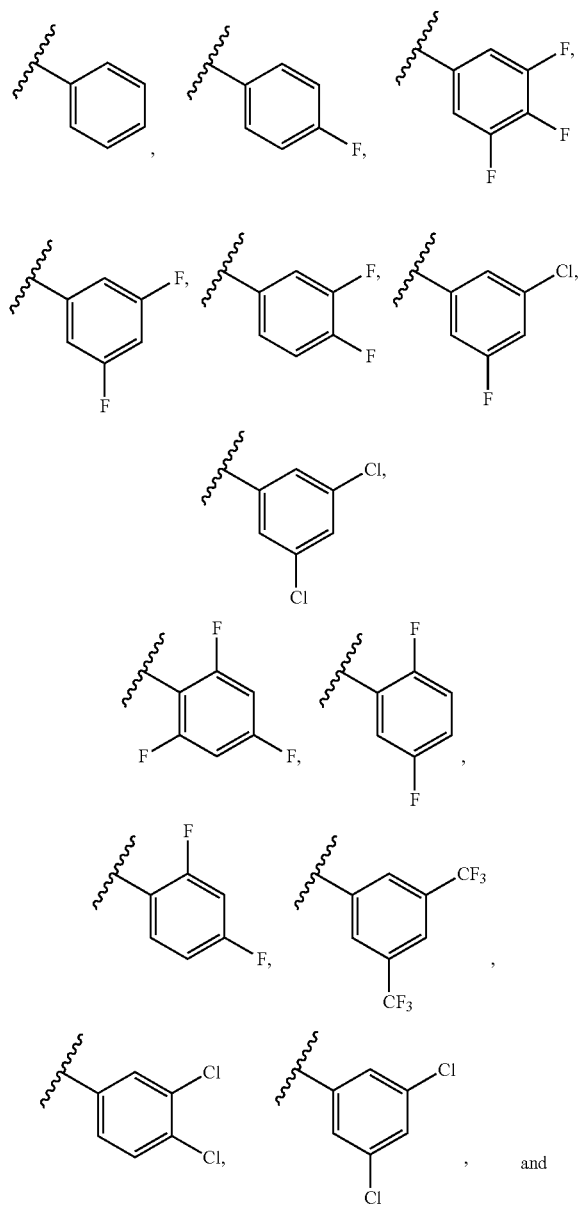

-continued

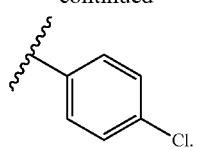

3. The compound of claim 1 or a pharmaceutically acceptable salt thereof, wherein L is selected from the group consisting of:

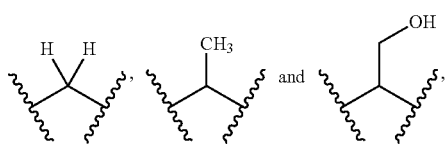

and $R^1$ selected from the group consisting of:

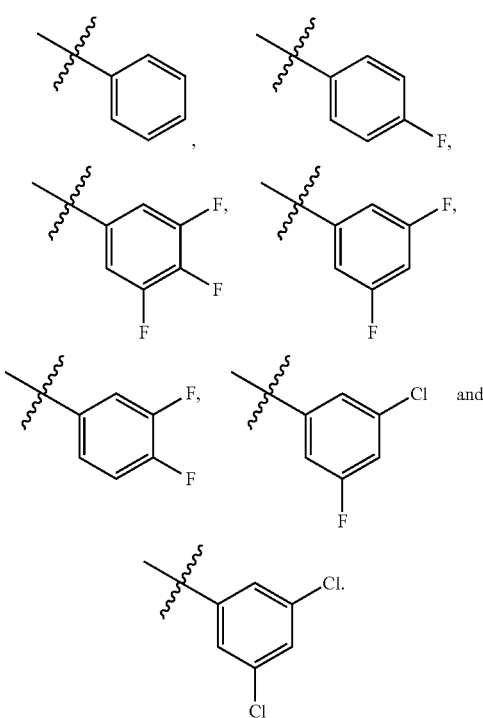

4. The compound of claim 1 or a pharmaceutically acceptable salt thereof, wherein the $R^4$—$R^3$— moiety is:

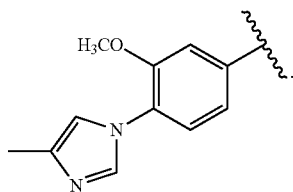 [SMILES: *c1ccc(-n2cnc(C)c2)c(OC)c1]

5. The compound of claim 1 or a pharmaceutically acceptable salt thereof, wherein:
(a) the $R^4$—$R^3$— moiety is selected from the group consisting of:

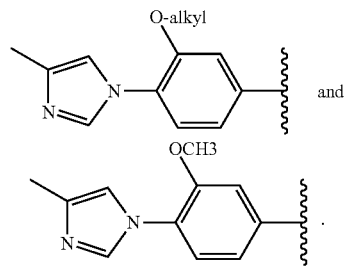

6. The compound of claim 1 or a pharmaceutically acceptable salt thereof, wherein:
(a) L is —C($R^6$)($R^7$)— wherein $R^6$ and $R^7$ are independently selected from the group consisting of:
H and alkyl; or
(b) L is —C($R^6$)($R^7$)— wherein $R^6$ is taken together with $R^1$ and the carbon to which they are bound to form a cycloalkyl, cycloalkenyl, heterocycloalkyl or heterocycloalkenyl ring fused to said $R^1$ ring, said fused ring is optionally substituted with 1 to 5 independently selected $R^{21}$ groups; or
(c) L is is —N($R^5$)—, and $R^5$ taken together with $R^1$ and the nitrogen to which they are bound form a heterocycloalkyl or heterocycloalkenyl ring fused to said $R^1$ ring.

7. The compound of claim 1 or a pharmaceutically acceptable salt thereof, selected from the group consisting of:

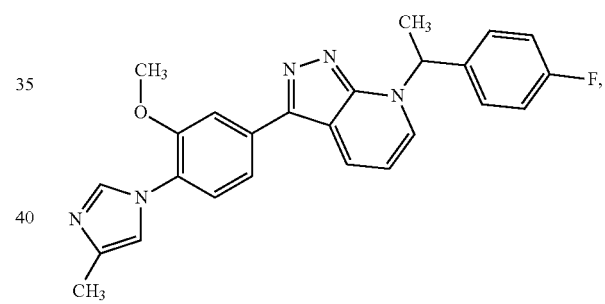

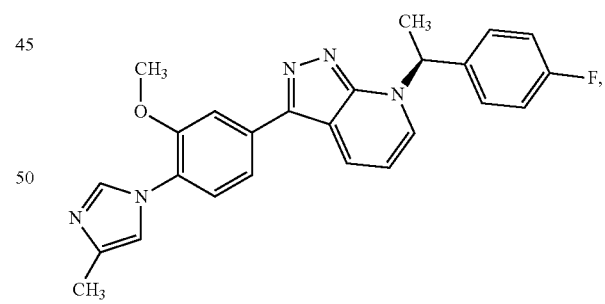

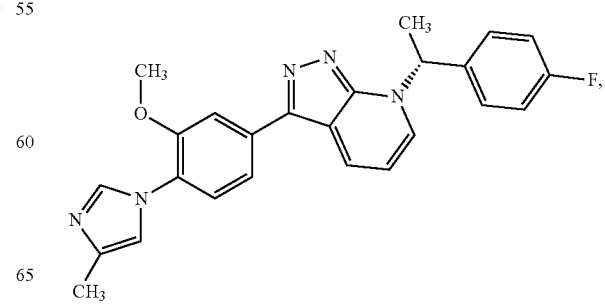

301
-continued
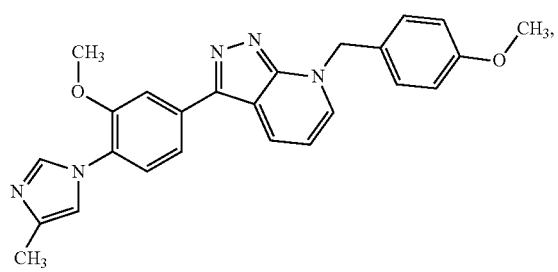
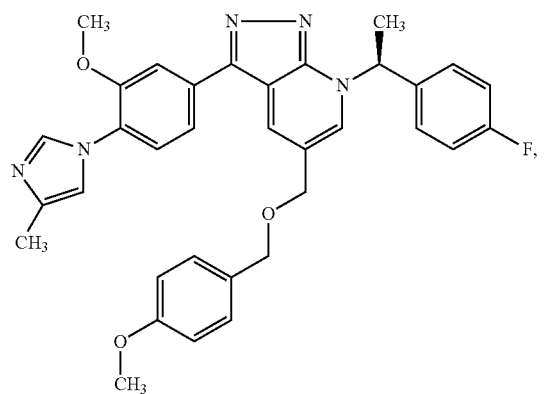
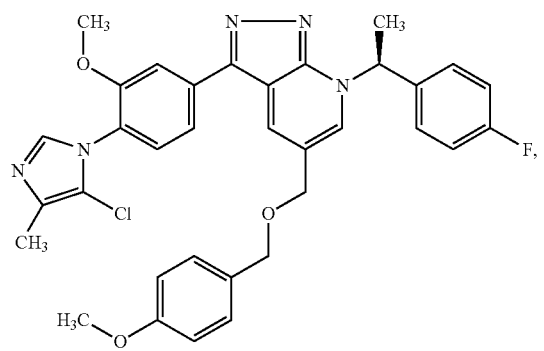
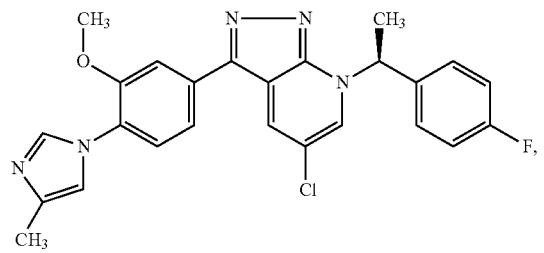
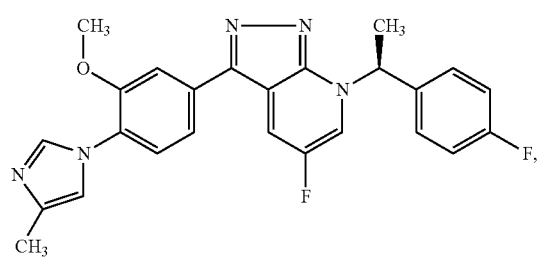
302
-continued
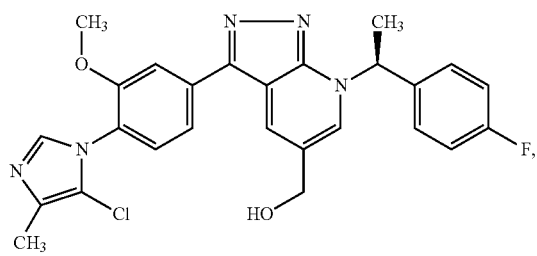
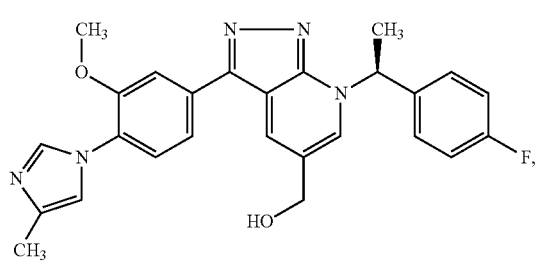
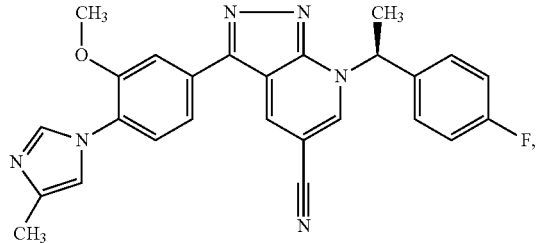
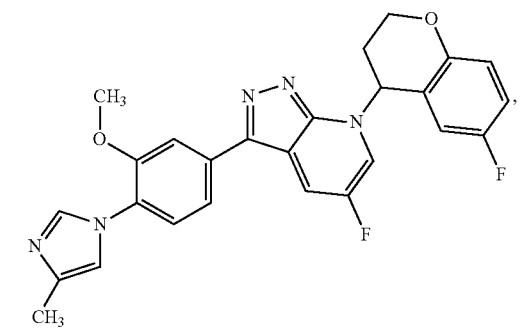
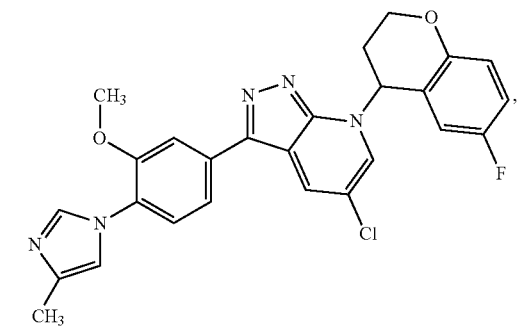

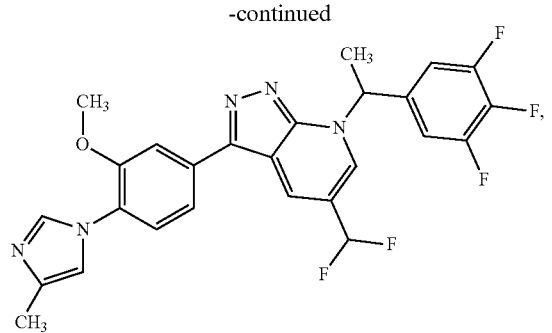
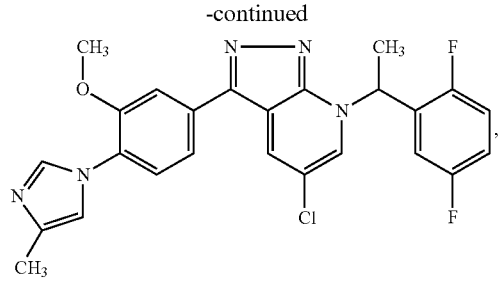
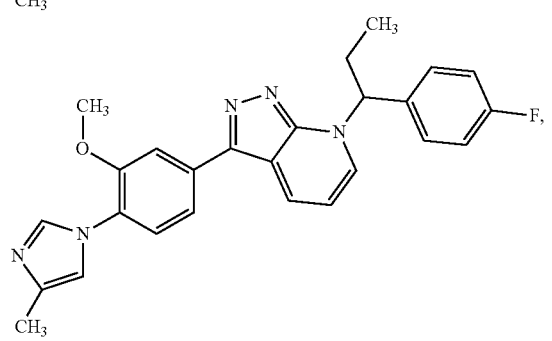
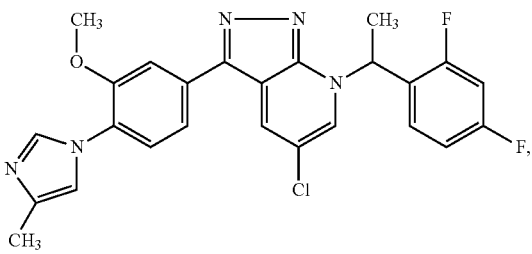
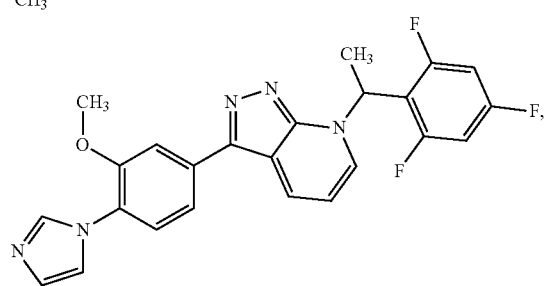
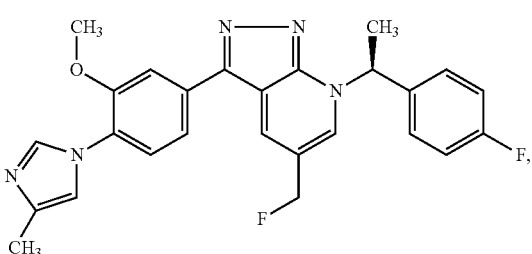
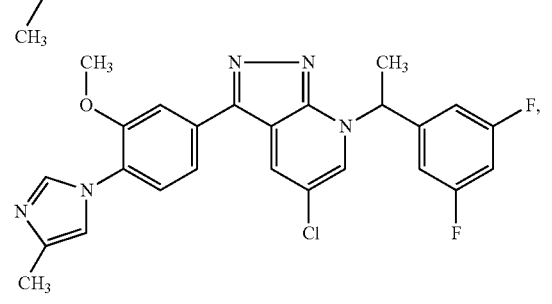
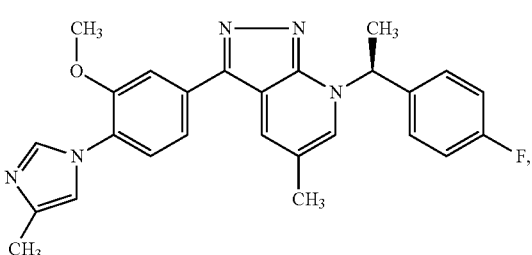
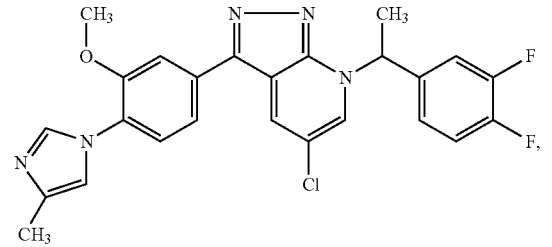
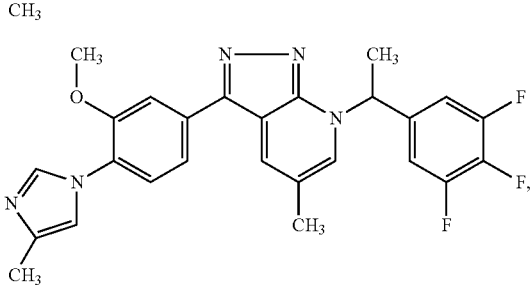
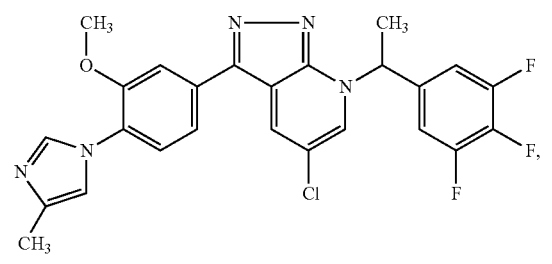
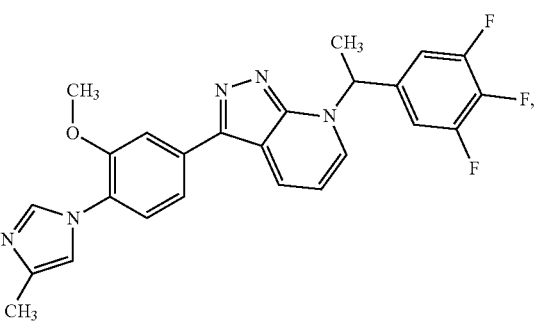

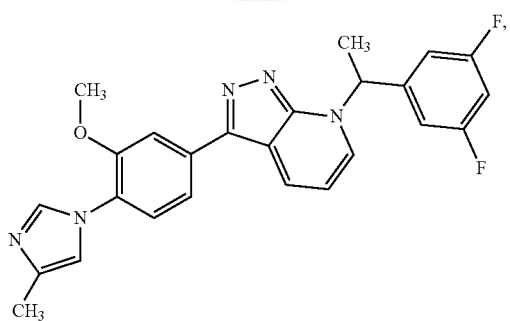
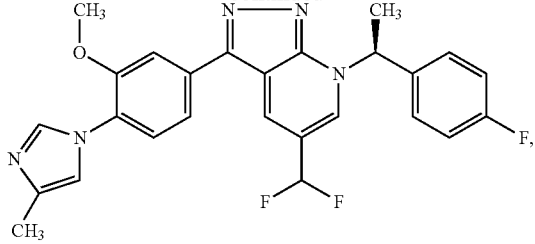
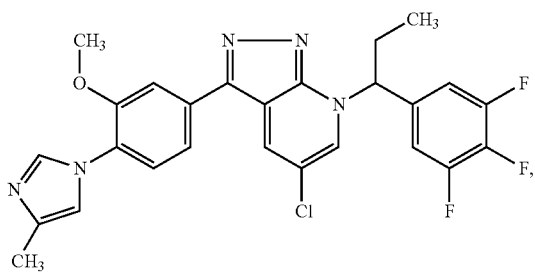
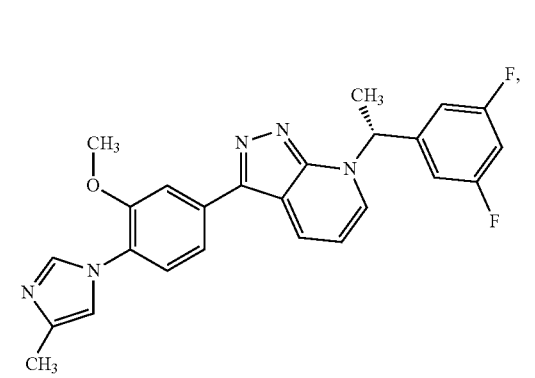
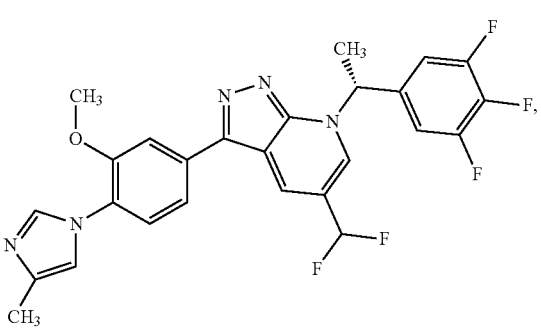
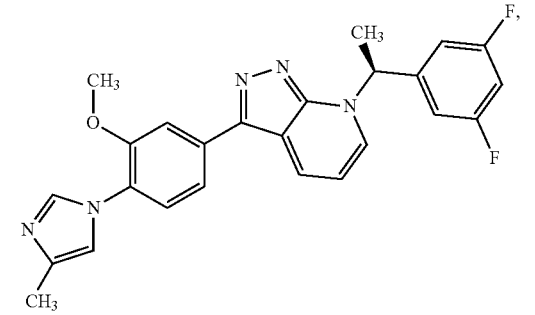

-continued
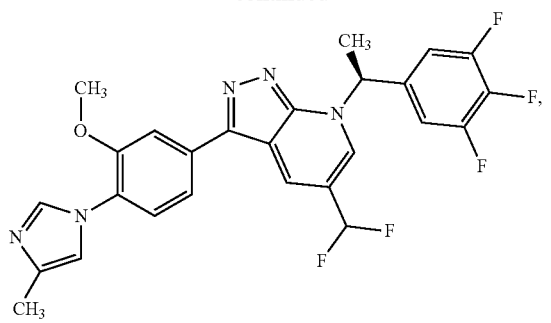
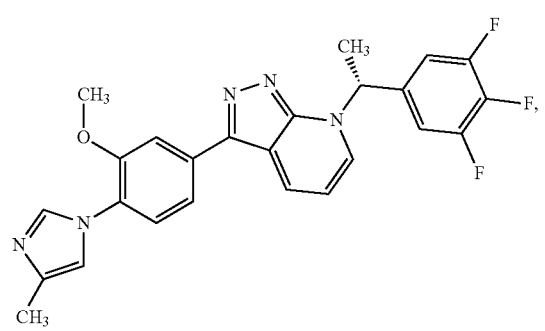
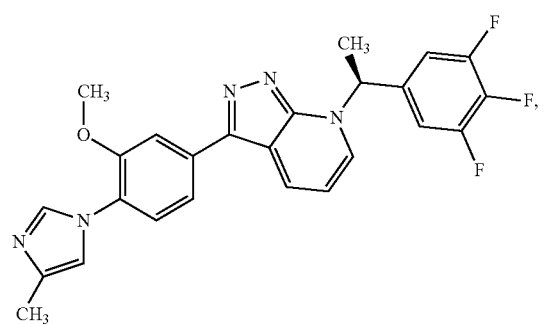
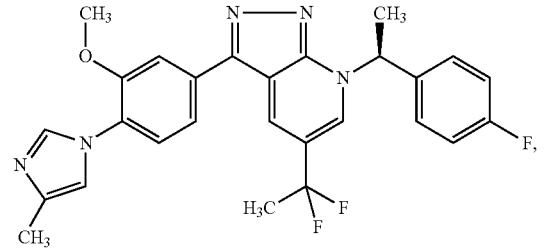
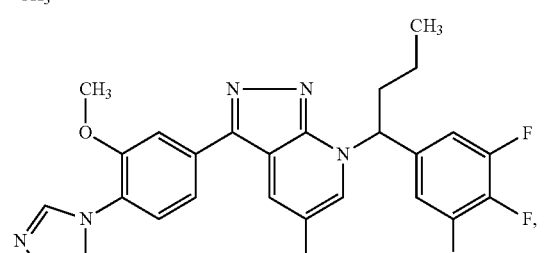
-continued
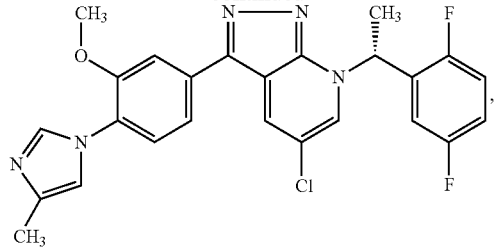
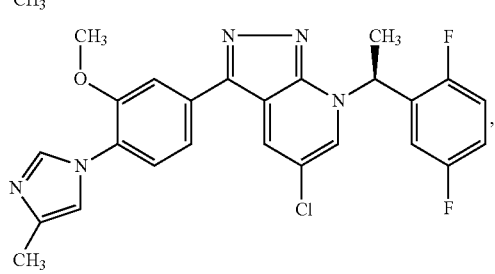
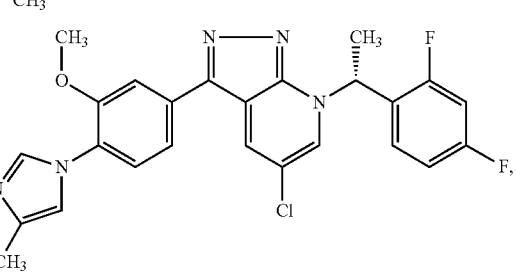
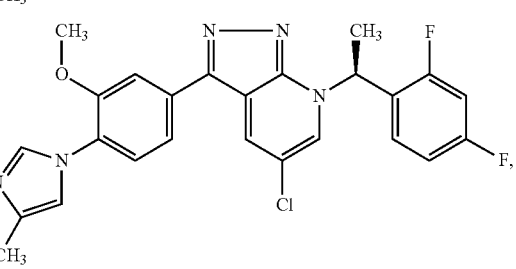
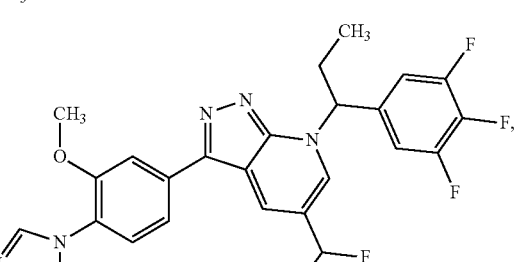
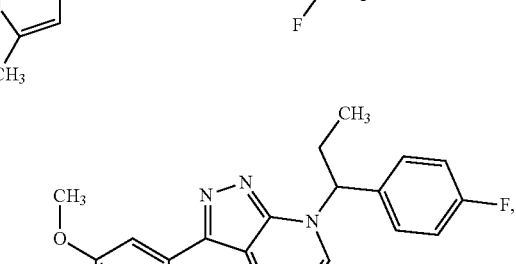

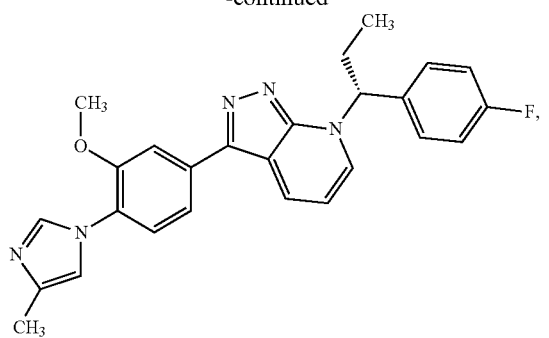
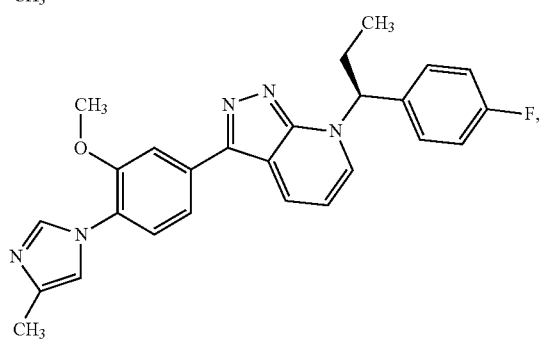
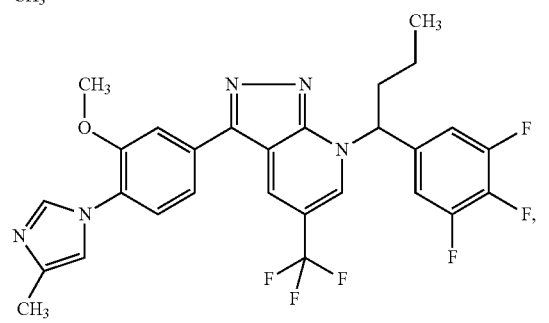
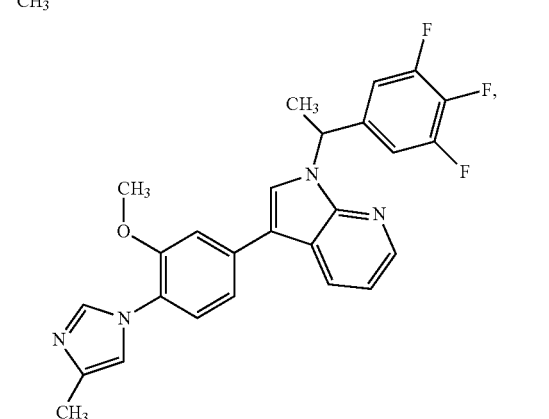
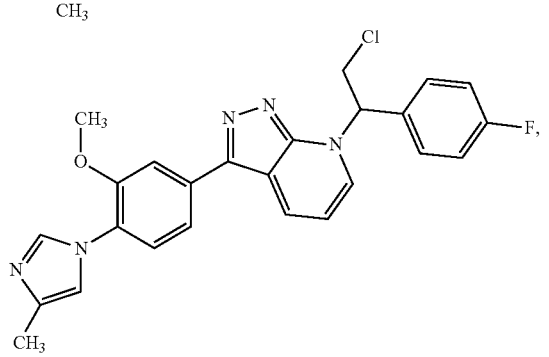
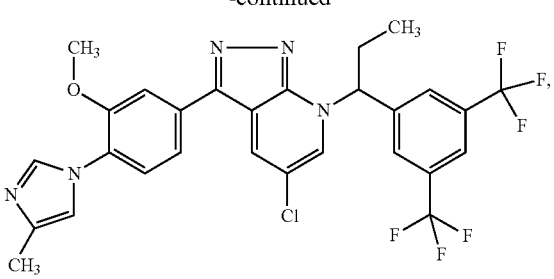
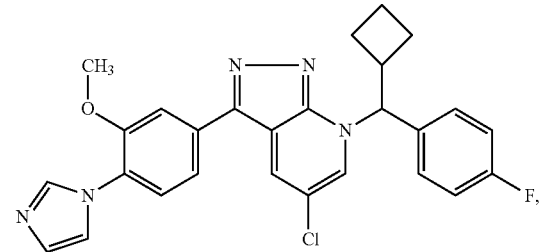
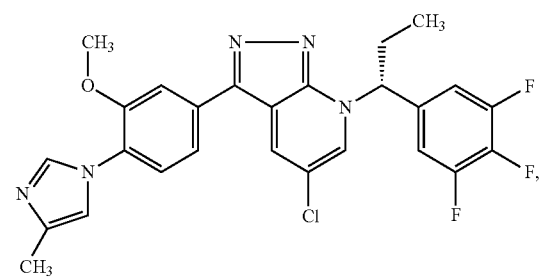
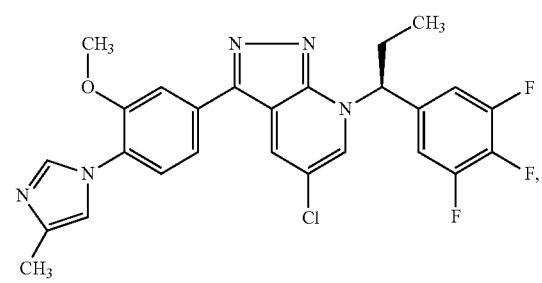
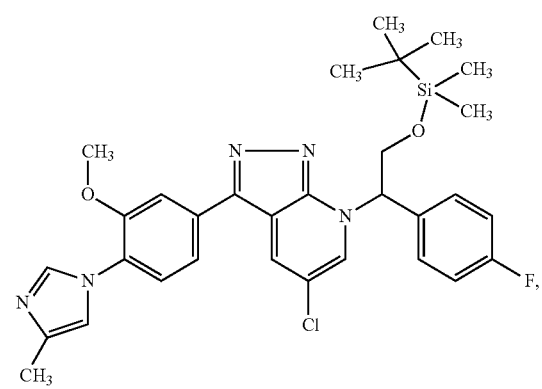

311
-continued
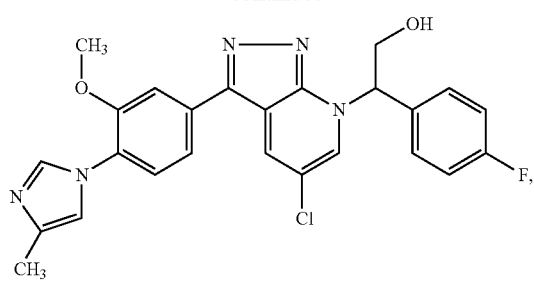
312
-continued
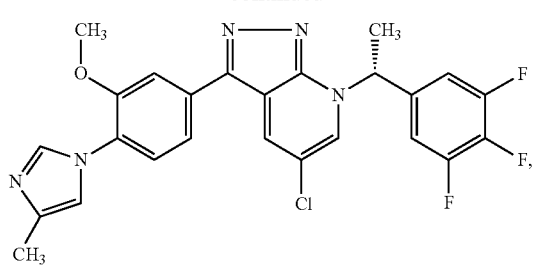
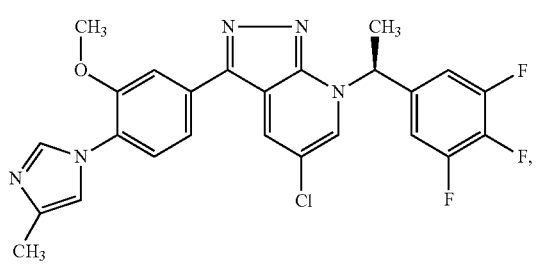
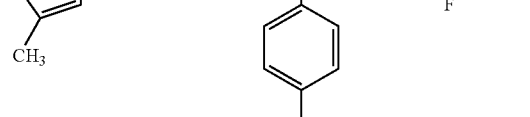
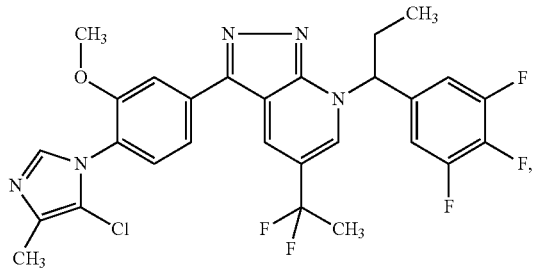
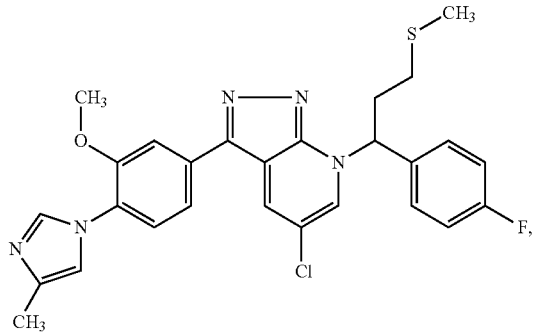

313
-continued
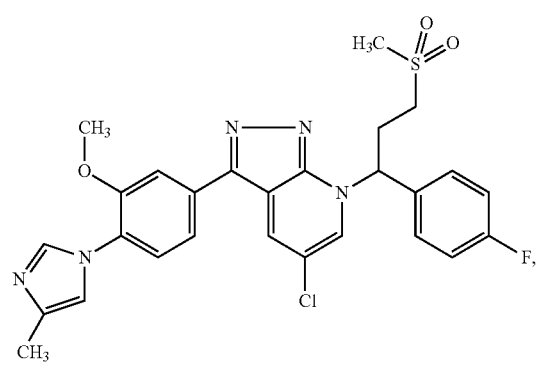
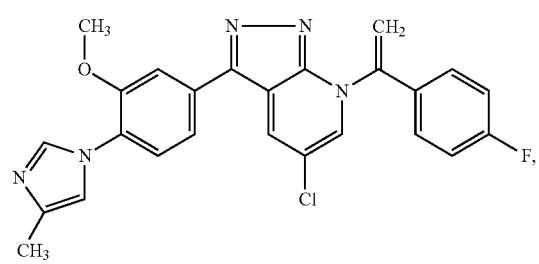
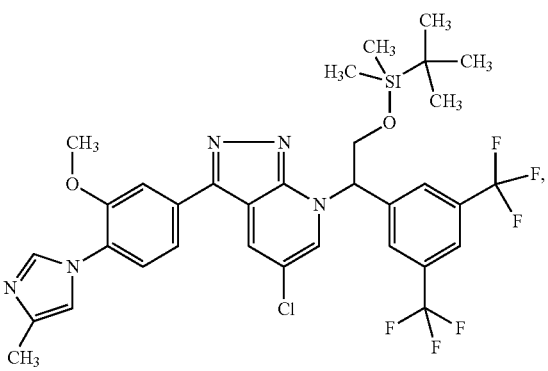
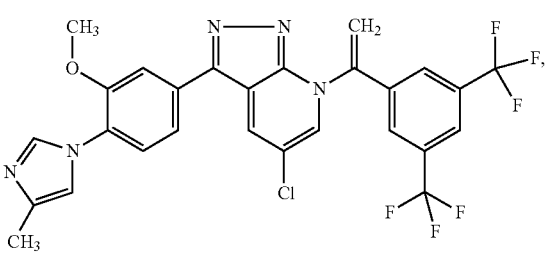
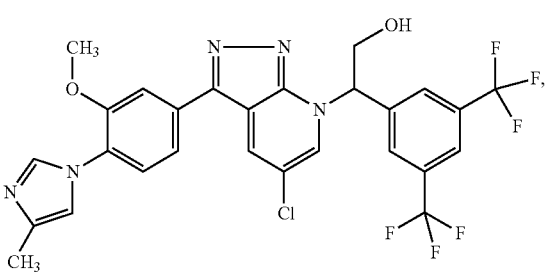
314
-continued
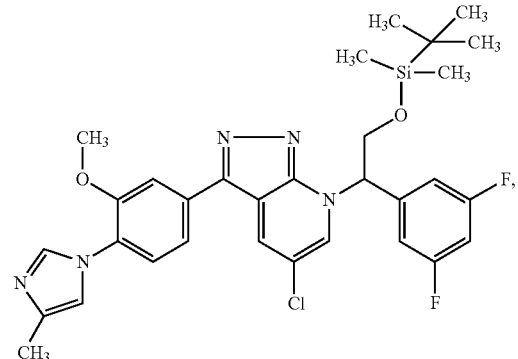
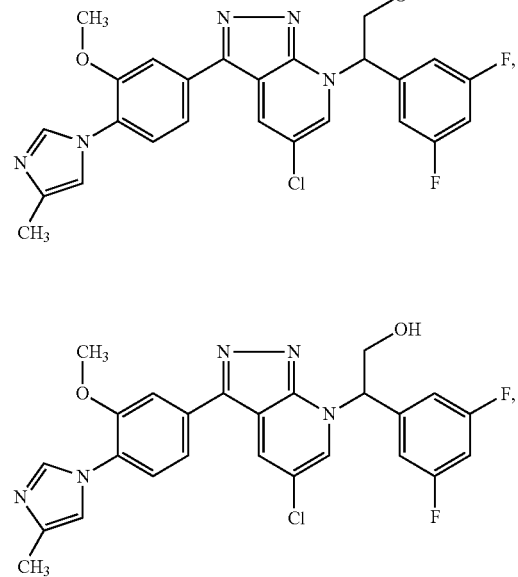
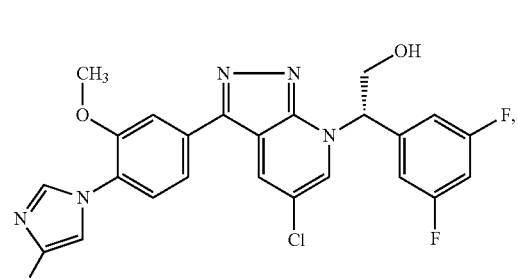
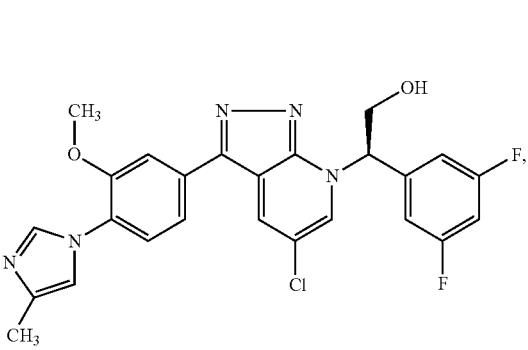
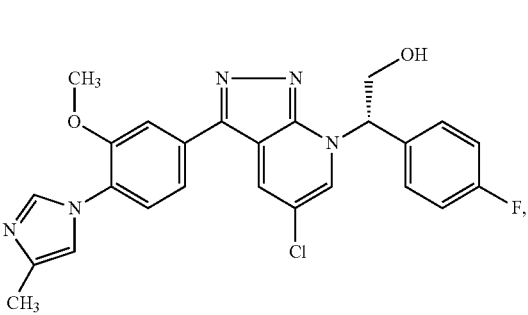

315
-continued
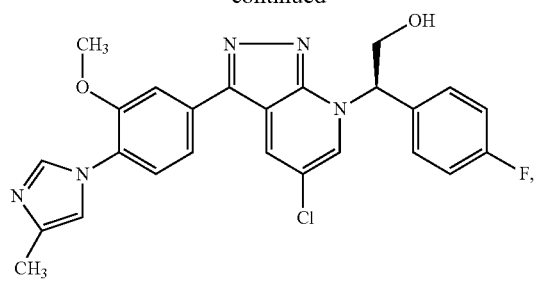
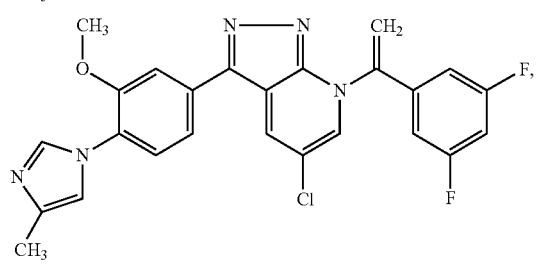
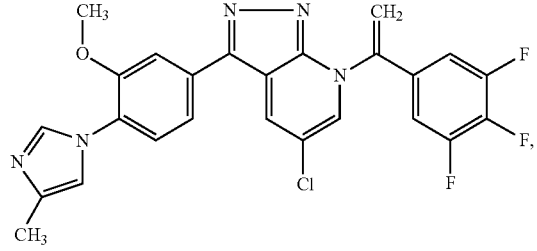
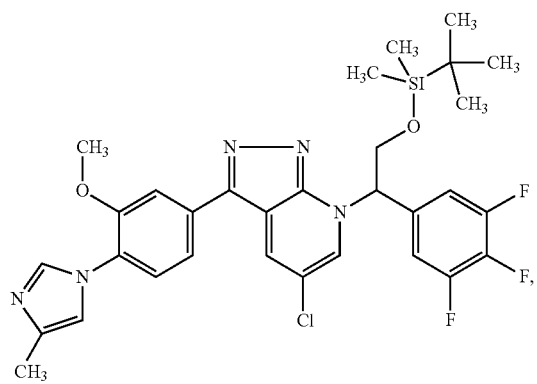
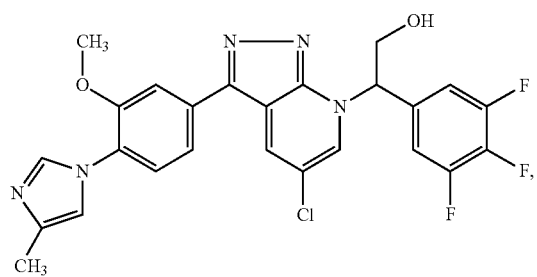
316
-continued
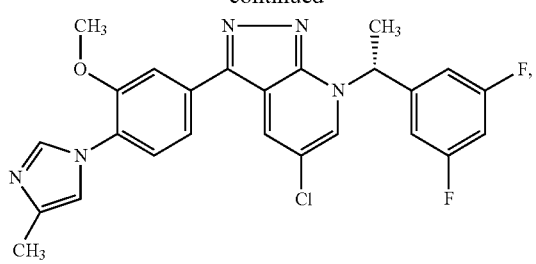
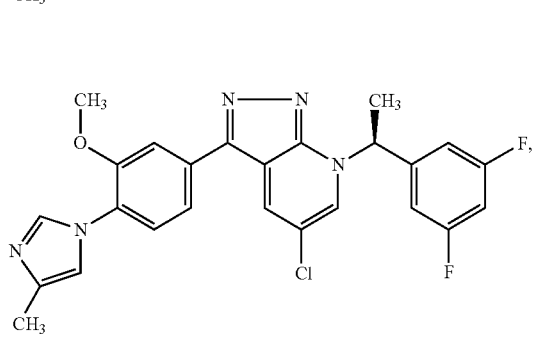
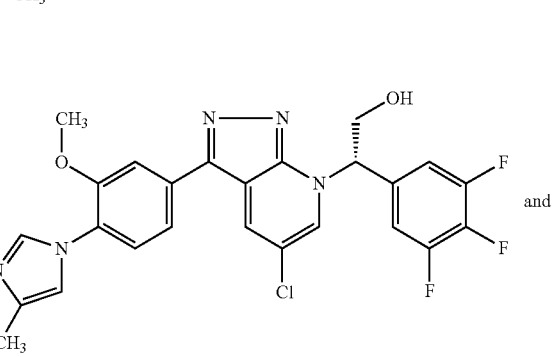
and
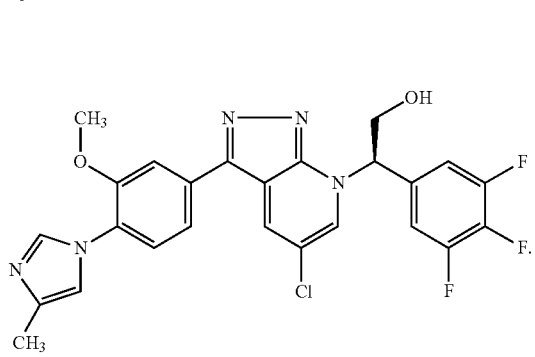
8. A pharmaceutical composition comprising: a therapeutically effective amount of at least one compound of claim 1 or a pharmaceutically acceptable salt thereof and a pharmaceutically acceptable carrier.
* * * * *

UNITED STATES PATENT AND TRADEMARK OFFICE
CERTIFICATE OF CORRECTION

| | |
|---|---|
| PATENT NO. | : 8,450,343 B2 |
| APPLICATION NO. | : 12/746041 |
| DATED | : May 28, 2013 |
| INVENTOR(S) | : Huang et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this
Second Day of December, 2014

Michelle K. Lee
*Deputy Director of the United States Patent and Trademark Office*